United States Patent
Ghezala et al.

(10) Patent No.: US 12,226,460 B2
(45) Date of Patent: Feb. 18, 2025

(54) ENZYMATIC METHODS FOR TREATING NEURODEGENERATIVE DISORDERS

(71) Applicant: Biome-ase Research, LLC, Bradenton, FL (US)

(72) Inventors: Ghania Ait Ghezala, Sarasota, FL (US); Ariane Menden, Palmetto, FL (US)

(73) Assignee: Biome-ase Research, LLC, Bradenton, FL (US)

( * ) Notice: Subject to any disclaimer, the term of this patent is extended or adjusted under 35 U.S.C. 154(b) by 0 days.

(21) Appl. No.: 18/606,664

(22) Filed: Mar. 15, 2024

(65) Prior Publication Data

US 2024/0307510 A1   Sep. 19, 2024

Related U.S. Application Data

(60) Provisional application No. 63/563,643, filed on Mar. 11, 2024, provisional application No. 63/491,004, filed on Mar. 17, 2023.

(51) Int. Cl.
*A61P 25/00* (2006.01)
*A61K 38/46* (2006.01)
*A61P 25/28* (2006.01)

(52) U.S. Cl.
CPC ............ *A61K 38/465* (2013.01); *A61P 25/28* (2018.01); *C12Y 301/01003* (2013.01)

(58) Field of Classification Search
CPC ....... C12P 7/62; C12Y 301/01; C12Y 301/00; C12N 9/20; C12N 9/16; C07K 2319/00
USPC ......................................................... 435/198
See application file for complete search history.

(56) References Cited

U.S. PATENT DOCUMENTS

| | | | |
|---|---|---|---|
| 2017/0000809 A1 | 5/2017 | Komorowski | |
| 2021/0403556 A1 | 12/2021 | Cadavid et al. | |
| 2022/0323529 A1 | 10/2022 | Cumberford et al. | |

OTHER PUBLICATIONS

Menden et al. (Nature 2022, 12(4797) pp. 1-17.*
Afgan et al., "The Galaxy platform for accessible, reproducible and collaborative biomedical analyses: 2018 update," *Nucleic Acids Res* 46, pp. W537-W544 (May 2018) (Oxford, England, UK).
Askarova et al., "The Links Between the Gut Microbiome, Aging, Modern Lifestyle and Alzheimer's Disease," *Front. Cell Infect. Microbiol.* 10(104), 12 pages (Mar. 2020) (Lausanne, Switzerland).
Barnes et al., "Selective improvement of aged rat short-term spatial memory by 3,4-diaminopyridine," *Neurobiology of Aging* 10(4), pp. 337-341 (Jul.-Aug. 1989) (Oxford, England, UK).
Borson et al., "The Mini-Cog as a Screen for Dementia: Validation in a Population-Based Sample," *J Am Geriatr Soc* 51(10), pp. 1451-1454 (Oct. 2003) (New York, New York, US).
Brandscheid et al., "Altered Gut Microbiome Composition and Tryptic Activity of the 5xFAD Alzheimer's Mouse Model," *Journal of Alzheimer's Disease* 56(2), pp. 775-788, (Dec. 2016) (Amsterdam, The Netherlands).
Bray et al., "An Ordination of the Upland Forest Communities of Southern Wisconsin," *Ecological Monographs* 27(4), pp. 325-349 (Oct. 1957) (Hoboken New Jersey, US).
Buysse et al., "The Pittsburgh Sleep Quality Index: A New Instrument for Psychiatric Practice and Research," *Psychiatry Research* 28(2), pp. 198-213 (May 1989) (Amsterdam, The Netherlands).
Caporaso et al., "QIIME allows analysis of high-throughput community sequencing data," *Nat. Methods* 7(5), pp. 335-336 (Apr. 2010) (Baden-Wuerttemberg, Germany).
Carabotti et al., "The gut-brain axis: interactions between enteric microbiota, central and enteric nervous systems," *Ann. Gastroenterol.* 28:203-209 (2015) (Heraklion, Crete, Greece).
Cattaneo et al., "Association of brain amyloidosis with proinflammatory gut bacterial taxa and peripheral inflammation markers in cognitively impaired elderly," *Neurobiology of Aging* 49, pp. 60-68 (Jan. 2017) (Amsterdam, The Netherlands).
Chang et al., "Plasma and Serum Alpha-Synuclein as a Biomarker of Diagnosis in Patients with Parkinson's Disease," *Frontiers in Neurology* 10(1388), 7 pages (Jan. 2020) (Lausanne, Switzerland).
Chen et al., "Plasma Levels of α-Synuclein, Aβ-40 and T-tau as Biomarkers to Predict Cognitive Impairment in Parkinson's Disease," *Front. Aging Neurosci.* 12(112), 8 pages (Apr. 2020) (Lausanne, Switzerland).
Chen et al., "Enrichr; interactive and collaborative HTML5 gene list enrichment analysis tool," *BMC Bioinform.* 14(128), 14 pages (Apr. 2013) (London, England, UK).
Chong et al., "Using MetaboAnalyst 4.0 for Metabolomics Data Analysis, Interpretation, and Integration with Other Omics Data," *Methods Mol. Biol.* 2104, pp. 337-360 (Jan. 2020) (Baden-Wuerttemberg, Germany).
Cleusix et al., "Glycerol induces reuterin production and decreases *Escherichia coli* population in an in vitro model of colonic fermentation with immobilized human feces," *FEMS Microbiol. Ecol.* 63(1), pp. 56-64 (Jan. 2008) (Zurich, Switzerland).
"The CNS Vital Signs Neurocognitive Testing Report," CNS Vital Signs Interpretation Guide, available online at www[dot]cnsv[dot]com/SampleReports/CNS%20VS%20Example%20Report.pdf; Test Date Mar. 28, 2015, accessed and downloaded Mar. 18, 2024, 2 pages.
Cummings, "New approaches to symptomatic treatments for Alzheimer's disease," *Mol. Neurodegener.* 16{2}, 13 pages (Jan. 2021) (electronic publication), available online at https://doi[dot]org/10.1186/s13024-021-00424-9.

(Continued)

*Primary Examiner* — Tekchand Saidha
*Assistant Examiner* — Mohammad Y Meah
(74) *Attorney, Agent, or Firm* — Arnold & Porter Kaye Scholer LLP

(57) ABSTRACT

The present disclosure relates to methods for treating, managing, or reducing the severity of one or more neurodegenerative disorders by administration of *Candida rugosa* lipase (CRL) to a patient in need thereof. The present disclosure also relates to pharmaceutical compositions comprising CRL for treating, managing, or reducing the severity of one or more neurodegenerative disorders. The present disclosure also relates to dietary supplements comprising CRL for improving memory and/or cognitive function in a subject in need thereof.

25 Claims, 82 Drawing Sheets

(56) References Cited

OTHER PUBLICATIONS

De Boever et al., "Fermentation by Gut Microbiota Cultured in a Simulator of the Human Intestinal Microbial Ecosystem Is Improved by Supplementing a Soygerm Powder," *The Journal of Nutrition* 130(10), pp. 2599-2606 (Oct. 2000) (Amsterdam, The Netherlands).
Depommier et al., "Supplementation with *Akkermansia muciniphila* in overweight and obese human volunteers: A proof-of-concept exploratory study," *Nature Medicine* 25, pp. 1096-1103 (May 2019) (Baden-Wuerttemberg, Germany).
Dhariwal et al., "MicrobiomeAnalyst: A web based tool for comprehensive statistical, visual and meta-analysis of microbiome data." *Nucleic Acids Res.* 45, pp. W180-W188 (Apr. 2017) (Oxford, England, UK).
Engels et al., "Acrolein contributes strongly to antimicrobial and heterocyclic amine transformation activities of reuterin," *Sci Rep.* 6(36246), 13 pages (Nov. 2016) (Baden-Wuerttemberg, Germany).
Fang et al., "The microbiome as a modifier of neurodegenerative disease risk," *Cell Host. Microbe* 28, pp. 201-222 (Aug. 2020) (Cambridge, Massachusetts, US).
Ferrer et al., "Production of native and recombinant lipases by *Candida rugosa*," *Appl Biochem Biotechnol* 95, pp. 221-255 (Jul. 2001) (Totowa, New Jersey, US).
Fröhlich et al., "Cognitive impairment by antibiotic-induced gut dysbiosis: Analysis of gut microbiota-brain communication," *Brain Behav. and Immun.* 56, pp. 140-155 (Aug. 2016) (Amsterdam, The Netherlands).
"Frontal Systems Behavior Scale (FrSBe)," Available online at movingahead[dot]Psy[dot]unsw[dot]edu.au/documents/research/outcome%20measures/adult/Behavioral%20Function/Website%20FrSBe.pdf, accessed and printed Mar. 20, 2024, 3 pages.
Ghyselinck et al., "A 4-strain Probiotic Supplement Influences Gut Microbiota Composition and Gut Wall Function in Patients with Ulcerative Colitis," *Int J Pharm* 587(119648), 37 pages, (Sep. 2020) (electronic publication), available online at https://doi[dot]org/10.1016/j.ijpharm.2020.119648.
Giovannini et al., "The Microbiota-Gut-Brain Axis and Alzheimer Disease. From Dysbiosis to Neurodegeneration: Focus on the Central Nervous System Glial Cells," *Journal of Clinical Medicine* 10(2358), 19 pages (May 2021) (electronic publication), available online at doi[dot]org/10.3390/jcm10112358.
Goetz et al., "Movement Disorder Society-Sponsored Revision of the Unified Parkinson's Disease Rating Scale (MDS-UPDRS): Scale Presentation and Clinimetric Testing Results," *Movement Disorders* 23(15), pp. 2129-2170 (Nov. 2008) (Milwaukee, Wisconsin, US).
Govindarajan et al., "Sodium Butyrate Improves Memory Function in an Alzheimer's Disease Mouse Model When Administered at an Advanced Stage of Disease Progression," *J. Alzheimers Dis.* 26(1), pp. 187-197 (Aug. 2011) (Amsterdam, The Netherlands).
Gualtieri et al., "Reliability and validity of a computerized neurocognitive test battery, CNS Vital Signs," *Archives of Clinical Neuropsychology*, 21(7), pp. 623-643 (May 2006) (Amsterdam, The Netherlands).
Harach et al., "Reduction of Abeta amyloid pathology in APPPS1 transgenic mice in the absence of gut microbiota," *Sci Rep.* 7(41802), 15 pages (Feb. 2017) (Baden-Wuerttemberg, Germany).
Harrison et al., "Endogenous anxiety and stress responses in water maze and Barnes maze spatial memory tasks," *Behavioral Brain Research* 198(1), pp. 247-251 (Oct. 2008) (electronic publication), available online: DOI: 10.1016/j.bbr.2008.10.015.
Hu et al., "Standardized preparation for fecal microbiota transplantation in pigs," *Front. Microbiol.* 9(1328), 10 pages, (Jun. 2018) (Lausanne, Switzerland).
Ianiro et al., "Digestive Enzyme Supplementation in Gastrointestinal Diseases," *Curr. Drug Metab.* 17, pp. 187-193 (Nov. 2016) (Sharjah, Sharjah, United Arab Emirates).
Joshi et al., "A permethrin metabolite is associated with adaptive immune responses in Gulf War Illness," *Brain Behav. Immun.* 81, pp. 545-559 (Oct. 2019) (Amsterdam, The Netherlands).
Kang et al., "Microbiota Transfer Therapy alters gut ecosystem and improves gastrointestinal and autism symptoms: an open-label study," *Microbiome* 5(10), pp. 16 pages (Jan. 2017) (London, England, UK).
Kao et al., "Lipids and Alzheimer's Disease," *Int. J. Mol. Sci.* 21(4),1505, 37 pages (Feb. 2020) (electronic publication), available online at https://doi[dot]org/10.3390/ijms21041505.
Kim et al., "HISAT: A fast spliced aligner with low memory requirements," *Nat. Methods* 12(4), pp: 357-360 (Apr. 2015) (Baden-Wuerttemberg, Germany).
Lee et al., "Analysis of the Gene Family Encoding Lipases in *Candida rugosa* by Competitive Reverse Transcription-PCR," *Appl. Environ. Microbiol.* 65(9), pp. 3888-3895 (Sep. 1999) (Washington, DC, US).
Lee et al., "Frozen vs Fresh Fecal Microbiota Transplantation and Clinical Resolution of Diarrhea in Patients With Recurrent *Clostridium difficile* Infection: A Randomized Clinical Trial," *JAMA* 315(2), pp. 142-149 (Jan. 2016) (electronic publication), available online at DOI: 10.1001/jama.2015.18098.
Liao et al., "featureCounts: An efficient general purpose program for assigning sequence reads to genomic features," *Bioinformatics* 30(7), pp. 923-930 (Apr. 2014) (Oxford, England, UK).
Liu et al., "Altered microbiomes distinguish Alzheimer's disease from amnestic mild cognitive impairment and health in a Chinese cohort," *Brain, Behavior, and Immunity* 80, pp. 633-643 (Aug. 2019) (Amsterdam, The Netherlands).
Liu et al., "Gut Microbiota and Dysbiosis in Alzheimer's Disease: Implications for Pathogenesis and Treatment," *Molecular Neurobiology* 57, pp. 5026-5043 (Aug. 2020) (Baden-Wuerttemberg, Germany).
Liu et al., "Gut microbiota mediates intermittent-fasting alleviation of diabetes-induced cognitive impairment," *Nature Communications* 11(855), 14 pages (Feb. 2020) (Baden-Wuerttemberg, Germany).
Menden et al., "A fast, miniaturized in-vitro assay developed for quantification of lipase enzyme activity," *Journal of Enzyme Inhibition and Medicinal Chemistry* 34(1), pp. 1474-1480 (2019) (Milton Park, Oxfordshire, UK).
Menden et al., "*Candida rugosa* lipase alters the gastrointestinal environment in wild-type mice," *Biomedicine & Pharmacotherapy* 130(110579) (Aug. 2020) (Amsterdam, The Netherlands).
Moens et al., "A four-strain probiotic exerts positive immunomodulatory effects by enhancing colonic butyrate production in vitro," *International Journal of Pharmaceutics* 555, pp: 1-10 (Jan. 2019) (Amsterdam, The Netherlands).
Morris et al., "Choosing and using diversity indices: Insights for ecological applications from the German Biodiversity Exploratories," *Ecology and Evolution* 4(18), pp. 3514-3524 (Sep. 2014) (Hoboken New Jersey, US).
Nasreddine et al., "The Montreal Cognitive Assessment, MoCA: A Brief Screening Tool For Mild Cognitive Impairment," *J. Am. Geriatr. Soc.* 53(4), pp. 695-699 (Apr. 2005) (electronic publication), available online at https://doi[dot]org/10.1111/j.1532-5415.2005.53221.x.
Natto et al., "Omega-3 Fatty Acids Effects on Inflammatory Biomarkers and Lipid Profiles among Diabetic and Cardiovascular Disease Patients: A Systematic Review and Meta-Analysis," *Sci Rep.* 9(18867), 10 pages (2019) (Baden-Wuerttemberg, Germany).
Nishiyama et al., "Supplementation of pancreatic digestive enzymes alters the composition of intestinal microbiota in mice," *Biochem. Biophys. Res. Commun.* 495(1), pp. 273-279 (Jan. 2018) (Amsterdam, The Netherlands).
Pitts, "Barnes Maze Procedure for Spatial Learning and Memory in Mice," *Bio Protoc.* 8(5):e2744, 11 pages (Mar. 2018) (electronic publication), available online at DOI:10.21769/BioProtoc.2744.
Prakash et al., "p-tau/Aβ42 Ratio Associates with Cognitive Decline in Alzheimer's disease, Mild Cognitive Impairment, and Cognitively Unimpaired Older Adults," *medRxiv*, Version Oct. 16, 2020, 28 pages, available online at https://doi[dot]org/10.1101/2020.10.13.20211375.
Remond et al., "Understanding the gastrointestinal tract of the elderly to develop dietary solutions that prevent malnutrition,"

(56) References Cited

OTHER PUBLICATIONS

*Oncotarget* 6(16), pp. 13858-13898 (May 2015) (electronic publication) available online at DOI: 10.18632/oncotarget.4030.

Robinson et al., "edgeR: A Bioconductor package for differential expression analysis of digital gene expression data," *Bioinformatics* 26(1), pp. 139-140 (Jan. 2010) (Oxford, England, UK).

Rodriguez-Carrio et al., "Free Fatty Acids Profiles Are Related to Gut Microbiota Signatures and Short-Chain Fatty Acids," *Front. Immunol.* 8(823), 13 pages (Jul. 2017) (Lausanne, Switzerland).

Rohart et al., "mixOmics: An R package for 'omics feature selection and multiple data integration," *PLoS Comput. Biol.* 13(11): e1005752, 19 pages (Nov. 2017) (San Francisco, CA, US).

Sato et al., "The roles of lipid and glucose metabolism in modulation of β-amyloid, tau, and neurodegeneration in the pathogenesis of Alzheimer disease," *Front. Aging Neurosci.* 7(199) (Oct. 2015) (Lausanne, Switzerland).

Schneeberger et al., "Akkermansia muciniphila inversely correlates with the onset of inflammation, altered adipose tissue metabolism and metabolic disorders during obesity in mice," *Sci Rep.* 5(16643), 14 pages (Nov. 2015) (Baden-Wuerttemberg, Germany).

Sheridan et al., "Normative Symbol Digit Modalities Test performance in a community-based sample," *Archives of Clinical Neuropsychology* 21(1), pp: 23-28 (Jan. 2006) (Amsterdam, The Netherlands).

Shi et al., "Variable selection and validation in multivariate modelling," *Bioinformatics* 35(6), pp: 972-980 (Mar. 2019) (Oxford, England, UK).

Singh et al., "DIABLO: an integrative approach for identifying key molecular drivers from multi-omics assays," *Bioinformatics* 35(17), pp. 3055-3062 (Sep. 2019) (Oxford, England, UK).

Smets et al., "The multidimensional Fatigue Inventory (MFI) psychometric qualities of an instrument to assess fatigue," *Journal of Psychosomatic Research* 39(3), pp. 315-325 (Apr. 1995) (Amsterdam, The Netherlands).

Smith et al., "XCMS: Processing Mass Spectrometry Data for Metabolite Profiling Using Nonlinear Peak Alignment, Matching, and Identification," *Anal. Chem.* 78(3), pp. 779-787 (Jan. 2006) (Washington, DC, US).

Somaraju et al., "Pancreatic enzyme replacement therapy for people with cystic fibrosis," *Cochrane Database of Systematic Reviews* 10(CD008227), 48 pages (Oct. 2014) (Hoboken, New Jersey, US).

Stout et al., "Factor Analysis of the Frontal Systems Behavior Scale (FrSBe)," *Assessment* 10(1), pp. 79-85 (Mar. 2003) (Thousand Oaks, California, US).

Tombaugh et al., "The Mini-Mental Status Examination: A Comprehensive Review," *Journal of the American Geriatrics Society* 40(9), pp. 922-935 (Sep. 1992) (Hoboken New Jersey, US).

Trapnell et al., "Efficacy and safety of Creon® 24,000 in subjects with exocrine pancreatic insufficiency due to cystic fibrosis," *Journal of Cystic Fibrosis* 8(6), pp. 370-377 (Dec. 2009) (Amsterdam, The Netherlands).

Van den Abbeele et al., "Incorporating a mucosal environment in a dynamic gut model results in a more representative colonization by lactobacilli," *Microbial Biotechnology* 5(1), pp. 106-115 (Jan. 2012) (Oxford, England, UK).

Vandeputte et al., "Quantitative microbiome profiling links gut community variation to microbial load," *Nature* 551(7681), pp. 507-511 (Nov. 2017) (Baden-Wuerttemberg, Germany).

Vinolo et al., "Regulation of Inflammation by Short Chain Fatty Acids," *Nutrients* 3(10), pp. 858-876 (Oct. 2011) (electronic publication), available online at https://doi[dot]org/10.3390/nu3100858.

Vogt et al., "Gut microbiome alterations in Alzheimer's disease," *Sci Rep.* 7(13537), 11 pages (Oct. 2017) (electronic publication), available online at https://doi[dot]org/10.1038/s41598-017-13601-y.

Wrzosek et al., "Transplantation of human microbiota into conventional mice durably reshapes the gut microbiota," *Sci. Rep.* 8(6854), 9 pages (May 2018) (electronic publication), available online at https://doi[dot]org/10.1038/s41598-018-25300-3.

Zarrinpar et al., "Antibiotic-induced microbiome depletion alters metabolic homeostasis by affecting gut signaling and colonic metabolism," *Nat. Commun.* 9(2872), 13 pages (Jul. 2018) (Baden-Wuerttemberg, Germany).

International Search Report dated Aug. 26, 2024, issued in Int'l. Appln. PCT/US2024/020114.

Malloy et al., "A Review of Rating Scales for Measuring Behavior Change Due to Frontal Systems Damage," Cog Behav Neurol 18(1), pp. 18-27 (Mar. 2005) (electronic publication).

\* cited by examiner

| Pathway | Overlap | Raw p | -log10(p) | FDR | Impact |
|---|---|---|---|---|---|
| Glycerophospholipid | 1/36 | 0.0006 | 3.2545 | 0.0256 | 0.0132 |
| Linoleic acid | 1/5 | 0.0015 | 2.8175 | 0.0284 | 1 |
| Glycerolipid | 2/16 | 0.0019 | 2.7151 | 0.0284 | 0.3302 |
| FA elongation | 1/39 | 0.0049 | 2.3072 | 0.0284 | 0 |
| FA degradation | 1/39 | 0.0049 | 2.3072 | 0.0284 | 0 |
| Biosynthesis of UFAs | 4/36 | 0.0087 | 2.0592 | 0.0401 | 0 |
| FA biosynthesis | 2/47 | 0.0191 | 1.7202 | 0.0548 | 0.0147 |

FIG. 1L

| Pairwise comparison | Pathway name | p value |
|---|---|---|
| Wt+CRL vs. Wt | Linoleic acid metabolism | 0.009934 |
| | alpha-Linolenic acid metabolism | 0.02569 |
| | Arachidonic acid metabolism | 0.070058 |
| | Glycerophospholipid metabolism | 0.070058 |
| APP/PS1+CRL vs. APP/PS1 | alpha-Linolenic acid metabolism | 0.001411 |
| | Biosynthesis of unsaturated fatty acids | 0.010823 |

FIG. 2C

| Term | Overlap | Adjusted p value | Odds ratio | Combined score |
|---|---|---|---|---|
| Endocytosis | 42/269 | 0.0321 | 1.9919 | 18.1129 |
| Lysosome | 23/124 | 0.0481 | 2.4410 | 19.5219 |
| Glycerophospholipid metabolism | 19/97 | 0.0507 | 2.6082 | 19.6628 |

FIG. 3M

ENZYMATIC METHODS FOR TREATING NEURODEGENERATIVE DISORDERS

CROSS REFERENCE TO RELATED APPLICATIONS

This application claims priority to U.S. Provisional Application Ser. No. 63/491,004 filed Mar. 17, 2023, and U.S. Application Ser. No. 63/563,643 filed Mar. 11, 2024, the entireties of which are incorporated by reference herein.

FIELD OF THE INVENTION

The present disclosure relates to treating, managing, or reducing the severity of neurodegenerative disorders, such as Alzheimer's Disease, by rebalancing the gut microbiome via administration of *Candida rugosa* lipase (CRL) to a patient in need thereof. The present disclosure also relates to improving memory and/or cognitive function by administering a dietary supplement comprising CRL to a subject in need thereof.

BACKGROUND

Dementia affects more than 50 million people worldwide, with Alzheimer's Disease (AD) being the most common form of dementia. AD is a progressive neurodegenerative disorder characterized by cognitive and functional decline, accompanied by neuropsychiatric symptoms. To date, no disease-modifying treatments have been developed which can effectively slow down or stop progression of the disease. See, e.g., Oxford et al., "Clinical trials in Alzheimer's disease: A hurdle in the path of remedy," *Int. J. Alzheimers Dis.* 5380346 (2020). This lack of success has led to exploration of AD treatment strategies other than amyloid plaque removal or inhibition of 7-secretase activity.

One such alternate treatment strategy is regulation of the gut microbiome, due to its ability to systemically impact host physiology and metabolism. See Askarova et al., "The links between the gut microbiome, aging, modern lifestyle and Alzheimer's disease," *Front. Cell Infect. Microbiol.* 10:104 (2020); Liu et al., "Gut microbiota and dysbiosis in Alzheimer's disease: Implications for pathogenesis and treatment," *Mol. Neurobiol.* 57:5026-5043 (2020); and Giovannini et al., "The microbiota-gut-brain axis and Alzheimer disease. From dysbiosis to neurodegeneration: Focus on the central nervous system glial cells," *J. Clin. Med.* 10:66 (2021). Gut microbes have previously been demonstrated to play a role in brain-related disorders such as Parkinson's disease and multiple sclerosis, affecting disease onset and severity of neuropathology. See Fang et al., "The microbiome as a modifier of neurodegenerative disease risk," *Cell Host. Microbe* 28: 201-222 (2020).

In AD patients, gut dysbiosis has been identified and denoted by a decrease in the bacterial phyla Firmicutes and Actinobacteria and an increased abundance of Bacteroidetes. See Vogt et al., "Gut microbiome alterations in Alzheimer's disease," *Sci. Rep.* 7:13537 (2017); Liu et al., "Altered microbiomes distinguish Alzheimer's disease from amnestic mild cognitive impairment and health in a Chinese cohort," *Brain Behav. Immun.* 80:633-643 (2019); and Cattaneo et al., "Association of brain amyloidosis with pro-inflammatory gut bacterial taxa and peripheral inflammation markers in cognitively impaired elderly," *Neurobiol. Aging* 49:60-68 (2017). Similarly, mouse models of AD-like pathology have shown significant differences in the gut microbial composition when compared to wild-type controls. See Brandscheid et al., "Altered gut microbiome composition and tryptic activity of the 5×FAD Alzheimer's mouse model," *J. Alzheimers Dis.* 56:775-788 (2017); and Harach et al., "Reduction of Abeta amyloid pathology in APPPS1 transgenic mice in the absence of gut microbiota," *Sci. Rep.* 7:41802 (2017). Furthermore, decreased AD pathology has been observed in germ-free APP/PS1 mice when compared to conventionally raised controls, suggesting that the gut microbiome contributes to AD pathology. See Harach 2017. These and other studies suggest that the gut contributes to AD pathology via the gut-brain axis, and that compositional enhancement may reduce AD pathology. See, e.g., Cummings, "New approaches to symptomatic treatments for Alzheimer's disease," Mol. Neurodegener. 16:2 (2021).

Administration of exogenous enzymes such as proteases, amylases, and lipases have been shown to alter the gut microbiome composition and to improve digestive performance of healthy individuals as well as patients suffering from cystic fibrosis or pancreatic insufficiency. See Somaraju et al., "Pancreatic enzyme replacement therapy for people with cystic fibrosis," *Cochrane Database Syst. Rev* 10:CD008227 (2014); Ianiro et al., "Digestive enzyme supplementation in gastrointestinal diseases," *Curr. Drug Metab.* 17:187-193 (2016); and Nishiyama et al., "Supplementation of pancreatic digestive enzymes alters the composition of intestinal microbiota in mice," *Biochem. Biophys. Res. Commun.* 495:273-279 (2018). In a recent study, oral administration of *Candida rugosa* lipase (CRL) to wild type mice has been shown to alter gut microbial β-diversity and promote growth of some bacterial species, including *A. muciniphila* and *Anaerostipes*. See Menden et al., "*Candida rugosa* lipase alters the gastrointestinal environment in wild-type mice," *Biomed. Pharmacother.* 130:110579 (2020). Notably, *A. muciniphila* and *Anaerostipes* are associated with anti-inflammatory and anti-diabetic effects. See, e.g., Depommier et al., "Supplementation with *Akkermansia muciniphila* in overweight and obese human volunteers: A proof-of-concept exploratory study," *Nat. Med.* 25:1096-1103 (2019); Schneeberger et al., "*Akkermansia muciniphila* inversely correlates with the onset of inflammation, altered adipose tissue metabolism and metabolic disorders during obesity in mice," *Sci. Rep.* 5:16643 (2015); Moens et al., A four-strain probiotic exerts positive immunomodulatory effects by enhancing colonic butyrate production in vitro," *Int. J. Pharm.* 555:1-10 (2019); Rodriguez-Carrio et al., "Free fatty acids profiles are related to gut microbiota signatures and short-chain fatty acids," *Front. Immunol.* 8:823 (2017); and Govindarajan et al., "Sodium butyrate improves memory function in an Alzheimer's disease mouse model when administered at an advanced stage of disease progression," *J. Alzheimers Dis.* 26:187-197 (2011).

Without being limited by theory, CRL has been shown to have a broad specificity range for triglyceride and cholesterol ester hydrolysis, and induces the release of fatty acids, cholesterol, and glycerol into the gut lumen. See Ianiro et al. 2016; and Lee et al., "Analysis of the gene family encoding lipases in *Candida rugosa* by competitive reverse transcription-PCR," *Appl. Environ. Microbiol.* 65:3888-3895 (1999). Further, lipase hydrolysis products can be absorbed by the host or gut microbiota to enhance their growth and metabolite production, and the microbial associated metabolites that are generated can exert anti-inflammatory and anti-bacterial properties potentially ameliorating AD-like pathology. See Cleusix et al., "Glycerol induces reuterin production and decreases *Escherichia coli* population in an in vitro model of colonic fermentation with immobilized human feces,"

FEMS Microbiol. Ecol. 63:56-64 (2008); Engels et al., "Acrolein contributes strongly to antimicrobial and heterocyclic amine transformation activities of reuterin," Sci. Rep. 6:36246 (2016); Vinolo et al., "Regulation of inflammation by short chain fatty acids," Nutrients 3:858-876 (2011); and Natto et al., "Omega-3 fatty acids effects on inflammatory biomarkers and lipid profiles among diabetic and cardiovascular disease patients: A systematic review and meta-analysis," Sci. Rep. 9:18867 (2019). Additionally, breakdown products directly absorbed by the host can impact lipid and cholesterol homeostasis, which have been associated with AD pathology and represent pivotal targets for potentially altering AD pathology. See Kao et al., "Lipids and Alzheimer's disease," Int. J. Mol. Sci. 21(4):1505 (2020).

SUMMARY

The present specification addresses the need to develop effective dementia and AD treatments. In an aspect, the present specification provides, and includes, methods of regulating the gut-brain axis of afflicted patients through administration of Candida rugosa lipase (CRL).

The present disclosure provides for, and includes, a method for treating, managing, or reducing the severity of a neurodegenerative disorder in a patient in need thereof, comprising administering a pharmaceutical composition comprising a therapeutically effective amount of CRL to the patient.

The present disclosure provides for, and includes, a method for treating, managing, or reducing the severity of Alzheimer's disease in a patient in need thereof, comprising administering a pharmaceutical composition comprising a therapeutically effective amount of CRL to the patient.

The present disclosure provides for, and includes, a method for improving cognitive function in a subject in need thereof, comprising administering a dietary supplement comprising Candida rugosa lipase (CRL) to the subject.

The present disclosure provides for, and includes, a pharmaceutical composition for use in treating, managing, or reducing the severity of a neurodegenerative disorder in a patient in need thereof, wherein the pharmaceutical composition comprises a therapeutically effective amount of CRL.

The present disclosure provides for, and includes, a method for improving memory in a subject in need thereof, comprising administering a dietary supplement comprising Candida rugosa lipase (CRL) to the subject.

The present disclosure provides for, and includes, a method for increasing levels of one or more gut bacteria in a patient having a neurodegenerative disorder, comprising administering a pharmaceutical composition comprising a therapeutically effective amount of Candida rugosa lipase (CRL) to the patient.

The present disclosure provides for, and includes, a method for enhancing gut microbiome diversity in a patient having a neurodegenerative disorder, comprising administering a pharmaceutical composition comprising a therapeutically effective amount of Candida rugosa lipase (CRL) to the patient.

The present disclosure provides for, and includes, a method for increasing levels of one or more gut bacteria in a subject in need thereof, comprising administering a dietary supplement comprising Candida rugosa lipase (CRL) to the subject.

The present disclosure provides for, and includes, a method for enhancing gut microbiome diversity in a subject in need thereof, comprising administering a dietary supplement comprising Candida rugosa lipase (CRL) to the subject.

BRIEF DESCRIPTION OF THE DRAWINGS

FIG. 1L presents a metabolome pathway analysis of the metabolites for which elevated levels are observed in the metabolomics study of FIG. 1K. (FDR=False Discovery Rate).

FIG. 2C presents a pathway analysis of untargeted plasma metabolomics data, which identifies significant changes in the metabolism of unsaturated fatty acids and glycerophospholipids result from CRL treatment of Wt and APP/PS1 mice.

FIG. 3M presents an enrichment analysis of significant uncorrected cortical transcriptomic data of treated and untreated APP/PS1 mice, which suggests that microglia activity, astrocyte activity, and glycerophospholipid metabolism are altered due to CRL treatment.

FIG. 6 (right panel) presents a graphical summary of results of the fecal matter transplantation study. Transplantation of fecal matter from APP/PS1+CRL mice from the study of FIG. 1A into antibiotic-depleted wildtype mice leads to enhanced memory function, while transplantation of fecal matter from untreated APP/PS1 mice from the study of FIG. 1A maintain memory deficits.

FIG. 7A shows a pH assessment of all three phases. FIG. 7B shows a pressure analyses of a supplemented colonic vessel with Product B compared to Blank. FIGS. 7C to 7G provide lactate and fatty acid profile analyses to assess functionality of microbial metabolism in the presence of Product B. FIGS. 7H and 7I provide ammonium and bSCFA analyses to determine adverse effects due to Product B exposure. Results in FIGS. 7A to 7I are presented as mean±stdev (n=3). Statistical analysis is performed throughout the entire 48 h (except for lactate 0-2 h) of incubation using 2-way ANOVA with Tukey correction.

DETAILED DESCRIPTION

A. Compositions and formulations

Figure 1A:
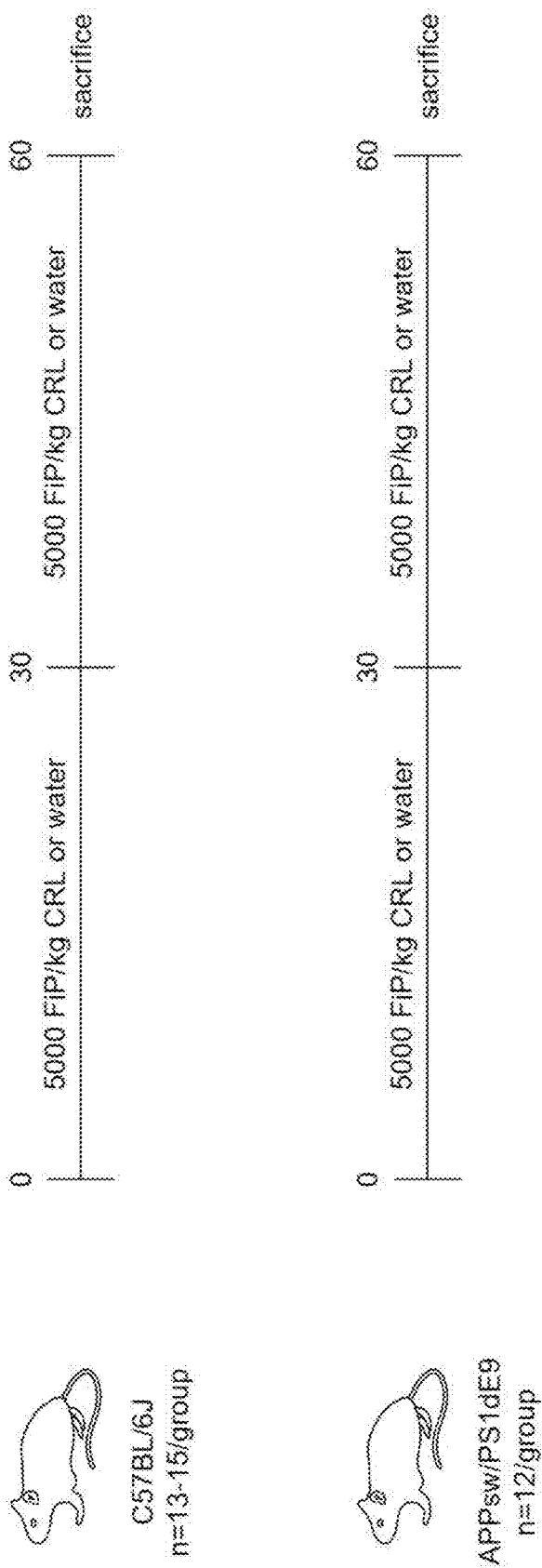
FIG. 1A presents a study design to examine whether CRL treatment in APPswe/PS1-dE9 (APP/PS1) mice induces gut microbial and metabolic changes that may ameliorate Alzheimer's Disease-like pathology. (C57BL/6J=wild type (Wt); FIP/kg=Fédération Internationale Pharmaceutique dose per kilogram; CRL=Candida rugosa Lipase).

The present disclosure provides for, and includes, CRL for treating, managing, or reducing the severity of a neurodegenerative disorder. The present disclosure also provides for, and includes, a pharmaceutical composition comprising CRL for treating, managing, or reducing the severity of a neurodegenerative disorder. In an aspect, the neurodegenerative disorder is dementia, Parkinson's disease, Alzheimer's disease, Huntington's disease, amyotrophic lateral sclerosis (ALS), schizophrenia, multiple sclerosis, traumatic brain injury (TBI), or any combination thereof.

The pharmaceutical compositions used in the methods provided herein, in one aspect, comprise an effective amount of CRL and a pharmaceutically acceptable carrier, adjuvant or diluent. A "pharmaceutically acceptable carrier, adjuvant or diluent" can refer to one or more compatible solid or liquid fillers or gel substances which are suitable for use in the human body. The "compatible" herein refers to that all ingredients in a composition can be mixed with each other and can be mixed with the compounds according to the present disclosure, while the medicinal effect of the compounds is not significantly reduced. Some non-limiting examples of the pharmaceutically acceptable carrier, adjuvant or diluents include cellulose and derivatives thereof (e.g., sodium carboxymethyl cellulose, sodium ethyl cellulose, and cellulose acetate), gelatin, talc, solid lubricants (e.g., stearic acid and magnesium stearate), calcium sulfate, plant oils (e.g., soybean oil, sesame oil, peanut oil, and olive oil), polyols (e.g., propylene glycol, glycerin, mannitol, and sorbitol), emulsifiers (e.g., Tween), wetting agents (e.g., sodium dodecyl sulfate), coloring agents, flavoring agents, stabilizing agents, antioxidants, preservatives, pyrogen-free water, and the like. In an aspect, the pharmaceutically acceptable carrier, adjuvant or diluent is sterile saline. In an aspect, the pharmaceutically acceptable carrier, adjuvant or diluent is phosphate-buffered saline (PBS).

Procedures for the selection and preparation of suitable pharmaceutical formulations, depending on the route of administration, are described in, for example, "Pharmaceuticals—The Science of Dosage Form Designs", M. E. Aulton, Churchill Livingstone, 2$^{nd}$ Ed. 2002, incorporated by reference herein in its entirety for all purposes.

The present disclosure contemplates that CRL may be present in a pharmaceutical composition as a pharmaceutically acceptable salt. For reviews on suitable salts, and pharmaceutically acceptable salts amenable for use herein, see Berge et al., "Pharmaceutical salts," *J. Pharm. Sci.* 66(1):1-19 (1997); and "Handbook of Pharmaceutical Salts: Properties, selection and use", P. H. Stahl, P. G. Vermuth, IUPAC, Wiley-VCH (2002), each of which is incorporated by reference herein in their entireties for all purposes. In one aspect, the pharmaceutical composition comprises an effective amount of CRL.

In an aspect, a pharmaceutical composition of the present disclosure comprises a combination of CRL and other lipase strains. In an aspect, a pharmaceutical composition of the present disclosure comprises a combination of CRL and two other lipase strains. In an aspect, a pharmaceutical composition of the present disclosure comprises CRL, a lipase from a yeast such as *Candida rugosa* (also known as *C. cylindracea*), a lipase from a fungus such as *Rhizopus oryzae*, and a filler (e.g., Lipase 1000). Without being limited by theory, a lipase from *Candida rugosa* can hydrolyze triacylglycerols into fatty acids and glycerol, and a lipase from *Rhizopus oryzae* can hydrolyze the ester bonds of 1- and 3-triglycerides. While CRL is active at a pH range of 4.0 to 7.0, inclusion of the two additional lipase strains may enable maintenance of activity at a more broad pH range of about 4.0 to about 9.0.

In an aspect, a dietary supplement of the present disclosure comprises CRL. In an aspect, a dietary supplement of the present disclosure comprises a combination of CRL and other lipase strains. In an aspect, a dietary supplement of the present disclosure comprises a combination of CRL and two other lipase strains. In an aspect, a dietary supplement of the present disclosure comprises CRL, a lipase from a yeast such as *Candida rugosa* (also known as *C. cylindracea*), a lipase from a fungus such as *Rhizopus oryzae*, and a filler (e.g., Lipase 1000).

In an aspect, a pharmaceutical composition of the present disclosure comprises a combination of CRL and one or more other enzymes. In an aspect, a pharmaceutical composition of the present disclosure comprises a combination of CRL, a protease, and an amylase. In an aspect, a dietary supplement of the present disclosure comprises CRL and one or more enzymes targeting lipid digestion. In an aspect, a dietary supplement of the present disclosure comprises CRL, a protease, and an amylase.

In an aspect, CRL is in a solid dosage form. Solid dosage forms used for oral administration may include capsules, tablets, pills, powders, and granules. Among these solid dosage forms, an active compound is mixed with at least one conventional inert excipient (or vehicle), such as sodium citrate or dicalcium phosphate, or mixed with the following ingredients: (a) a filler or a compatibilizer, such as starch, lactose, sucrose, glucose, mannitol, and silicic acid; (b) a bonding agent, such as hydroxymethyl cellulose, alginate, gelatin, polyvinylpyrrolidone, sucrose, and gum arabic; (c) a moisturizer, such as glycerin; (d) a disintegrant, such as agar, calcium carbonate, potato starch or tapioca starch, alginic acid, some composite silicates, and sodium carbonate; I a slow solvent, such as paraffin; (f) an absorbing accelerator, such as quaternary amine compounds; (g) a wetting agent, such as cetyl alcohol and glyceryl monostearate; (h) an adsorbent, such as kaolin; and (i) a lubricant, such as talc, calcium stearate, magnesium stearate, solid polyethylene glycol, sodium dodecyl sulfate, or a mixture thereof. Dosage forms of capsules, tablets, and pills may also contain a buffer agent.

In an aspect, solid dosage forms such as tablets, sugared pills, capsules, pills, and granules may be prepared using coatings and shells, such as enteric coatings and other materials known in the art. The solid dosage forms may contain opacifiers, and moreover, active compounds or compounds in such compositions may be released in a portion of the digestive tract in a delayed manner. Non-limiting examples of embedding components that can be employed are polymeric materials and waxy materials. The active compounds may also be formed into microcapsules with one or more of the above excipients.

In an aspect, CRL is in tablet form. In an aspect, a pharmaceutical composition comprising CRL is in tablet form. In an aspect, a CRL-containing dietary supplement is in tablet form. In an aspect, CRL is in capsule form. In an aspect, a pharmaceutical composition comprising CRL is in capsule form. In an aspect, a CRL-containing dietary supplement is in capsule form. In aspects, the CRL, the pharmaceutical composition, or the CRL-containing dietary supplement in tablet form further comprises a tablet coating.

In an aspect, CRL is in a liquid dosage form. Liquid dosage forms for oral administration include pharmaceutically acceptable emulsions, solutions, suspensions, syrups, or tincture. In addition to CRL, a liquid dosage form may contain inert diluents conventionally employed in the art, such as water or other solvents, solubilizers, and emulsifiers, like ethanol, isopropanol, ethyl carbonate, ethyl acetate, propylene glycol, 1,3-butanediol, dimethylformamide, and oils, in particular cottonseed oil, peanut oil, corn germ oil, olive oil, castor oil, sesame oil, or a mixture of these substances.

In an aspect, liquid preparations for oral application may be in the form of syrups, solutions or suspensions. Solutions, for example, may contain the compound used in the methods of the present disclosure, the balance being sugar and a mixture of ethanol, water, glycerol and propylene glycol. Optionally such liquid preparations may contain coloring agents, flavoring agents, saccharine and/or carboxymethylcellulose as a thickening agent. Furthermore, other excipients known to those skilled in art may be used when making formulations for oral use. In addition, liquid suspensions for oral application may contain a suspending agent, such as ethoxylated isostearyl alcohol, polyoxyethylene sorbitol, sorbitan ester, microcrystalline cellulose, aluminum methoxide, agar, or a mixture of these substances.

In an aspect, for oral administration, CRL may be admixed with one or more pharmaceutically acceptable adjuvants, diluents or carriers, for example, lactose, saccharose, sorbitol, mannitol; starch, for example, potato starch, corn starch or amylopectin; cellulose derivative; binder, for example, gelatin or polyvinylpyrrolidone; disintegrant, for example cellulose derivative, and/or lubricant, for example, magnesium stearate, calcium stearate, polyethylene glycol, wax, paraffin, and the like, and then compressed into tablets. If coated tablets are required, the cores, prepared as described above, may be coated with a suitable polymer dissolved or dispersed in water or readily volatile organic solvent(s). Alternatively, the tablet may be coated with a concentrated sugar solution which may contain, for example, gum arabic, gelatin, talcum and titanium dioxide.

In an aspect, an oral dosage form is a film-coated oral tablet. In an aspect, the dosage form is an immediate release dosage form with rapid dissolution characteristics under in vitro test conditions.

In an aspect, for the preparation of soft gelatin capsules, CRL may be admixed with, for example, a vegetable oil or polyethylene glycol. Hard gelatin capsules may contain granules of the compound using pharmaceutical excipients like the above-mentioned excipients for tablets. Also, liquid or semisolid formulations of CRL may be filled into hard gelatin capsules.

In an aspect, CRL is provided as an oral disintegrating tablet (ODT). ODTs differ from traditional tablets in that they are designed to be dissolved on the tongue rather than swallowed whole.

In an aspect, CRL is provided as an oral thin film or an oral disintegrating film (ODF). Without being limited by theory, such oral formulations, when placed on the tongue, hydrate via interaction with saliva, and releases the active compound from the dosage form. The ODF, in one aspect, contains a film-forming polymer such as hydroxypropyl methylcellulose (HPMC), hydroxypropyl cellulose (HPC), pullulan, carboxymethyl cellulose (CMC), pectin, starch, polyvinyl acetate (PVA) or sodium alginate.

The dosage of CRL administered may vary with the route of administration. In an aspect, if CRL is administered orally, then the daily dosage of CRL used in the methods of the present disclosure may be in the range of 30,000 Fédération International Pharmaceutique (FIP) units to 45,000 FIP units. In an aspect, if CRL is administered orally, then the daily dosage of CRL used in the methods of the present disclosure may be in the range of 30,000 FIP units to 60,000 FIP units. In an aspect, if CRL is administered orally, then the daily dosage of CRL used in the methods of the present disclosure may be in the range of 30,000 FIP units to 75,000 FIP units. In an aspect, if CRL is administered orally, then the daily dosage of CRL used in the methods of the present disclosure may be in the range of 30,000 FIP units to 90,000 FIP units. In an aspect, if CRL is administered orally, then the daily dosage of CRL used in the methods of the present disclosure may be in the range of 30,000 FIP units to 105,000 FIP units. In an aspect, if CRL is administered orally, then the daily dosage of CRL used in the methods of the present disclosure may be in the range of 45,000 FIP units to 60,000 FIP units. In an aspect, if CRL is administered orally, then the daily dosage of CRL used in the methods of the present disclosure may be in the range of 45,000 FIP units to 75,000 FIP units. In an aspect, if CRL is administered orally, then the daily dosage of CRL used in the methods of the present disclosure may be in the range of 45,000 FIP units to 90,000 FIP units. In an aspect, if CRL is administered orally, then the daily dosage of CRL used in the methods of the present disclosure may be in the range of 45,000 FIP units to 105,000 FIP units. In an aspect, if CRL is administered orally, then the daily dosage of CRL used in the methods of the present disclosure may be in the range of 60,000 FIP units to 75,000 FIP units. In an aspect, if CRL is administered orally, then the daily dosage of CRL used in the methods of the present disclosure may be in the range of 60,000 FIP units to 90,000 FIP units. In an aspect, if CRL is administered orally, then the daily dosage of CRL used in the methods of the present disclosure may be in the range of 60,000 FIP units to 105,000 FIP units. In an aspect, if CRL is administered orally, then the daily dosage of CRL used in the methods of the present disclosure may be in the range of 75,000 FIP units to 90,000 FIP units. In an aspect, if CRL is administered orally, then the daily dosage of CRL used in the methods of the present disclosure may be in the range of 75,000 FIP units to 105,000 FIP units. In an aspect if CRL is administered orally, then the daily dosage of CRL used in the methods of the present disclosure may be in the range of 90,000 FIP units to 105,000 FIP units. In an aspect, if CRL is administered orally, then the daily dosage of CRL used in the methods of the present disclosure is about 30,000 FIP units. In an aspect, if CRL is administered orally, then the daily dosage of CRL used in the methods of the present disclosure is about 45,000 FIP units. In an aspect, if CRL is administered orally, then the daily dosage of CRL used in the methods of the present disclosure is about 60,000 FIP units. In an aspect, if CRL is administered orally, then the daily dosage of CRL used in the methods of the present disclosure is about 75,000 FIP units. In an aspect, if CRL is administered orally, then the daily dosage of CRL used in the methods of the present disclosure is about 90,000 FIP units. In an aspect, if CRL is administered orally, then the daily dosage of CRL used in the methods of the present disclosure is about 105,000 FIP units.

In an aspect, a tablet for oral administration comprises about 10,000 FIP units of CRL, about 15,000 FIP units of CRL, about 20,000 FIP units of CRL, about 25,000 FIP units of CRL, about 30,000 FIP units of CRL, about 35,000 FIP units of CRL, about 40,000 FIP units of CRL, or about 45,000 FIP units of CRL. In an aspect, one, two, three, or four tablets are administered at a time. In an aspect, a total of one, two, three, four, five, six, seven, eight, nine, or ten tablets are administered daily.

In an aspect, a capsule for oral administration comprises about 10,000 FIP units of CRL, about 15,000 FIP units of CRL, about 20,000 FIP units of CRL, about 25,000 FIP units of CRL, about 30,000 FIP units of CRL, about 35,000 FIP units of CRL, about 40,000 FIP units of CRL, or about 45,000 FIP units of CRL. In an aspect, one, two, three, or four capsules are administered at a time. In an aspect, a total of one, two, three, four, five, six, seven, eight, nine, or ten capsules are administered daily.

In an aspect, a dietary supplement for oral administration comprises about 10,000 FIP units of CRL, about 15,000 FIP units of CRL, about 20,000 FIP units of CRL, about 25,000 FIP units of CRL, about 30,000 FIP units of CRL, about 35,000 FIP units of CRL, about 40,000 FIP units of CRL, or about 45,000 FIP units of CRL. In an aspect, one, two, three, or four capsules are administered at a time. In an aspect, a total of one, two, three, four, five, six, seven, eight, nine, or ten capsules are administered daily. In an aspect, the dietary supplement is in tablet form. In an aspect, the dietary supplement is in capsule form.

In the methods provided herein, CRL, a pharmaceutical composition comprising CRL, or a CRL-containing dietary supplement may be administered to a patient on an ongoing basis or for a discrete treatment period. In an aspect, the treatment period is at least one (1) month, at least three (3) months, at least six (6) months, at least twelve (12) months, at least eighteen (18) months, at least twenty-four (24) months, at least thirty (30) months, or at least thirty-six (36) months. In an aspect, the treatment period is about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, or about 20 years.

In an aspect, CRL, a pharmaceutical composition comprising CRL, or a CRL-containing dietary supplement is administered once daily. In an aspect, CRL, a pharmaceutical composition comprising CRL, or a CRL-containing dietary supplement is administered once daily as an oral composition. In an aspect, the oral composition is administered once daily in tablet form at approximately the same time every day, e.g., prior to a breakfast. In an aspect, the oral composition is administered once daily in capsule form at approximately the same time every day. In an aspect, the daily dose of CRL is between 45,000 FIP units to 90,000 FIP units. In an aspect, the daily dose of CRL is between 30,000 FIP units to 90,000 FIP units. In an aspect, the daily dose of CRL is between 30,000 FIP units to 45,000 FIP units. In an aspect, the daily dose of CRL is at least 30,000 FIP units. In an aspect, the daily dose of CRL is between 30,000 FIP units to 60,000 FIP units.

In an aspect, CRL, a pharmaceutical composition comprising CRL, or a CRL-containing dietary supplement is administered twice daily. In an aspect, CRL, a pharmaceutical composition comprising CRL, or a CRL-containing dietary supplement is administered twice daily as an oral composition. In an aspect, the oral composition is administered twice daily in tablet form at approximately the same times every day. In an aspect, the oral composition is administered twice daily in capsule form at approximately the same time every day. In an aspect, the daily dose of CRL is between 45,000 FIP units to 90,000 FIP units. In an aspect, the daily dose of CRL is between 30,000 FIP units to 90,000 FIP units. In an aspect, the daily dose of CRL is between 30,000 FIP units to 45,000 FIP units. In an aspect, the daily dose of CRL is between 15,000 FIP units to 30,000 FIP units. In an aspect, the daily dose of CRL is between 15,000 FIP units to 45,000 FIP units.

In an aspect, CRL, a pharmaceutical composition comprising CRL, or a CRL-containing dietary supplement is administered three times a day. In an aspect, CRL, a pharmaceutical composition comprising CRL, or a CRL-containing dietary supplement is administered three times a day as an oral composition. In an aspect, the oral composition is administered three times a day in tablet form at approximately the same times every day. In an aspect, the oral composition is administered three times a day in capsule form at approximately the same time every day. In an aspect, the daily dose of CRL is between 45,000 FIP units to 90,000 FIP units. In an aspect, the daily dose of CRL is between 30,000 FIP units to 90,000 FIP units. In an aspect, the daily dose of CRL is between 30,000 FIP units to 45,000 FIP units. In an aspect, the daily dose of CRL is between 15,000 FIP units to 30,000 FIP units. In an aspect, the daily dose of CRL is between 15,000 FIP units to 45,000 FIP units.

In an aspect, CRL, a pharmaceutical composition comprising CRL, or a CRL-containing dietary supplement is administered 1× per week, every other day, every third day, 2× per week, 3× per week, 4× per week, or 5× per week. In an aspect, CRL, a pharmaceutical composition comprising CRL, or a CRL-containing dietary supplement is administered on an empty stomach. In an aspect, CRL, a pharmaceutical composition comprising CRL, or a CRL-containing dietary supplement is administered before a meal. In an aspect, CRL is administered after a meal. In aspects, CRL is administered without food. In an aspect, CRL, a pharmaceutical composition comprising CRL, or a CRL-containing dietary supplement is administered with food.

B. Methods and Uses

In the methods provided herein, a pharmaceutical composition comprising an effective amount of CRL is administered to a patient in need of treatment of a neurodegenerative disorder. In the methods provided herein, a pharmaceutical composition comprising an effective amount of CRL is administered to a patient in need of management of a neurodegenerative disorder. In the methods provided herein, a pharmaceutical composition comprising an effective amount of CRL is administered to a patient in need of amelioration of a neurodegenerative disorder. In the methods provided herein, a pharmaceutical composition comprising an effective amount of CRL is administered to a patient in need of a reduction in the severity of a neurodegenerative disorder. In an aspect, the neurodegenerative disorder is selected from the group consisting of dementia, Alzheimer's disease, Parkinson's disease, Huntington's disease, amyotrophic lateral sclerosis (ALS), schizophrenia, multiple sclerosis, cerebral palsy, ataxia, spasticity, traumatic brain injury (TBI), and any combination thereof.

In the methods provided herein, a pharmaceutical composition comprising an effective amount of CRL is administered to a patient in need of treatment of dementia. In the methods provided herein, a pharmaceutical composition comprising an effective amount of CRL is administered to a patient in need of management of dementia. In the methods provided herein, a pharmaceutical composition comprising an effective amount of CRL is administered to a patient in need of amelioration of dementia. In the methods provided herein, a pharmaceutical composition comprising an effective amount of CRL is administered to a patient in need of a reduction in the severity of dementia. In an aspect, the dementia is early-stage dementia, middle-stage dementia, or late-stage dementia. In an aspect, the dementia is selected from the group consisting of Parkinson's disease dementia, Huntington's disease dementia, vascular dementia, dementia with Lewy bodies (DLB), frontotemporal dementia, alcohol-related dementia, HIV-associated dementia, early-onset dementia, Alzheimer's disease, Creutzfeldt-Jakob disease (CJD), and any combination thereof.

In the methods provided herein, a pharmaceutical composition comprising an effective amount of CRL is administered to a patient in need of treatment of Alzheimer's disease. In the methods provided herein, a pharmaceutical composition comprising an effective amount of CRL is administered to a patient in need of management of Alzheimer's disease. In the methods provided herein, a pharmaceutical composition comprising an effective amount of CRL is administered to a patient in need of amelioration of Alzheimer's disease. In the methods provided herein, a pharmaceutical composition comprising an effective amount of CRL is administered to a patient in need of a reduction in the severity of Alzheimer's disease. In the methods provided herein, a pharmaceutical composition comprising an effective amount of CRL is administered to an Alzheimer's disease patient in need thereof to slow the progression of Alzheimer's disease in the patient. In the methods provided herein, a pharmaceutical composition comprising an effective amount of CRL is administered to an Alzheimer's disease patient in need thereof to improve the patient's cognitive function. In an aspect, the Alzheimer's disease is early-onset Alzheimer's disease or late-onset Alzheimer's disease. In an aspect, the Alzheimer's disease is mild Alzheimer's disease, moderate Alzheimer's disease, or severe Alzheimer's disease.

Without being limited by theory, two major proteins implicated in the Alzheimer's disease pathological process are amyloid-β 42 (Aβ42) and phosphorylated tau (P-tau). In Alzheimer's disease, increased Aβ42 is negatively correlated with Aβ42 levels in the cerebrospinal fluid (CSF), while P-tau levels in the CSF are positively correlated with P-tau levels in the brain. The Aβ42/P-tau ratio in the CSF has been shown to be predictive of the conversion of mild cognitive impairment into Alzheimer's disease. See Prakash et al., "p-tau/Aβ42 Ratio Associates with Cognitive Decline in Alzheimer's disease, Mild Cognitive Impairment, and Cognitively Unimpaired Older Adults," medRxiv 2020.10.13.20211375. In an aspect, the Alzheimer's disease patient has a increased level of amyloid-β 42 (Aβ42) deposit (plaques) in the brain, an increased level of total tau (T-tau) in the brain, an increased level of phosphorylated tau (P-tau), Hyperphosphorylation of the protein tau, renders tau prone to aggregate that forms neurofibrillary tangles (NFTs) of hyperphosphorylated tau in the brain, or any combination thereof, compared to a normal patient. In an aspect, the Alzheimer's disease patient has a decreased level of amyloid-β42 (Aβ42) in the CSF, an increased level of total tau (T-tau) in the CSF, an increased level of phosphorylated tau (P-tau) in the CSF, or any combination thereof, compared to a normal patient. In order to determine the levels of Aβ42, T-tau, and/or P-tau in the CSF, CSF must be collected from the patient. The most common procedure for collecting CSF from a patient is by lumbar puncture (spinal tap). In an aspect, the Alzheimer's disease patient has an increased ratio of t-Tau/Aβ42 compared to a normal patient. In an aspect, molecular imaging of the Alzheimer's disease patient's brain indicated the presence of amyloid plaques, neurofibrillary fibers (neurofibrillary tangles), or a combination thereof.

In the methods provided herein, a pharmaceutical composition comprising an effective amount of CRL that is administered to an Alzheimer's disease patient increases the level of amyloid-β 42 (Aβ42) in the CSF of the patient. In an aspect, the level of Aβ42 in the CSF of the Alzheimer's disease patient is increased about 1.5-fold after administration of the pharmaceutical composition. In an aspect, the level of Aβ42 in the CSF of the Alzheimer's disease patient is increased about 2-fold after administration of the pharmaceutical composition. In an aspect, the level of Aβ42 in the CSF of the Alzheimer's disease patient is increased about 2.5-fold after administration of the pharmaceutical composition. In an aspect, the level of Aβ42 in the CSF of the Alzheimer's disease patient is increased about 3-fold after administration of the pharmaceutical composition. In an aspect, the level of Aβ42 in the CSF of the Alzheimer's disease patient is increased between 1.5-fold to 3-fold after administration of the pharmaceutical composition. In an aspect, the level of Aβ42 in the CSF of the Alzheimer's disease patient is between about 500 to about 1,400 picograms per milliliter (pg/ml) after administration of the pharmaceutical composition. In an aspect, the level of Aβ42 in the CSF of the Alzheimer's disease patient is between about 700 to about 2,000 picograms per milliliter (pg/ml) after administration of the pharmaceutical composition. In an aspect, the level of Aβ42 in the CSF of the Alzheimer's disease patient is between about 700 to about 1,500 picograms per milliliter (pg/ml) after administration of the pharmaceutical composition. In an aspect, the level of Aβ42 in the CSF of the Alzheimer's disease patient is between about 1,000 to about 2,000 picograms per milliliter (pg/ml) after administration of the pharmaceutical composition. In an aspect, the level of Aβ42 in the CSF of the Alzheimer's disease patient is between about 200 to about 700 pg/ml before administration of the pharmaceutical composition. In an aspect, the level of Aβ42 in the CSF of the Alzheimer's disease patient is between about 200 to about 500 pg/ml before administration of the pharmaceutical composition. In an aspect, the level of Aβ42 in the CSF of the Alzheimer's disease patient is between about 300 to about 600 pg/ml before administration of the pharmaceutical composition.

In the methods provided herein, a pharmaceutical composition comprising an effective amount of CRL that is administered to an Alzheimer's disease patient reduces the level of total tau (T-tau) in the CSF of the patient. In an aspect, the level of T-tau in the CSF of the Alzheimer's disease patient is reduced about 2-fold after administration of the pharmaceutical composition. In an aspect, the level of T-tau in the CSF of the Alzheimer's disease patient is reduced about 2.5-fold after administration of the pharmaceutical composition. In an aspect, the level of T-tau in the CSF of the Alzheimer's disease patient is reduced about 3-fold after administration of the pharmaceutical composition. In an aspect, the level of T-tau in the CSF of the Alzheimer's disease patient is reduced about 3.5-fold after administration of the pharmaceutical composition. In an aspect, the level of T-tau in the CSF of the Alzheimer's disease patient is reduced between 2-fold and 3.5-fold after administration of the pharmaceutical composition. In an aspect, the level of T-tau in the CSF of the Alzheimer's disease patient is between about 180 to about 900 picogram per milliliter (pg/ml) before administration of the pharmaceutical composition. In an aspect, the level of T-tau in the CSF of the Alzheimer's disease patient is between about 90 to 450 pg/ml after administration of the pharmaceutical composition. In an aspect, the level of T-tau in the CSF of the Alzheimer's disease patient is between about 90 to 350 pg/ml after administration of the pharmaceutical composition. In an aspect, the level of T-tau in the CSF of the Alzheimer's disease patient is between about 90 to 250 pg/ml after administration of the pharmaceutical composition. In an aspect, the level of T-tau in the CSF of the Alzheimer's disease patient is between about 90 to 180 pg/ml after administration of the pharmaceutical composition. In an aspect, the level of T-tau in the CSF of the Alzheimer's disease patient is between about 60 to 300 pg/ml after administration of the pharmaceutical composition. In an aspect, the level of T-tau in the CSF of the Alzheimer's disease patient is between about 60 to 200 pg/ml after administration of the pharmaceutical composition. In an aspect, the level of T-tau in the CSF of the Alzheimer's disease patient is between about 60 to 180 pg/ml after administration of the pharmaceutical composition.

In the methods provided herein, a pharmaceutical composition comprising an effective amount of CRL that is administered to an Alzheimer's disease patient reduces the level of phosphorylated tau (P-tau) in the CSF of the patient. In an aspect, the level of P-tau in the CSF of the Alzheimer's disease patient is reduced about 1.5-fold after administration of the pharmaceutical composition. In an aspect, the level of P-tau in the CSF of the Alzheimer's disease patient is reduced about 2-fold after administration of the pharmaceutical composition. In an aspect, the level of P-tau in the CSF of the Alzheimer's disease patient is reduced about 2.5-fold after administration of the pharmaceutical composition. In an aspect, the level of P-tau in the CSF of the Alzheimer's disease patient is reduced about 3-fold after administration of the pharmaceutical composition. In an aspect, the level of P-tau in the CSF of the Alzheimer's disease patient is reduced between 1.5-fold and 3-fold after administration of the pharmaceutical composition. In an aspect, the level of P-tau in the CSF of the Alzheimer's disease patient is between about 30 to about 100 picogram per milliliter (pg/ml) before administration of the pharmaceutical composition. In an aspect, the level of P-tau in the CSF of the Alzheimer's disease patient is between about 15 to 50 pg/ml after administration of the pharmaceutical composition. In an aspect, the level of P-tau in the CSF of the Alzheimer's disease patient is between about 15 to 40 pg/ml after administration of the pharmaceutical composition. In an aspect, the level of P-tau in the CSF of the Alzheimer's disease patient is between about 15 to 30 pg/ml after administration of the pharmaceutical composition. In an aspect, the level of P-tau in the CSF of the Alzheimer's disease patient is between about 20 to 35 pg/ml after administration of the pharmaceutical composition.

In the methods provided herein, a pharmaceutical composition comprising an effective amount of CRL that is administered to an Alzheimer's disease patient decreases the ratio of t-Tau/Aβ42 in the CSF of the patient. In an aspect, the ratio of t-Tau/Aβ42 in the CSF of the Alzheimer's disease patient is decreased about 5-fold after administration of the pharmaceutical composition. In an aspect, the ratio of t-Tau/Aβ42 in the CSF of the Alzheimer's disease patient is decreased about 7.5-fold after administration of the pharmaceutical composition. In an aspect, the ratio of t-Tau/Aβ42 in the CSF of the Alzheimer's disease patient is decreased about 10-fold after administration of the pharmaceutical composition. In an aspect, the ratio of t-Tau/Aβ42 in the CSF of the Alzheimer's disease patient is decreased between about 5-fold to about 10-fold after administration of the pharmaceutical composition. In an aspect, the ratio of t-Tau/Aβ42 in the CSF of the Alzheimer's disease patient is decreased between about 5-fold to about 10-fold after administration of the pharmaceutical composition. In an aspect, the ratio of t-Tau/Aβ42 in the CSF of the Alzheimer's disease patient is decreased between about 5-fold to about 20-fold after administration of the pharmaceutical composition. In an aspect, the ratio of t-Tau/Aβ42 in the CSF of the Alzheimer's disease patient is decreased between about 10-fold to about 20-fold after administration of the pharmaceutical composition. In an aspect, the ratio of t-Tau/Aβ42 in the CSF of the Alzheimer's disease patient is between about to 0.2 to 3.0 before administration of the pharmaceutical composition. In an aspect, the ratio of t-Tau/Aβ42 in the CSF of the Alzheimer's disease patient is between about to 0.5 to 2.5 before administration of the pharmaceutical composition. In an aspect, the ratio of t-Tau/Aβ42 in the CSF of the Alzheimer's disease patient is greater than about 0.5 before administration of the pharmaceutical composition. In an aspect, the ratio of t-Tau/Aβ42 in the CSF of the Alzheimer's disease patient is between about 0.1 to about 0.4 after administration of the pharmaceutical composition. In an aspect, the ratio of t-Tau/Aβ42 in the CSF of the Alzheimer's disease patient is between about 0.2 to about 0.4 after administration of the pharmaceutical composition.

In an aspect, the ratio of t-Tau/Aβ42 in the CSF of the Alzheimer's disease patient is between about 0.1 to about 0.3 after administration of the pharmaceutical composition. In an aspect, the ratio of t-Tau/Aβ42 in the CSF of the Alzheimer's disease patient is less than 0.5 after administration of the pharmaceutical composition. In an aspect, the ratio of t-Tau/Aβ42 in the CSF of the Alzheimer's disease patient is 0.4 or less after administration of the pharmaceutical composition.

In the methods provided herein, a pharmaceutical composition comprising an effective amount of CRL that is administered to an Alzheimer's disease patient increases the ratio of Aβ42/p-Tau in the CSF of the patient. In an aspect, the ratio of Aβ42/p-Tau in the CSF of the Alzheimer's disease patient is increased about 5-fold after administration of the pharmaceutical composition. In an aspect, the ratio of Aβ42/p-Tau in the CSF of the Alzheimer's disease patient is increased about 7.5-fold after administration of the pharmaceutical composition. In an aspect, the ratio of Aβ42/p-Tau in the CSF of the Alzheimer's disease patient is increased about 10-fold after administration of the pharmaceutical composition. In an aspect, the ratio of Aβ42/p-Tau in the CSF of the Alzheimer's disease patient is increased between about 5-fold to about 10-fold after administration of the pharmaceutical composition. In an aspect, the ratio of Aβ42/p-Tau in the CSF of the Alzheimer's disease patient is increased between about 5-fold to about 10-fold after administration of the pharmaceutical composition. In an aspect, the ratio of Aβ42/p-Tau in the CSF of the Alzheimer's disease patient is increased between about 5-fold to about 20-fold after administration of the pharmaceutical composition. In an aspect, the ratio of Aβ42/p-Tau in the CSF of the Alzheimer's disease patient is increased between about 10-fold to about 20-fold after administration of the pharmaceutical composition. In an aspect, the ratio of Aβ42/p-Tau in the CSF of the Alzheimer's disease patient is between about 1.0 to 17.5 before administration of the pharmaceutical composition. In an aspect, the ratio of Aβ42/p-Tau in the CSF of the Alzheimer's disease patient is between about 15 to about 47.5 after administration of the pharmaceutical composition. In an aspect, the ratio of Aβ42/p-Tau in the CSF of the Alzheimer's disease patient is greater than 17.5 after administration of the pharmaceutical composition.

In the methods provided herein, a pharmaceutical composition comprising an effective amount of CRL that is administered to an Alzheimer's disease patient decreases the ratio of p-Tau/Aβ42 in the CSF of the patient. In an aspect, the ratio of p-Tau/Aβ42 in the CSF of the Alzheimer's disease patient is decreased by at least 5% after administration of the pharmaceutical composition. In an aspect, the ratio of p-Tau/Aβ42 in the CSF of the Alzheimer's disease patient is decreased by at least 10% after administration of the pharmaceutical composition. In an aspect, the ratio of p-Tau/Aβ42 in the CSF of the Alzheimer's disease patient is decreased by at least 25% after administration of the pharmaceutical composition. In an aspect, the ratio of p-Tau/Aβ42 in the CSF of the Alzheimer's disease patient is decreased by at least 50% after administration of the pharmaceutical composition. In an aspect, the ratio of p-Tau/Aβ42 in the CSF of the Alzheimer's disease patient is decreased by between 5 to 50% after administration of the pharmaceutical composition. In an aspect, the ratio of p-Tau/Aβ42 in the CSF of the Alzheimer's disease patient is decreased by between 5 to 95% after administration of the pharmaceutical composition. In an aspect, the ratio of p-Tau/Aβ42 in the CSF of the Alzheimer's disease patient is decreased by between 50 to 95% after administration of the pharmaceutical composition. In an aspect, the ratio of p-Tau/Aβ42 in the CSF of the Alzheimer's disease patient is between about 0.06 to 1.0 before administration of the pharmaceutical composition. In an aspect, the ratio of p-Tau/Aβ42 in the CSF of the Alzheimer's disease patient is greater than 0.06 before administration of the pharmaceutical composition. In an aspect, the ratio of p-Tau/Aβ42 in the CSF of the Alzheimer's disease patient is between about 0.02 to 0.07 after administration of the pharmaceutical composition. In an aspect, the ratio of p-Tau/Aβ42 in the CSF of the Alzheimer's disease patient is less than 0.06 after administration of the pharmaceutical composition.

In the methods provided herein, a pharmaceutical composition comprising an effective amount of CRL that is administered to an Alzheimer's disease patient reduces the amount of amyloid plaques in the brain by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% following administration. In an aspect, no amyloid plaques are detected in the brain of the Alzheimer's disease patient after administration of the pharmaceutical composition.

In the methods provided herein, a pharmaceutical composition comprising an effective amount of CRL that is administered to an Alzheimer's disease patient reduces the quantity of neurofibrillary fibers in the brain by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% following administration. In an aspect, no neurofibrillary fibers are detected in the brain of the Alzheimer's disease patient after administration of the pharmaceutical composition.

In the methods provided herein, a pharmaceutical composition comprising an effective amount of CRL is administered to a patient in need of treatment of Parkinson's disease. In the methods provided herein, a pharmaceutical composition comprising an effective amount of CRL is administered to a patient in need of management of Parkinson's disease. In the methods provided herein, a pharmaceutical composition comprising an effective amount of CRL is administered to a patient in need of amelioration of Parkinson's disease. In the methods provided herein, a pharmaceutical composition comprising an effective amount of CRL is administered to a patient in need of a reduction in the severity of Parkinson's disease. In the methods provided herein, a pharmaceutical composition comprising an effective amount of CRL is administered to a Parkinson's disease patient in need thereof to slow the progression of Parkinson's disease in the patient. In an aspect, the Parkinson's disease is selected from the group consisting of corticobasal degeneration (CBD), dementia with Lewy Bodies (DLB), drug-induced parkinsonism, multiple system atrophy (MSA), progressive supranuclear palsy (PSP), vascular (arteriosclerotic) parkinsonism, essential tremor, and any combination thereof.

Physical symptoms of Parkinson's disease may include shaking (tremors), slowness of movement (bradykinesia), rigidity, and posture instability. In an aspect, the Parkinson's disease patient in need of treatment has Stage One Parkinson's disease, where the patient experiences mild symptoms which may include tremor and other movement symptoms which occur on one side of the body only, and changes in posture, walking and facial expressions. In an aspect, the Parkinson's disease patient in need of treatment has Stage Two Parkinson's disease, where the patient experiences tremor, rigidity and other movement symptoms on both sides of the body. In an aspect, the Parkinson's disease patient in need of treatment has Stage Three Parkinson's disease, where the patient experiences loss of balance and slowness of movements, falls are common, and activities such as dressing and eating are significantly impaired. In an aspect, Parkinson's disease patient in need of treatment has Stage Four Parkinson's disease, where compromised motor symptoms are severe and limiting in the patient, the patient may stand without help but usually requires a walker, and the patient is unable to live alone and requires assistance with daily activities. In an aspect, Parkinson's disease patient in need of treatment has Stage Five Parkinson's disease, where stiffness in the legs makes it impossible for the patient to stand or walk, the patient is bedridden or requires a wheelchair, the patient may experience hallucinations and delusions, and the patient requires nursing care for all daily activities. In an aspect, the patient has been diagnosed with Parkinson's disease by a physical and neurological examination conducted by a doctor or health care practitioner.

In the methods provided herein, a pharmaceutical composition comprising an effective amount of CRL that is administered to a Parkinson's disease patient reduces the occurrence of shaking (tremors) over a period of time by at least 5%, at least 10%, at least 15%, at least 20%, at least 25%, at least about 30%, at least 35%, at least 40%, at least 45%, at least 50%, at least 55%, at least 60%, at least 65%, at least 70%, or at least 75%, as compared an identical period of time prior to treatment with CRL. In the methods provided herein, a pharmaceutical composition comprising an effective amount of CRL that is administered to a Parkinson's disease reduces the frequency of shaking (tremors) over a period of time by about 5%, about 10%, about 15%, about 20%, about 25%, about 30%, about 35%, about 40%, about 45%, about 50%, about 55%, about 60%, about 65%, about 70%, or about 75%, as compared to an identical period of time prior to treatment with CRL. In the methods provided herein, a pharmaceutical composition comprising an effective amount of CRL that is administered to a Parkinson's disease reduces the frequency of shaking (tremors) over a period of time by between 10% and 20%, between 20% and 30%, between 30% and 40%, between 40% and 50%, between 50% and 60%, between 60% and 70%, between 5% and 25%, between 10% and 30%, between 20% and 40%, between 30% and 50%, between 40% and 60%, between 50% and 75%, between 10% to 50%, between 20% to 60%, between 30% to 70%, or between 5% and 75%, as compared to an identical period of time prior to treatment with CRL. In an aspect, a period of time is 30 minutes, one hour, two hours, three hours, four hours, five hours, six hours, eight hours, nine hours, 10 hours, 11 hours, 12 hours, one day, two days, three days, four days, five days, six days, or one week. In an aspect, the frequency of shaking (tremors) may be quantified in a Parkinson's disease patient using motion capture equipment, such as an accelerometer, laser displacement sensors, or combinations of accelerometers, gyroscopes, and magnetometers. Electromyography (EMG), a technique for evaluating and recording the electrical activity produced by skeletal muscles, may also be used to measure tremor occurrence and frequency.

The MDS-UPDRS is a comprehensive 50 question assessment of both motor and non-motor symptoms associated with Parkinson's disease. The maximum overall MDS-UPDRS score is 199, indicating the most severe level of disability due to Parkinson's disease. See e.g., Goetz et al., "Movement Disorder Society-Sponsored Revision of the Unified Parkinson's Disease Rating Scale (MDS-UPDRS): Scale Presentation and Clinimetric Testing Results," *Movement Disorders* 23(15):2129-2170 (2008). In the methods provided herein, a pharmaceutical composition comprising an effective amount of CRL that is administered to a Parkinson's disease patient improves the Movement Disorder Society Unified Parkinson's Disease Rating Scale (MDS-UPDRS) rating of the patient as compared to the MDS-UPDRS rating of the patient. In the methods provided herein, a pharmaceutical composition comprising an effective amount of CRL that is administered to a Parkinson's disease reduces the patient's overall MDS-UPDRS score by at least 5 points, at least 10 points, at least 15 points, at least 20 points, at least 25 points, at least 30 points, at least 35 points, at least 40 points, at least 45 points, at least 50 points, at least 55 points, at least 60 points, at least 65 points, at least 70 points, at least 75 points, at least 80 points, at least 85 points, at least 90 points, at least 95 points, at least 100 points, at least 110 points, at least 120 points, at least 130 points, at least 140 points, at least 150 points, at least 160 points, at least 170 points, at least 180 points, or at least 190 points as compared to the patient's overall MDS-UPDRS score prior to treatment with CRL. In the methods provided herein, a pharmaceutical composition comprising an effective amount of CRL that is administered to a Parkinson's disease reduces the patient's overall MDS-UPDRS score by about 5 points, about 10 points, about 15 points, about 20 points, about 25 points, about 30 points, about 35 points, about 40 points, about 45 points, about 50 points, about 55 points, about 60 points, about 65 points, about 70 points, about 75 points, about 80 points, about 85 points, about 90 points, about 95 points, about 100 points, about 110 points, about 120 points, about 130 points, about 140 points, about 150 points, about 160 points, about 170 points, about 180 points, or about 190 points as compared to the patient's overall MDS-UPDRS score prior to treatment with CRL. In the methods provided herein, a pharmaceutical composition comprising an effective amount of CRL that is administered to a Parkinson's disease reduces the patient's overall MDS-UPDRS score by between 5 and 25 points, between 25 and 50 points, between 50 and 75 points, between 75 and 100 points, between 100 and 125 points, between 125 and 150 points, between 150 and 175 points, between 175 and 195 points, between 10 and 50 points, between 50 and 100 points, between 100 and 150 points, between 150 and 190 points, between 10 and 100 points, between 100 and 190 points, between 10 and 190 points, or between 5 and 195 points as compared to the patient's overall MDS-UPDRS score prior to treatment with CRL. In an aspect, a Parkinson's disease patient has an overall MDS-UPDRS score of between 5- and 150-points following treatment with CRL.

Alpha synuclein (α-Syn) is a presynaptic neuronal protein that has been linked genetically and neuropathologically to Parkinson's disease and has been shown to aggregate in the brains of Parkinson's disease patients. See e.g., Chang et al., "Plasma and Serum Alpha-Synuclein as a Biomarker of Diagnosis in Patients with Parkinson's disease," *Front. Neurol.* 10:1388 (2020). In the methods provided herein, a pharmaceutical composition comprising an effective amount of CRL that is administered to a Parkinson's disease patient decreases the levels of α-Syn in the plasma and/or serum of the patient. In an aspect, the mean level of α-Syn in the plasma of a Parkinson's disease prior to treatment with CRL is between 1.0 picograms per milliliter (pg/mL) and 6.1 pg/mL. In an aspect, the mean level of α-Syn in the serum of a Parkinson's disease prior to treatment with CRL is between 0.01 pg/mL and 0.07 pg/mL. In the methods provided herein, a pharmaceutical composition comprising an effective amount of CRL that is administered to a Parkinson's disease patient reduces the plasma level of α-Syn by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% following administration. In the methods provided herein, a pharmaceutical composition comprising an effective amount of CRL that is administered to a Parkinson's disease patient reduces the serum level of α-Syn by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% following administration. In an aspect, no α-Syn is detected in the serum the Parkinson's disease patient after administration of the pharmaceutical composition.

Levels of amyloid-β 40 (Aβ40) and total tau (T-tau) in plasma have also been shown to be predictive of Parkinson's disease and associated cognitive symptoms. See e.g., Chen et al., "Plasma Levels of α-Synuclein, A3-40 and T-tau as Biomarkers to Predict Cognitive Impairment in Parkinson's disease," *Front. Aging Neurosci.* 12:112 (2020). In an aspect, the level of Aβ40 in the plasma of a Parkinson's disease prior to treatment with CRL is between about 30 picograms per milliliter (pg/mL) and about 45 pg/mL. In an aspect, the level of Aβ40 in the plasma of a Parkinson's disease after treatment with CRL is between about 45 picograms per milliliter (pg/mL) and about 70 pg/mL. In an aspect, the level of Aβ40 in the plasma of the Parkinson's disease patient is increased about 1.25-fold after administration of the pharmaceutical composition. In an aspect, the level of Aβ40 in the plasma of the Parkinson's disease patient is increased about 1.5-fold after administration of the pharmaceutical composition. In an aspect, the level of Aβ40 in the plasma of the Parkinson's disease patient is increased about 1.75-fold after administration of the pharmaceutical composition. In an aspect, the level of Aβ40 in the plasma of the Parkinson's disease patient is increased about 2-fold after administration of the pharmaceutical composition. In an aspect, the level of T-tau in the plasma of a Parkinson's disease prior to treatment with CRL is between about 25 pg/mL and about 40 pg/mL. In an aspect, the level of T-tau in the plasma of a Parkinson's disease after treatment with CRL is between about 10 pg/mL and about 25 pg/mL. In an aspect, the level of T-tau in the plasma of the Parkinson's disease patient is reduced by about 10%, about 15%, about 20%, about 25%, about 30%, about 35%, about 40%, about 45%, about 50%, about 55%, about 60%, about 65%, about 70%, about 75%, or about 80% after administration of the pharmaceutical composition. In an aspect, the level of T-tau in the plasma of the Parkinson's disease patient is reduced by between 25% and 50% after administration of the pharmaceutical composition. In an aspect, the level of T-tau in the plasma of the Parkinson's disease patient is reduced by between 25% and 75% after administration of the pharmaceutical composition.

In the methods provided herein, a pharmaceutical composition comprising an effective amount of CRL is administered to a patient in need of improved memory function. In the methods provided herein, a pharmaceutical composition comprising an effective amount of CRL is administered to a patient in need thereof to improve memory function. In the methods provided herein, a pharmaceutical composition comprising an effective amount of CRL is administered to a patient in need thereof to enhance cognition. In the methods provided herein, a pharmaceutical composition comprising an effective amount of CRL is administered to a patient in need thereof to enhance the patient's ability to encode, store, retrieve information. Cognitive testing may be used to assess memory function in patients administered CRL. Cognitive tests assess mental functions through a series of questions and/or simple tasks, and commonly used cognitive tests include a Montreal Cognitive Assessment (MoCA), a Mini-Mental State Exam (MMSE), and a Mini-Cog. In an aspect, the memory function of the patient in need thereof is assessed by a MoCA, a MMSE, a Mini-Cog, or any combination thereof. In an aspect, the memory function of the patient in need thereof is assessed by a MoCA. In an aspect, the memory function of the patient in need thereof is assessed by a MMSE. In an aspect, the memory function of the patient in need thereof is assessed by a Mini-Cog. In an aspect, the memory function of the patient in need thereof is assessed by both a MoCA and a MMSE. In an aspect, the memory function of the patient in need thereof is assessed by both a MoCA and a Mini-Cog. In an aspect, the memory function of the patient in need thereof is assessed by both a MMSE and a Mini-Cog. In an aspect, the memory function of the patient in need thereof is assessed by all three of a MoCA, a MMSE, and a Mini-Cog. In an aspect, the memory function of the patient in need thereof is assessed by CNS Vitals, a Symbol Digit Modalities Test (SDMT), a Profile of Mood States (POMS), a Pittsburgh Sleep Quality Index (PSQI), a Multidimensional Fatigue Inventory Questionnaire (MFI-20), a Frontal Systems Behavioral Scales (FrSBe), or any combination thereof. In an aspect, the memory function of the patient in need thereof is assessed by CNS Vitals. In an aspect, the memory function of the patient in need thereof is assessed by a SDMT. In an aspect, the memory function of the patient in need thereof is assessed by a POMS. In an aspect, the memory function of the patient in need thereof is assessed by a PSQI. In an aspect, the memory function of the patient in need thereof is assessed by a MFI-20. In an aspect, the memory function of the patient in need thereof is assessed by a FrSBe. In an aspect, the memory function of the patient is improved by at least 5% after the administration. In an aspect, the memory function of the patient is improved by at least 10% after the administration. In an aspect, the memory function of the patient is improved by at least 15% after the administration. In an aspect, the memory function of the patient is improved by at least 20% after the administration. In an aspect, the memory function of the patient is improved by at least 25% after the administration. In an aspect, the memory function of the patient is improved by at least 30% after the administration. In an aspect, the memory function of the patient is improved by at least 35% after the administration. In an aspect, the memory function of the patient is improved by at least 40% after the administration. In an aspect, the memory function of the patient is improved by at least 45% after the administration. In an aspect, the memory function of the patient is improved by at least 50% after the administration. In an aspect, the memory function of the patient is improved by at least 55% after the administration. In an aspect, the memory function of the patient is improved by at least 60% after the administration. In an aspect, the memory function of the patient is improved by at least 65% after the administration. In an aspect, the memory function of the patient is improved by at least 70% after the administration. In an aspect, the memory function of the patient is improved by at least 75% after the administration. In an aspect, the memory function of the patient is improved by at least 80% after the administration. In an aspect, the memory function of the patient is improved by at least 80% after the administration. In an aspect, the memory function of the patient is improved by between 5% to 15% after the administration. In an aspect, the memory function of the patient is improved by between 5% to 25% after the administration. In an aspect, the memory function of the patient is improved by between 5% to 50% after the administration. In an aspect, the memory function of the patient is improved by between 10% to 20% after the administration. In an aspect, the memory function of the patient is improved by between 10% to 50% after the administration. In an aspect, the memory function of the patient is improved by between 50% to 75% after the administration. In an aspect, the memory function of the patient is improved by between 5% to 75% after the administration. In an aspect, the memory function of the patient is improved by between 10% to 80% after the administration. In an aspect, the administration is for a time period of at least 1 month. In an aspect, the administration is for a time period of at least 2 months. In an aspect, the administration is for a time period of at least 3 months. In an aspect, the administration is for a time period of at least 4 months. In an aspect, the administration is for a time period of at least 5 months. In an aspect, the administration is for a time period of at least 6 months. In an aspect, the administration is for a time period of at least 7 months. In an aspect, the administration is for a time period of at least 8 months. In an aspect, the administration is for a time period of at least 9 months. In an aspect, the administration is for a time period of at least 10 months. In an aspect, the administration is for a time period of at least 11 months. In an aspect, the administration is for a time period of at least 1 year. In an aspect, the administration is for a time period of at least 1.5 years. In an aspect, the administration is for a time period of at least 2 years. In an aspect, the administration is for a time period of at least 2.5 years. In an aspect, the administration is for a time period of at least 3 years. In an aspect, the administration is for a time period of at least 3.5 years. In an aspect, the administration is for a time period of at least 4 years. In an aspect, the administration is for a time period of at least 4.5 years. In an aspect, the administration is for a time period of at least 5 years. In an aspect, the improved memory function of the patient persists throughout the administration time period.

In the methods provided herein, a dietary supplement comprising CRL is administered to a subject in need of improved memory function. In the methods provided herein, a dietary supplement comprising CRL is administered to a subject in need thereof to improve memory function. In the methods provided herein, a dietary supplement comprising CRL is administered to a subject in need thereof to enhance cognition. In the methods provided herein, a dietary supplement comprising CRL is administered to a subject in need thereof to enhance the subject's ability to encode, store, retrieve information. Cognitive testing may be used to assess memory function in subjects administered a dietary supplement comprising CRL. In an aspect, the memory function of the subject in need thereof is assessed by CNS Vitals, a Symbol Digit Modalities Test (SDMT), a Profile of Mood States (POMS), a Pittsburgh Sleep Quality Index (PSQI), a Multidimensional Fatigue Inventory Questionnaire (MFI-20), a Frontal Systems Behavioral Scales (FrSBe), or any combination thereof. In an aspect, the memory function of the subject in need thereof is assessed by CNS Vitals. In an aspect, the CNS-Vitals score of the subject in need thereof is 85 or less prior to the administering. In an aspect, the CNS-Vitals score of the subject in need thereof is increased after the administering. In an aspect, the CNS-Vitals score of the subject in need thereof is at least 90 after the administering. In an aspect, the CNS-Vitals score of the subject in need thereof is between 90 to 109 after the administering. In an aspect, the memory function of the subject in need thereof is assessed by a SDMT. In an aspect, the SDMT score of the subject in need thereof is 40 or less prior to the administering. In an aspect, the SDMT score of the subject in need thereof is increased after the administering. In an aspect, the SDMT score of the subject in need thereof is at least 50 after the administering. In an aspect, the SDMT score of the subject in need thereof is between 45 to 50 after the administering. In an aspect, the memory function of the subject in need thereof is assessed by a POMS. In an aspect, the POMS is a POMS short form. In an aspect, the POMS short form score of the subject in need thereof is elevated prior to the administering. In an aspect, the POMS short form score of the subject in need thereof is decreased after the administering. In an aspect, the POMS short form score of the subject in need thereof is lower than the original score after the administering. In an aspect, the POMS short form score measures the negative mood scores of the subject in need thereof. In an aspect, the memory function of the subject in need thereof is assessed by a PSQI. In an aspect, the memory function of the subject in need thereof is assessed by a MFI-20. In an aspect, the memory function of the subject in need thereof is assessed by a FrSBe. In an aspect, the memory function of the subject is improved by at least 5% after the administration. In an aspect, the memory function of the subject is improved by at least 10% after the administration. In an aspect, the memory function of the subject is improved by at least 15% after the administration. In an aspect, the memory function of the subject is improved by at least 20% after the administration. In an aspect, the memory function of the subject is improved by at least 25% after the administration. In an aspect, the memory function of the subject is improved by at least 30% after the administration. In an aspect, the memory function of the subject is improved by at least 35% after the administration. In an aspect, the memory function of the subject is improved by at least 40% after the administration. In an aspect, the memory function of the subject is improved by at least 45% after the administration. In an aspect, the memory function of the subject is improved by at least 50% after the administration. In an aspect, the memory function of the subject is improved by at least 55% after the administration. In an aspect, the memory function of the subject is improved by at least 60% after the administration. In an aspect, the memory function of the subject is improved by at least 65% after the administration. In an aspect, the memory function of the subject is improved by at least 70% after the administration. In an aspect, the memory function of the subject is improved by at least 75% after the administration. In an aspect, the memory function of the subject is improved by at least 80% after the administration. In an aspect, the memory function of the subject is improved by at least 80% after the administration. In an aspect, the memory function of the subject is improved by between 5% to 15% after the administration. In an aspect, the memory function of the subject is improved by between 5% to 25% after the administration. In an aspect, the memory function of the subject is improved by between 5% to 50% after the administration. In an aspect, the memory function of the subject is improved by between 10% to 20% after the administration. In an aspect, the memory function of the subject is improved by between 10% to 50% after the administration. In an aspect, the memory function of the subject is improved by between 50% to 75% after the administration. In an aspect, the memory function of the subject is improved by between 5% to 75% after the administration. In an aspect, the memory function of the subject is improved by between 10% to 80% after the administration. In an aspect, the administration is for a time period of at least 1 month. In an aspect, the administration is for a time period of at least 2 months. In an aspect, the administration is for a time period of at least 3 months. In an aspect, the administration is for a time period of at least 4 months. In an aspect, the administration is for a time period of at least 5 months. In an aspect, the administration is for a time period of at least 6 months. In an aspect, the administration is for a time period of at least 7 months. In an aspect, the administration is for a time period of at least 8 months. In an aspect, the administration is for a time period of at least 9 months. In an aspect, the administration is for a time period of at least 10 months. In an aspect, the administration is for a time period of at least 11 months. In an aspect, the administration is for a time period of at least 1 year. In an aspect, the administration is for a time period of at least 1.5 years. In an aspect, the administration is for a time period of at least 2 years. In an aspect, the administration is for a time period of at least 2.5 years. In an aspect, the administration is for a time period of at least 3 years. In an aspect, the administration is for a time period of at least 3.5 years. In an aspect, the administration is for a time period of at least 4 years. In an aspect, the administration is for a time period of at least 4.5 years. In an aspect, the administration is for a time period of at least 5 years. In an aspect, the improved memory function of the subject persists throughout the administration time period.

In the methods provided herein, the improved memory function of a patient administered a pharmaceutical composition comprising an effective amount of CRL is assessed by a Montreal Cognitive Assessment (MoCA). In an aspect, the MoCA score of the patient is 15 or less prior to the administration. In an aspect, the MoCA score of the patient is 20 or less prior to the administration. In an aspect, the MoCA score of the patient is 25 or less prior to the administration. In an aspect, the MoCA score of the patient is increased after the administration. In an aspect, the MoCA score of the patient is increased by at least 1 point after the administration. In an aspect, the MoCA score of the patient is increased by at least 2 points after the administration. In an aspect, the MoCA score of the patient is increased by at least 3 points after the administration. In an aspect, the MoCA score of the patient is increased by at least 4 points after the administration. In an aspect, the MoCA score of the patient is increased by at least 5 points after the administration. In an aspect, the MoCA score of the patient is increased by at least 6 points after the administration. In an aspect, the MoCA score of the patient is increased by at least 7 points after the administration. In an aspect, the MoCA score of the patient is increased by at least 8 points after the administration. In an aspect, the MoCA score of the patient is increased by at least 9 points after the administration. In an aspect, the MoCA score of the patient is increased by at least 10 points after the administration. In an aspect, the MoCA score of the patient is increased by between 1 point and 5 points after the administration. In an aspect, the MoCA score of the patient is increased by between 1 point and 10 points after the administration. In an aspect, the MoCA score of the patient is increased by between 5 points and 10 points after the administration. In an aspect, the MoCA score of the patient is at least 20 after the administration. In an aspect, the MoCA score of the patient is at least 22 after the administration. In an aspect, the MoCA score of the patient is at least 24 after the administration. In an aspect, the MoCA score of the patient is at least 25 after the administration. In an aspect, the MoCA score of the patient is at least 26 after the administration. In an aspect, the MoCA score of the patient is at least 27 after the administration. In an aspect, the MoCA score of the patient is at least 28 after the administration. In an aspect, the MoCA score of the patient is at least 29 after the administration. In an aspect, the MoCA score of the patient is 30 after the administration. In an aspect, the MoCA score of the patient is between 20 and 25 after the administration. In an aspect, the MoCA score of the patient is between 25 and 30 after the administration. In an aspect, the MoCA score of the patient is between 26 and 30 after the administration. In an aspect, the MoCA score of the patient is between 27 and 30 after the administration. In an aspect, the MoCA score of the patient is between 28 and 30 after the administration. In an aspect, the increased MoCA score of the patient persists throughout the administration time period, as assessed by periodic MoCA testing of the patient.

In the methods provided herein, the improved memory function of a patient administered a pharmaceutical composition comprising an effective amount of CRL is assessed by a Mini-Mental State Exam (MMSE). In an aspect, the MMSE score of the patient is 15 or less prior to the administration. In an aspect, the MMSE score of the patient is 20 or less prior to the administration. In an aspect, the MMSE score of the patient is 22 or less prior to the administration. In an aspect, the MMSE score of the patient is increased after the administration. In an aspect, the MMSE score of the patient is increased by at least 1 point after the administration. In an aspect, the MMSE score of the patient is increased by at least 2 points after the administration. In an aspect, the MMSE score of the patient is increased by at least 3 points after the administration. In an aspect, the MMSE score of the patient is increased by at least 4 points after the administration. In an aspect, the MMSE score of the patient is increased by at least 5 points after the administration. In an aspect, the MMSE score of the patient is increased by at least 6 points after the administration. In an aspect, the MMSE score of the patient is increased by at least 7 points after the administration. In an aspect, the MMSE score of the patient is increased by at least 8 points after the administration. In an aspect, the MMSE score of the patient is increased by at least 9 points after the administration. In an aspect, the MMSE score of the patient is increased by at least 10 points after the administration. In an aspect, the MMSE score of the patient is increased by between 1 point and 5 points after the administration. In an aspect, the MMSE score of the patient is increased by between 1 point and 10 points after the administration. In an aspect, the MMSE score of the patient is increased by between 5 points and 10 points after the administration. In an aspect, the MMSE score of the patient is at least 24 after the administration. In an aspect, the MMSE score of the patient is at least 25 after the administration. In an aspect, the MMSE score of the patient is at least 26 after the administration. In an aspect, the MMSE score of the patient is at least 27 after the administration. In an aspect, the MMSE score of the patient is at least 28 after the administration. In an aspect, the MMSE score of the patient is at least 29 after the administration. In an aspect, the MMSE score of the patient is 30 after the administration. In an aspect, the MMSE score of the patient is between 24 and 28 after the administration. In an aspect, the MMSE score of the patient is between 25 and 28 after the administration. In an aspect, the MMSE score of the patient is between 25 and 30 after the administration. In an aspect, the MMSE score of the patient is between 26 and 30 after the administration. In an aspect, the MMSE score of the patient is between 27 and 30 after the administration. In an aspect, the MMSE score of the patient is between 28 and 30 after the administration. In an aspect, the increased MMSE score of the patient of the patient persists throughout the administration time period, as assessed by periodic MMSE testing of the patient.

In the methods provided herein, the improved memory function of a patient administered a pharmaceutical composition comprising an effective amount of CRL is assessed by a Mini-Cog. In an aspect, the Mini-Cog score of the patient is 0, 1, or 2 prior to the administration. In an aspect, the Mini-Cog score of the patient in need thereof is 2 or less prior to the administration. In an aspect, the Mini-Cog score of the patient in need thereof is increased after the administration. In an aspect, the Mini-Cog score of the patient in need thereof is increased by at least 1 point after the administration. In an aspect, the Mini-Cog score of the patient in need thereof is increased by 1 point after the administration. In an aspect, the Mini-Cog score of the patient in need thereof is increased by at least 2 points after the administration. In an aspect, the Mini-Cog score of the patient in need thereof is increased by 2 points after the administration. In an aspect, the Mini-Cog score of the patient in need thereof is increased by at least 3 points after the administration. In an aspect, the Mini-Cog score of the patient in need thereof is increased by 3 points after the administration. In an aspect, the Mini-Cog score of the patient in need thereof is increased by at least 4 points after the administration. In an aspect, the Mini-Cog score of the patient in need thereof is increased by 4 points after the administration. In an aspect, the Mini-Cog score of the patient in need thereof is increased by 5 points after the administration. In an aspect, the Mini-Cog score of the patient in need thereof is increased by 1 point or 2 points after the administration. In an aspect, the Mini-Cog score of the patient in need thereof is increased by between 1 point and 3 points after the administration. In an aspect, the Mini-Cog score of the patient in need thereof is increased by between 1 point and 4 points after the administration. In an aspect, the Mini-Cog score of the patient in need thereof is increased by between 1 point and 5 points after the administration. In an aspect, the Mini-Cog score of the patient in need thereof is increased by between 2 points or 3 points after the administration. In an aspect, the Mini-Cog score of the patient in need thereof is increased by between 2 points and 4 points after the administration. In an aspect, the Mini-Cog score of the patient in need thereof is increased by between 2 points and 5 points after the administration. In an aspect, the Mini-Cog score of the patient in need thereof is increased by 3 points or 4 points after the administration. In an aspect, the Mini-Cog score of the patient in need thereof is increased by between 3 points and 5 points after the administration. In an aspect, the Mini-Cog score of the patient in need thereof is increased by 4 points or 5 points after the administration. In an aspect, the Mini-Cog score of the patient in need thereof is at least 2 after the administration. In an aspect, the Mini-Cog score of the patient in need thereof is at least 3 after the administration. In an aspect, the Mini-Cog score of the patient in need thereof is at least 4 after the administration. In an aspect, the Mini-Cog score of the patient in need thereof is 5 after the administration. In an aspect, the MMSE score of the patient in need thereof is between 2 and 4 after the administration. In an aspect, the MMSE score of the patient in need thereof is between 2 and 5 after the administration. In an aspect, the MMSE score of the patient in need thereof is between 3 and 5 after the administration. In an aspect, the increased Mini-Cog score of the patient of the patient persists throughout the administration time period, as assessed by periodic Mini-Cog testing of the patient.

In the methods provided herein, administering CRL, or a pharmaceutical composition comprising CRL, to a patient in need thereof increases levels of one or more gut bacteria in the patient. In an aspect, the levels of one or more gut bacteria in the patient are measured by analysis of a fecal sample obtained from the patient. In an aspect, the one or more gut bacteria with increased levels are selected from Clostridiales lostridiales vadinBB60 group bacterium 1, Clostridiales vadinBB60 group bacterium 2, Acetatifactor, *Bifidobacterium pseudolongum*, Rikinellaceae, *Allobaculum*, *Akkermansia muciniphila*, *Anaerostipes*, and Christensenellaceae. In an aspect, the one or more gut bacteria with increased levels is Clostridiales lostridiales vadinBB60 group bacterium 1. In an aspect, the one or more gut bacteria with increased levels is Clostridiales vadinBB60 group bacterium 2. In an aspect, the one or more gut bacteria with increased levels is Acetatifactor. In an aspect, the one or more gut bacteria with increased levels is *Bifidobacterium pseudolongum*. In an aspect, the one or more gut bacteria with increased levels is Rikinellaceae. In an aspect, the one or more gut bacteria with increased levels is *Allobaculum*. In an aspect, the one or more gut bacteria with increased levels is *Akkermansia muciniphila*. In an aspect, the one or more gut bacteria with increased levels is *Anaerostipes*. In an aspect, the one or more gut bacteria with increased levels is Christensenellaceae. In an aspect, the one or more gut bacteria with increased levels are Clostridiales lostridiales vadinBB60 group bacterium 1, Clostridiales vadinBB60 group bacterium 2, and Acetatifactor. In an aspect, the one or more gut bacteria with increased levels are one, two, three, four, five, six, seven, eight, or nine different bacteria. In an aspect, the levels of the one or more gut bacteria are independently increased by at least 10%. In an aspect, the levels of the one or more gut bacteria are independently increased by about 10%. In an aspect, the levels of the one or more gut bacteria are independently increased by at least 20%. In an aspect, the levels of the one or more gut bacteria are independently increased by about 20%. In an aspect, the levels of the one or more gut bacteria are independently increased by at least 30%. In an aspect, the levels of the one or more gut bacteria are independently increased by about 30%. In an aspect, the levels of the one or more gut bacteria are independently increased by at least 40%. In an aspect, the levels of the one or more gut bacteria are independently increased by about 40%. In an aspect, the levels of the one or more gut bacteria are independently increased by at least 50%. In an aspect, the levels of the one or more gut bacteria are independently increased by about 50%. In an aspect, the levels of the one or more gut bacteria are independently increased by at least 60%. In an aspect, the levels of the one or more gut bacteria are independently increased by about 60%. In an aspect, the levels of the one or more gut bacteria are independently increased by at least 70%. In an aspect, the levels of the one or more gut bacteria are independently increased by about 70%. In an aspect, the levels of the one or more gut bacteria are independently increased by at least 80%. In an aspect, the levels of the one or more gut bacteria are independently increased by about 80%. In an aspect, the levels of the one or more gut bacteria are independently increased by at least 90%. In an aspect, the levels of the one or more gut bacteria are independently increased by about 90%. In an aspect, the levels of the one or more gut bacteria are independently increased by at least 95%. In an aspect, the levels of the one or more gut bacteria are independently increased by about 95%. In an aspect, the levels of the one or more gut bacteria are independently increased by about 100%. In an aspect, the levels of the one or more gut bacteria are independently increased by about 110%. In an aspect, the levels of the one or more gut bacteria are independently increased by about 120%. In an aspect, the levels of the one or more gut bacteria are independently increased by about 130%. In an aspect, the levels of the one or more gut bacteria are independently increased by about 140%. In an aspect, the levels of the one or more gut bacteria are independently increased by about 150%. In an aspect, the levels of the one or more gut bacteria are independently increased by between 10% and 25%. In an aspect, the levels of the one or more gut bacteria are independently increased by between 10% and 50%. In an aspect, the levels of the one or more gut bacteria are independently increased by between 10% and 75%. In an aspect, the levels of the one or more gut bacteria are independently increased by between 25% and 50%. In an aspect, the levels of the one or more gut bacteria are independently increased by between 25% and 75%. In an aspect, the levels of the one or more gut bacteria are independently increased by between 50% and 75%. In an aspect, the levels of the one or more gut bacteria are independently increased by between 50% and 95%. In an aspect, the levels of the one or more gut bacteria are independently increased by between 10% and 90%. In an aspect, the levels of the one or more gut bacteria are independently increased by between 10% and 95%. In an aspect, the levels of the one or more gut bacteria are independently increased by at least one-fold. In an aspect, the levels of the one or more gut bacteria are independently increased by at least two-fold. In an aspect, the levels of the one or more gut bacteria are independently increased by at least three-fold. In an aspect, the levels of the one or more gut bacteria are independently increased by at least four-fold. In an aspect, the levels of the one or more gut bacteria are independently increased by at least five-fold. In an aspect, the levels of the one or more gut bacteria are independently increased by at least six-fold. In an aspect, the levels of the one or more gut bacteria are independently increased by at least seven-fold. In an aspect, the levels of the one or more gut bacteria are independently increased by at least eight-fold. In an aspect, the levels of the one or more gut bacteria are independently increased by at least nine-fold. In an aspect, the levels of the one or more gut bacteria are independently increased by at least ten-fold. In an aspect, the levels of the one or more gut bacteria are independently increased by between one-fold and 1.5-fold. In an aspect, the levels of the one or more gut bacteria are independently increased by between one-fold and two-fold. In an aspect, the levels of the one or more gut bacteria are independently increased by between one-fold and 2.5-fold. In an aspect, the levels of the one or more gut bacteria are independently increased by between one-fold and three-fold. In an aspect, the levels of the one or more gut bacteria are independently increased by between one-fold and 3.5-fold. In an aspect, the levels of the one or more gut bacteria are independently increased by between one-fold and four-fold. In an aspect, the levels of the one or more gut bacteria are independently increased by between one-fold and five-fold. In an aspect, the levels of the one or more gut bacteria are independently increased by between 1.5-fold and 2.5-fold. In an aspect, the levels of the one or more gut bacteria are independently increased by between 1.5-fold and three-fold. In an aspect, the levels of the one or more gut bacteria are independently increased by between 1.5-fold and four-fold. In an aspect, the levels of the one or more gut bacteria are independently increased by between 1.5-fold and five-fold. In an aspect, the levels of the one or more gut bacteria are independently increased by between two-fold and three-fold. In an aspect, the levels of the one or more gut bacteria are independently increased by between two-fold and 3.5-fold. In an aspect, the levels of the one or more gut bacteria are independently increased by between two-fold and four-fold. In an aspect, the levels of the one or more gut bacteria are independently increased by between two-fold and five-fold. In an aspect, the levels of the one or more gut bacteria are independently increased by between 2.5-fold and 3.5-fold. In an aspect, the levels of the one or more gut bacteria are independently increased by between 2.5-fold and four-fold. In an aspect, the levels of the one or more gut bacteria are independently increased by between 2.5-fold and five-fold. In an aspect, the levels of the one or more gut bacteria are independently increased by between three-fold and four-fold. In an aspect, the levels of the one or more gut bacteria are independently increased by between three-fold and five-fold. In an aspect, the levels of the one or more gut bacteria are independently increased by between 3.5-fold and 4.5-fold. In an aspect, the levels of the one or more gut bacteria are independently increased by between 3.5-fold and five-fold. In an aspect, the levels of the one or more gut bacteria are independently increased by between four-fold and five-fold. In an aspect, the levels of the one or more gut bacteria are independently increased by between one-fold and ten-fold. In an aspect, the levels of the one or more gut bacteria are independently increased by between five-fold and ten-fold. In an aspect, the patient is a dementia patient. In an aspect, the patient is an Alzheimer's disease patient. In an aspect, the patient is a Parkinson's disease patient.

In an aspect, a pharmaceutical composition comprising an effective amount of CRL may be used for the treatment of a neurodegenerative disorder in a patient of need thereof. In an aspect, a pharmaceutical composition comprising an effective amount of CRL is used for the management of a neurodegenerative disorder in a patient of need thereof. In an aspect, a pharmaceutical composition comprising an effective amount of CRL is used to reduce the severity of a neurodegenerative disorder in a patient of need thereof. In an aspect, the neurodegenerative disorder is selected from the group consisting of dementia, Alzheimer's disease, Parkinson's disease, Huntington's disease, amyotrophic lateral sclerosis (ALS), schizophrenia, multiple sclerosis, cerebral palsy, ataxia, spasticity, traumatic brain injury (TBI), and any combination thereof.

In an aspect a pharmaceutical composition comprising an effective amount of CRL is used for the manufacture of a medicament for the treatment of a neurodegenerative disorder in a patient of need thereof. In an aspect, a pharmaceutical composition comprising an effective amount of CRL is used for the manufacture of a medicament for the management of a neurodegenerative disorder in a patient of need thereof. In an aspect, a pharmaceutical composition comprising an effective amount of CRL is used for the manufacture of a medicament for reducing the severity of a neurodegenerative disorder in a patient of need thereof. In an aspect, the neurodegenerative disorder is selected from the group consisting of dementia, Alzheimer's disease, Parkinson's disease, Huntington's disease, amyotrophic lateral sclerosis (ALS), schizophrenia, multiple sclerosis, cerebral palsy, ataxia, spasticity, traumatic brain injury (TBI), and any combination thereof.

The skilled person will recognize that CRL may be prepared by fermentation according to the methods set forth in, for example, Ferrer et al., "Production of native and recombinant lipases by *Candida rugosa*," *Appl Biochem Biotechnol.* 95(3):221-255 (2001), which is incorporated by reference herein in its entirety for all purposes. In an aspect, CRL is produced from the yeast *Candida rugosa* by fermentation. In an aspect, CRL is mixed with one or more additives following isolation. In an aspect, the additive is maltodextrin.

C. Definitions

The term "and/or" when used in a list of two or more items, means that any one of the listed items can be employed by itself or in combination with any one or more of the listed items. For example, the expression "A and/or B" is intended to mean either or both of A and B, i.e., A alone, B alone, or A and B in combination. The expression "A, B and/or C" is intended to mean A alone, B alone, C alone, A and B in combination, A and C in combination, B and C in combination, or A, B, and C in combination.

As used herein, terms in the singular and the singular forms "a," "an," and "the," for example, include plural referents unless the content clearly dictates otherwise.

Where a range of values is provided, it is understood that each intervening value, between the upper and lower limit of that range and any other stated or intervening value in that stated range is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure. Whenever the phrase "comprising" is used, variations such as "consisting essentially of" and "consisting of" are also contemplated.

As used herein, the term "about" refers to a range extending to +/−10% of the specified value.

Unless defined otherwise herein, terms are to be understood according to conventional usage by those of ordinary skill in the relevant art. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), or the "McGraw-Hill Dictionary of Scientific and Technical Terms" (6th edition, 2002, McGraw-Hill, New York).

As used herein, the terms "gut microbiome" refers to the group of microorganisms ("gut microbiota"), including bacteria and archaea, inhabiting the gastrointestinal tract (gut) of a host animal. In humans, the gut microbiome includes trillions of microorganisms, including approximately 300 to 500 different types of bacteria. The bacteria located within the human gastrointestinal tract fall into five main phyla: (1) Bacteroidetes, (2) Firmicutes, (3) Actinobacteria, (4), Proteobacteria, and (5) Verrucomicrobia. Of these, Bacteroidetes and Firmicutes are most common. The gut microbiome forms a complex ecological community which, through its collective activities and interactions, influences host physiology, function, and susceptibility to disease.

As used herein, "neurodegenerative disorder" is a disease, disorder, or condition in which nerve cells in the brain lose function over time and ultimately die. Cognitive effects of neurodegenerative disorders include general cognitive dysfunction and impairment, memory loss, memory impairment, agitation, moodiness, anxiety, mood changes, depression, forgetfulness, apathy, and any combination thereof. Neurodegenerative disorders may also disrupt body activities, including balance, movement, speech, swallowing, breathing, bladder and bowel function, blood pressure stabilization, heart function, muscle activity and control, posture, and sleep. Non-liming examples of neurodegenerative disorders include dementia, Parkinson's disease, Alzheimer's disease, Huntington's disease, amyotrophic lateral sclerosis (ALS), schizophrenia, multiple sclerosis, cerebral palsy, ataxia, motor neuron disease (MND), and spasticity.

As used herein, "biodiversity" is a measure of variation with an ecosystem at the genetic or species level, and "gut biodiversity" refers to the variety of species of microorganisms within a host's gut microbiome. Various methods are known in the art to assess biodiversity within a single sample, referred to as "α-diversity." The α-diversity of a sample or community estimates the richness (number) and/or distribution (evenness) of species within that sample or community. One common method for estimating α-diversity is the Shannon index, which is a weighted geometric mean of the proportional abundances of the various species within the sample which gives a higher weight to species richness. Shannon's diversity (H') is calculated according to formula (I)

$$H' = -\sum P_i \ln(P_i) \qquad (I)$$

where $P_i$ is the proportion of individuals belonging to species i. See Morris et al., "Choosing and using diversity indices: Insights for ecological applications from the German Biodiversity Exploratories," *Ecology and Evolution*, 4(18):3514-3524 (2014). Larger H' values indicate higher levels of α-diversity. A second method for determining α-diversity is by the Simpson index. The Simpson index considers both species richness and relative species abundance but gives a higher weight to relative abundance. In this model, Simpson's diversity (D1) is calculated according to formula (II)

$$D_1 = 1 - \sum P_i^2 \qquad (II)$$

where $P_i$ is the proportion of individuals belonging to species i. See Morris et al. 2014. Rare species make less of a contribution to a sample's α-diversity score if analyzed by the Simpson index as compared to the Shannon index. Biodiversity between two different samples, groups, or systems is referred to as "β-diversity." A commonly used method to assess β-diversity is the Bray-Curtis dissimilarity index, which is based on the Sorenson index and considers species abundance. In this model, the Bray-Curtis dissimilarity for two samples i and j (BCij) is calculated according to formula (III)

$$BC_{ij} = 1 - \frac{2C_{ij}}{S_i + S_j} \quad \text{(III)}$$

where $S_i$ is the total number of specimens collected in sample i, $S_j$ is the total number of specimens collected in sample j, and $C_{ij}$ is the sum of only the lesser counts for each species found in both samples. The Bray-Curtis dissimilarity ranges from 0 (the two samples share all species) to 1 (the two samples share no species). See Bray et al., "An ordination of upland forest communities of southern Wisconsin," *Ecological Monographs* 27:325-349 (1957).

As used herein, "dysbiosis" refers to an imbalance between the types of organisms present in a person's natural microflora, particularly in the gut.

As used herein, "effective amount" or "therapeutically effective amount" refers to the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

As used herein, "Federation International Pharmaceutique" or "FIP" is a measure of lipase enzyme activity, and refers to the quantity of a standard lipase preparation (Fungi Lipase-International FIP Standard) that liberates the equivalent of 1 micromole (mol) of fatty acid per minute from a substrate emulsion at pH 7.00 and 37° C.

As used herein, "patient" or "subject" or "individual" refers to a human or non-human animal selected for treatment or therapy, or receiving a dietary supplement. In an aspect, a subject receiving a dietary supplement is a healthy subject. In an aspect, a subject receiving a dietary supplement is a subject having impaired cognitive function or poor memory.

As used herein, "pharmaceutical agent" refers to a substance that provides a therapeutic benefit when administered to an individual. For example, in certain aspects, CRL is pharmaceutical agent.

As used herein, "pharmaceutical composition" refers to a mixture of substances suitable for administering to an individual. For example, a pharmaceutical composition can comprise one or more active agents and a sterile aqueous solution.

As used herein, "treat" or "treatment" or "treating" refers to administering a pharmaceutical composition to affect an alteration or improvement of a disease, disorder, or condition.

As used herein, "co-administration" refers to administration of two or more agents to an individual. The two or more agents can be in a single pharmaceutical composition, or can be in separate pharmaceutical compositions. Each of the two or more agents can be administered through the same or different routes of administration. Co-administration encompasses simultaneous or sequential administration.

As used herein, "dietary supplement" refers to a composition or manufactured product intended to improve or complete one or more aspects of a subject's health or well-being.

All publications, patents, and patent applications mentioned in this disclosure are herein incorporated by reference to the same extent as if each individual publication, patent, or patent application was specifically and individually indicated to be incorporated by reference.

Having now generally described the disclosure, the same will be more readily understood through reference to the following examples that are provided by way of illustration, and are not intended to be limiting of the present disclosure, unless specified.

D. EMBODIMENTS

Embodiment 1. A method for treating, managing, or reducing the severity of a neurodegenerative disorder in a patient in need thereof, comprising administering a pharmaceutical composition comprising a therapeutically effective amount of *Candida rugosa* lipase (CRL) to the patient.

Embodiment 2. The method of Embodiment 1, wherein the neurodegenerative disorder is selected from the group consisting of dementia, Parkinson's disease, Alzheimer's disease, Huntington's disease, amyotrophic lateral sclerosis (ALS), schizophrenia, multiple sclerosis, traumatic brain injury (TBI), and any combination thereof.

Embodiment 3. The method of Embodiment 2, wherein the neurodegenerative disorder is dementia.

Embodiment 4. The method of Embodiment 2, wherein the neurodegenerative disorder is Alzheimer's disease.

Embodiment 5. The method of Embodiment 2, wherein the neurodegenerative disorder is Parkinson's disease.

Embodiment 6. The method of any one of Embodiments 1 to 5, wherein the therapeutically effective amount of CRL is between 45,000 and 90,000 Fédération International Pharmaceutique (FIP) units of CRL per day.

Embodiment 7. The method of any one of Embodiments 1 to 6, wherein the administering is once per day.

Embodiment 8. The method of any one of Embodiments 1 to 6, wherein the administering is twice per day.

Embodiment 9. The method of any one of Embodiments 1 to 6, wherein the administering is three times per day.

Embodiment 10. The method of Embodiment 9, wherein the therapeutically effective amount of CRL is administered to the patient in three doses, each of the three doses comprising 15,000 FIP units of CRL or 30,000 FIP units of CRL.

Embodiment 11. The method of Embodiment 10, wherein each of the doses is administered to the patient without food.

Embodiment 12. The method of Embodiment 10 or Embodiment 11, wherein each of the doses is administered orally to the patient as a capsule.

Embodiment 13. The method of Embodiment 10 or Embodiment 11, wherein each of the doses is administered orally to the patient as a tablet.

Embodiment 14. The method of any one of Embodiments 1 to 13, wherein the administering alters the gut microbiome of the patient.

Embodiment 15. The method of Embodiment 14, wherein the patient's fecal α-diversity, fecal β-diversity, or both is increased after the administering.

Embodiment 16. The method of any one of Embodiments 1 to 15, wherein levels of one or more gut bacteria in the patient are increased after the administering.

Embodiment 17. The method of Embodiment 16, wherein the one or more gut bacteria is selected from the group consisting of Clostridiales lostridiales vadinBB60 group bacterium 1, Clostridiales vadinBB60 group bacterium 2, Acetatifactor, *Bifidobacterium pseudolongum*, Rikinellaceae, *Allobaculum, Akkermansia muciniphila, Anaerostipes,* and Christensenellaceae.

Embodiment 18. The method of Embodiment 16, wherein the one or more gut bacteria are Clostridiales lostridiales vadinBB60 group bacterium 1, Clostridiales vadinBB60 group bacterium 2, and Acetatifactor.

Embodiment 19. The method of any one of Embodiments 16 to 18, wherein the levels of the one or more gut bacteria are each independently increased by between 10% to 90% after the administering.

Embodiment 20. The method of any one of Embodiments 16 to 19, wherein the levels of the one or more gut bacteria are measured by analysis of a fecal sample obtained from the patient.

Embodiment 21. The method of any one of Embodiments 1 to 20, wherein the administering increases circulating levels of very low-density and low-density lipoprotein (VLDL/HDL) cholesterol, VLDL/HDL cholesterol esters, or both.

Embodiment 22. The method of Embodiment 21, wherein the circulating levels of VLDL/HDL cholesterol are increased by 5% to 40% after the administering.

Embodiment 23. The method of Embodiment 21, wherein the circulating levels of VLDL/HDL cholesterol esters are increased by 5% to 35% after the administering.

Embodiment 24. The method of any one of Embodiments 1 to 23, wherein the patient exhibits improved cognition after the administering.

Embodiment 25. The method of Embodiment 24, wherein said improved cognition is a reduction in memory loss, a reduction in memory impairment, or both.

Embodiment 26. The method of any one of Embodiments 1 to 25, wherein the patient exhibits an improvement of one or more neurological parameters after said administering.

Embodiment 27. The method of Embodiment 26, wherein the one or more neurological parameters are selected from the group consisting of balance, movement, speech, swallowing, breathing, bladder function, bowel function, blood pressure stabilization, heart function, muscle activity, muscle control, posture, and sleep.

Embodiment 28. A method for treating, managing, or reducing the severity of Alzheimer's disease in a patient in need thereof, comprising administering a pharmaceutical composition comprising a therapeutically effective amount of *Candida rugosa* lipase (CRL) to the patient.

Embodiment 29. The method of any one of Embodiment 28, wherein the therapeutically effective amount of CRL is between 45,000 and 90,000 Fédération International Pharmaceutique (FIP) units of CRL per day.

Embodiment 30. The method of Embodiment 28 or Embodiment 29, wherein the administering is once per day.

Embodiment 31. The method of Embodiment 28 or Embodiment 29, wherein the administering is twice per day.

Embodiment 32. The method of Embodiment 28 or Embodiment 29, wherein the administering is three times per day.

Embodiment 33. The method of Embodiment 32, wherein the therapeutically effective amount of CRL is administered to the patient in three doses, each of the three doses comprising 15,000 FIP units of CRL or 30,000 FIP units of CRL.

Embodiment 34. The method of Embodiment 33, wherein each of the doses is administered to the patient without food.

Embodiment 35. The method of Embodiment 33 or Embodiment 34, wherein each of the doses is administered orally to the patient as a capsule.

Embodiment 36. The method of Embodiment 33 or Embodiment 34, wherein each of the doses is administered orally to the patient as a tablet.

Embodiment 37. The method of any one of Embodiments 28 to 36, wherein the administering alters the gut microbiome of the patient.

Embodiment 38. The method of Embodiment 37, wherein the patient's fecal α-diversity, fecal β-diversity, or both is increased after the administering.

Embodiment 39. The method of any one of Embodiments 28 to 38, wherein levels of one or more gut bacteria in the patient are increased after the administering.

Embodiment 40. The method of Embodiment 39, wherein the one or more gut bacteria is selected from the group consisting of Clostridiales lostridiales vadinBB60 group bacterium 1, Clostridiales vadinBB60 group bacterium 2, Acetatifactor, *Bifidobacterium pseudolongum*, Rikinellaceae, *Allobaculum, Akkermansia muciniphila, Anaerostipes*, and Christensenellaceae.

Embodiment 41. The method of Embodiment 39, wherein the one or more gut bacteria are Clostridiales lostridiales vadinBB60 group bacterium 1, Clostridiales vadinBB60 group bacterium 2, and Acetatifactor.

Embodiment 42. The method of any one of Embodiments 28 to 41, wherein the levels of the one or more gut bacteria are each independently increased by between 10% to 90% after said administering.

Embodiment 43. The method of any one of Embodiments 28 to 42, wherein a level of an Alzheimer's disease biomarker in a cerebral spinal fluid (CSF) sample of the patient is altered after said administering, wherein the Alzheimer's disease biomarker is selected from the group consisting of amyloid-β 42 (Aβ42), total tau (T-tau), phosphorylated tau (P-tau), and any combination thereof.

Embodiment 44. The method of Embodiment 43, wherein the level of amyloid-β 42 (Aβ42) is increased between 1.5-fold to 2.5-fold after the administering.

Embodiment 45. The method of Embodiment 43, wherein the level of total tau (T-tau) is decreased between 2-fold to 3-fold after the administering.

Embodiment 46. The method of Embodiment 43, wherein the level phosphorylated tau (P-tau) is decreased between 1.5-fold to 2.5-fold after the administering.

Embodiment 47. The method of any one of Embodiments 43 to 46, wherein a ratio of total tau (T-tau) to amyloid-β 42 (Aβ42) is decreased between about 5-fold to about 10-fold after the administering.

Embodiment 48. The method of any one of Embodiments 43 to 47, wherein a ratio of amyloid-β 42 (Aβ42) to phosphorylated tau (P-tau) is increased between about 5-fold to about 10-fold after the administering.

Embodiment 49. The method of any one of Embodiments 43 to 48, wherein the cerebral spinal fluid (CSF) sample is collected from the patient by lumbar puncture.

Embodiment 50. The method of any one of Embodiments 28 to 49, wherein the quantity of amyloid plaques in the brain of the patient is reduced by at least 20% after the administering.

Embodiment 51. The method of Embodiment 50, wherein the quantity of amyloid plaques is determined by molecular imaging of the brain of the patient.

Embodiment 52. The method of any one of Embodiments 28 to 51, wherein the quantity of neurofibrillary fibers in the brain of the patient is reduced by at least 20% after the administering.

Embodiment 53. The method of Embodiment 52, wherein the quantity of neurofibrillary fibers is determined by molecular imaging of the brain of the patient.

Embodiment 54. The method of any one of Embodiments 28 to 53, wherein circulating levels of very low-density and low-density lipoprotein (VLDL/HDL) cholesterol, VLDL/HDL cholesterol esters, or both, are increased after the administering.

Embodiment 55. The method of Embodiment 54, wherein the circulating levels of VLDL/HDL cholesterol are increased by 5% to 40% after the administering.

Embodiment 56. The method of Embodiment 55, wherein the circulating levels of VLDL/HDL cholesterol esters are increased by 5% to 35% after the administering.

Embodiment 57. The method of any one of Embodiments 28 to 56, wherein the patient exhibits improved cognition after the administering.

Embodiment 58. The method of Embodiment 57, wherein said improved cognition is a reduction in memory loss, a reduction in memory impairment, or both.

Embodiment 59. A pharmaceutical composition for use in treating, managing, or reducing the severity of a neurodegenerative disorder in a patient in need thereof, wherein the pharmaceutical composition comprises a therapeutically effective amount of *Candida rugosa* lipase (CRL).

Embodiment 60. The pharmaceutical composition of Embodiment 59, wherein the therapeutically effective amount of CRL is between 45,000 and 90,000 Fédération International Pharmaceutique (FIP) units of CRL per day.

Embodiment 61. A method for increasing levels of one or more gut bacteria in a patient having a neurodegenerative disorder, comprising administering a pharmaceutical composition comprising a therapeutically effective amount of *Candida rugosa* lipase (CRL) to the patient.

Embodiment 62. The method of Embodiment 61, wherein the therapeutically effective amount of CRL is between 45,000 and 90,000 Fédération International Pharmaceutique (FIP) units of CRL per day.

Embodiment 63. A method for enhancing gut microbiome diversity in a patient having a neurodegenerative disorder, comprising administering a pharmaceutical composition comprising a therapeutically effective amount of *Candida rugosa* lipase (CRL) to the patient.

Embodiment 64. The method of Embodiment 63, wherein the therapeutically effective amount of CRL is between 45,000 and 90,000 Fédération International Pharmaceutique (FIP) units of CRL per day.

Embodiment 65. A method for improving memory function in a subject in need thereof, comprising administering a dietary supplement comprising *Candida rugosa* lipase (CRL) to the subject.

Embodiment 66. The method of Embodiment 65, wherein the memory function of the subject in need thereof is assessed by a CNS-Vitals, The Symbol Digit Modalities Test (SDMT), The Profile of Mood States (POMS) or any combination thereof.

Embodiment 67. The method of Embodiment 66, wherein the CNS-Vitals score of the subject in need thereof is 85 or less prior to the administering.

Embodiment 68. The method of Embodiment 66 or Embodiment 67, wherein the CNS-Vitals score of the subject in need thereof is increased after the administering.

Embodiment 69. The method of any one of Embodiments 66 to 68, wherein the CNS-Vitals score of the subject in need thereof is at least 90 after the administering.

Embodiment 70. The method of any one of Embodiments 66 to 68, wherein the CNS-Vitals score of the subject in need thereof is between 90 to 109 after the administering.

Embodiment 71. The method of any one of Embodiments 66 to 70, wherein the Symbol Digit Modalities Test score of the subject in need thereof is 40 or less prior to the administering.

Embodiment 72. The method of any one of Embodiments 66 to 71, wherein the Symbol Digit Modalities Test score of the subject in need thereof is increased after the administering.

Embodiment 73. The method of any one of Embodiments 66 to 72, wherein the Symbol Digit Modalities Test score of the subject in need thereof is at least 50 after the administering.

Embodiment 74. The method of any one of Embodiments 66 to 72, wherein the Symbol Digit Modalities Test score of the subject in need thereof is between 45 to 50 after the administering.

Embodiment 76. The method of any one of Embodiments 66 to 75, wherein the Profile of Mood States short form score of the subject in need thereof is elevated prior to the administering.

Embodiment 77. The method of any one of Embodiments 66 to 76, wherein the Profile of Mood States short form score of the subject in need thereof is decreased after the administering.

Embodiment 78. The method of any one of Embodiments 66 to 77, wherein the Profile of Mood States short form score of the subject in need thereof is lower than the original score after the administering.

Embodiment 79. The method of any one of Embodiments 76 to 78, wherein the Profile of Mood States short form score comprises measurements of one or more negative mood factors.

Embodiment 80. The method of Embodiment 65, wherein the memory function of the subject in need thereof is assessed by battery of neuropsychological tests.

Embodiment 81. The method of Embodiment 80, wherein the neuropsychological tests measure verbal memory, visual memory, processing speed, attention, executive function, reaction time, or any combination thereof.

Embodiment 82. The method of Embodiment 80 or Embodiment 81, wherein the battery of neuropsychological tests is CNS Vitals, and wherein CNS Vitals measures a standard score (SS), a percentile range (PR), or both for each of the neuropsychological tests.

Embodiment 83. The method of Embodiment 82, wherein the SS of one or more of the neuropsychological tests increases by 10 or more after the administering, the PR of one or more of the neuropsychological tests increases by 5 or more after the administering, or both.

Embodiment 84. The method of Embodiment 82 or Embodiment 83, wherein the SS of one or more of the neuropsychological tests increases by 20 or more after the administering, the PR of one or more of the neuropsychological tests increases by 10 or more after the administering, or both.

Embodiment 85. The method of Embodiment 65, wherein the memory function of the subject in need thereof is assessed by a Symbol Digit Modalities Test (SDMT).

Embodiment 86. The method of Embodiment 85, wherein the SDMT score of the subject in need thereof increases by 10 or more after the administering.

Embodiment 87. The method of Embodiment 85 or Embodiment 86, wherein the SDMT score of the subject in need thereof increases by 20 or more after the administering.

Embodiment 88. The method of Embodiment 65, wherein the memory function of the subject in need thereof is assessed by a Profile of mood state (POMS).

Embodiment 89. The method of Embodiment 88, wherein POMS measures one or more primary mood factors selected from the group consisting of tension-anxiety, depression-dejection, anger-hostility, vigor-activity, fatigue-inertia, and confusion-bewilderment, and wherein each of the primary mood factors is scored on a Likert scale.

Embodiment 90. The method of Embodiment 89, wherein the subject in need thereof shows an improvement in the score of one or more of the primary mood factors after the administering.

Embodiment 91. The method of Embodiment 65, wherein the memory function of the subject in need thereof is assessed by a Pittsburgh Sleep Quality Index (PSQI).

Embodiment 92. The method of Embodiment 91, wherein the PSQI measures one or more sleep quality components selected from the group consisting of subjective sleep quality, sleep latency, sleep duration, sleep efficiency, sleep disturbances, use of sleep medication, and daytime dysfunction, and wherein each of the sleep quality components is scored on a Likert scale.

Embodiment 93. The method of Embodiment 92, wherein the subject in need thereof shows an improvement in the score of one or more of the sleep quality components after the administering.

Embodiment 94. The method of Embodiment 65, wherein the memory function of the subject in need thereof is assessed by a Multidimensional Fatigue Inventory Questionnaire (MFI-20).

Embodiment 95. The method of Embodiment 94, wherein the MFI-20 measures one or more fatigue dimensions selected from the group consisting of general fatigue, physical fatigue, mental fatigue, reduced motivation, and reduced activity, and wherein each of the fatigue dimensions is scored on a Likert scale.

Embodiment 96. The method of Embodiment 95, wherein the subject in need thereof shows an improvement in the score of one or more of the fatigue dimensions after the administering.

Embodiment 97. The method of Embodiment 65, wherein the memory function of the subject in need thereof is assessed by a Frontal Systems Behavioral Scales (FrSBe).

Embodiment 98. The method of Embodiment 97, wherein the FrSBe measures one or more primary domains of behavior selected from the group consisting of apathy, disinhibition, and executive dysfunction.

Embodiment 99. The method of Embodiment 97 or Embodiment 98, wherein a FrSBe total score of the subject in need thereof is decreased by 10 points or more after the administering.

Embodiment 100. The method of any one of Embodiments 97 to 99, wherein a FrSBe total score of the subject in need thereof is decreased by 20 points or more after the administering.

Embodiment 101. The method of Embodiment 65, wherein the memory function of the subject in need thereof is assessed by CNS Vitals, a Symbol Digit Modalities Test (SDMT), a Profile of Mood States (POMS), a Pittsburgh Sleep Quality Index (PSQI), a Multidimensional Fatigue Inventory Questionnaire (MFI-20), a Frontal Systems Behavioral Scales (FrSBe), or any combination thereof.

Embodiment 102. The method of any one of Embodiments 65 to 101, wherein the administering is for a period of 1 month to 5 years.

Embodiment 103. The method of any one of Embodiments 65 to 102, wherein the improved memory function in the subject in need thereof persists for a time period of at least 1 month, at least 2 months, at least 3 months, at least 6 months, at least 1 year, at least 18 months, at least 2 years, at least 2.5 years, at least 3 years, at least 3.5 years, at least 4 years, at least 4.5 years, or at least 5 years.

Embodiment 104. A method for improving cognitive function in a subject in need thereof, comprising administering a dietary supplement comprising *Candida rugosa* lipase (CRL) to the subject.

Embodiment 105. The method of Embodiment 104, wherein the cognitive function of the subject in need thereof is assessed by a Montreal Cognitive Assessment, a Mini-Mental State Exam, a Mini-Cog, or any combination thereof.

Embodiment 106. The method of Embodiment 104, wherein the cognitive function of the subject in need thereof is assessed by CNS Vitals, a Symbol Digit Modalities Test (SDMT), a Profile of Mood States (POMS), a Pittsburgh Sleep Quality Index (PSQI), a Multidimensional Fatigue Inventory Questionnaire (MFI-20), a Frontal Systems Behavioral Scales (FrSBe), or any combination thereof.

Embodiment 107. The method of any one of Embodiments 104 to 106, wherein the administering is for a period of 1 month to 5 years.

Embodiment 108. The method of any one of Embodiments 104 to 107, wherein the improved cognitive function in the subject in need thereof persists for a time period of at least 1 month, at least 2 months, at least 3 months, at least 6 months, at least 1 year, at least 18 months, at least 2 years, at least 2.5 years, at least 3 years, at least 3.5 years, at least 4 years, at least 4.5 years, or at least 5 years.

EXAMPLES

Example 1: Materials and Methods for Mouse Microbiome and Cognition Studies with CRL Animals are kept in an Association for Assessment and Accreditation of Laboratory Animal Care International (AAALAC) accredited vivarium at the Roskamp Institute. Experiments with mice are reviewed and approved by the Institutional Animal Care and Use Committee (IACUC) of the Roskamp Institute before implementation and conducted in compliance with the National Institutes of Health Guidelines for the Care and Use of Laboratory Animals. All wild type (Wt) and APPswe/PSlde9 (APP/PS1) mice are obtained from in-house breeding. Mice are maintained on a 12 h/12 h light/dark cycle and received food and water ad-libitum. All studies are reported in accordance with the ARRIVE guidelines.

CRL Treatment Study

Mice (Wt or APP/PS1, 8 months of age, n=12-15/group) are obtained from an internal breeding protocol, and randomly subdivided into CRL treated and untreated groups. Mice receive 5000 Fidiration Internationale Pharmaceutique (FIP)/kg body weight CRL (300,000 FIP/g, Enzymedica, FL, USA) in drinking water for 2 months, or regular water. This dose is extrapolated from Creon, a human digestive enzyme treatment for pancreatic insufficiency. See Trapnell et al., "Efficacy and safety of Creon 24,000 in subjects with exocrine pancreatic insufficiency due to cystic fibrosis," *J. Cyst. Fibros.* 8:370-377 (2009). Drinking water, CRL-treated or untreated, is changed twice a week. See Menden et al., "A fast, miniaturised in-vitro assay developed for quantification of lipase enzyme activity," *J. Enzyme Inhib. Med. Chem.* 34:1474-1480 (2019). Beginning four weeks before treatment, started nesting and bedding materials are exchanged between all groups and throughout the study within groups twice a week, to normalize endogenous gut microbial variance and to prevent cage effects. Four groups are assessed (APP/PS1 n=12, APP/PS1+CRL n=12, Wt n=13, Wt+CRL n=15). Fecal samples are collected at 0, 4, and 8 weeks of treatment and in addition, three times per week during treatment week 5 and 8 for the subsequent fecal matter transplant study described below. In the last two weeks of treatment, mice are trained and assessed for spatial learning and memory in a Barnes maze, as described below. On the last day of treatment, gut integrity is assessed. Animals are then humanely euthanized after anesthesia with 2% isoflurane (Patterson veterinary, Greeley, CO) in oxygen via cardiac puncture-induced exsanguination and subsequent perfusion with phosphate buffered saline (PBS) in accordance with the approved IACUC protocol. Right hemispheres of the brain are fixed in 4% paraformaldehyde (Sigma, St. Louis, MO) for 24 h for immunohistochemical analysis. The left-brain hemisphere, gastrointestinal tract, and plasma are collected and immediately flash frozen in liquid nitrogen and stored at −80° C.

Fecal Matter Transplant (FMT) Study

Fecal samples are collected from the mice of the CRL treatment study described above three times a week between treatment week 5 to 8 for each group, and immediately homogenized 1:5 (w/V) in 0.9% sodium chloride (Sigma, St. Louis, MO) solution containing 10% glycerol (Sigma, St. Louis, MO) to stabilize fecal bacteria during storage and shorten oxygen exposure. Before usage, all samples of the same group are flash thawed and combined. See Hu et al., "Standardized preparation for fecal microbiota transplantation in pigs," *Front. Microbiol.* 9; 1328 (2018). The fecal pool of each group is strained through a 40 μM nylon filter (Fisher Scientific, Waltham, MA) by centrifugation at 350 g until a viscous layer forms. The cell density of the flow-through is measured with a cell counter (APP/PS1: $6.74 \times 10^6$/50 μL; APP/PS1+CRL: $5.04 \times 10^6$/50 μL; Wt: $7.47 \times 10^6$/50 μL; Wt+CRL: $8.68 \times 10^6$/50 μL) and adjusted to $5 \times 10^6$ cells/50 μL. Samples are divided in 700 50 μL aliquots, flash frozen in liquid nitrogen and stored at −80° C. and used for FMT treatment.

Wt mice (n=72, aged 13-14 weeks) are randomly subdivided into 6 groups with 12 mice per group (Sham, ABX, FMT:APP/PS1, FMT:APP/PS1+CRL, FMT:Wt, FMT:Wt+CRL). The bedding and nesting materials are exchanged between all groups four weeks prior to the study as well as within groups twice a week throughout the study to prevent cage effects. Briefly, the strategy used is adapted from the transplantation procedures of Zarrinpar et al., "Antibiotic-induced microbiome depletion alters metabolic homeostasis by affecting gut signaling and colonic metabolism," *Nat. Commun.* 9:2872 (2018); Wrzosek et al. Transplantation of human microbiota into conventional mice durably reshapes the gut microbiota. *Sci. Rep.* 8:6854 (2018); and Kang et al. Microbiota transfer therapy alters gut ecosystem and improves gastrointestinal and autism symptoms: an open-label study. *Microbiome* 5:10 (2017). Mice are treated with an antibiotic cocktail (Neomycin:Ampicillin:Metronidazole: Vancomycin (Sigma, St. Louis, MO) in 1:1:1:0.25 ratio of 200 mg/kg in drinking water containing 2% sucrose (or sucrose only for control mice) for a period of two weeks. See Zarrinpar et al. 2018; and Kang et al. 2017. Water is changed twice a week. Mice also receive 100 μg Amphotericin B (Sigma, St. Louis, MO) in 5% dimethyl sulfoxide ("DMSO," Sigma, St. Louis, MO), or 5% DMSO only for Sham mice, twice a week in water via oral gavage (20 G, 38 mm, 2 mm tip, straight; GavageNeedle[dot]com, Phoenix, AZ) to prevent fungal overgrowth in the depleted gut microbial environment. See Zarrinpar et al. 2018. During the oral gavage procedure, mice are non-anaesthetized. The mice are scruffed to overstretch their heads, which allows the operator to insert the oral gavage needle into the esophagus and down to the stomach. The appropriate amount of enzyme is then immediately released and the needle is removed from the upper digestive system. Mice are observed for adverse events for 5 min following oral gavage and then returned to their cage.

After antibiotic treatment on day 15, mice are allowed to fast for a period of 1 h (no water and food) and then receive four oral gavage injections of 200 μL each of 400 g/L Macrogol 4000 (Sigma, St. Louis, MO), or four oral gavage injections of 200 μL each of water for control (Sham mice), 20 min apart to further remove gut microbiota and residual antibiotics prior to transplantation. See Wrzosek et al. 2018; and Kang et al. 2017. All mice are then allowed to fast for a period of 4 h (no water or food).

Next, the live stocks or buffering solution of live stocks (sham) described above are transplanted into the antibiotic-treated, bowel cleansed AIMD Wt mice. Mice receive a first FMT of $5.00 \times 10^6$ cells in 50 μL per FMT, or 10% glycerol in 0.9% NaCl for Sham and ABX mice, via oral gavage. See Hu et al. 2018; and Lee et al., "Frozen vs fresh fecal microbiota transplantation and clinical resolution of diarrhea in patients with recurrent *Clostridium difficile* infection: A randomized clinical trial," *JAMA* 315:142-149 (2016). The three subsequent gavages are administered once weekly thereafter. Fecal samples are collected before antibiotic treatment (Baseline, 0d), after antibiotic treatment and bowel cleanse (ABX/PEG, 15 d), and after 4 weeks of weekly FMT administration.

One week after the last FMT, mice are trained and evaluated in a Barnes maze to determine the effects of the FMTs on spatial memory and learning. After behavioral testing, animals are humanely euthanized after anesthesia with 2% isoflurane (Patterson veterinary, Greeley, CO) in oxygen via cardiac puncture-induced exsanguination in accordance with the approved IACUC protocol. Tissues are then collected for 16S sequencing analysis.

Microbiome Analysis

DNA (n=6 per group for either of the CRL treatment and FMT studies) is extracted from feces (20-100 mg/pellet) and cecum (30 mg) samples using the Fast DNA stool mini kit (Qiagen, Germantown, MD) according to the manufacturer's protocol. Volumes are adjusted to account for lower sample weight. DNA extracts are analyzed by V3-V4 region 16S rRNA gene amplicon sequencing using the Illumina MiSeq sequencing platform (Illumina, San Diego, CA) following the Earth Micro-biome Project protocols. See Menden et al., "*Candida rugosa* lipase alters the gastrointestinal environment in wild-type mice," *Biomed. Pharmacother.* 130:110579 (2020). In addition, the MicrobiomeAnalyst interface is used to identify differential abundant microbial genera with the LEfSe application. See Dhariwal et al., "MicrobiomeAnalyst: A web-based tool for comprehensive statistical, visual and meta-analysis of microbiome data." *Nucleic Acids Res.* 45:W180-W188 (2017). Data is plotted in GraphPad Prism 8 (GraphPad, San Diego, CA), and β-diversity plots were acquired in Qiime2 using the Emperor suite. See Caporaso et al., "QIIME allows analysis of high-throughput community sequencing data," *Nat. Methods* 7:335-336 (2010).

Pro-Inflammatory Cytokine Panel

Cortex and plasma cytokine levels (n=6 per group in the CRL treatment study) are analyzed with the V-PLEX Plus Proinflammatory Panell Mouse Kit (MSD, Rockville, MD) according to the manufacturer's protocol. Plasma and cortex lysate are diluted 1:2 in Diluent 41, added in duplicates, and incubated overnight at 4° C. Cortex cytokines are then normalized to protein content of lysates, which is determined by bicinchoninic protein assay (Thermo Fisher, Waltham, MA) analysis. Data is plotted and analyzed via 2-way ANOVA and Tukey correction in GraphPad Prism 8 (GraphPad, San Diego, CA).

Cecum Metabolomics Analysis

Cecal metabolites (n=4 per group in the CRL treatment study) are investigated by gas chromatography mass spectrometry (GCMS) analysis. 50 mg of cecum is mixed with 50 µL of an internal standard mix consisting of 10 µg/mL 6,6-D2-glucose and 300 µg/mL D6-7-aminobutyric acid (each from Sigma, St. Louis, MO); 20 µg/mL 2,2,4,4-D4-citric acid, 10 µg/mL 2,3-D2-fumaric acid, 50 µg/mL U-13C-α-ketoglutaric acid, 50 µg/mL 13C3-malonic acid, 500 µg/mL 3,3,3-D3-lactate, 100 µg/mL 13C3-pyruvate, 10 µg/mL D4-succinic acid, 5 µg/mL D5-phenylalanine, 200 µg/mL 2,3-13C-phosphoenol pyruvate, and 100 µg/mL 2,4,4-D3-glutamic acid (all from Cambridge Isotope Laboratories, Tewksbury, MA); 2.5 µg/mL D4-O-hydroxybutyric acid (Cayman Chemicals, Ann Arbor, MI); and 20 µg/mL D27-myristic acid (Indofine Chemical Company, Somerville, NJ). Cecal content (30 mg) is homogenized in 50 µL phosphate buffered saline (PBS). Samples are extracted by protein precipitation through sample adjustment to 80% methanol and incubation at 80° C. for 3 min (200 µL, Thermo Fisher, Waltham, MA). Samples are then incubated at room temperature for 30 min. Next, samples are methoximated with 10 µL of 40 mg/mL methoxamine hydrochloride in pyridine (Sigma, St. Louis, MO) and incubated at 30° C. for 90 min. Finally, samples are trimethylsilylated for 60 min at 40° C. by adding 50 µL of N-Methyl-(N-trimethylsilyl) trifluoroacetamide (MSTFA, Thermo Fisher, Waltham, MA) and 1% chlorotrimethylsilane (TMSCl, Thermo Fisher, Waltham, MA) with subsequent overnight incubation at room temperature. Samples (100 nL: 1 µL split 1:10) are injected and analyzed on an Agilent 7890A (Agilent Technologies, Santa Clara, CA) GC-MS instrument using the Agilent metabolomics protocol, with a flow rate of 1.0246 mL/min. Samples are separated on a Rxi-5 ms fused silica column (30 m×0.25 mm, 0.25 um, Restek, Bellefonte, PA) in hexane with a temperature gradient separation over a 33 minute time period: 0-5 min at 80° C., 5-8 min at 100° C., 8-33 min with a 10° C. increase per minute up to a final temperature of 350° C. Quality control samples are generated by combining 5 µL of each sample, and are subsequently injected after each batch. Samples are identified using the National Institute of Standards and Technology (NIST) database in Automated Mass Spectrometry Deconvolution and Identification System (AMDIS) (NIST, Gaithersburg, MD) and deconvoluted with XCMS. See Smith et al., "XCMS: processing mass spectrometry data for metabolite profiling using nonlinear peak alignment, matching, and identification," *Anal. Chem.* 78:779-787 (2006). Data and statistical analysis are performed in MetaboAnalyst, and treatment and control groups are combined for determination of treatment-specific effects. See Chong et al., "*Using MetaboAnalyst* 4.0 for metabolomics data analysis, interpretation, and integration with other Omics data," *Methods Mol. Biol.* 2104:337-360 (2020).

Plasma Metabolomics Analysis

Plasma metabolites (n=4 per group in the CRL treatment study) are sent to Creative Proteomics (Shirley, NY) for sample preparation, untargeted liquid chromatography mass spectrometry analysis in both positive and negative modes, metabolite identification, and pathway analysis. Data is plotted and analyzed via 2-way ANOVA and Tukey correction in GraphPad Prism 8 (GraphPad, San Diego, CA).

Barnes Maze Experiment

To analyze memory and learning, a Barnes maze is used. See Barnes et al., "Selective improvement of aged rat short-term spatial memory by 3,4-diaminopyridine," *Neurobiol Aging* 10(4):337-341 (1989); Pitts, "Barnes Maze Procedure for Spatial Learning and Memory in Mice," *Bio Protoc.* 8(5):e2744 (2018); Harrison et al., "Endogenous anxiety and stress responses in water maze and Barnes maze spatial memory tasks," *Behav Brain Res.* 198(1):247-251 (2008). There are 18 equally spaced holes around the outer perimeter of the maze (n=11-15 mice per group for the CRL treatment study; n=11-12 mice per group for the FMT study). The target hole has a box positioned directly beneath it that allows the mice to exit the maze. Distinct visual cues are positioned on each of the four walls. Mice are trained for 4 days (3 min/trial/day) to use the cues to locate the target hole and escape the maze, which is achieved when the mouse enters the target box positioned under the target hole. On day 5, the target box is removed to evaluate for learning and spatial memory in a 90-s probe trial. Each trial is tracked and recorded using EthoVision XT 14 software. Data plotting and statistical analysis is performed in GraphPad Prism 8 (GraphPad, San Diego, CA) with 3-way ANOVA testing for acquisition and one- or two-way ANOVA dependent on the respective parameter on the probe day with post-hoc multiple comparisons.

The Barnes Maze experiment generally assesses exploratory behavior in mammals to evaluate their reactions to novel settings. The test measures the mammal's behavior directed toward acquiring information about the environment, ambulatory tendencies, and fear of novelty (neophobia). During exploration, multiple contacts with objects located in the environment take place via the phenomenon of habituation, part of a more general process of knowledge acquisition. In settings previously encountered, re-exploration or dishabituation occurs. Thus, novelty in an environment exists normally through reference to stored memories of previously explored or familiar places; if novelty is detected and exploration behaviors are triggered, it is implied that some representation of the initial situation has been constructed. Such exploratory behavior is assumed by neuropsychologists to be an updating activity of the currently stored cognitive map or spatial representation. When experiencing a new environment, a mismatch between what is stored in the cognitive map or spatial representation and what is observed triggers exploration. Subsequently, once that memory is trigged, there is no more need for exploration and reduced exploration results.

Enhanced memory results from increased neuroplasticity, a mechanism by which the brain encodes experiences, learns new behaviors, and relearns lost behaviors if the brain has been damaged, as in Alzheimer disease. In humans, cognitive testing is used to assess memory function (although cognitive testing cannot identify the specific cause of impairment). Commonly-used human cognitive tests measure mental functions through a series of questions and/or simple tasks. One such human cognitive test is a Montreal Cognitive Assessment (MoCA) test, which is a 10-to-15-minute test that includes memorizing a short list of words, identifying a picture of an animal, and copying a drawing of a shape or object. See, e.g., Nasreddine et al., "The Montreal Cognitive Assessment. MoCA: a brief screening tool for mild cognitive impairment, *JAm Geriatr Soc* 53(4):695-699 (2005). The MoCA is scored between 0 and 30, where a score of 26 or more is indicative of normal cognitive function. Another human cognitive test is a Mini-Mental State Exam (MMSE), which is a 7-to-10-minute test that includes naming the current date, counting backward, and identifying everyday objects like a pencil or watch. See, e.g., Tombaugh et al., "The mini-mental Status Examination: A comprehensive Review," *JAm Geriatr Soc* 40(9):922-935 (1992). The MMSE is scored up to 30, and a score of 24 or more indicates normal cognitive ability. A third human cognitive test is a Mini-Cog, which is a 3-to-5-minute test that includes recalling a three-word list of objects and drawing a clock. See, e.g., Borson et al., "The Mini-Cog as a screen for dementia: Validation in a population-based sample," *JAm Geriatr Soc* 51(10):1451-1454 (2003). The Mini-Cog test is scored between 0 and 5, where a score of 0, 1, or 2 is indicative of clinically relevant cognitive impairment. Enhanced human cognition, as assessed by, e.g., a MoCA, a MMSE, and/or a Mini-Cog, correlates to increased exploratory behavior and enhanced memory function in animals in a Barnes Maze animal experiment. Similarly, reduced human cognition, as assessed by e.g., a MoCA, a MMSE, and/or a Mini-Cog, correlates to reduced exploratory behavior and reduced memory function in a Barnes Maze animal experiment.

Example 2: Administration of CRL to APP/PS1 Mice Alters Gut Microbiome and Gut Metabolite Distribution Assessment of Gut Integrity In the CRL treatment study of Example 1, prior to euthanasia, mice (APP/PS1 n=6, APP/PS1+CRL n=5, Wt n=3, and Wt+CRL n=3) are starved (food and water) for 5 h. Next, 4 kDa fluorescein isothiocyanate (FITC)-dextran (0.6 mg/g body weight, Sigma, St. Louis, MO) is orally administered via oral gavage. After 60 min, mice are humanely euthanized. Following euthanasia, plasma as collected, flash frozen in liquid nitrogen, and then stored at −80° C. For analysis, plasma samples are diluted 1:5 in PBS pH 7.4. 100 µL of water and 50 µL of sample, or standard (0-40 µL/mL 4 kDa FITC-dextran), are added to a black 96-well µ-clear bottom plate (Greiner Bio-One, Monroe, NC). Fluorescence is immediately measured at 485/528 nm and FITC dextran concentration was examined in each sample. Data is analyzed with 2-way ANOVA and Tukey multiple comparisons correction and plotted in GraphPad Prism 8 (GraphPad, San Diego, CA).

Figure 1B:
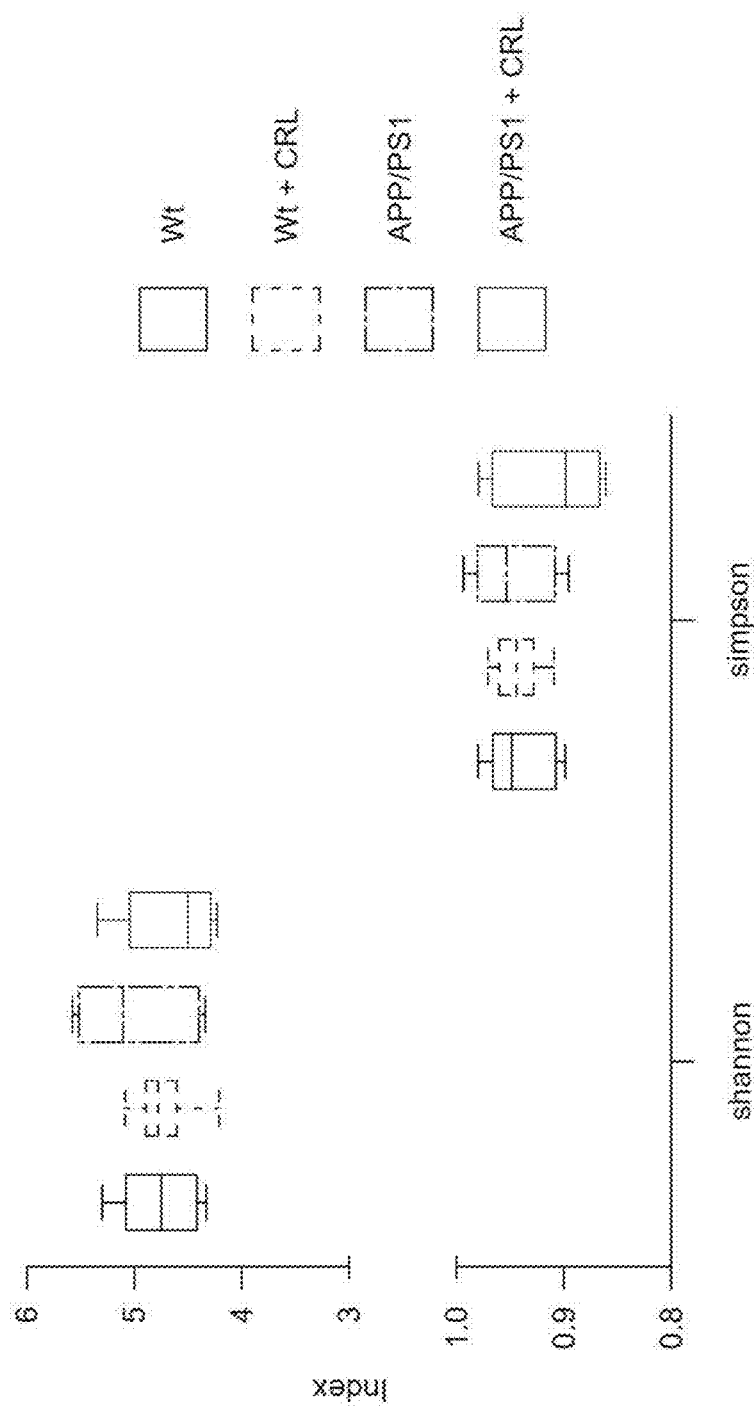
FIG. 1B presents a fecal $\alpha$-diversity analysis, as determined by the Shannon and Simpson indices. (shannon=Shannon Diversity Index; simpson=Simpson Diversity Index). Significance for $\alpha$-diversity was assessed by Kruskal-Wallis H test and pairwise comparisons.
Figure 1C:
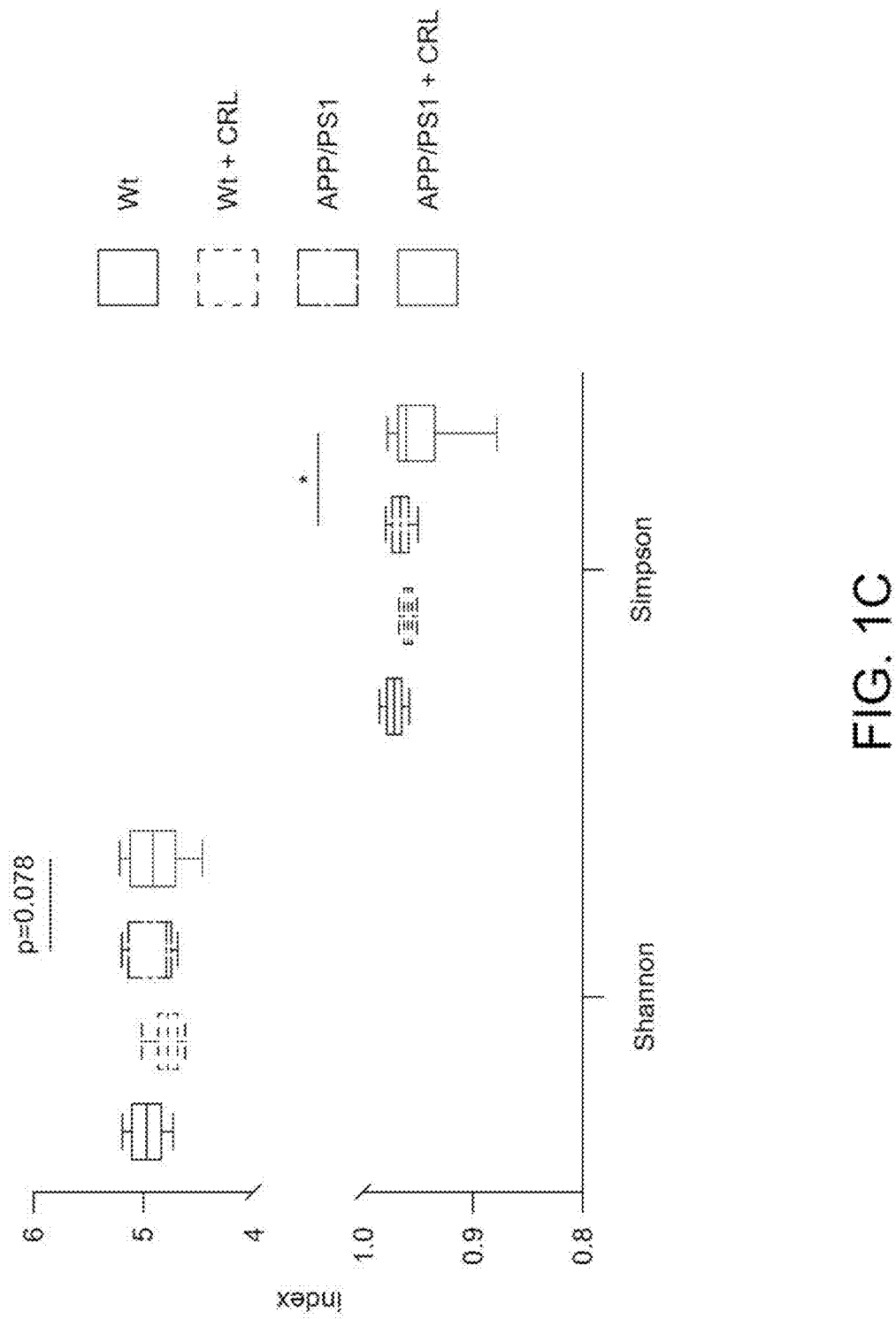
FIG. 1C presents a cecal $\alpha$-diversity analysis, as determined by the Shannon and Simpson indices. Significance of $\alpha$-diversity is assessed by the Kruskal-Wallis H test and pairwise comparisons. (Shannon=Shannon Diversity Index; Simpson=Simpson Diversity Index; Significance: *=$p<0.05$).
Figure 1D:
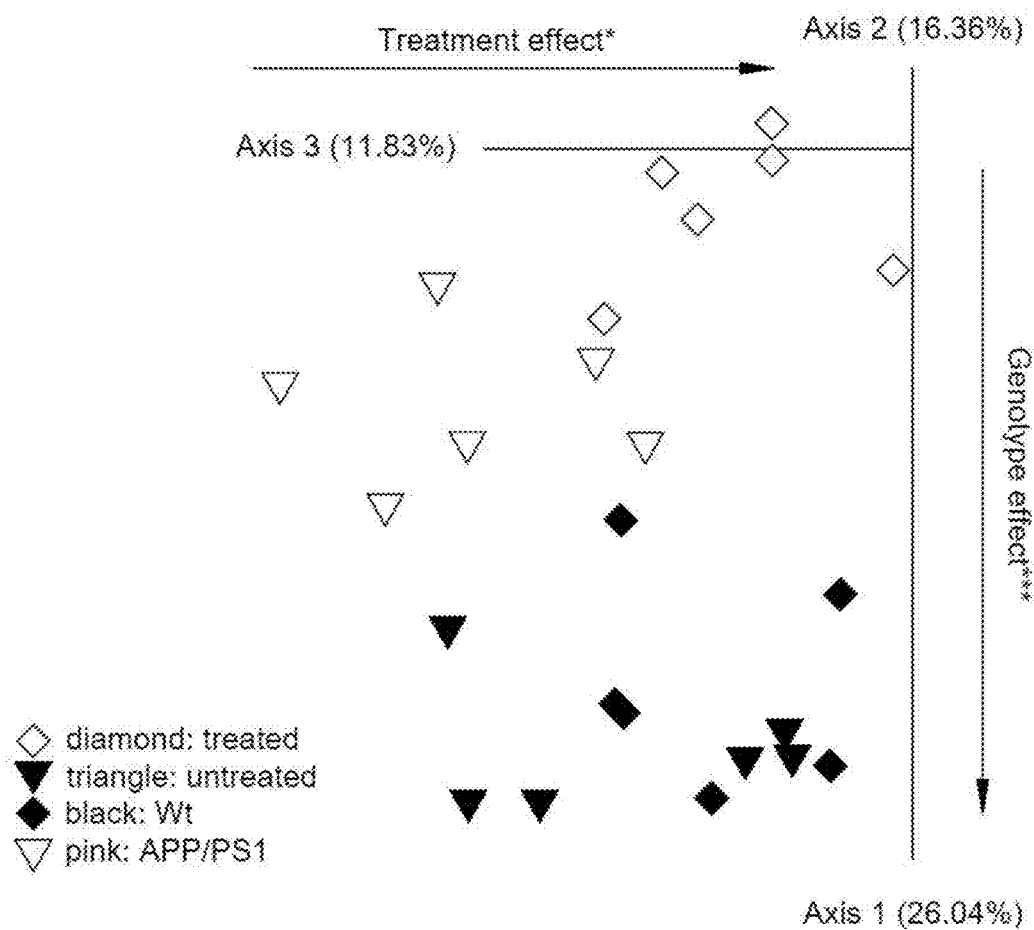
FIG. 1D presents a fecal $\beta$-diversity analysis, as determined by Bray-Curtis dissimilarity and distances of fecal matter. Significance of $\beta$-diversity is assessed by permutational multivariate analysis of variance (PERMANOVA). (Significance: *=$p<0.05$; ***=$p<0.001$).
Figure 1E:
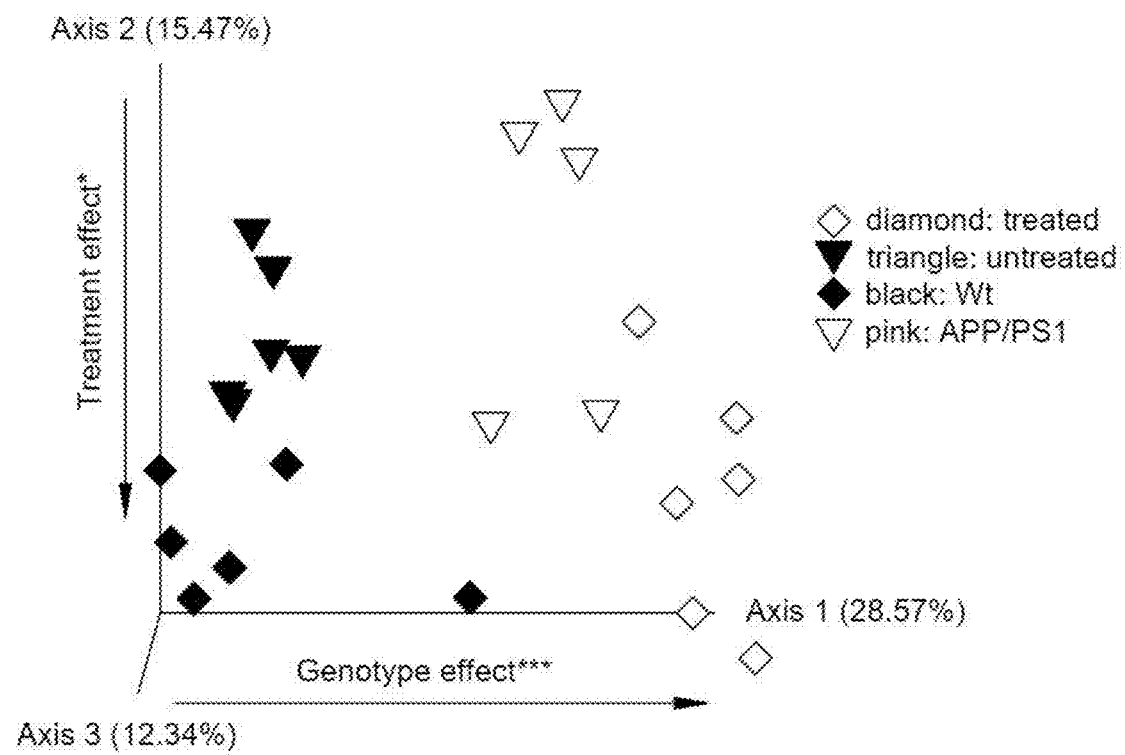
FIG. 1E presents a cecal $\beta$-diversity analysis, as determined by Bray-Curtis dissimilarity and distances of cecal matter. Significance of $\beta$-diversity is assessed by PERMANOVA. (Significance: *=$p<0.05$; ***=$p<0.001$).
Figure 1F:
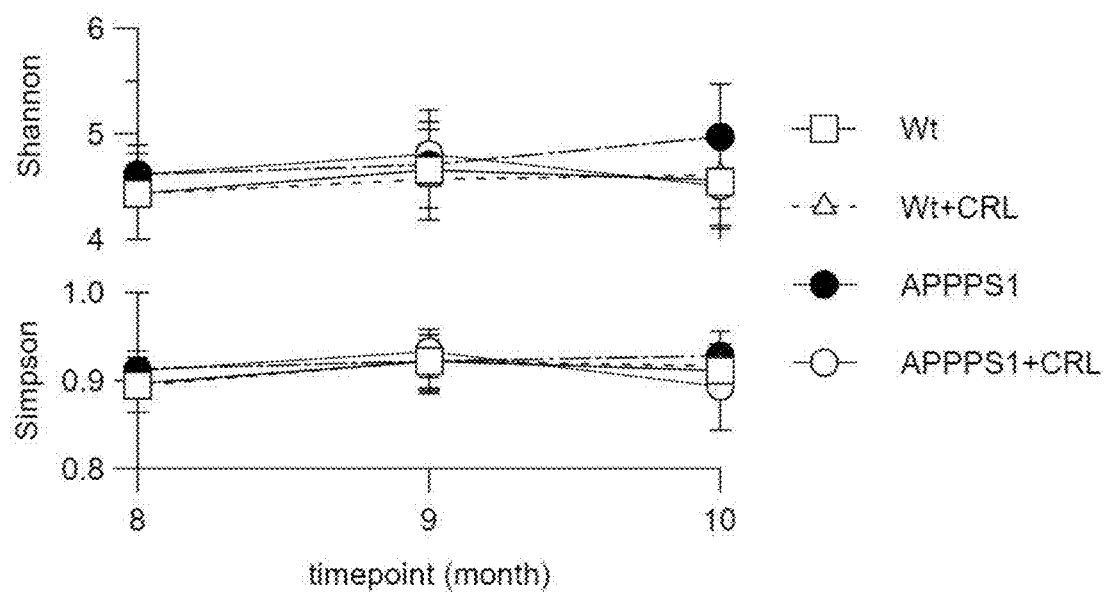
FIG. 1F displays changes in fecal $\alpha$-diversity over time, as determined by the Shannon and Simpson indices. Significance of $\alpha$-diversity is assessed by the Kruskal-Wallis H test and pairwise comparisons.
Figure 1G:
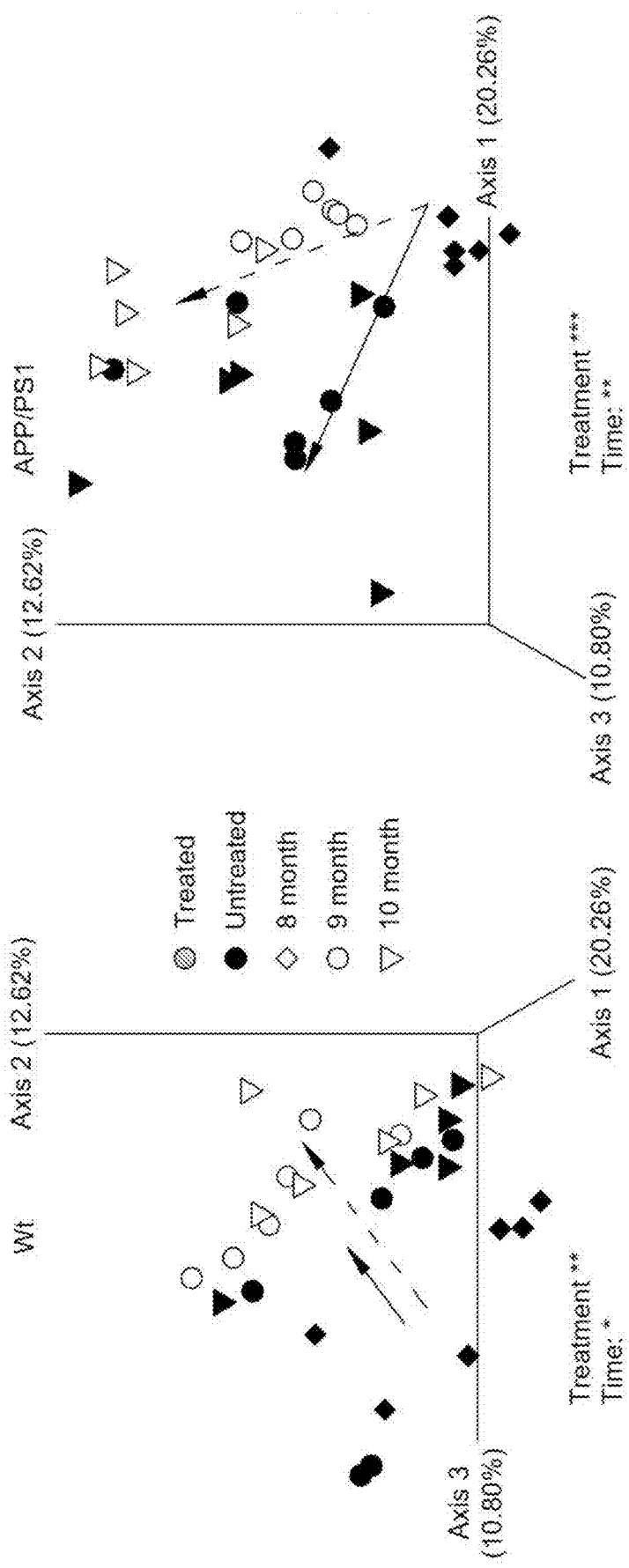
FIGS. 1G-1H display changes in fecal $\beta$-diversity over time, as determined by Bray-Curtis dissimilarity and distances of fecal matter. Significance of $\beta$-diversity is assessed by PERMANOVA. (Significance: *=$p<0.05$; =$p<0.01$; *=$p<0.001$).
Figure 1H:
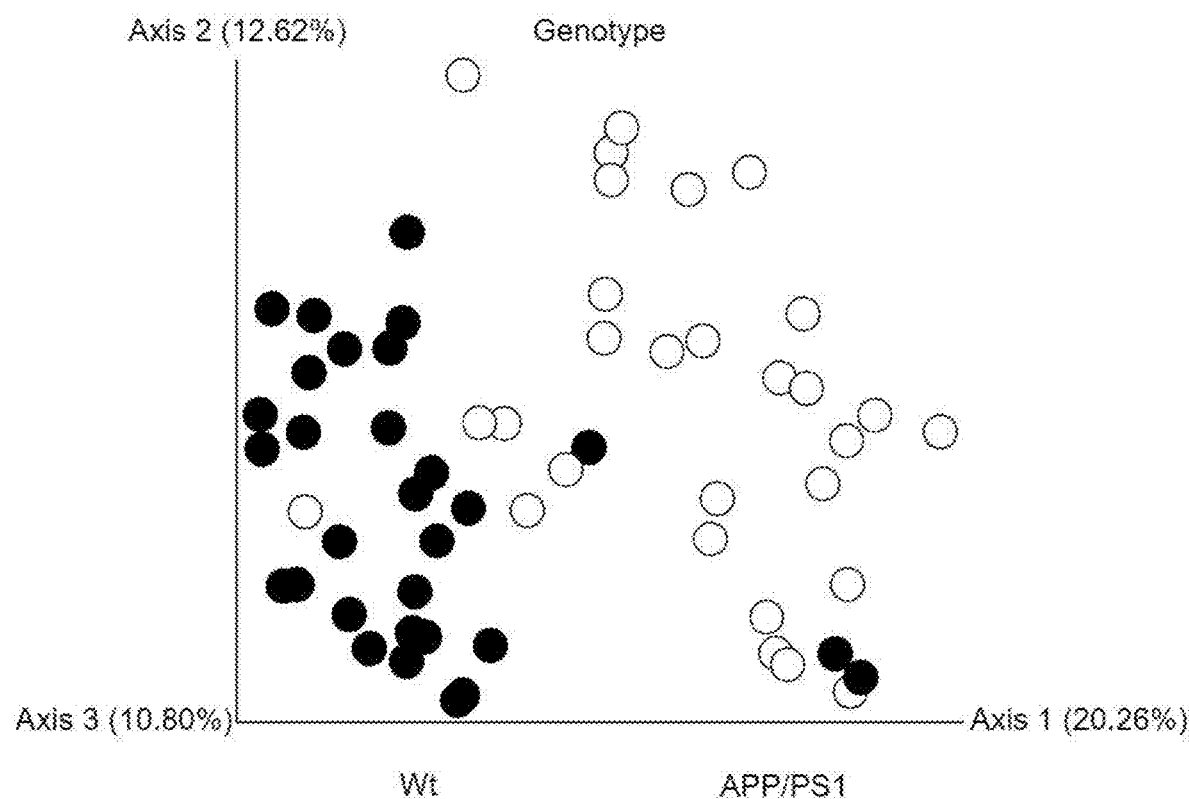

The hypothesis that the most prominent changes in response to CRL treatment would be observed in the gut environment where the enzyme is physically present and active is explored according to the study design shown in FIG. 1A, where Wt mice (n=13-15, 8 months of age) and APP/PS1 mice (n=12, 8 months of age) received 5000 PIP/kg CRL for two consecutive months, or regular water for two consecutive months, before sacrifice. The fecal microbiome and the gut metabolome, as well as gut integrity in the gut post treatment, are investigated as described in Example 1 and compared to untreated age-matched controls. In the fecal microbiome, no changes in α-diversity in fecal matter, as analyzed by Shannon and Simpson indices, are observed between the treatment groups. This observation is consistent across both cecal data after two months of treatment (FIG. 1C) and fecal data after 0, 1 and 2 months of treatment (FIG. 1B) between Wt mice and APP/PS1 mice (genotype-dependent), as well as between treated and untreated animals (treatment-dependent). In contrast, β-diversity analysis by Bray-Curtis dissimilarity shows genotype-dependent and treatment-dependent dissimilarities in both fecal matter (p=0.001 and p=0.031, respectively; FIG. 1D) and cecal matter (p=0.001 and p=0.017, respectively; FIG. 1E) after two months of treatment. Also, while no significant longitudinal changes of fecal α-diversity are observed (FIG. 1F), longitudinal dissimilarities of fecal β-diversity (at 0, 1 and 2 months of treatment) are observed between all groups (FIGS. 1G-H), where changes are most pronounced between genotypes (p=0.001) and treatment groups (APP/PS1: p=0.001; Wt: p=0.017).

Figure 1I:
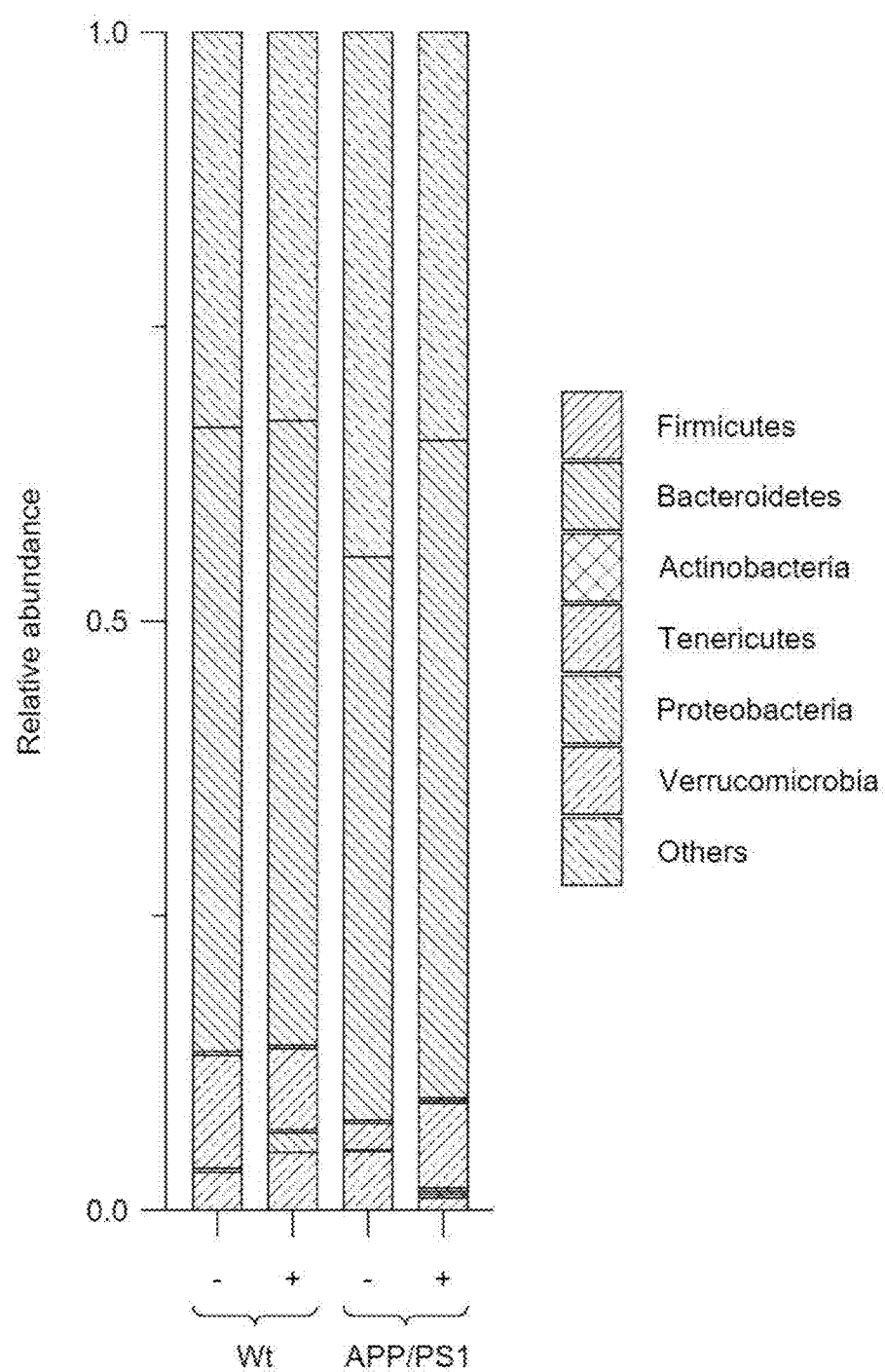
FIG. 1I presents a taxonomy analysis of phyla abundance in fecal matter by alignment with the GreenGenes 16S rRNA gene database.

After two months of treatment, taxonomic analysis of fecal samples on the phyla level by alignment with Greengenes database indicates differences between untreated Wt and APP/PS1 animals, while the fecal microbiome of CRL-treated APP/PS1 mice is reshaped towards Wt taxa composition (FIG. 1I). As also shown in FIG. 1I, two months of CRL treatment increased Proteobacteria levels in both genotypes, but this increase appears to be more pronounced in the fecal samples of treated Wt mice over treated APP/PS1 mice.

Figure 1J:
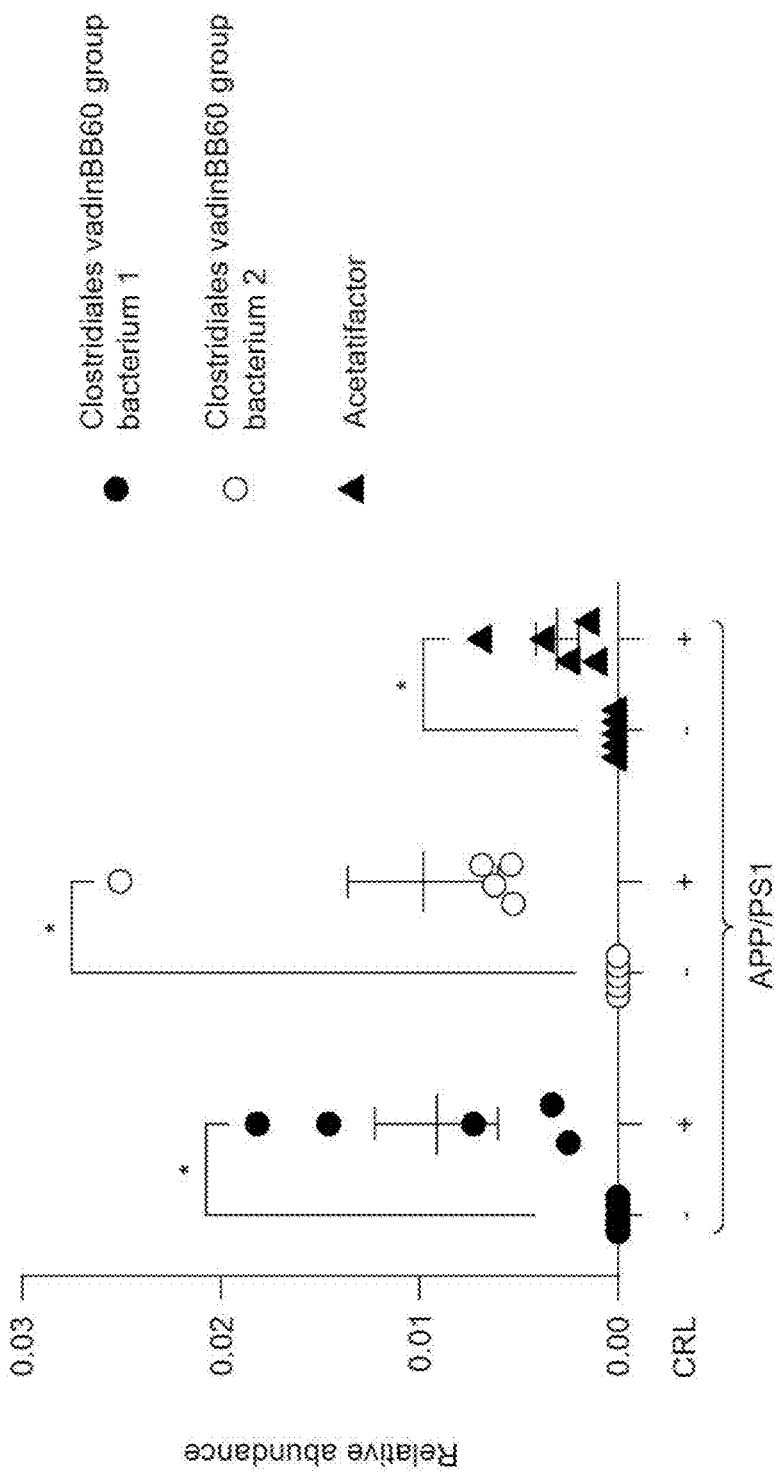
FIG. 1J presents results of genus-level Linear discriminant analysis Effect Size (LEfSe) applied to fecal samples of APP/PS1 mice after two months of treatment. This analysis identifies three bacterial genera (Clostridiales vadinBB60 group bacterium 1, Clostridiales vadinBB60 group bacterium 2, and Acetatifactor) having increased abundance in the fecal samples of CRL-treated APP/PS1 mice. LEfSe results were analyzed using 2-way ANOVA and FDR correction Significance: *=$p<0.05$.
Figure 1K:
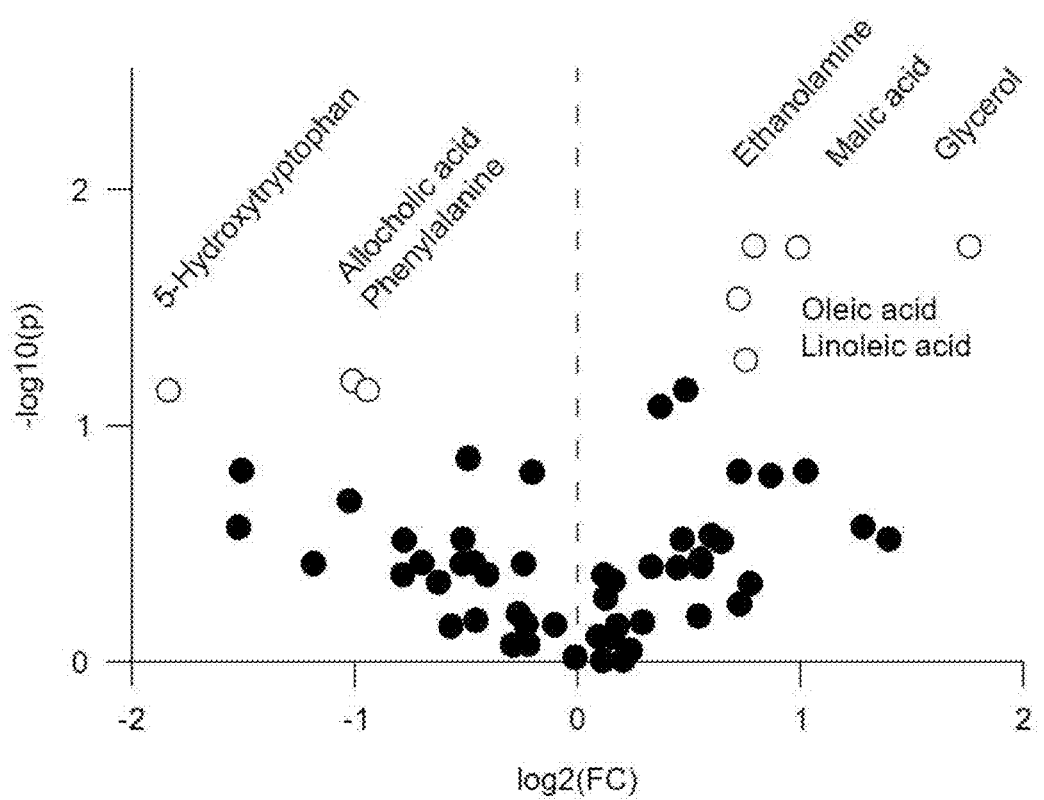
FIG. 1K presents a metabolomics analysis of cecal matter of CRL-treated APP/PS1 mice. Metabolites with increased abundance are identified by name on the plot. Data was analyzed using 2-way ANOVA and FDR correction, significance: red dots $p<0.05$.

Next, microbes in fecal samples of APP/PS1 mice after two months of CRL treatment are analyzed by Linear discriminant analysis Effect Size (LEfSe), and Clostridiales vadin BB60 group and Acetatifactor genera are identified as being significantly increased in the CRL-treated animals (FIG. 1J). As described in Example 1, gas-chromatography mass-spectrometry (GCMS) is used to examine whether these fecal microbial shifts are associated with alteration in the cecal gut metabolome after two months of treatment. The identified increase of the Acetatifactor genus in treated APP/PS1 mice is hypothesized to have occurred in response to lipase-dependent fatty acid release and other potential alterations of the gut metabolome. Therefore, treatment-dependent changes of the gut metabolite composition are investigated in APP/PS1 mice by GCMS, which shows an increased abundance of metabolites associated with lipid digestion (FIG. 1K). As shown in FIG. 1K, three metabolites are significantly decreased (5-hydroxytryptophan: fold change (FC)=0.280, $p_{false\ discovery\ rate\ (FDR)}$=0.071; allocholic acid FC=0.498, $p_{FDR}$=0.065; and phenylalanine FC=0.522, $p_{FDR}$=0.071), while five metabolites are significantly increased (malic acid, FC=1.988, $p_{FDR}$=0.018; ethanolamine, FC=1.732, $p_{FDR}$=0.017; linoleic acid, FC=1.690, $p_{FDR}$=0.052; oleic acid, FC=1.650, $p_{FDR}$=0.029; and glycerol, FC=3.393, $p_{FDR}$=0.017). An associated metabolome pathway analysis of identified metabolites to determine key pathways activated through lipase administration further identifies pathways associated with unsaturated fatty acids and lipid metabolism, indicating that CRL administration elevates fatty acid release in the gut lumen of APP/PS1 mice (FIG. 1L).

Figure 1M:
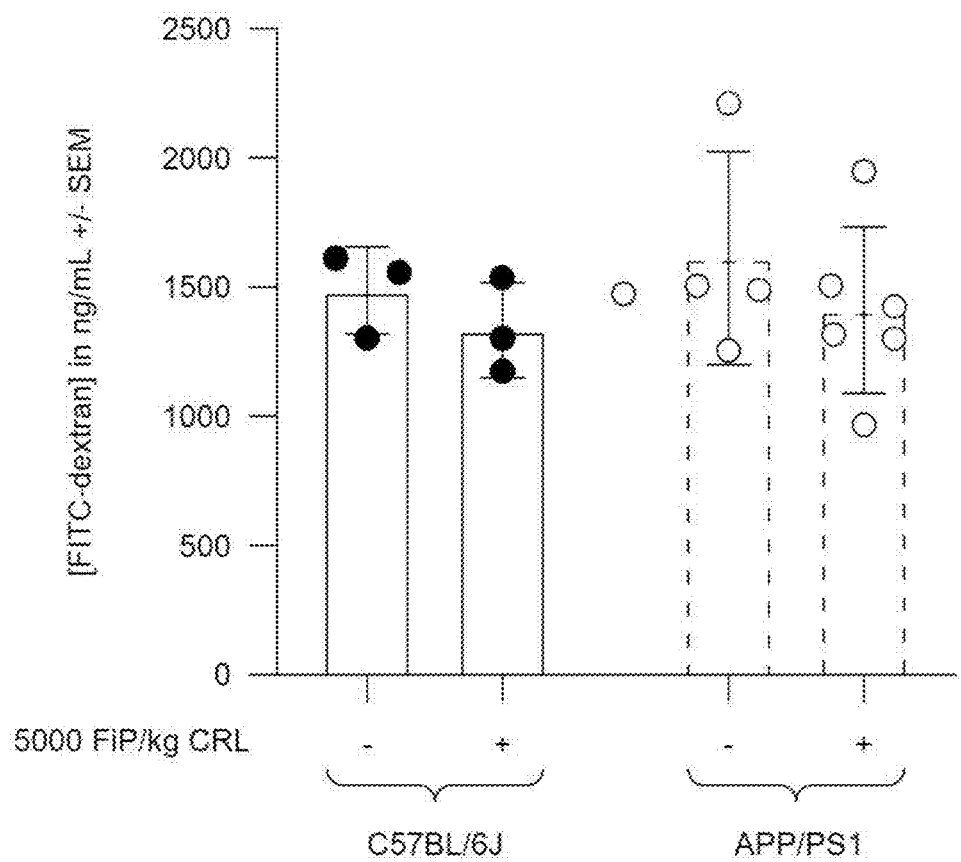
FIG. 1M presents the results of a gut integrity analysis treated and untreated wild type (C57BL/6J) and APP/PS1 mice, as determined by transition measurement of oral administered fluorescein isothiocyanate (FITC)-dextran dye into plasma. (SEM=standard error of the mean).

Finally, as shown in FIG. 1M, gut barrier integrity is assessed. No differences between treated and untreated animals or APP/PS1 and Wt animals are observed, suggesting that CRL treatment induces changes in the gut lumen that may be beneficial to the host.

In sum, the above studies of Example 2 show that CRL treatment alters the microbial β-diversity in fecal and cecal specimens of APP/PS1 mice, and that levels of two Clostridiales vadin BB60 genera as well as Acetatifactor are elevated.

Example 3: Administration of CRL to APP/PS1 Mice has No Significant Peripheral Immunological Effects Flow Cytometry Analysis Flow cytometry analysis of T lymphocytes is conducted according to the general protocol of Joshi et al., "A permethrin metabolite is associated with adaptive immune responses in Gulf War Illness," *Brain Behav. Immun.* 81:545-559 (2019). In brief, 200 μL of whole blood (n=6 per group in the CRL treatment study) is diluted 1:10 in red blood cell lysis buffer (RBC, Thermo Fisher, Waltham, MA), centrifuged and pellet resuspended in 500 μL 95% PBS and 5% fetal bovine serum (FBS). 100 μL suspensions are labeled with 0.25 μg of α-CD4-FITC antibody, 0.25 μg of α-CD8α-PE and/or 0.5 μg α-CD3-Cy7 antibody (11-0042-82, 12-0081-82 and 25-0032-80, respectively, Fisher Scientific, Waltham, MA) for 10 min, then 1 mL 95% PBS (Thermo Fisher, Waltham, MA) and 5% FBS (Thermo Fisher, Waltham, MA) is added to dilute each sample. The flow cytometry analysis is performed using the Attune® NxT Acoustic Focusing Flow Cytometer (Thermo Fisher, Waltham, MA, USA) using Attune® NxT software version 2.7 (Thermo Fisher Scientific, Waltham, MA, USA). The population is gated, subdivided by antibody staining, and quantified. Data is presented as percentage to absolute count for each channel and plotted and analyzed via 2-way ANOVA and Tukey correction in GraphPad Prism 8 (GraphPad, San Diego, CA).

Figure 2A:
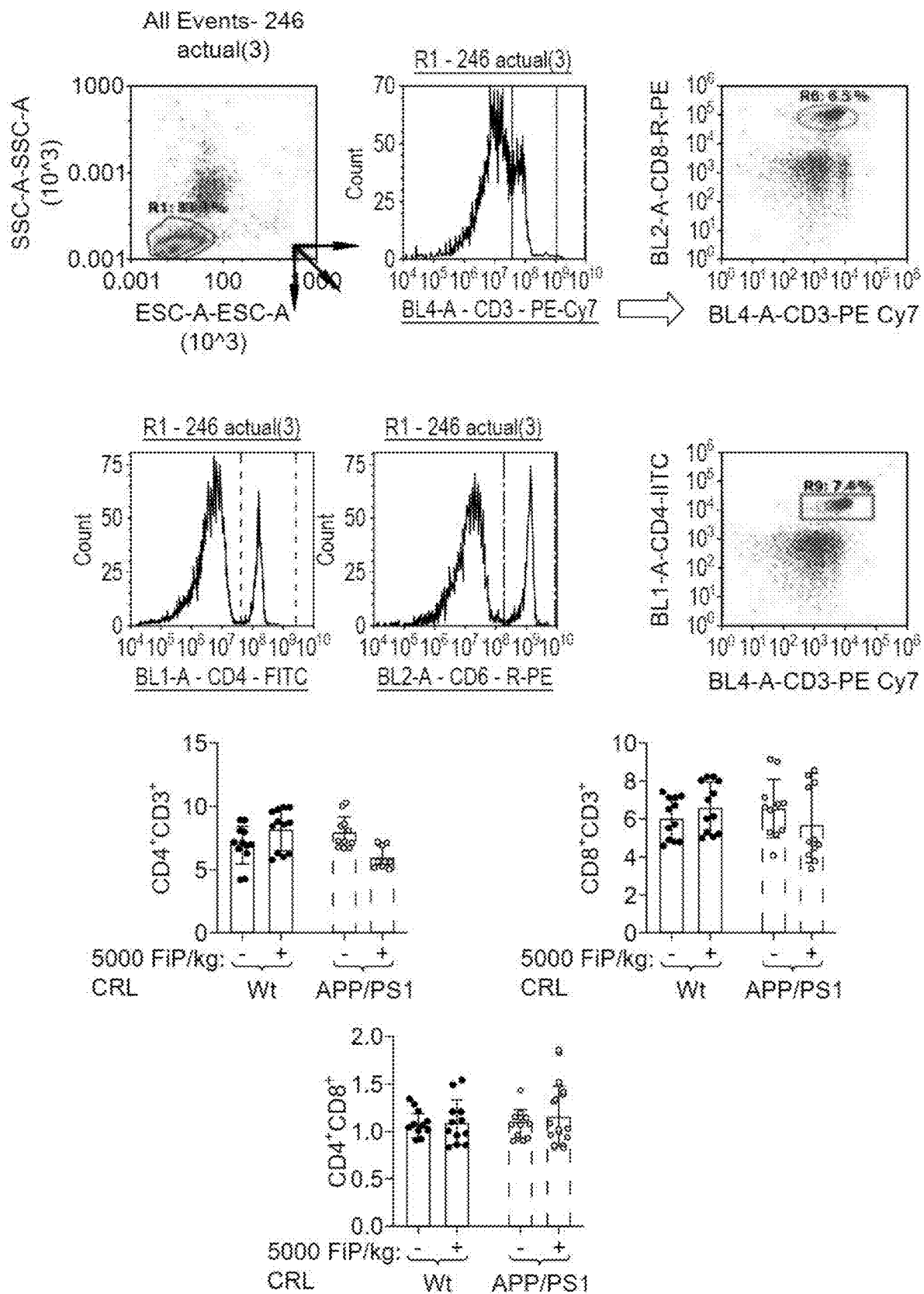
FIG. 2A presents a flow cytometric analysis of three immune cell populations for all treatment groups. The data generated by this analysis is presented in both scatter plot and bar graph formats.
Figure 2B:
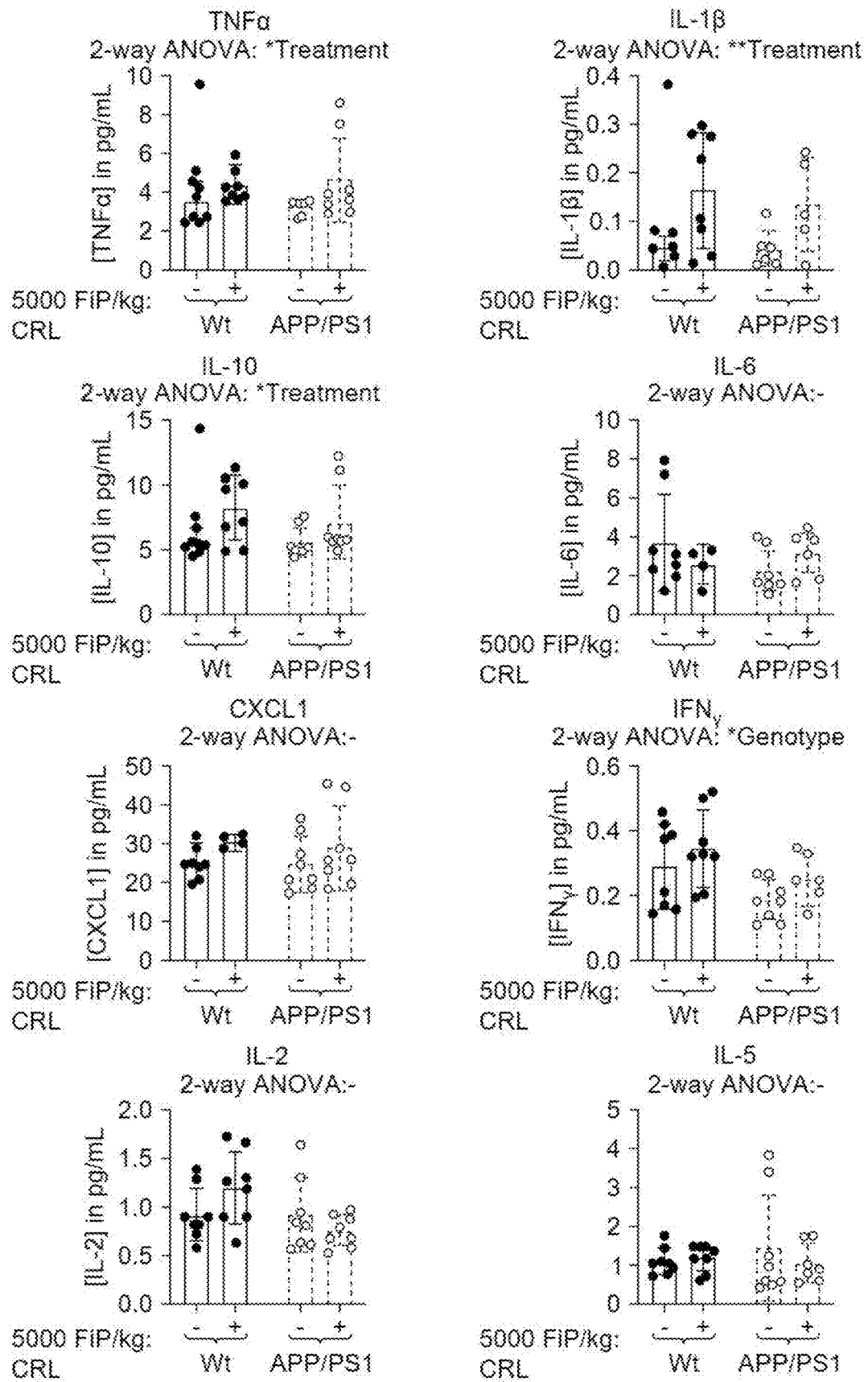
FIG. 2B displays plasma cytokine and chemokine levels. Significance is assessed by 2-way analysis of variance (ANOVA) and post-hoc Tukey correction. (pg/mL=picograms per milliliter; TNFα=tumor necrosis factor alpha; IL-I=interleukin 1 beta; IL-10=interleukin 10; IL-6=interleukin 6; CXCL1=CXC motif chemokine ligand 1; IFNγ=interferon gamma; IL-2=interleukin 2; IL-5=interleukin 5). Significance was assessed by 2-way ANOVA and post-hoc Tukey correction. Significance: $*p<0.05$, $**<0.01$, $*p<0.001$.

It is investigated whether the identified gut alterations identified in Example 2 are reflected in the host's peripheral circulation, which has been shown to be in direct exchange with the gut, through the gut-brain axes. See Carabotti et al., "The gut-brain axis: interactions between enteric microbiota, central and enteric nervous systems," *Ann. Gastroenterol.* 28:203-209 (2015). First, the immunological axis is analyzed to assess the treatment-dependent changes in plasma immune cells. Immune cell populations (T-helper: CD3+CD4+ and cytotoxic T cells: $CD3^+CD8^+$) in all groups are examined by flow cytometry. As shown in FIG. 2A, no difference is measured between untreated Wt and APP/PS1 mice, but a trend for decreased $CD3^+CD4^+$ and $CD3^+CD8^+$ populations is observed in treated APP/PS1 mice when compared to untreated animals; however, since the $CD4^+$/$CD8^+$ ratio is unaffected by CRL treatment compared to control groups, this analysis suggests that there are no significant treatment-dependent effects. Next, measurement of plasma cytokine levels as described in Example 1 can be used to assess treatment-dependent activity changes of immune cells. As shown in FIG. 2B, while levels of some multiple cytokines and chemokines are affected by CRL treatment (in particular, IL-1β), these results have negligible biological relevance due to overall low cytokine and chemokine concentrations. In view of these results, the immunological axis is considered to be independent of CRL treatment.

Example 4: Administration of CRL to APP/PS1 Mice Increases Peripheral Levels of Unsaturated Fatty Acids and VLDL/LDL Cholesterol Analysis of Cholesterol and Cholesterol Esters of Lipoproteins in Plasma For assessment of HDL and VLDL/LDL cholesterol and cholesterol esters in plasma, the Cholesterol Assay Kit (ab65390, Abcam, Cambridge, MA) is used. The assay is performed following the manufacturer's protocol.

Figure 2D:
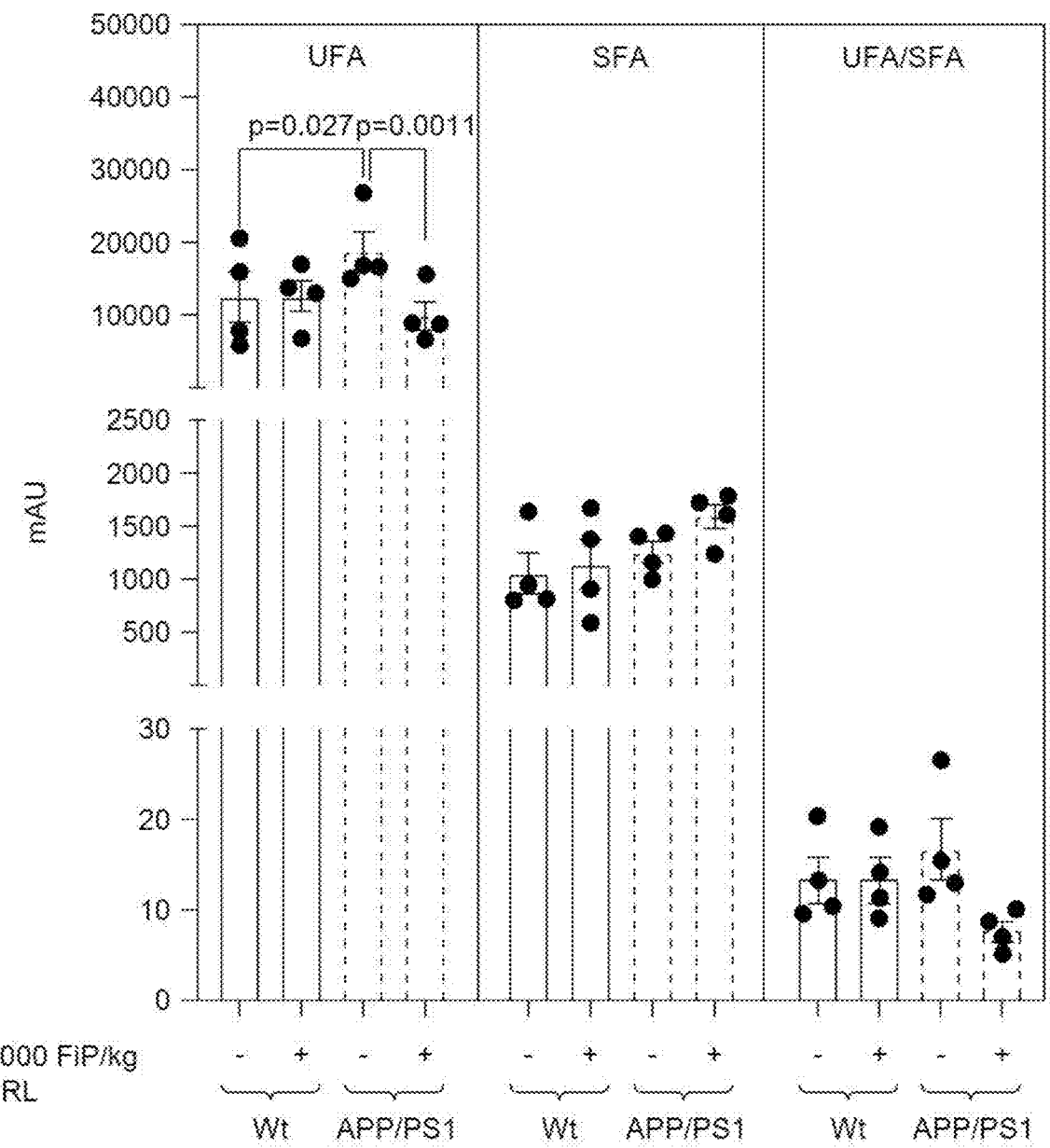
FIG. 2D shows comparative changes in saturated and unsaturated fatty acids, revealing an unsaturated fatty acid (UFA)-specific increase in untreated APP-PS1 mice. (SFA=saturated fatty acids; UFA/SFA=ratio of unsaturated fatty acids to saturated fatty acids). Significance was assessed by 2-way ANOVA and post-hoc Tukey correction. Significance: $*p<0.05$, $**<0.01$, $*p<0.001$).
Figure 2E:
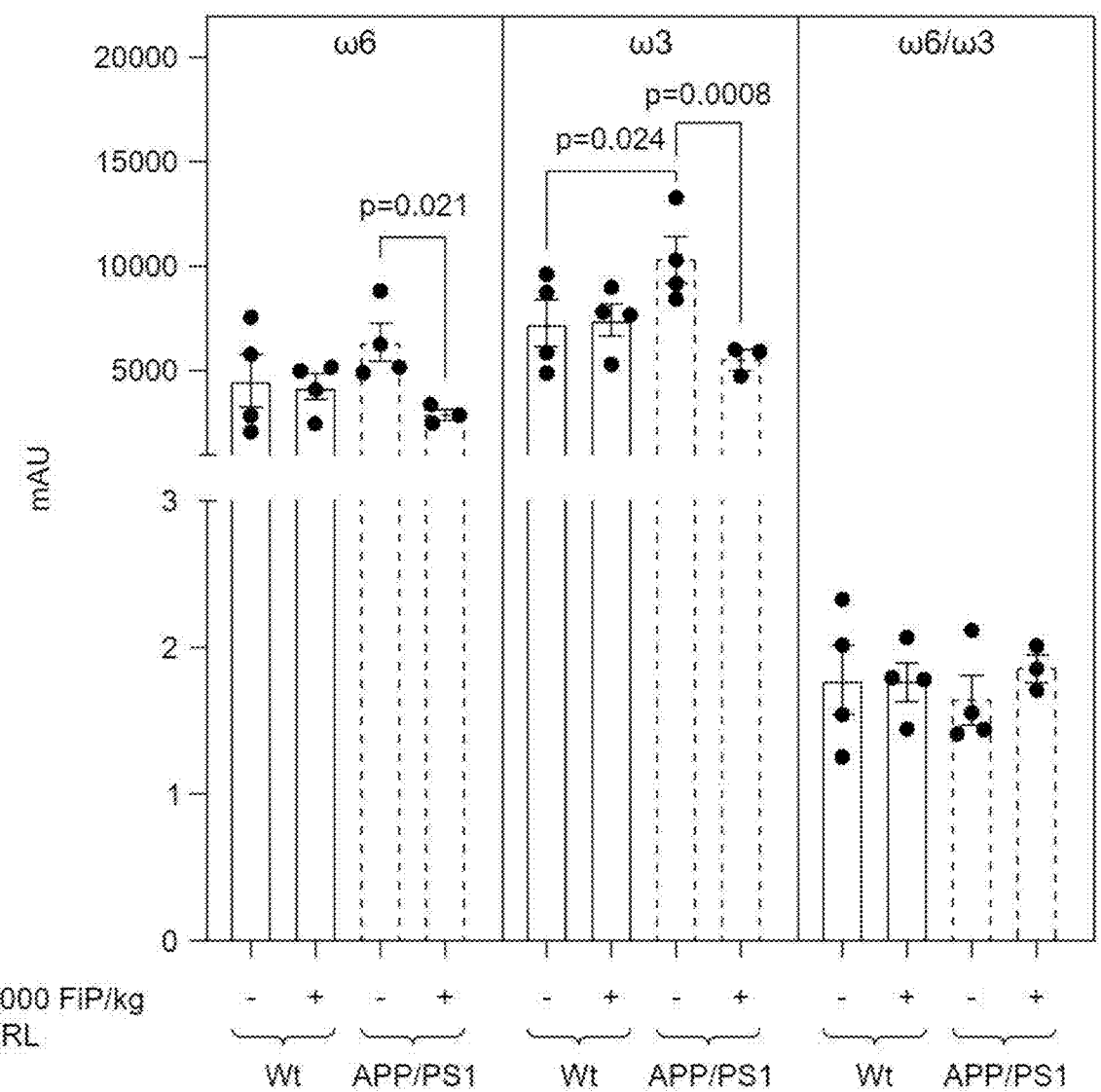
FIG. 2E shows changes in ω-3 and ω-6 fatty acid subgroups of unsaturated fatty acids, revealing that both ω-3 and ω-6 fatty acid levels are significantly increased in untreated APP/PS1 mice compared to CRL-treated APP/PS1 mice. Significance was assessed by 2-way ANOVA and post-hoc Tukey correction. Significance: $*p<0.05$, $**<0.01$, $*p<0.001$.
Figure 2F:
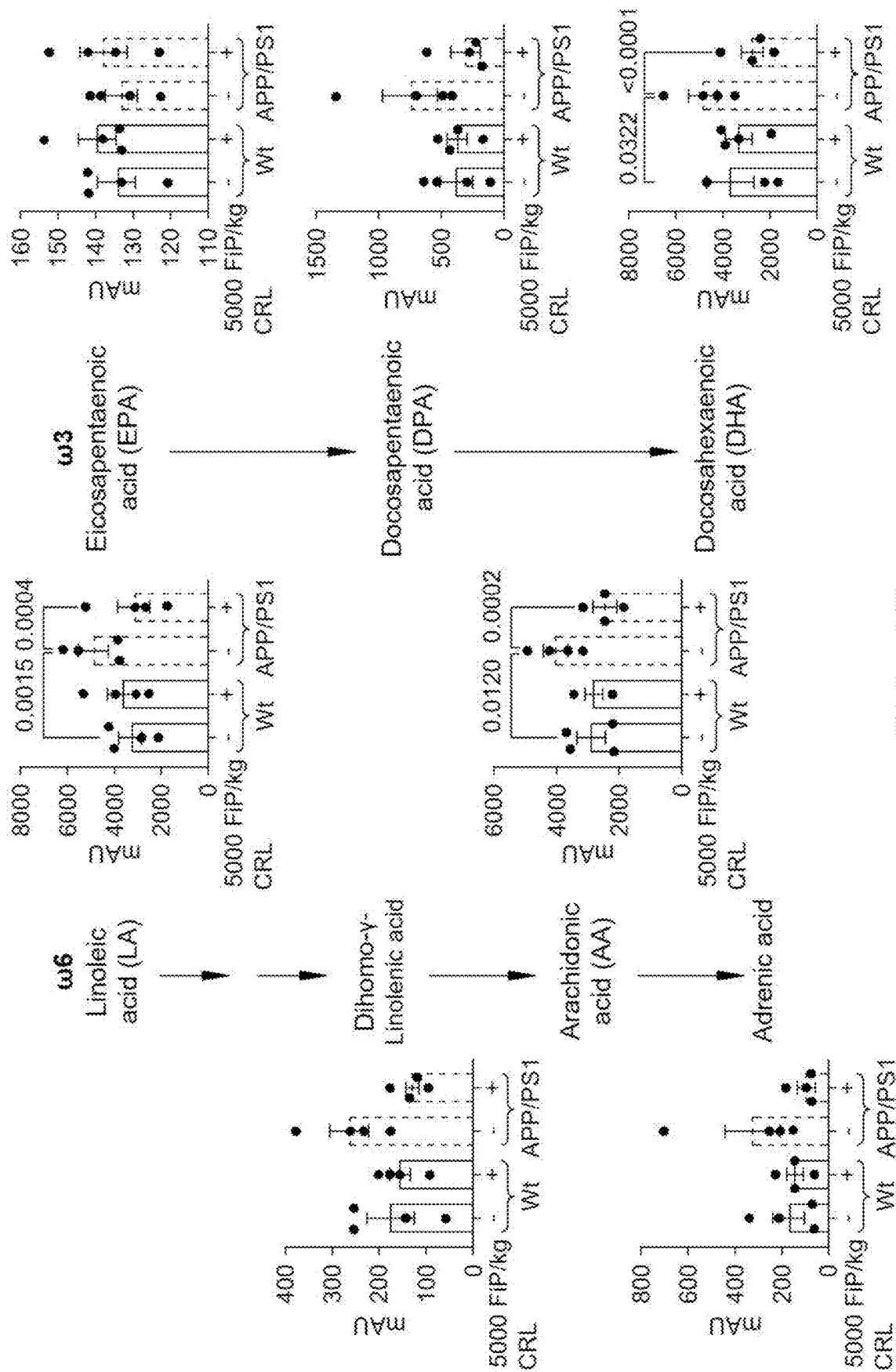
FIG. 2F presents plasma levels of ω-3 and ω-6 fatty acid levels and their downstream products, revealing significant reductions in some associated metabolites in CRL-treated APP/PS1 mice compared to untreated APP/PS1 mice. All downstream metabolites showed significant or trending normalization post-CRL treatment. (mAU=gas abundance). Significance was assessed by 2-way ANOVA and post-hoc Tukey correction. Significance: $*p<0.05$, $**<0.01$, $*p<0.001$.
Figure 2G:
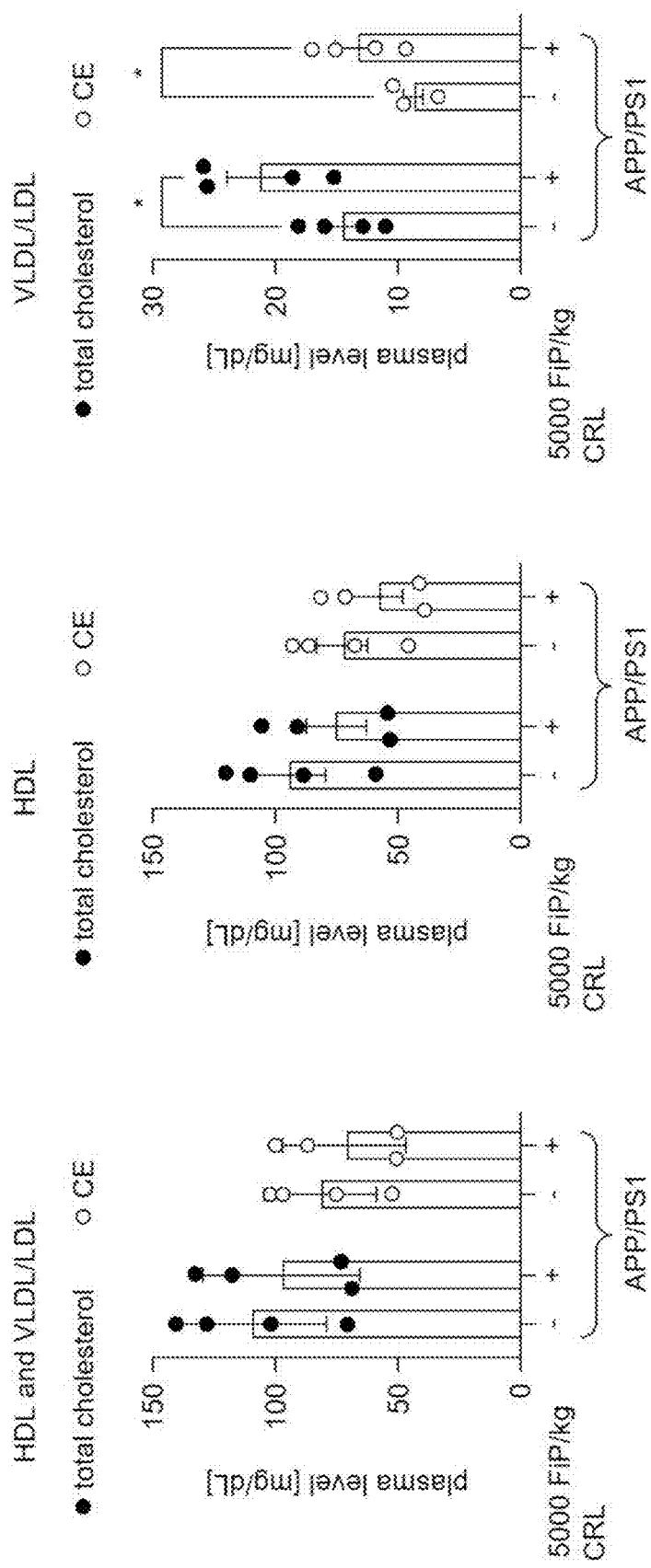
FIG. 2G presents plasma levels of HDL (high density lipoprotein) and VLDL/LDL (very low density lipoprotein/low density lipoprotein) cholesterol and cholesterol esters, revealing significant increases in VLDL/LDL cholesterol and VLDL/LDL cholesterol esters in APP/PS1 mice resulting from CRL treatment (right panel). (mg/dL=milligrams per deciliter). Significance was assessed by 2-way ANOVA and post-hoc Tukey correction. Significance: $*p<0.05$).

The metabolic axis is analyzed to identify any treatment-dependent changes in plasma by untargeted metabolomics. As shown in FIG. 2C, a metabolic pathway analysis as described in Example 1 reveals, for both genotypes, significant treatment-dependent alterations in pathways associated with unsaturated fatty acid metabolism. To identify further the direction of the identified alterations, the data was sub-grouped in total saturated fatty acids (SFAs) and unsaturated fatty acids (UFAs) as shown in FIG. 2D. While no significant genotype-dependent and treatment-dependent effects in SFAs and UFAs-to-SFAs ratio are observed, UFA levels are significantly increased in untreated compared to treated APP/PS1 mice (p=0.001). Further subdivision of UFAs into ω-3 and ω-6 fatty acids displays the same trend in both sub-groups (ω-3: p=0.0008; ω-6: p=0.021), but the effect was more pronounced in the ω-3 fatty acids subgroup (FIG. 2E). As shown in FIG. 2F, further analysis of specific unsaturated fatty acid levels and their downstream products reveals significant reductions in the following metabolites in treated APP/PS1 mice compared to untreated APP/PS1 mice: linoleic acid ($FC_{APP/PS1}$=0.651; p=0.0002), arachidonic acid ($FC_{APP/PS1}$=0.618; p=0.0001) and docosahexaenoic acid ($FC_{APP/PS1}$=0.569; p<0.0001). Finally, as shown in FIG. 2G, alterations in lipid transport favor the peripheral differences of UFAs in APP/PS1 mice measured by high-density lipoproteins (HDL) and very low-density and low-density lipoprotein (VLDL/LDL) cholesterol plasma levels. Here, as also shown in FIG. 2G, peripheral total cholesterol and cholesterol ester levels are unchanged, but cholesterol and cholesterol esters in HDL and VLDL/LDL fractions show treatment-dependent divergent differences. Only VLDL/LDL cholesterol and cholesterol ester levels are significantly increased post treatment (cholesterol: FC=1.459, p=0.031; cholesterol ester: FC=1.529, p=0.031).

In sum, the above studies of Examples 3 and 4 show that cecal levels of UFAs of treated APP/PS1 mice are elevated, peripheral levels of UFAs are normalized, and VLDL/LDL cholesterol and cholesterol esters are increased.

Example 5: Administration of CRL to APP/PS1 Mice Improves Memory and Learning in a Barnes Maze Test Next, CRL's treatment effect on memory and learning was examined via a Barnes maze test, as described in Example 1. The Barnes maze acquisition trials show some significant differences between untreated C57BL/6J (Wt) and APP/PS1 animals and trends for treatment-dependent improvements (FIGS. 3A-3E). Indeed, the probe trials of FIGS. 3A-3E show genotype-dependent differences in frequency to find the target hole, as well as latency to find the target hole (latency: p=0.114; frequency: p=0.043). Here, significant improvement of latency to find the target hole, as well as a trend for improvement in frequency of target hole investigations, is observed in treated APP/PS1 mice when compared to untreated littermates (latency: p=0.025; frequency: p=0.478). Also, CRL-treated Wt mice show a trend for improvement in latency and frequency when compared to untreated animals (latency: p=0.158; frequency: p=0.325). In addition, untreated APP/PS1 mice exhibit decreased velocity results in both acquisition and probe days, which is normalized upon treatment (velocity: p=0.045). This result is attributed to diminished exploratory behavior in the untreated APP/PS1 mice. As provided above, increased exploratory behavior and enhanced memory function in a Barnes Maze experiment in animals correlates to increased cognition in humans, as assessed by, e.g., a MoCA, a MMSE, and/or a Mini-Cog.

Example 6: Administration of CRL to APP/PS1
Mice Reduces Certain Neuroinflammatory Markers
and Modulates Certain Metabolic Pathways Immunohistochemistry Analysis The collected brain hemispheres of cohort 1 (n=4 per group in the CRL treatment study) are fixed in 4% paraformaldehyde solution for 24 h and subsequently dehydrated and embedded in paraffin. Brain hemispheres are cut into 9 μm Sects. (4 animals, 4 sections per hemisphere; 2 consecutive sections and 2 consecutive Sects. 90 μm apart) and deparaffinized, then rehydrated through Histo-Clear (Thermo Fisher, Waltham, MA) and ethanol gradient, and then treated with 0.3% hydrogen peroxide to reduce background staining. Sections are washed in PBS and incubated in blocking serum before an overnight incubation at 4° C. in a 1:8000 dilution of Glial Fibrillary Acidic Protein (GFAP) antibody (Polyclonal Rabbit Anti-GFAP, DAKO, Z0334) or 1:2000 dilution of Iba1 antibody (Polyclonal Rabbit Anti-Iba1, Abcam, Cambridge, MA). Next, the sections are washed with PBS and placed in secondary antibody Vectastain Elite ABC reagent (Vector Laboratories, Inc., Burlingame, CA) for 30 min. Iba1 slides are then stained with Congo Red for 10 min to stain A3 plaques. Then, all slides are incubated in 3,3'-diaminobenzidine (DAB) for 1-3 min. Subsequently, tissue sections are counterstained with hematoxylin, dehydrated through both an ethanol gradient and Histo-Clear, and mounted to coverslips. Upon drying of the slides, three random images at 20× magnification of the hippocampal area spanning CA1, CA2 and CA3, and cortical area spanning M1, S1, LPtA, MPtA, V2MM, are taken (without overlap) per section using an Olympus BX63 Intelligent microscope and quantified with ImageJ. Also, six images per section of 40× magnification of microglia surrounding Congo Red stained plaques in both hippocampus and cortex within the same area are taken, and plaque size areas are analyzed with ImageJ. Additionally, microglia that directly surround the associated plaque area are counted, and the ratio between plaque area and count is determined. Data is plotted and analyzed via 2-way ANOVA and Tukey correction in GraphPad Prism 8 (GraphPad, San Diego, CA). Transcriptomics analysis Cortex (n=4 per group for the CRL treatment study) is separated from one frozen hemisphere and immediately transferred into 1 mL of TRIzol (Thermo Fisher, Waltham, MA) under RNase free conditions. Samples are disrupted by ultrasonication. 100 μL 1-bromo-3-cholorpropane reagent (Sigma, St. Louis, MO) is subsequently added and samples are mixed and centrifuged at 12,000 g for 15 min. Finally, RNA is precipitated by addition of 500 μL ice-cold isopropanol, and washed with 75% ethanol in DEPC water (Thermo Fisher, Waltham, MA). The air-dried pellet is resuspended in DEPC water and RNA concentration is measured at Cytation 3 (BioTek, Winooski, VT). At least 500 ng RNA is subsequently sent to GENEWIZ LLC (South Plainfield, NJ) for sample processing and total RNA sequencing (20-30 million reads). The sequencing data was analyzed using the following applications from the Galaxy platform (See Afgan et al., "The Galaxy platform for accessible, reproducible and collaborative biomedical analyses: 2018 update," Nucleic Acids Res 46:W537-W544 (2018)): FastQC, MultiQC, Trimmomatic, HiSAT2 (See Kim et al., "HISAT: A fast spliced aligner with low memory requirements," Nat. Methods 12:357-360 (2015)), Mark-Duplicates, Feature Counts (See Liao et al., "featureCounts: An efficient general purpose program for assigning sequence reads to genomic features," Bioinformatics 30:923-930 (2014)), Column Join on Collections, annotateMyIDs, and edgeR (Robinson et al., "edgeR: A Bioconductor package for differential expression analysis of digital gene expression data," Bioinformatics 26:139-140 (2010)). Gene enrichment analysis is performed with EnrichR. See Chen, E. Y. et al., "Enrichr: Interactive and collaborative HTML5 gene list enrichment analysis tool," BMC Bioinform. 14:128 (2013). Examined cell-specific markers include: Aldh1l1, Atp1b2, Aqp4, Sox9, Slc4a4, Mlc1, and GFAP (astrocytes); Cx3cr1, P2ry12, TMEM119, Aif1, Olfm13, Ccl3, and Itgam (microglia); stmn2, Rbfox3, syt1, and syn1 (neurons); Pecam1 and Tie1 (endothelia); and Nfasc and Kndc1 (oligodendroglia). Data is plotted and analyzed via 2-way ANOVA and FDR correction in GraphPad Prism 8 (GraphPad, San Diego, CA).

Figure 3A:
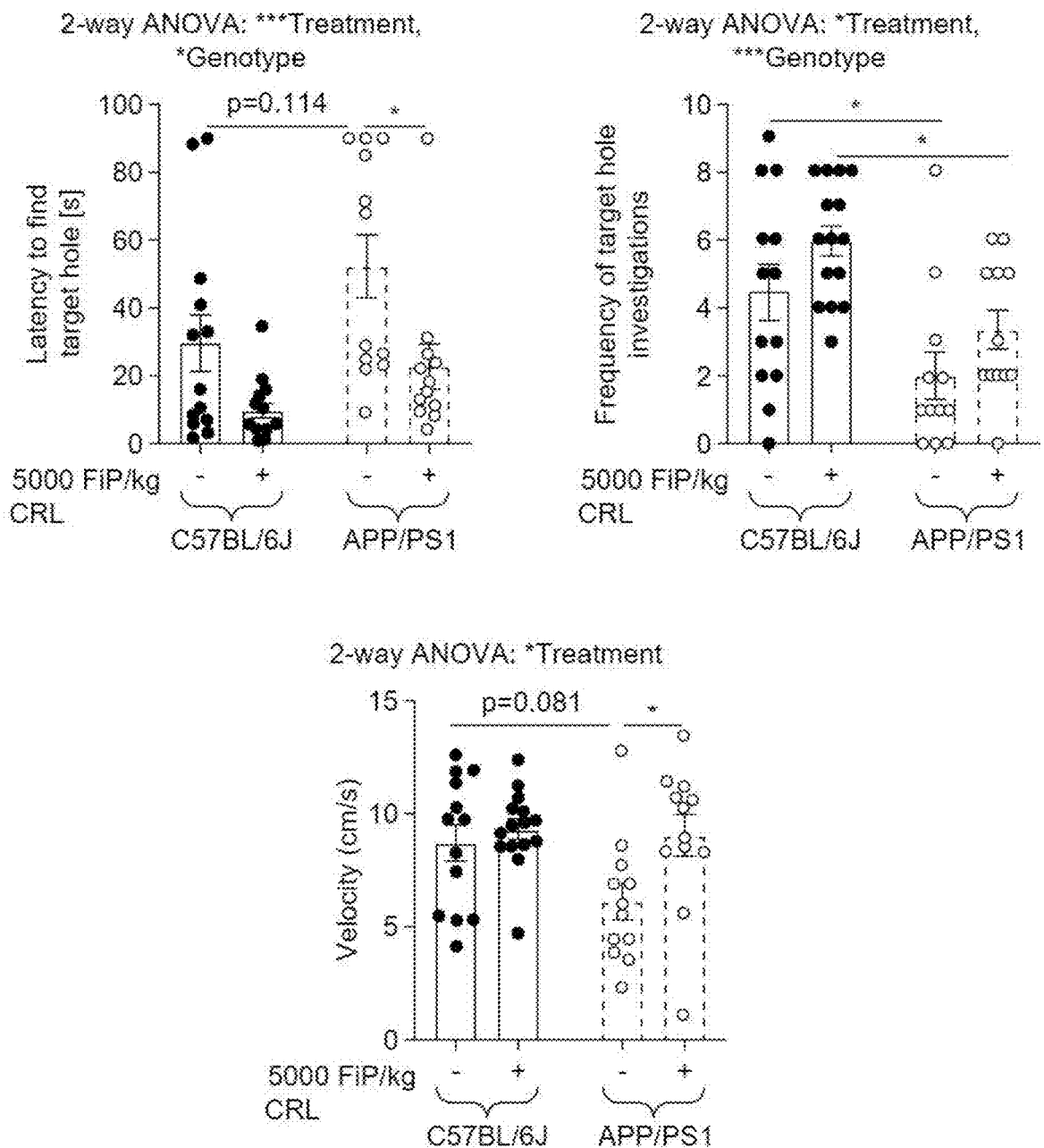
FIGS. 3A-3E present Barnes maze probe and acquisition results for all four treatment groups, investigating latency for the treated mice to locate the target hole, frequency of target hole investigations by the treated mice, velocity of the treated mice throughout the maze, maze escape latency, and cumulative distance from the target hole. Significance is assessed by 2-way (prob trial) or 3-way ANOVA (acquisition trial) with post-hoc Tukey correction. (s=seconds; cm=centimeters; cm/s=centimeters per second. Significance: $*=p<0.05$; $=p<0.01$; $*=p<0.001$; $****=p<0.0001$.
Figure 3B:
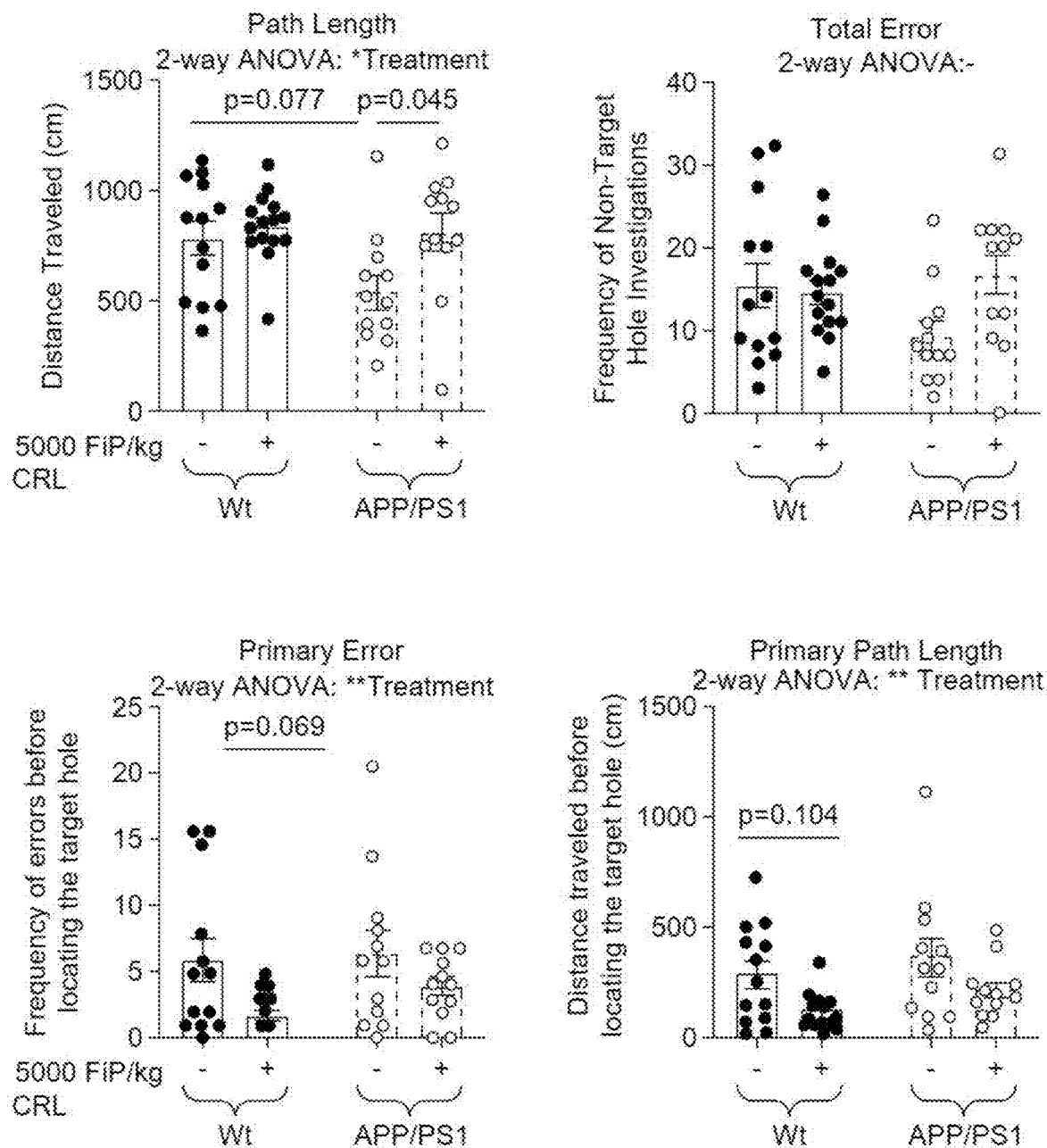
Figure 3C:
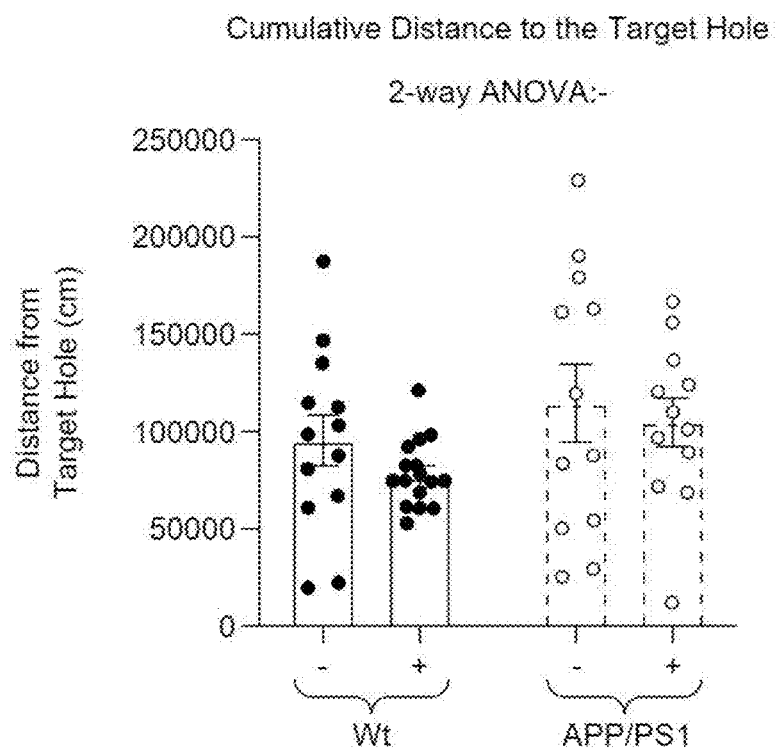
Figure 3C:
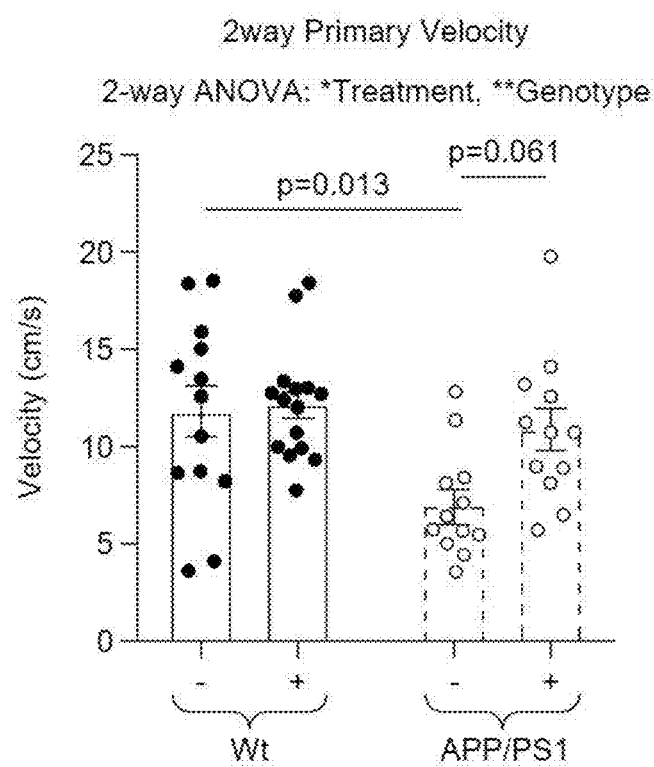
Figure 3D:
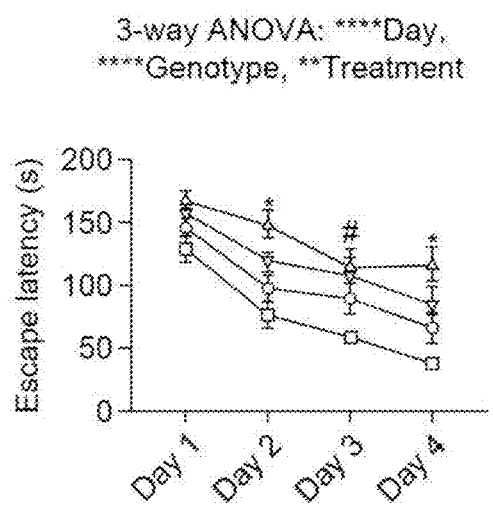
Figure 3D:
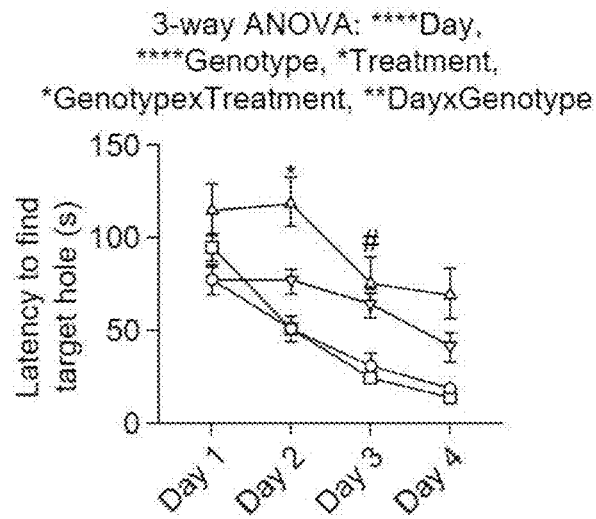
Figure 3D:
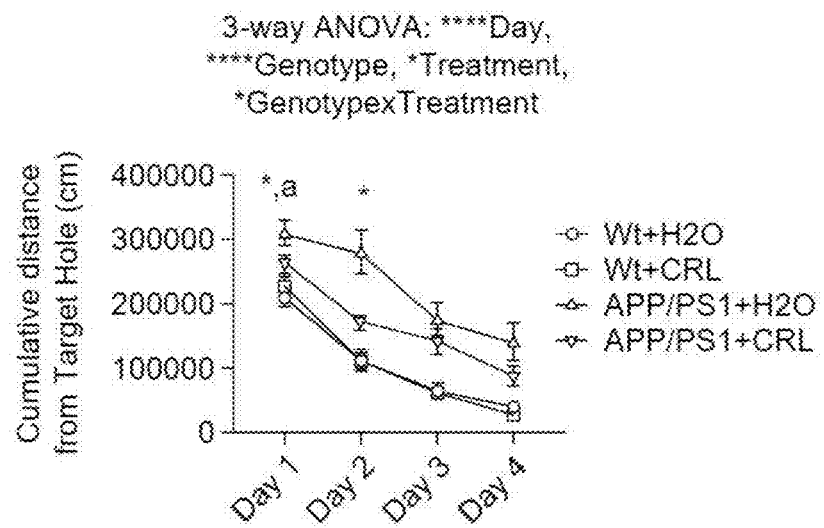
Figure 3E:
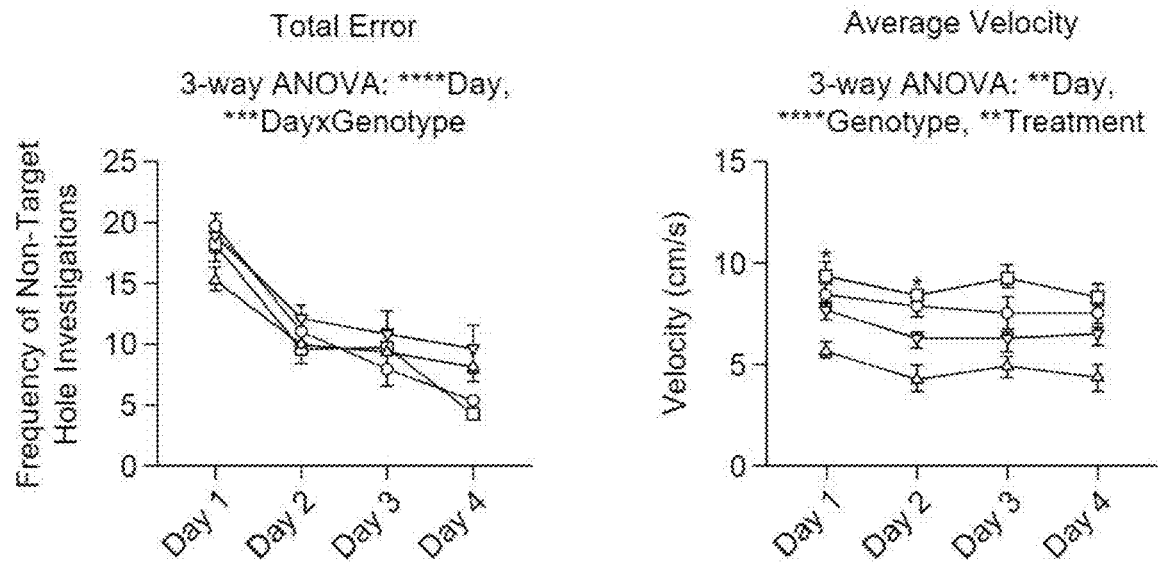
Figure 3E:
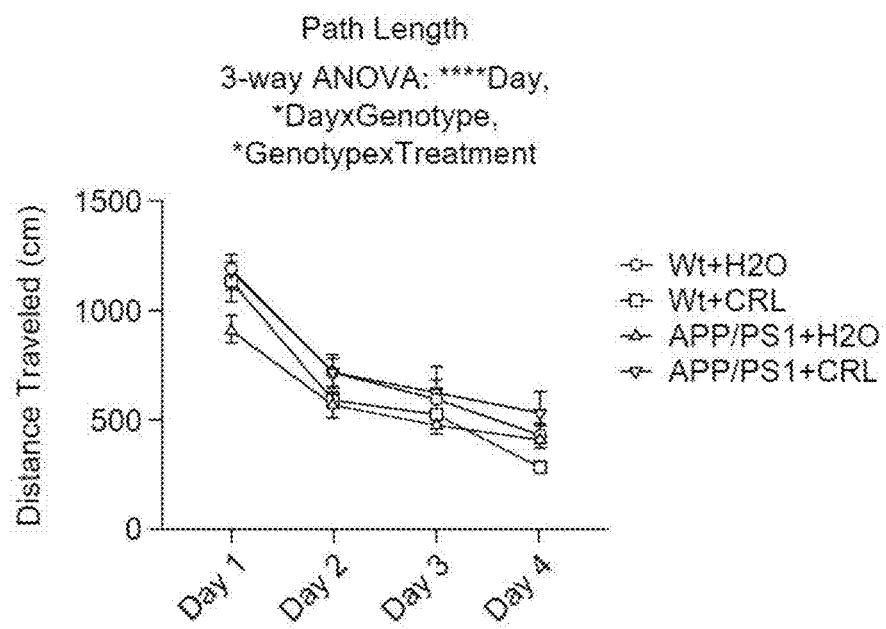
Figure 3F:
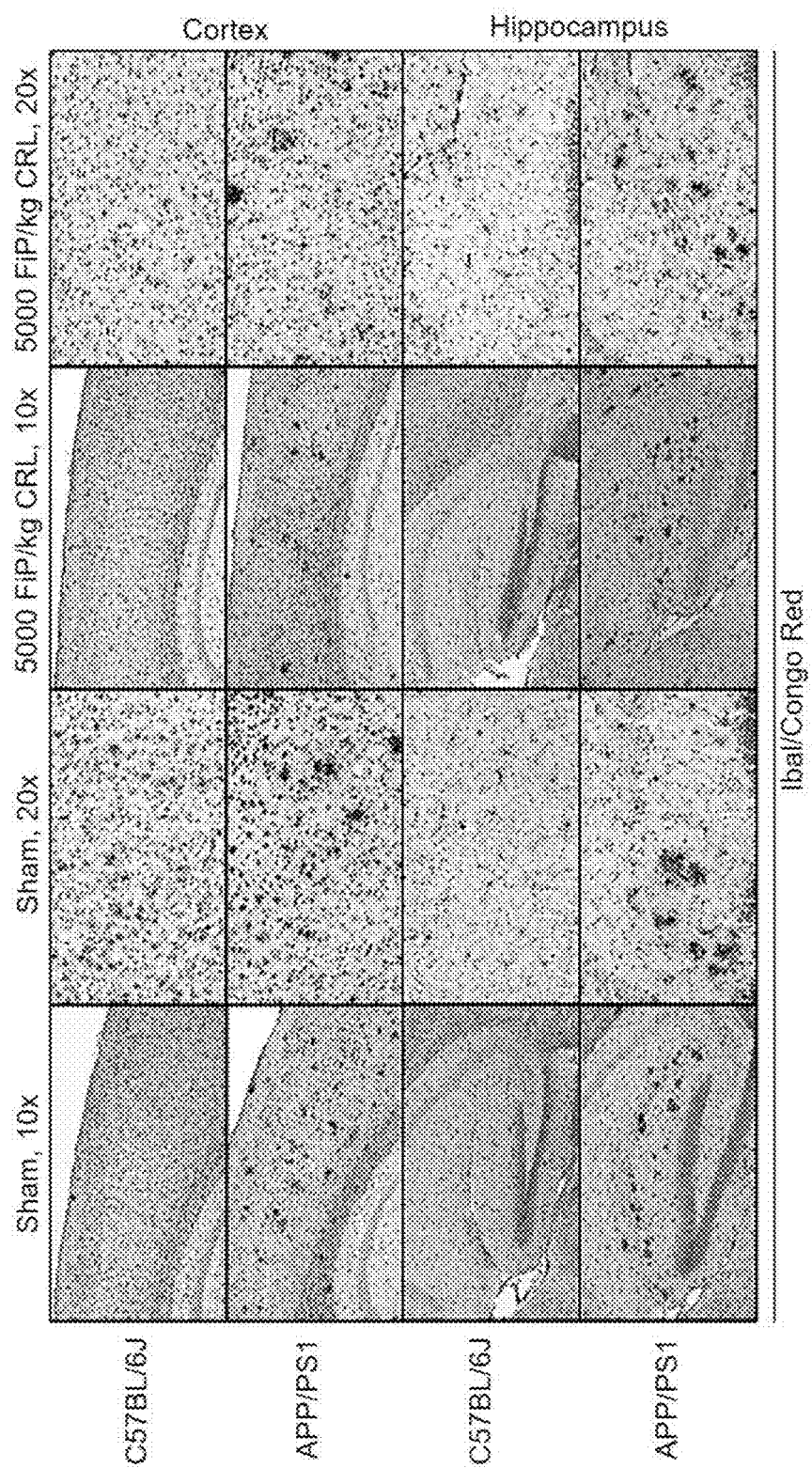
FIGS. 3F-3G present an immunohistochemical analysis of CRL treatment-dependent effects on microglia activation in the cortex and hippocampus by Iba1/Congo Red staining (×20 magnification: four animals per group with four tissue sections per animal and three images per section). Significance is assessed by 2-way ANOVA and post-hoc Tukey correction (SEM=standard error of the mean; Significance: $=p<0.01$; $**=p<0.0001$).
Figure 3G:
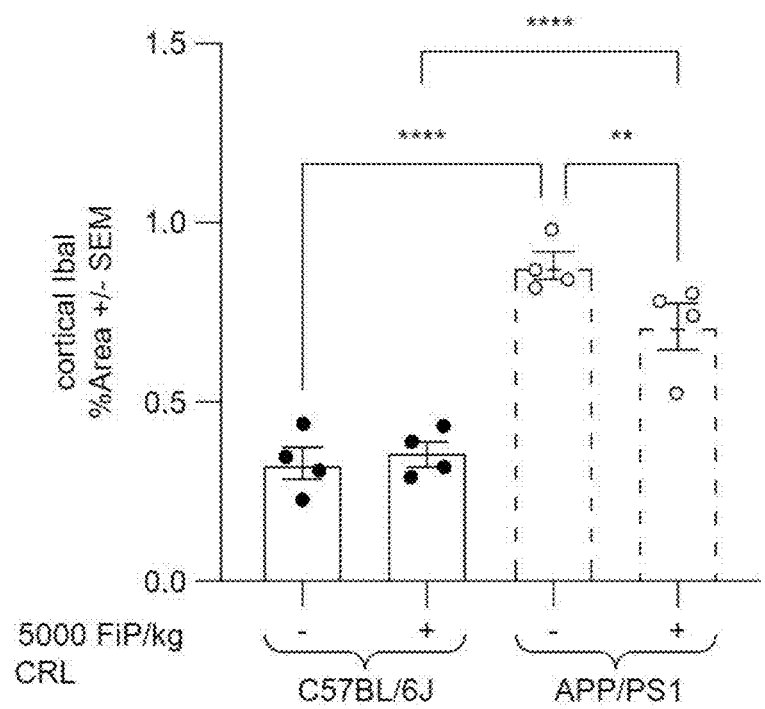
Figure 3G:
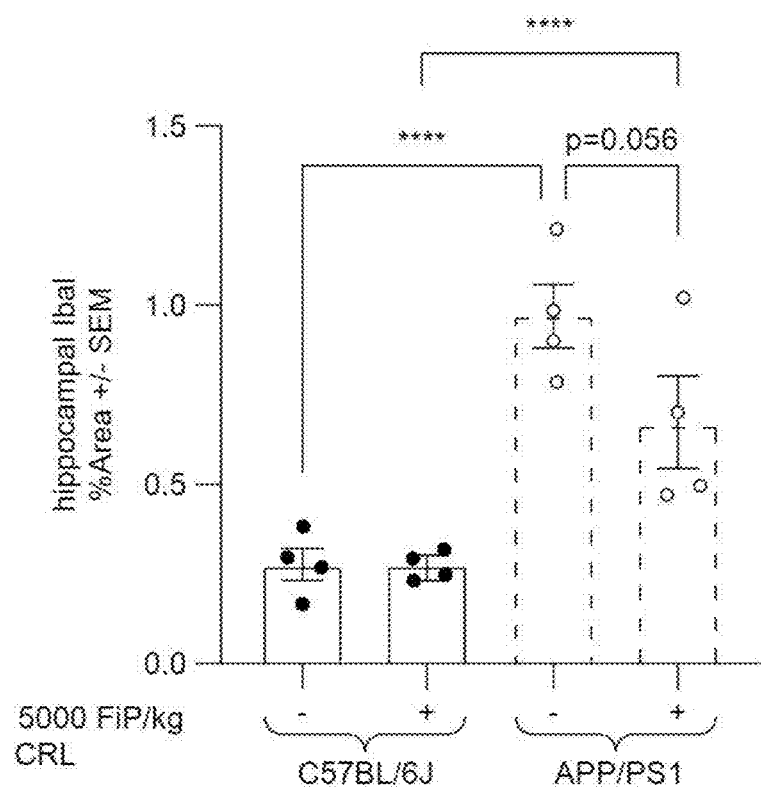
Figure 3H:
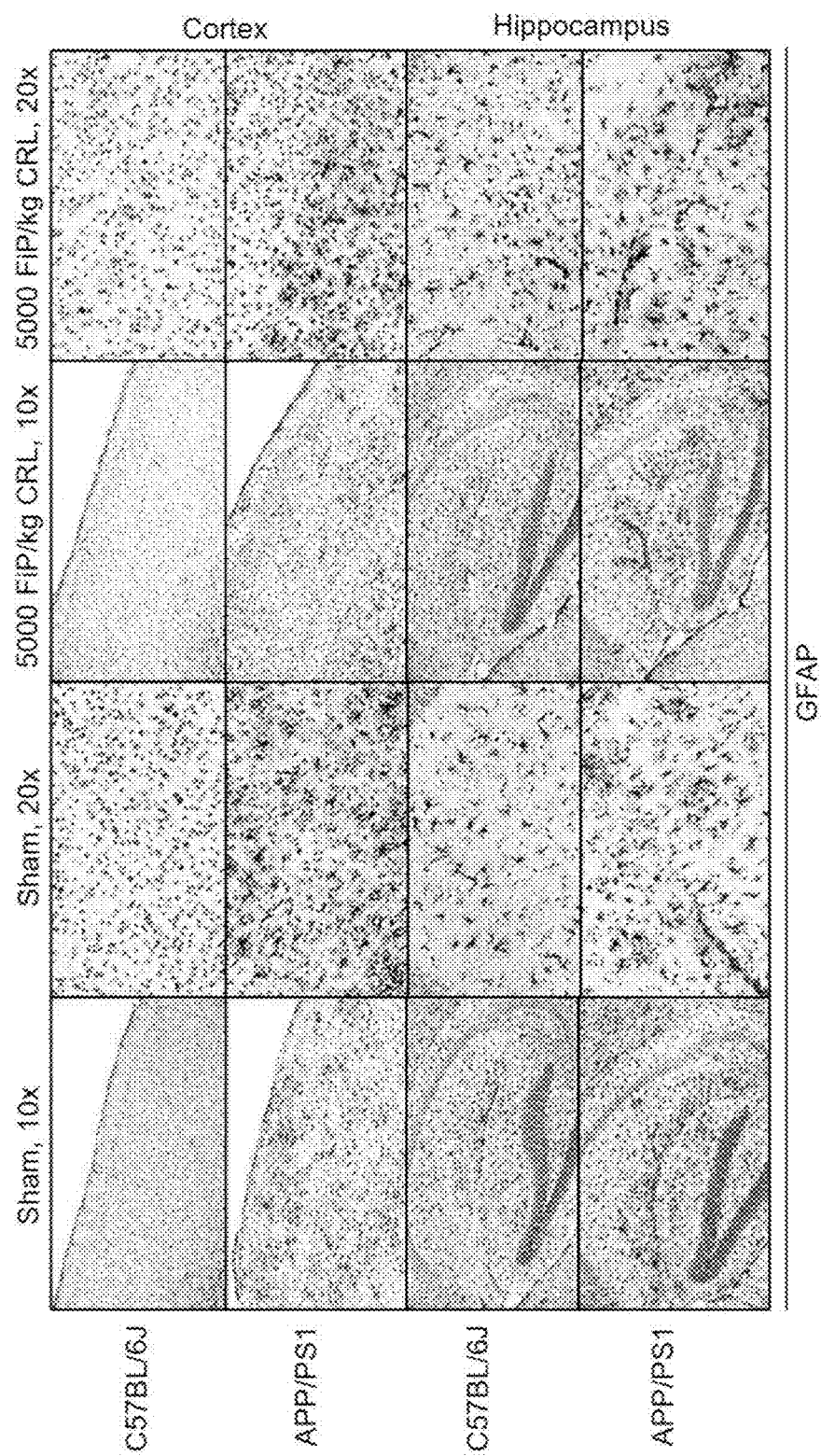
FIGS. 3H-3I present an immunohistochemical analysis of CRL treatment-dependent effects on astrocytosis in the cortex and hippocampus by Glial Fibrillary Acidic Protein (GFAP) staining (×20 magnification: four animals per group with four tissue sections per animal and three images per section). Significance is assessed by 2-way ANOVA and post-hoc Tukey correction. (SEM=standard error of the mean; Significance: $*=p<0.001$; $**=p<0.0001$).
Figure 3I:
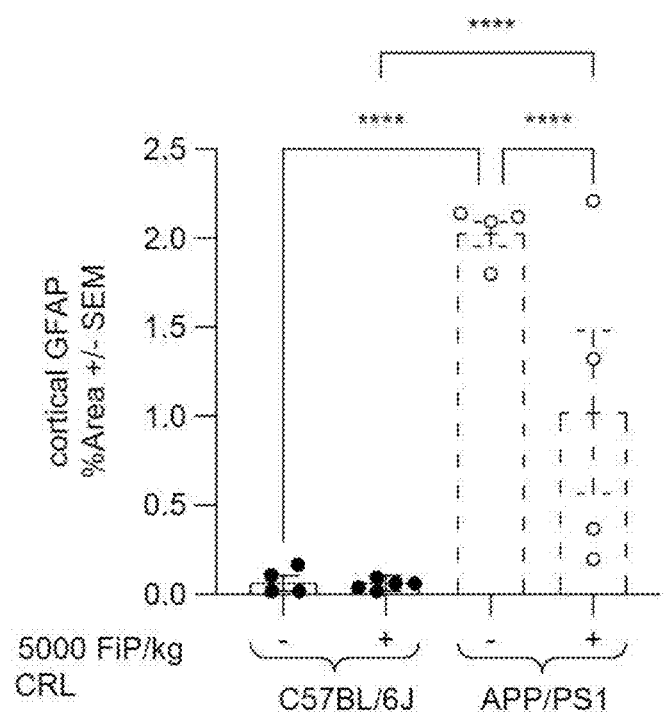
Figure 3I:
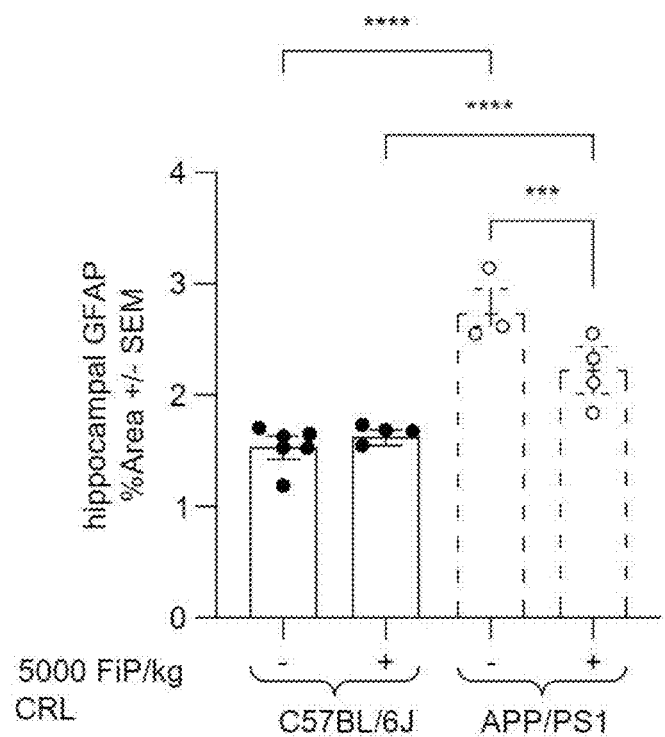
Figure 3J:
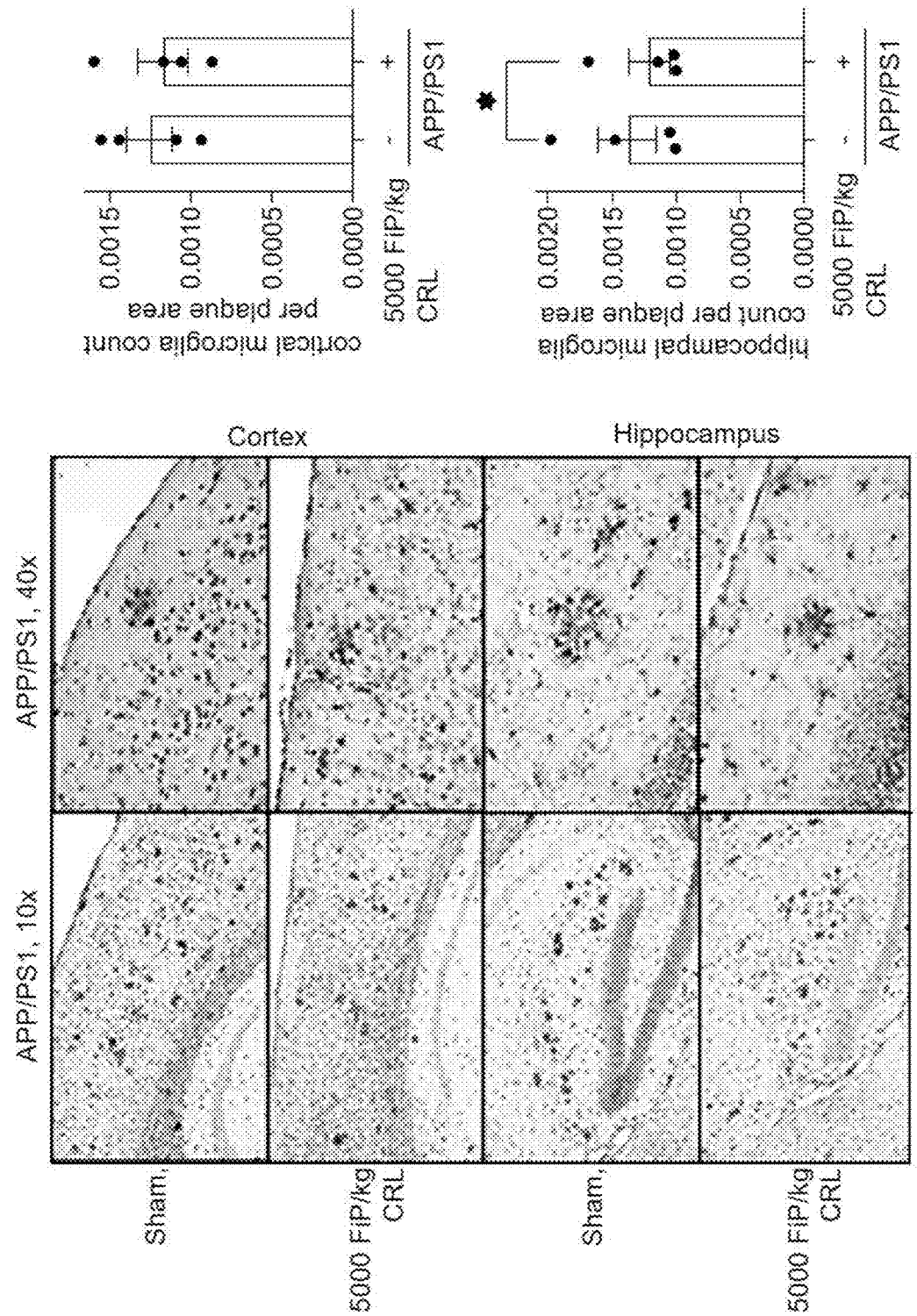
FIG. 3J compares amyloid plaque size to associated microglia counts to determine changes in inflammatory response and plaque burden (×40 magnification: four animals per group, four slides per animal, six images per tissue area). Significance is assessed by 2-way ANOVA and post-hoc Tukey correction (SEM=standard error of the mean; Significance: $*=p<0.001$; $**=p<0.0001$).

CRL's treatment effect on neuroinflammation and gene expression (RNAseq) is examined to assess whether the improvement of memory observed in Example 5 is associated with decreased neuroinflammation in the brain. The degree of microgliosis and astrocytosis are analyzed in the cortex and hippocampus by Iba1/Congo Red and GFAP staining (FIGS. 3F-3I). In the cortex, significant genotype-dependent differences are observed between treated Wt (C57BL/6J) and APP/PS1 mice (Iba1: p<0.0001, FIGS. 3F-3G; GFAP: p<0.0001, FIGS. 3H-3I), while no differences between treated and untreated Wt mice are observed. Indeed, a significant reduction of both GFAP and Iba1 staining is observed in the cerebral cortex in treated APP/PS1 mice (Iba1: p=0.0094, FIGS. 3F-3G; GFAP: p<0.0001, FIGS. 3H-3I). However, as shown in FIG. 3J, no differences in the ratio of Iba1 stained microglia counts surrounding amyloid plaques to the area of the respective Congo Red-stained amyloid plaques is found between treated and untreated APP/PS1 mice in the cerebral cortex, indicating that no increase in plaque burden has occurred. In the hippocampus, Iba1 and GFAP levels were also significantly different between treated Wt and APP/PS1 animals (Iba1: p<0.0001, FIGS. 3F-3G; GFAP: p<0.0001, FIGS. 3H-3I). No differences between untreated and treated Wt animals are observed in the hippocampus, while treated APP/PS1 animals show significant reductions of Iba1 and GFAP compared to untreated APP/PS1 animals, although these differences are less pronounced when compared to the cortical analyses (GFAP: p=0.0003, FIGS. 3H-3I). However, analysis of the ratio of microglia counts-to-proximal amyloid plaque area in the hippocampus of APP/PS1 animals indicates a significant reduction in this ratio in treated animals (p=0.015; FIG. 3J).

Figure 3K:
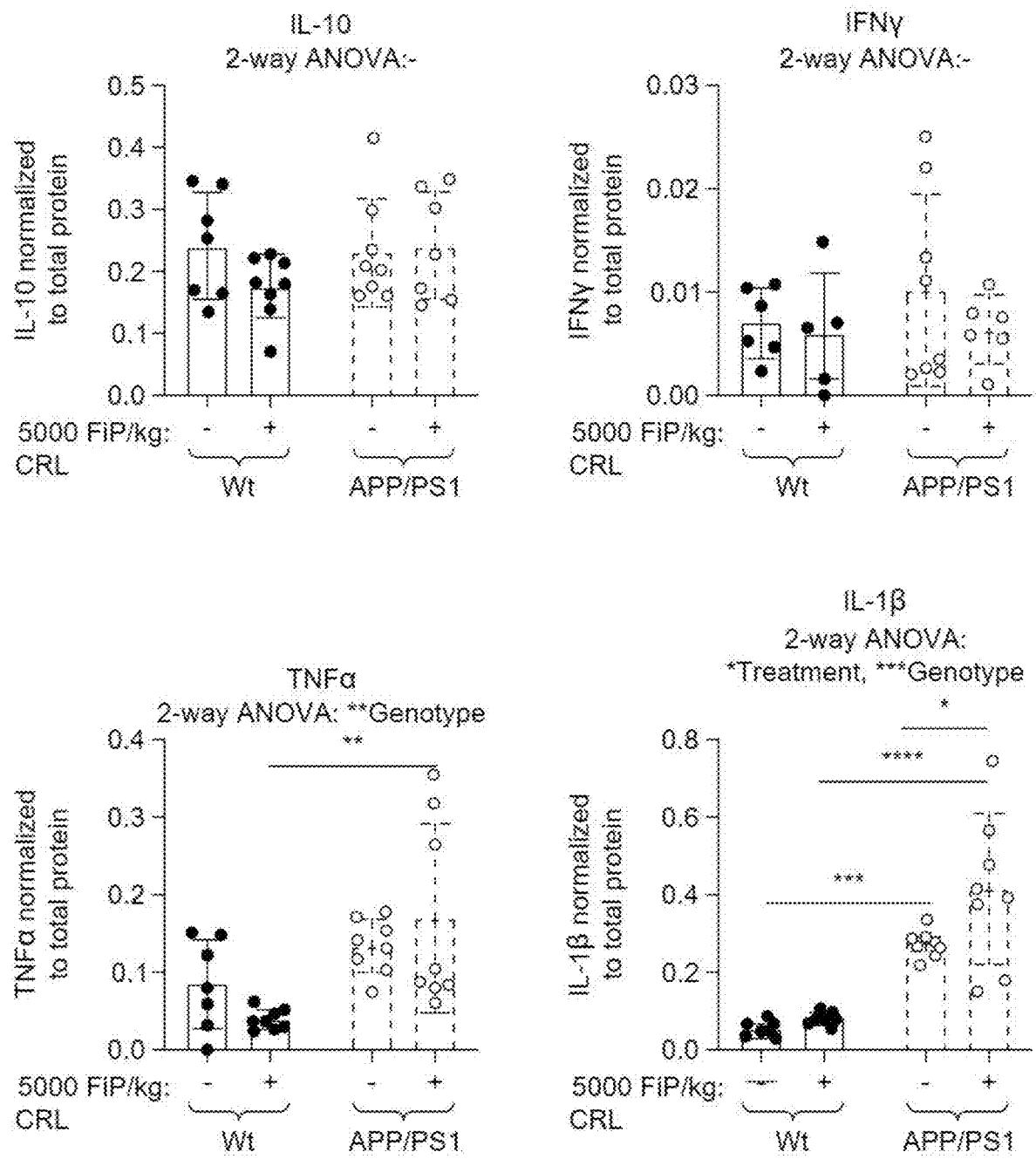
FIGS. 3K-3L display brain cytokine and chemokine levels. Significance is assessed by 2-way analysis of variance (ANOVA) and post-hoc Tukey correction. (IL-10=interleukin 10; TNFα=tumor necrosis factor alpha; IL-5=interleukin 5; IL-6=interleukin 6; IFNγ=interferon gamma; IL-1β=interleukin 1 beta; CXCL1=CXC motif chemokine ligand 1; Significance: $*=p<0.05$; $=p<0.01$; $*=p<0.001$).
Figure 3L:
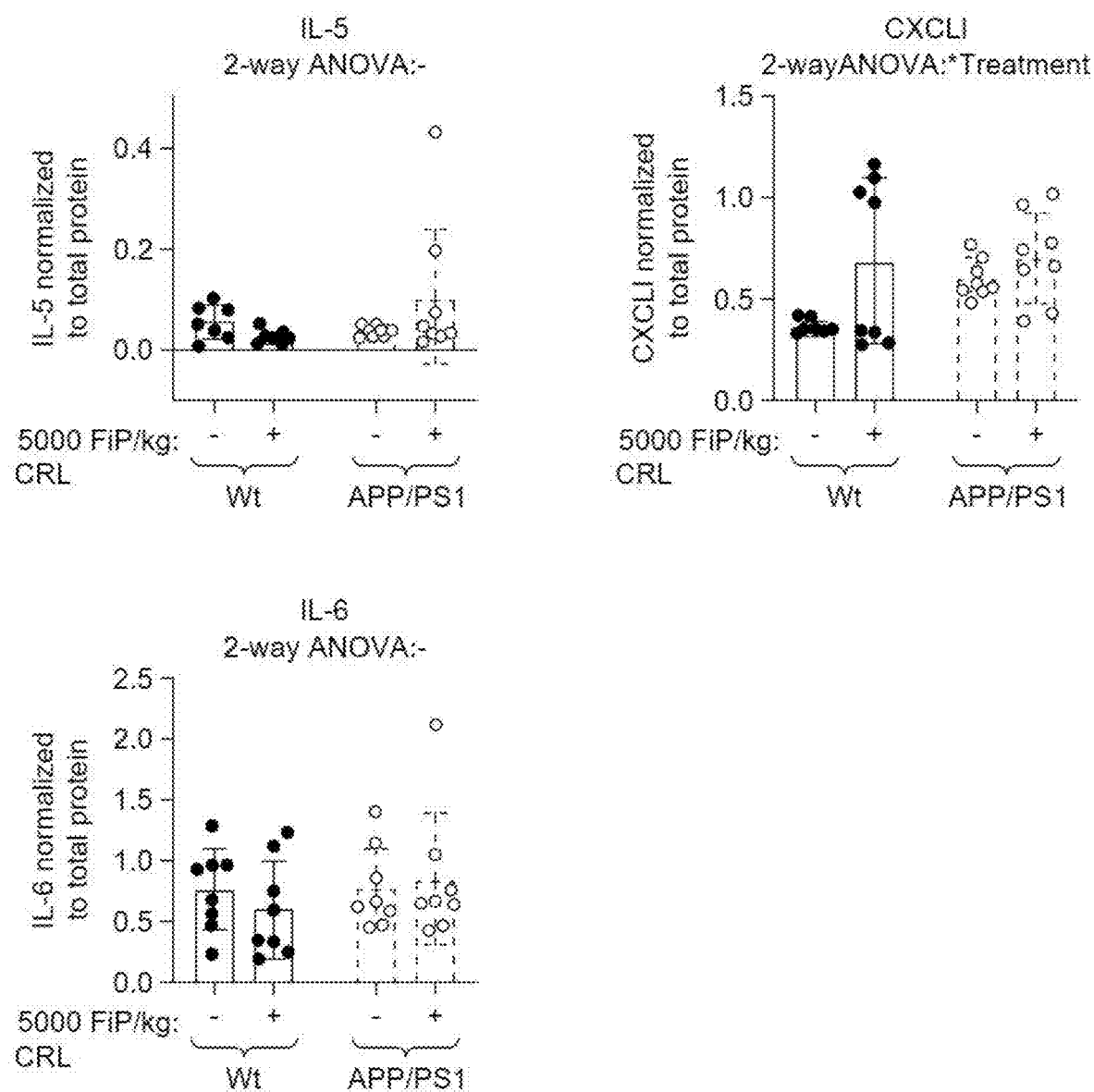
Figure 3N:
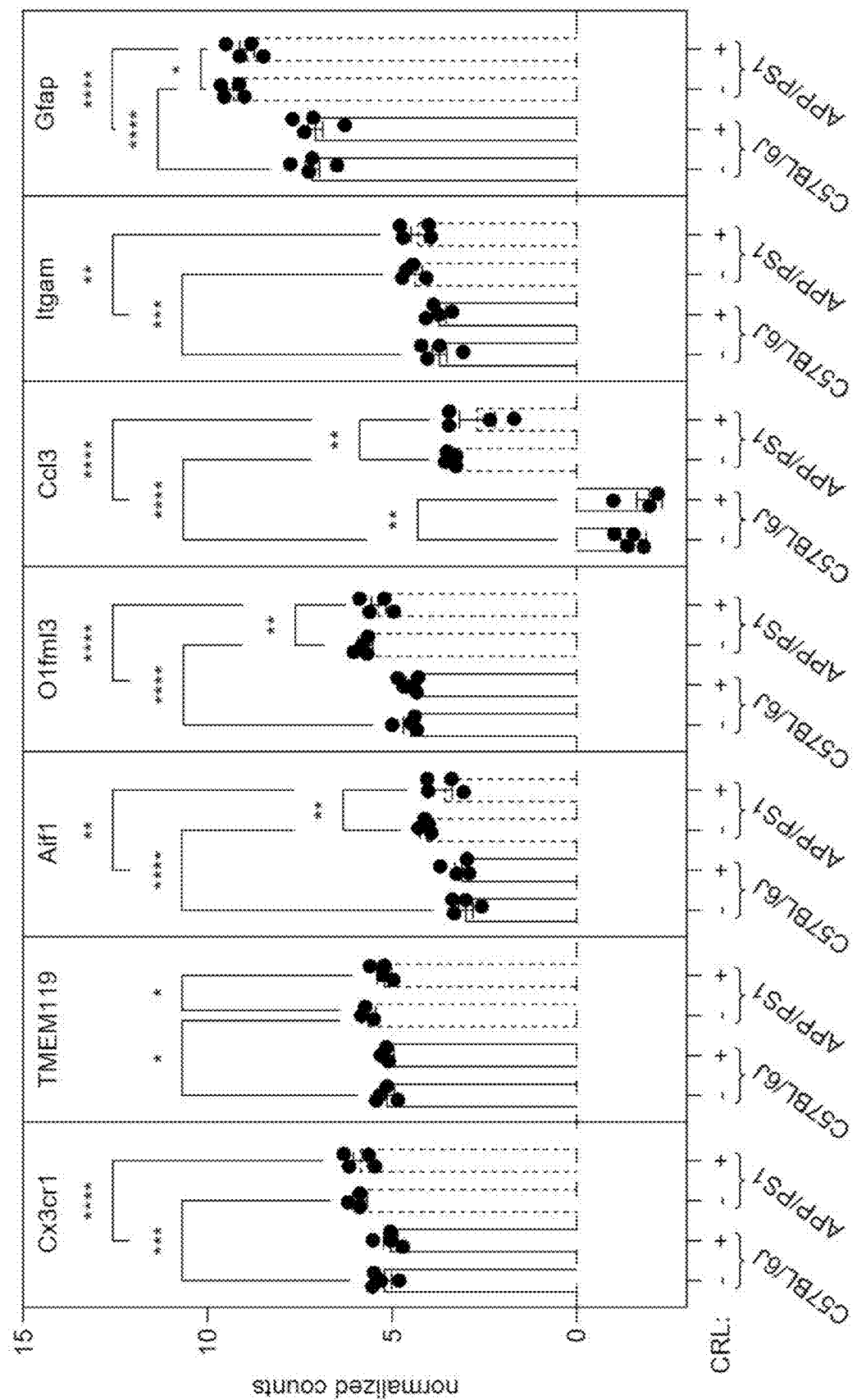
FIG. 3N presents a transcriptomics analysis of brain cell markers of whole cortical tissue, which reveals treatment-dependent changes in microglia-specific genes in APP/PS1 mice. Significance is assessed by 2-way ANOVA and FDR correction. (Cx3cr1=C-x3-C motif chemokine receptor 1; TMEM119=transmembrane protein 119; Aif1=allograft inflammatory factor 1; Olfm13=olfactomedin like 3; Ccl3=chemokine (C-C motif) ligand 3; Itgam=integrin subunit alpha M; GFAP=glial fibrillary acidic protein; Significance: $*=p<0.05$; $=p<0.01$; $*=p<0.001$; $****=p<0.0001$).

Due to the stronger impact of treatment on microglia and astrocyte markers in cortical tissue described above, treatment-dependent effects on cortical cytokine and chemokine levels and transcriptome are measured. As shown in FIGS. 3K-3L, of the seven cortex cytokines and chemokines measured, the level of IL-1 is significantly increased in treated versus untreated APP/PS1 mice, while IFNg levels are decreased, and IL-5 and TNFα levels are slightly increased in treated animals. However, the overall levels of cytokines and chemokines shown in FIGS. 3K-3L are low, indicating little biological relevance. Next, the total RNA expression of whole cortical tissue of treated and untreated APP/PS1mice is analyzed by a focused hypothesis-driven analysis (gene enrichment), and this analysis suggests that endocytosis, lysosomal activity, and glycerophospholipid metabolism are altered by CRL treatment (FIG. 3M). As endocytosis and lysosomal activity are particularly associated with glial cells, the dataset is reanalyzed for specific brain cell markers in FIG. 3N. This transcriptomics analysis shows differential expression of microglial and astrocytic cell markers GFAP, TMEM119, Aif1, Olfm13 and Ccl3 were shown to be differentially expressed in treated vs. untreated APP/PS1 mice ($p_{FDR}$=0.046, $p_{FDR}$=0.036, $p_{FDR}$=0.005, $p_{FDR}$=0.010, and $p_{FDR}$=0.002, respectively).

Example 7: Multi-Omics Analysis Suggests Negative Correlations Between Elevated Clostridiales and Acetatifactor in CRL-Treated APP/PS1 Mice with Certain Unsaturated Fatty Acids and Microglial Gene Expression Multi-Omics Analysis Multi-omics analysis is performed according to the protocol of Liu et al., "Gut microbiota mediates intermittent-fasting alleviation of diabetes-induced cognitive impairment," *Nat. Commun.* 11:855 (2020). All omics acquired datasets (metagenomics, metabolomics, and transcriptomics) are filtered and normalized prior to applying the mixOmics package for data integration. A repeated double cross validation random forest (rdCV-RF) analysis method is then applied to establish repeated measures and pathway modules with an inner tuning and outer testing loop of 100 repetitions and subsequent cross-validation with 1000 permutations to evaluate the quality of the datasets. See Shi et al., "Variable selection and validation in multivariate modelling," *Bioinformatics* 35:972-980 (2019). This is followed by Data Integration Analysis for Biomarker discovery using Latent cOmponents (DIABLO) in the R package mixOmics, an integrated package of R's Bioconductor (mixOmics) that applies superior unsupervised integrative methods achieving predictive performance that has been shown to be comparable to other supervised methods. See Rohart et al., "mixOmics: An R package for 'omics feature selection and multiple data integration," *PLoS Comput. Biol.* 13:e1005752 (2017); Singh et al., "DIABLO: an integrative approach for identifying key molecular drivers from multi-omics assays," Bioinformatics 1; 35(17):3055-3062 (2019). DIABLO allows quality assessment of each supplied datasets as well as identification of common information between different datatypes, which ultimately allows for selection of a subset of molecular features in dependence of grouping that show interdependency. In this analysis, the mixOmics package used for data integration allows classification of performance, and acquisition of the correlation structure between datasets and single variables within and between the different datatypes.

Figure 4A:
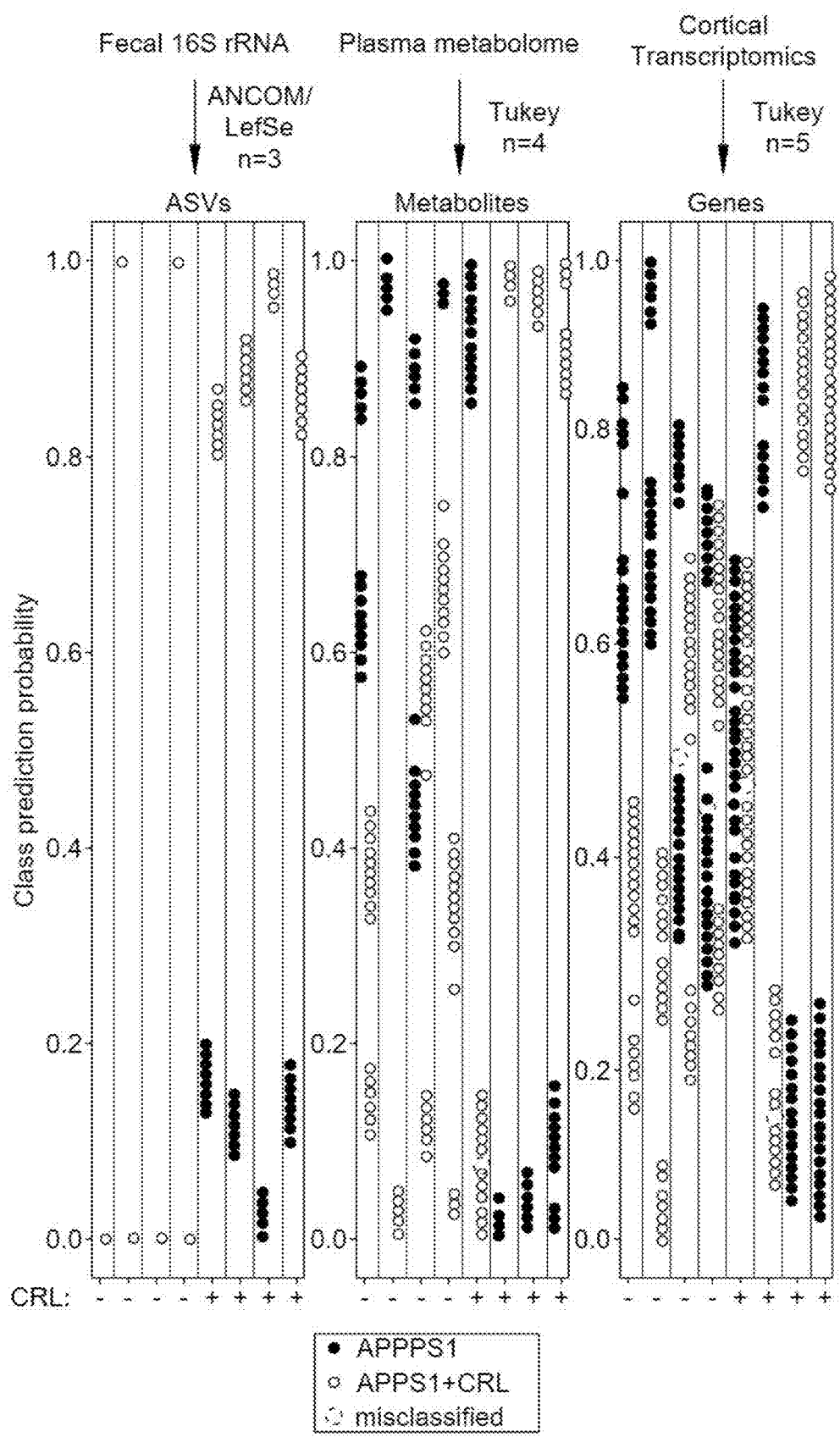
FIG. 4A presents results of a repeated double-cross validation with random forest (rdCV-RF) Multi-Omics analysis of metagenomic (fecal 16S rRNA), metabolomic (plasma untargeted metabolomics) and transcriptomic data (cortical RNAseq) displayed as a swim lane plot. Each swim lane displays one sample, and circled points indicate misclassified components. Each component is assessed by 200 double-cross validations to analyze class probabilities.

A total of three Omics datasets including metagenomic (fecal 16S rRNA), metabolomic (plasma untargeted metabolomics) and transcriptomic data (cortical RNAseq) are analyzed to investigate global treatment effects in APP/PS1 mice according to the Multi-Omics protocol described above. The focus of the integrated omics analysis is guided by the significant variables determined in the gut metagenomic, plasma metabolomic, and cortical transcriptomic datasets described above. However, to assess the variables' dependencies and strength in relation to CRL treatment, repeated double-cross validation with random forest (rdCV-RF) is applied on the identified significant features to prevent statistical overfitting. The rdCV-RF analysis reveals that 100% (determined by division of misclassified parameters and total number of parameters) of amplicon sequence variants (ASVs), 75% of metabolites, and 20% of transcripts are correctly classified, highlighting the weakness of the selected transcriptomic parameters (FIG. 4A). This is further established by examining the area under the curve (AUC) values used to evaluate model performance post rdCV-RF analysis. The ASVs and metabolite datasets have an AUC of 0.8 to 1, which suggests good model performance, while the transcriptomics dataset has only an AUC of 0.62, which suggests weak performance in accordance with the EdgeR analysis.

Figure 4B:
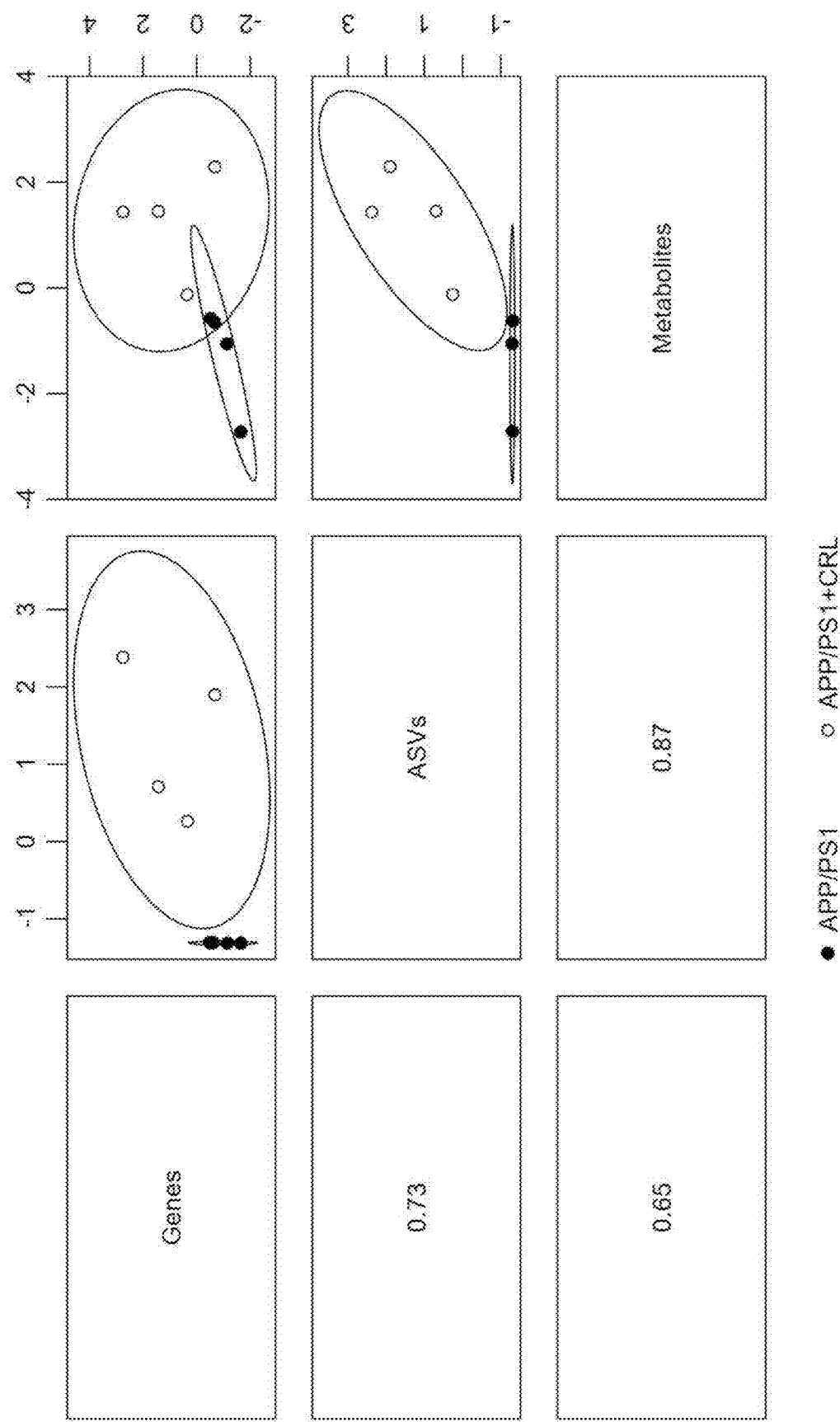
FIG. 4B displays a component correlation of the three datasets of FIG. 4A as determined by Data Integration Analysis for Biomarker discovery using a latent component method for Omics (DIABLO), identifying a strong correlation between amplicon sequence variants (ASVs) and metabolites.
Figure 4C:
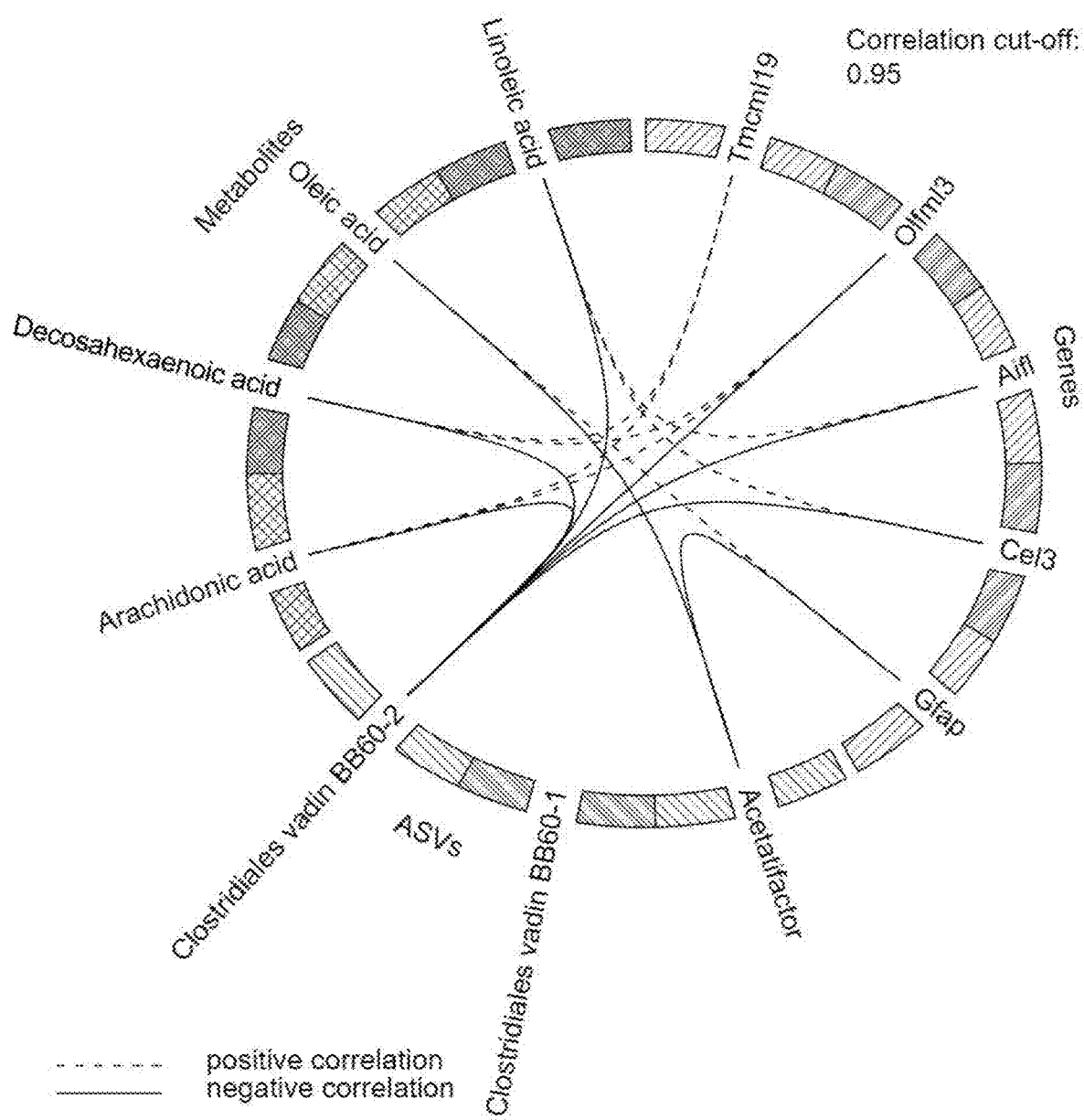
FIG. 4C is a Circos plot displaying the component correlations of FIG. 4B with a correlation cut-off of 0.95. A positive correlation pathway is indicated by a light line, and a negative correlation pathway is indicated by a dark line.

As shown in FIG. 4B, when determining correlations between the three datasets, the strongest correlation is observed between ASVs and metabolites (0.87), while metabolites and transcripts show the weakest interaction (0.65). That said, when correlations between variables are analyzed by DIABLO (with a correlation cut-off of 0.95), two separate, correlated pathways are identified: (1) Clostridiales vadin BB60 group uncultured bacterium 2 shows significant negative correlations with linoleic acid, arachidonic acid, docosahexaenoic acid, and genes associated with microglial gene expression, and (2) Acetatifactor is negatively correlated with GFAP and oleic acid (FIG. 4C). However, as noted above, the weakness of the transcriptomic dataset suggests that any correlations involving RNA transcripts be require further validation.

Example 8: Summary of Effects of CRL Treatment in APP/PS1 Mice

Figure 6:
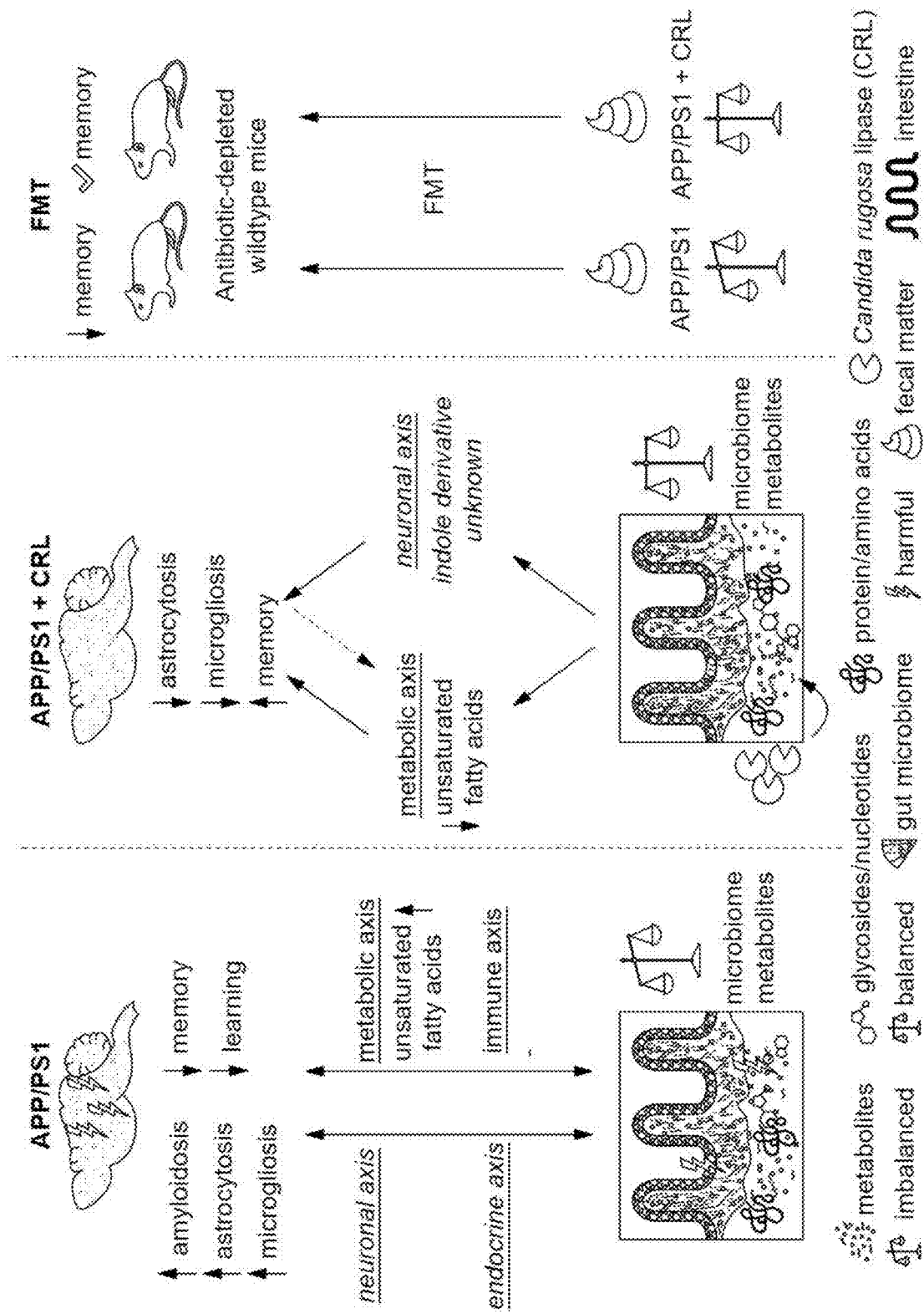
FIG. 6 (left and center panels) presents a graphical summary of results of the CRL treatment study in APP/PS1 mice having AD-like pathology. APP/PS1 mice treated with CRL (central panel) exhibit a balanced microbiome, decreased unsaturated fatty acids, decreased astrocytosis and microgliosis, and improved memory performance post-treatment.

The effects of CRL treatment in APP/PS1 mice having AD-like pathology are shown in FIG. 6 (left and center panels). As indicated in the figure, APP/PS1 mice treated with CRL for a two-month period exhibit improved microbiome and metabolite composition, improved astroglial and microglial activation, an improved fatty acids profile, and enhanced memory performance as compared to untreated APP/PS1 mice. These results establish that digestive enzymes are clinically relevant agents to treat neurodegenerative diseases such as AD, particularly in view of the fact that enzyme activity has been shown to decline with increasing age, potentially contributing to dysfunction of glucose and lipid metabolism. See Remond et al., "Understanding the gastrointestinal tract of the elderly to develop dietary solutions that prevent malnutrition," *Oncotarget* 6:13858-13898 (2015); Sato et al., "The roles of lipid and glucose metabolism in modulation of beta-amyloid, tau, and neurodegeneration in the pathogenesis of Alzheimer disease.," *Front. Aging Neurosci.* 7:199 (2015).

Example 9: Validation of Gut Changes Induced by CRL Treatment in APP/PS1 Mice in a Fecal Transplantation Model To categorially analyze whether the observed changes of AD-like pathology in APP/PS1 mice from the CRL treatment study were primarily driven by the gut-induced changes through CRL treatment, antibiotic-depleted wild-type mice (AIMD, disturbed microbiome) receive fecal matter transplants from the mice of the CRL treatment study. AIMD mice exhibit not only a disturbed microbiome, but also declined cognition post antibiotic treatment. It is hypothesized that fecal matter transplants to AIMD mice can, once the microbial communities establish themselves in the transplant recipients, mitigate cognition deficits if originating from Wt donors as well as treated APP/PS1 mice. It is also hypothesized that no improvement in cognition will occur in AIMD mice receiving fecal matter from untreated APP/PS1 mice or sham transplants.

Figure 5A:
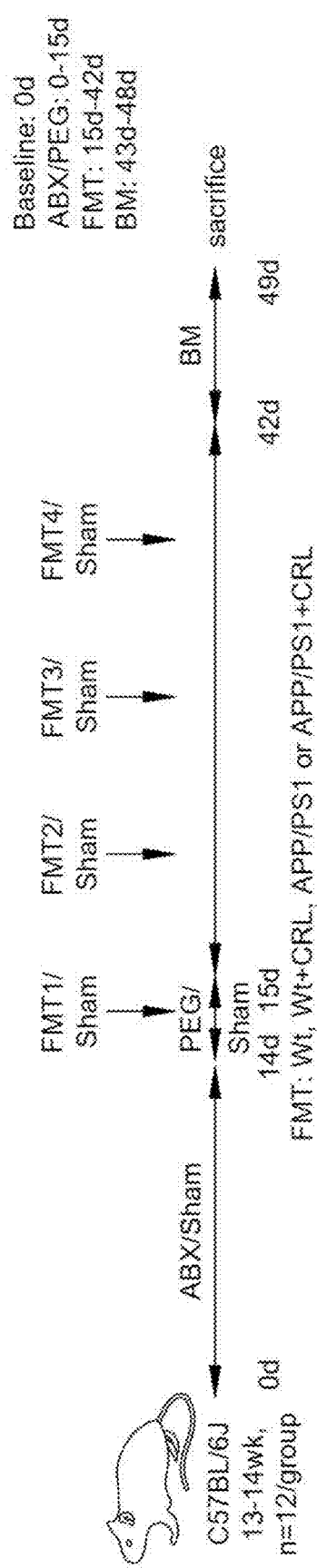
FIG. 5A presents a study design for fecal matter transplantation (FMT) of fecal samples collected at weeks 5 and 8 from all groups of mice in the study described in FIG. 1A into antibiotic-induced microbiome-depleted (AIMD) Wt mice. This study investigates whether the observed changes of AD-like pathology in APP/PS1 mice of the study of FIG. 1A are primarily driven by changes in the gut induced by CRL treatment. Prior to fecal matter transplantation (FMT), fecal samples of the AIMD Wt mice exhibit a 50% reduced amounts of amplicon sequence variants (ASVs). (ABX=antibiotics; PEG=polyethylene glycol; BM=Barnes Maze test).
Figure 5B:
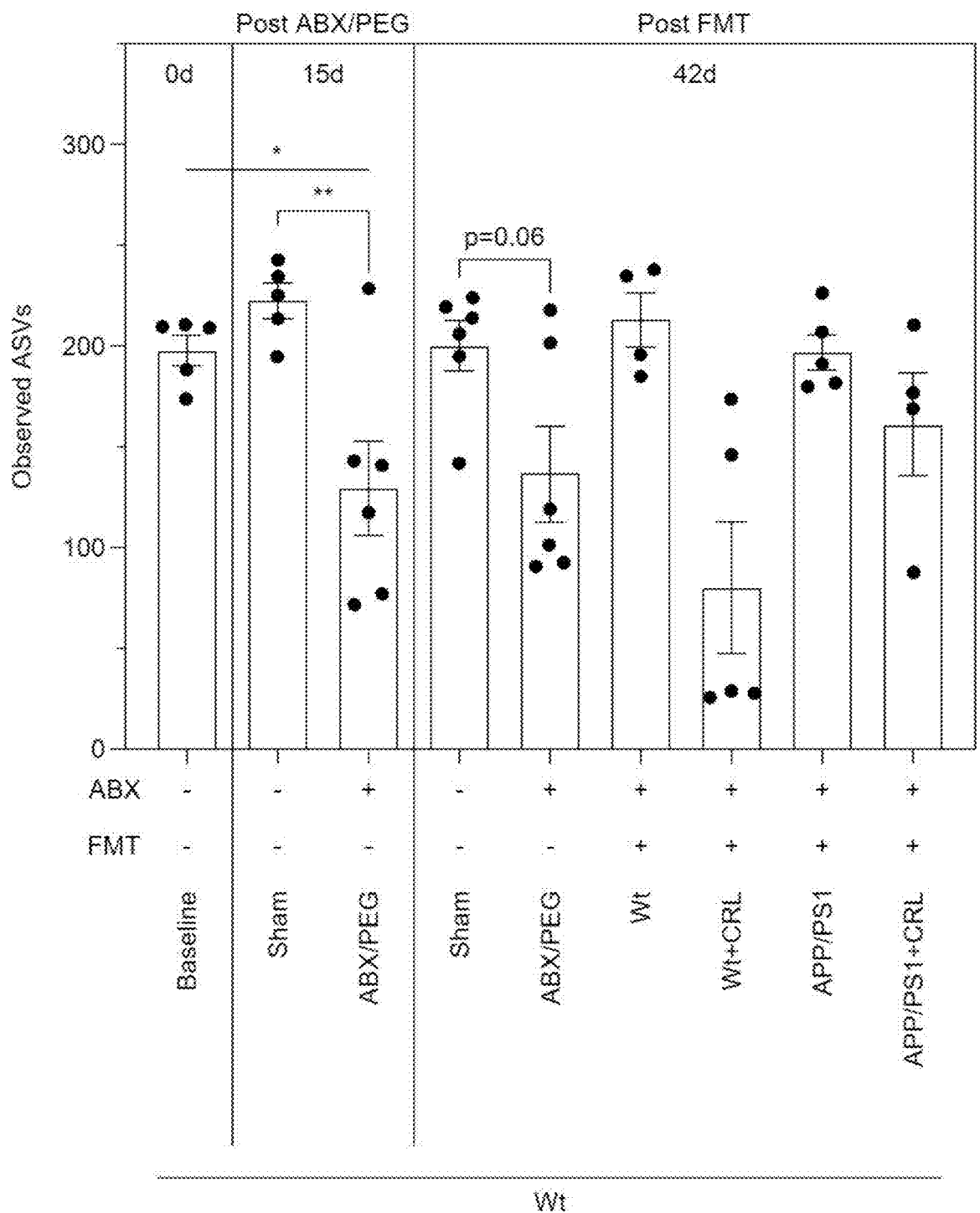
FIG. 5B presents a fecal α-diversity analysis in AIMD Wt mice at day 0, at day 15 post-antibiotic treatment and bowel cleanse, and at day 42 after four rounds of fecal matter transplantation. Fecal α-diversity is measured by counts of observed ASVs. Significance for α-diversity was assessed by Kruskal-Wallis H test and pairwise comparisons; *p<0.05, **p<0.01.
Figure 5C:
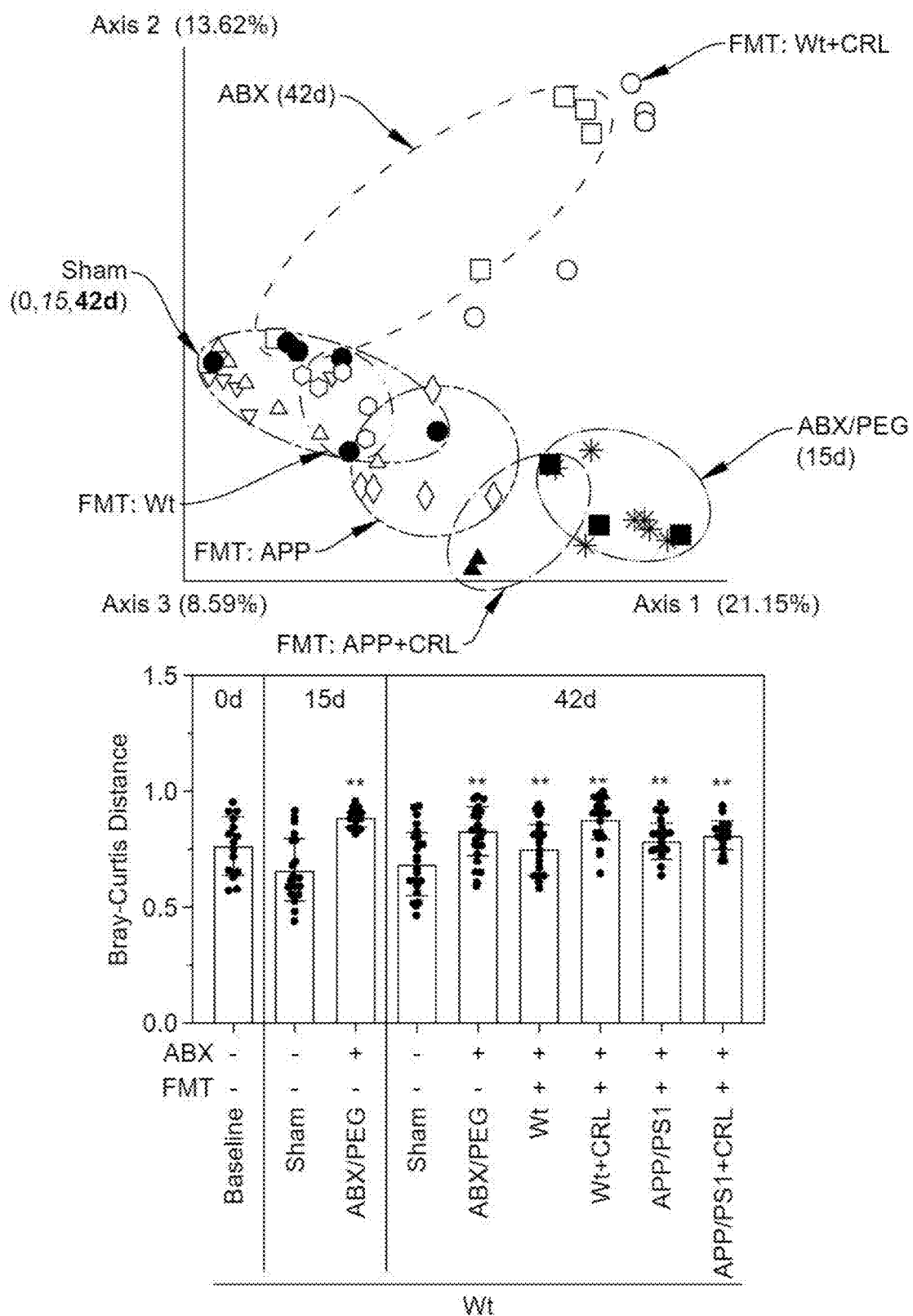
FIG. 5C presents a fecal β-diversity of all fecal matter transplant study groups analysis measured by Bray-Curtis distance. While Sham groups co-located and ABX and PEG groups co-located, animals receiving FMTs were distinct but located separately. The ABX group recovered partially. For analysis, the group receiving Wt+CRL FMT (abnormal α- and β-diversity) are fainted throughout microbial analysis, although no impact on behavioral data is observed. Significance of β-diversity is assessed by permutational multivariate analysis of variance (PERMANOVA). (Significance: *=p<0.05; **=p<0.01).

Microbial composition analysis (observed ASVs) shows 50% reduced amounts of observed ASVs in fecal samples post-antibiotic treatment (FIG. 5B). As shown in FIG. 5B, after fecal matter transplantation, at day 42 all animals receiving FMTs from Wt animals (untreated) and APP/PS1 animals (treated and untreated) exhibit comparable ASVs when compared to the Sham group. In contrast, the ABX group, which received sham FMTs, maintains a reduction of 30 to 40% observed ASV levels after 42 days. These results suggest that the gut microbiome was successfully disturbed after ABX treatment. Furthermore, as shown in FIG. 5C, fecal β-diversity of the Sham group which received neither antibiotics nor fecal matter transplants co-locates, and shows no distortion at all sampling timepoints (0, 15 and 42 days). However, the ABX (after antibiotics) and PEG (after bowel cleanse) group (day 14 and 15, respectively) show a significant dimensional separation of the Bray-Curtis distance from the Sham group. After 42 days, β-diversity in mice that received antibiotics and sham FMT (ABX), or antibiotics and FMT from treated Wt mice (Wt+CRL), also separate from the Sham group, while antibiotic-depleted mice receiving fecal matter from APP/PS1, APP/PS1+CRL and Wt mice shift back towards the Sham group. These results suggest partial recovery of microbiota in these groups post antibiotic exposure.

Figure 5D:
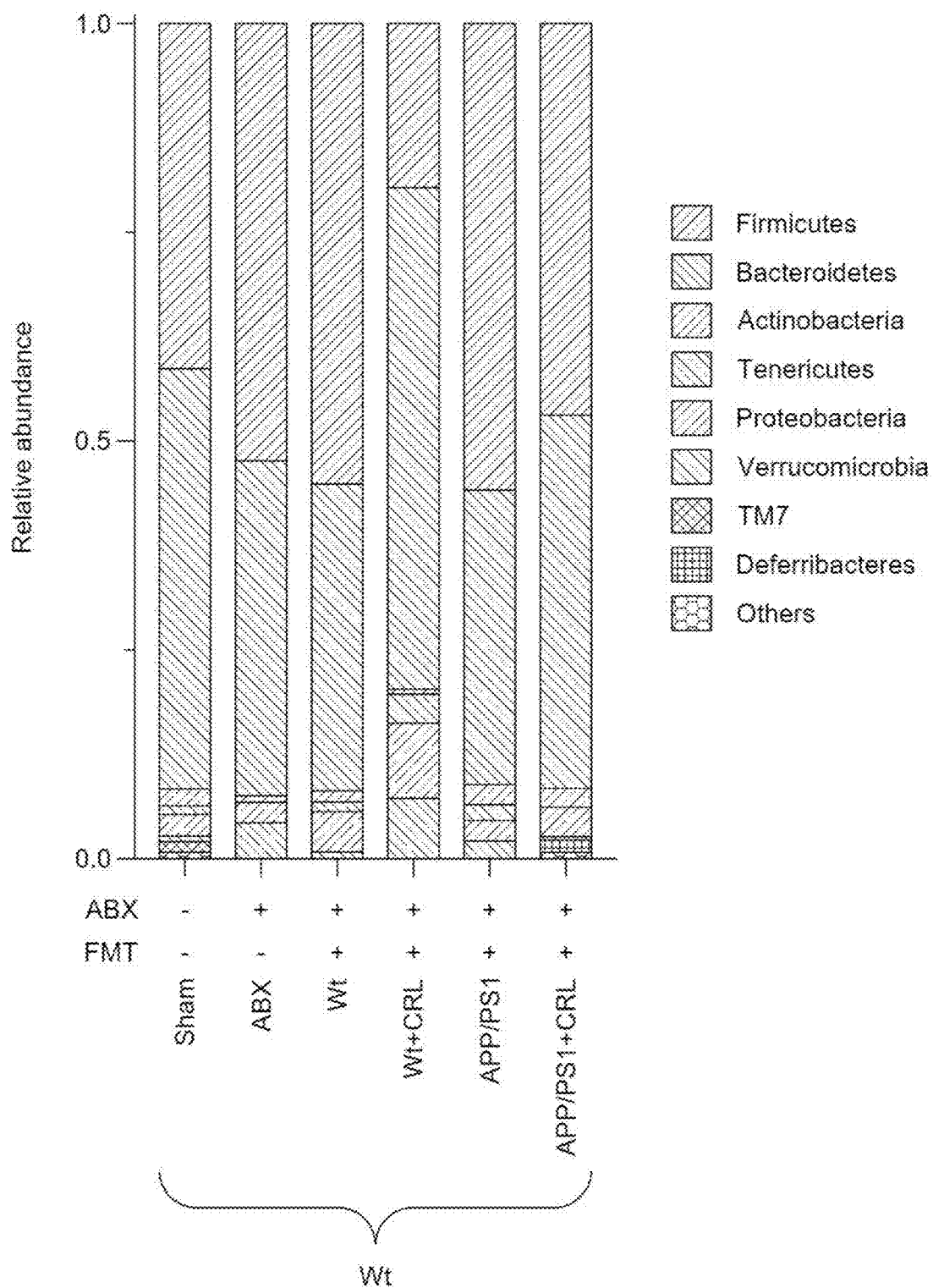
FIG. 5D presents a taxonomy analysis of phyla abundance in fecal samples post-transplantation. The most prominent taxonomical difference between the ABX, Wt+CRL and APP/PS1 groups compared to the other three groups is an increased abundance of each of Verrucomicrobia and Firmicutes, and a decreased abundance of Bacteroidetes.
Figure 5E:
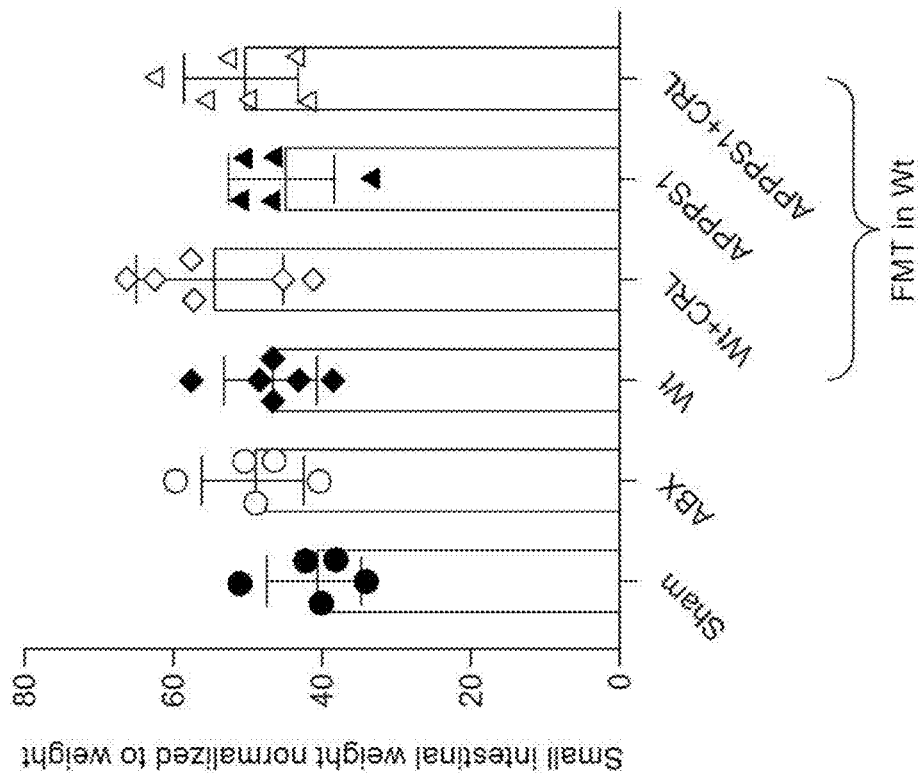
FIG. 5E compares cecal weight measurements and small intestinal weight measurements among all fecal matter transplant study groups, showing enlarged ceca in the Wt+CRL group. Significance is assessed by 2-way ANOVA and post-hoc Tukey correction. (Significance: ****=p<0.0001).
Figure 5E:
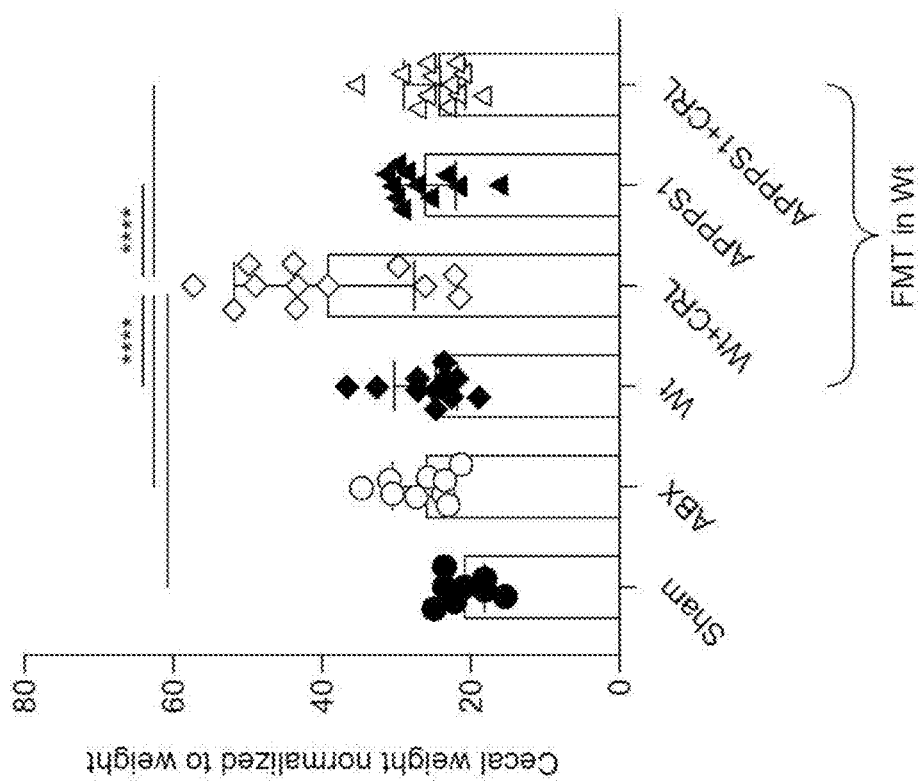
Figure 5F:
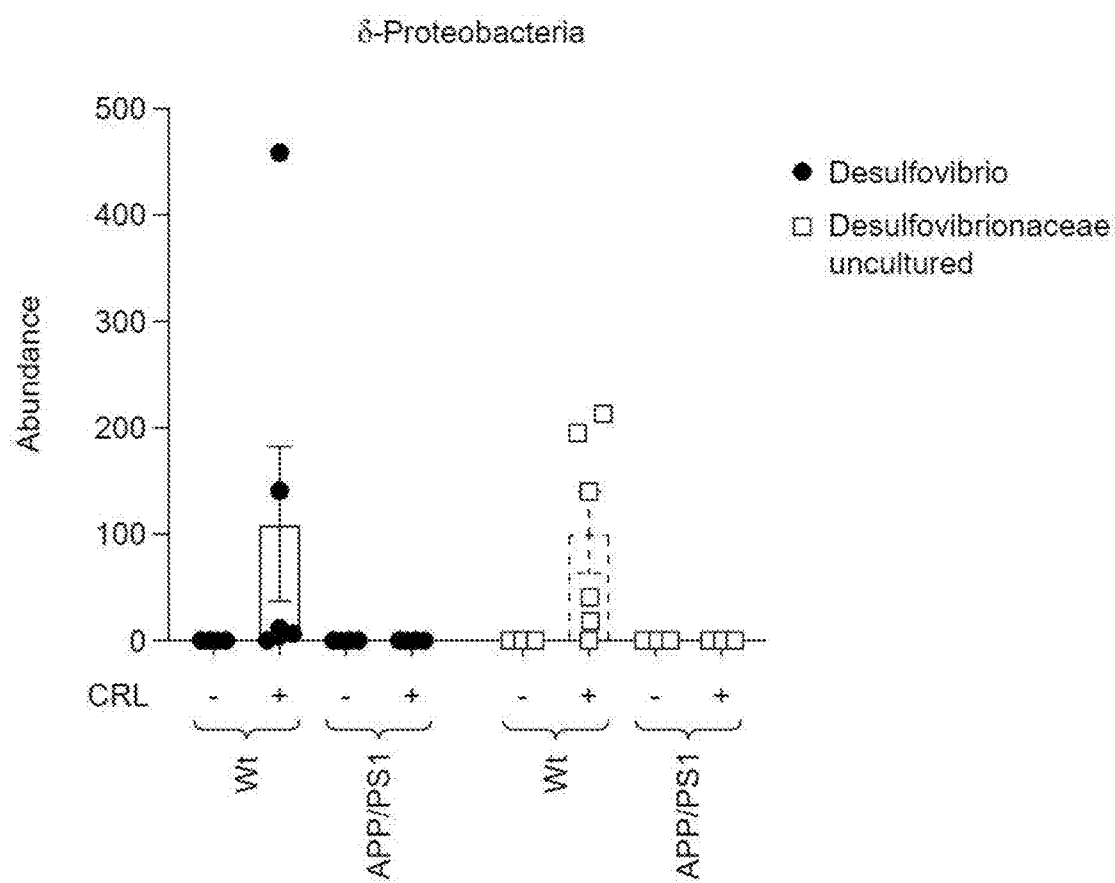
FIG. 5F presents an analysis of composition of microbiomes (ANCOM) of fecal matter transplant study taxonomical data, showing increased levels of 5-Proteobacteria in the Wt+CRL group.
Figure 5G:
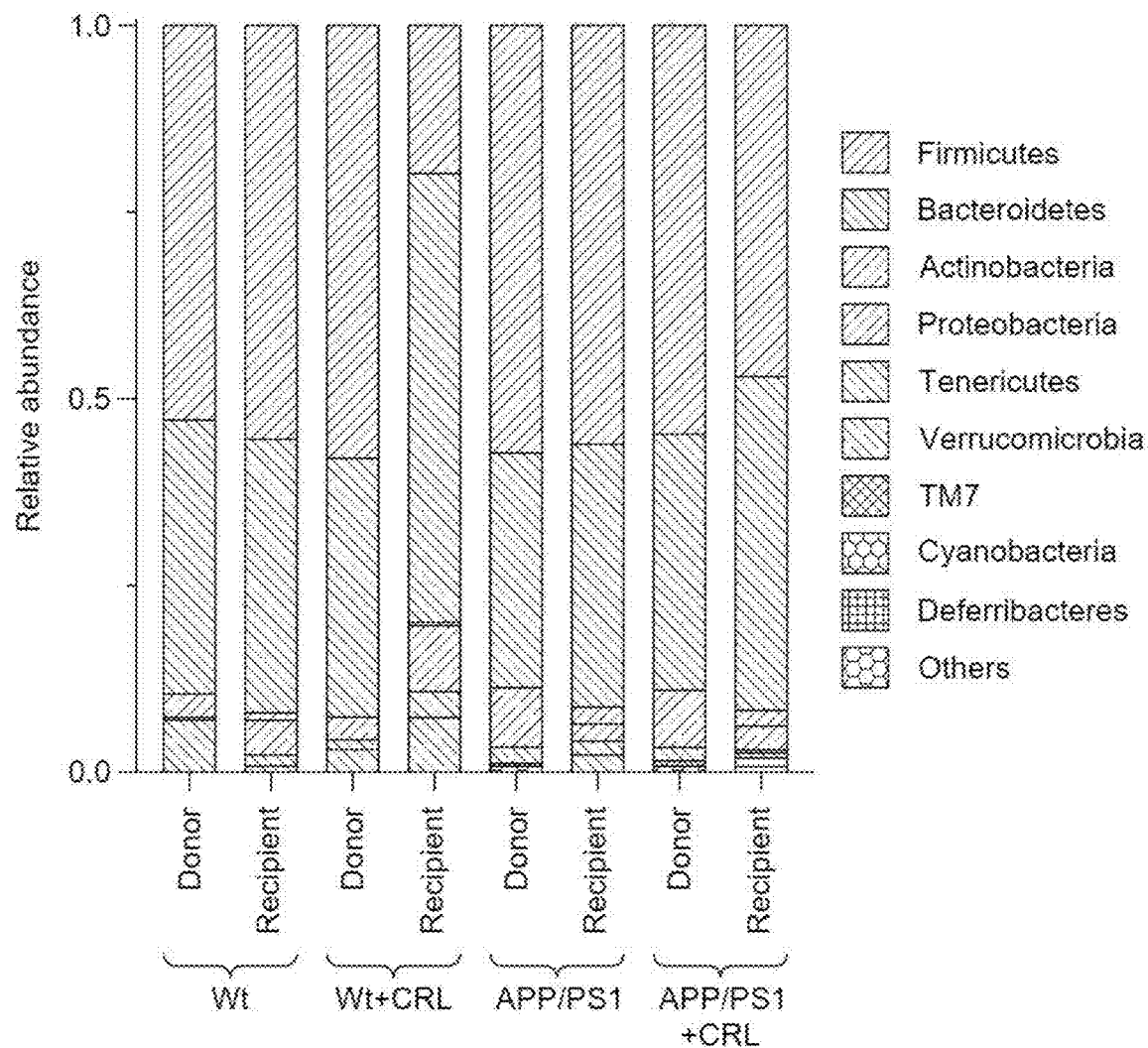
FIG. 5G presents a taxonomy analysis of donor and receiver fecal matter for all fecal matter transplant study groups, revealing an imbalance in the Wt+CRL recipient group. The taxonomic imbalance, along with the increased cecal weight and increased 5-Proteobacteria in Wt+CRL mice as provided in FIGS. 5E-5F, is indicative of an infection in the Wt+CRL recipient group, and may originate from the oral gavage procedure.

The most prominent taxonomical differences between ABX, Wt+CRL and APP/PS1 groups compared to the other three groups are an increased abundance of Verrucomicrobia and Firmicutes, and decreased Bacteroidetes FIG. 5D). Also, in view of the unusual results of the Wt+CRL group in shown FIG. 5D, additional analyses are performed, showing abnormal phyla levels, enlarged ceca, and increased levels of δ-Proteobacteria in this group, which suggests the occurrence of an infection in this group during FMT administration (FIGS. 5E-5G). For this reason, the data shown in FIGS. 5A-5D for Wt+CRL mice are excluded, as indicated by light grey data points/bars for this group. In addition, as shown in FIG. 5G, donor and recipient fecal material show no major differences between phyla for any recipient group other than the excluded Wt+CRL recipient group.

Figure 5H:
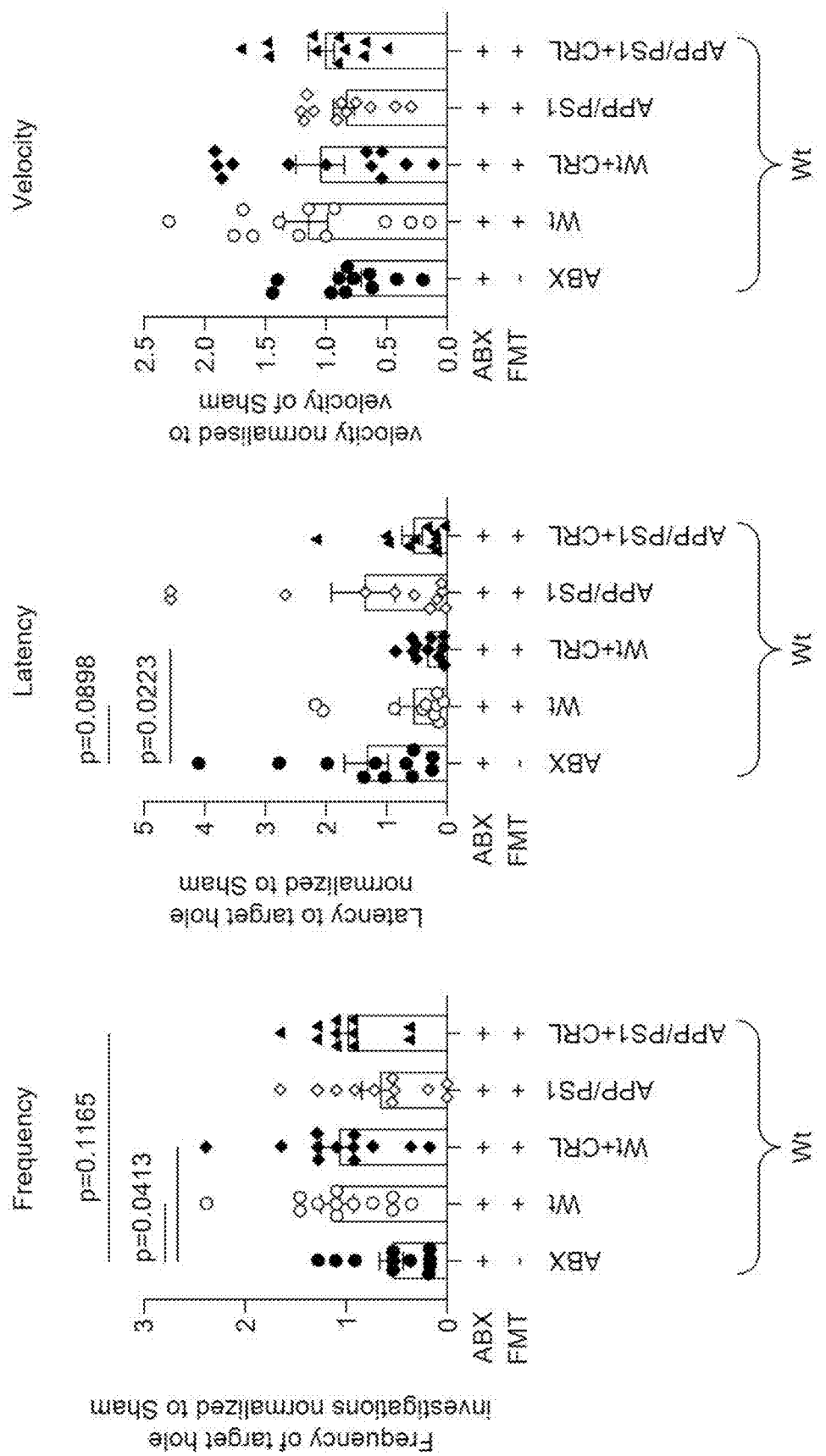
FIGS. 5H-5K presents Barnes maze probe and acquisition results for the fecal matter transplant study. Results are normalized to Sham group to reduce complexity of data analysis. Analysis of the data reveals that AIMD Wt mice receiving no FMTs, or alternatively, receiving FMTs from untreated APP/PS1 mice, perform similar or worse than all other groups in terms of frequency of target hole investigation, latency to locate the target hole, velocity, time spent at target hole, cumulative distance, and primary path length. Changes in latency, escape latency cumulative distance, velocity, and path length over a 4-day period are also investigated.
Figure 5I:
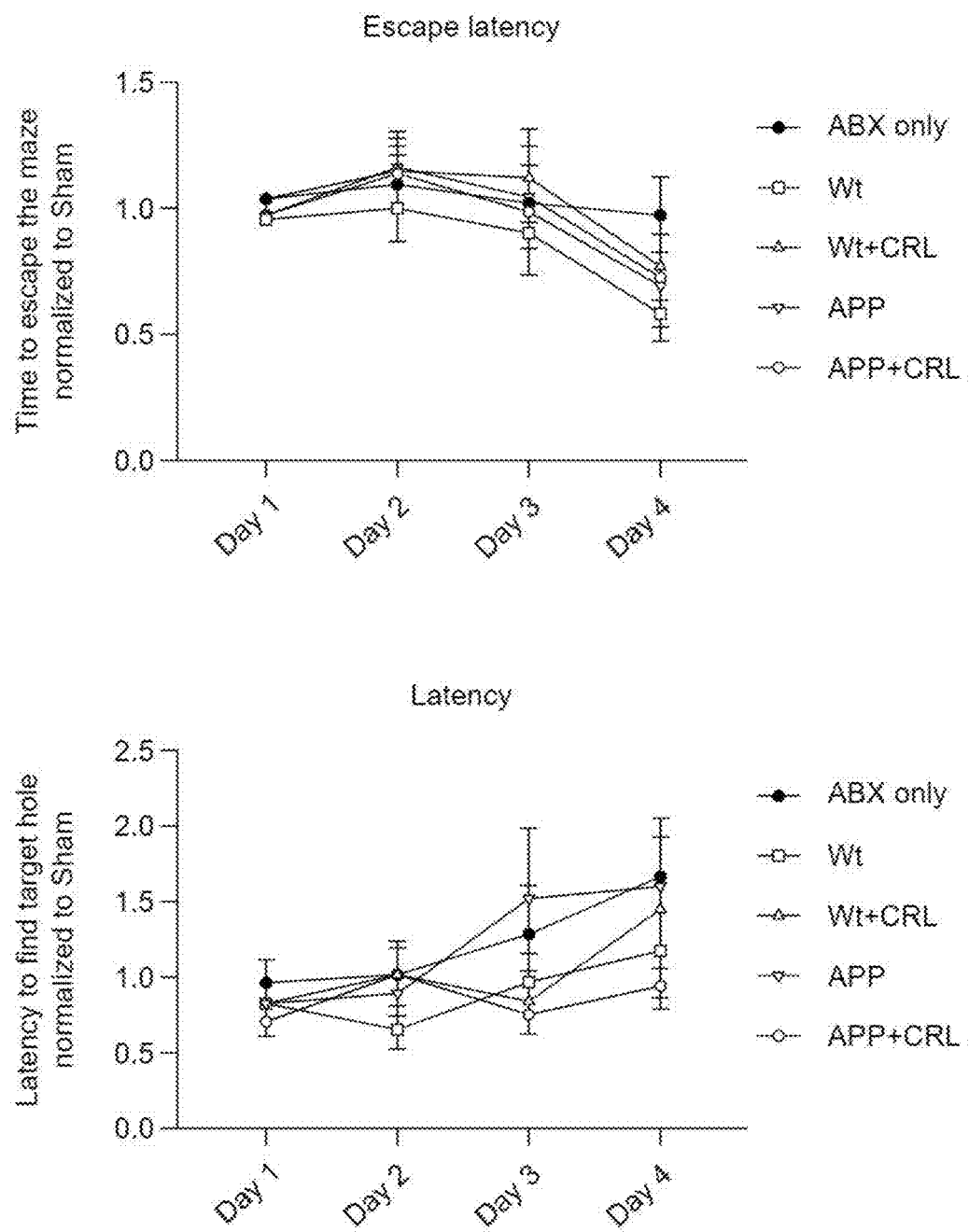
Figure 5J:
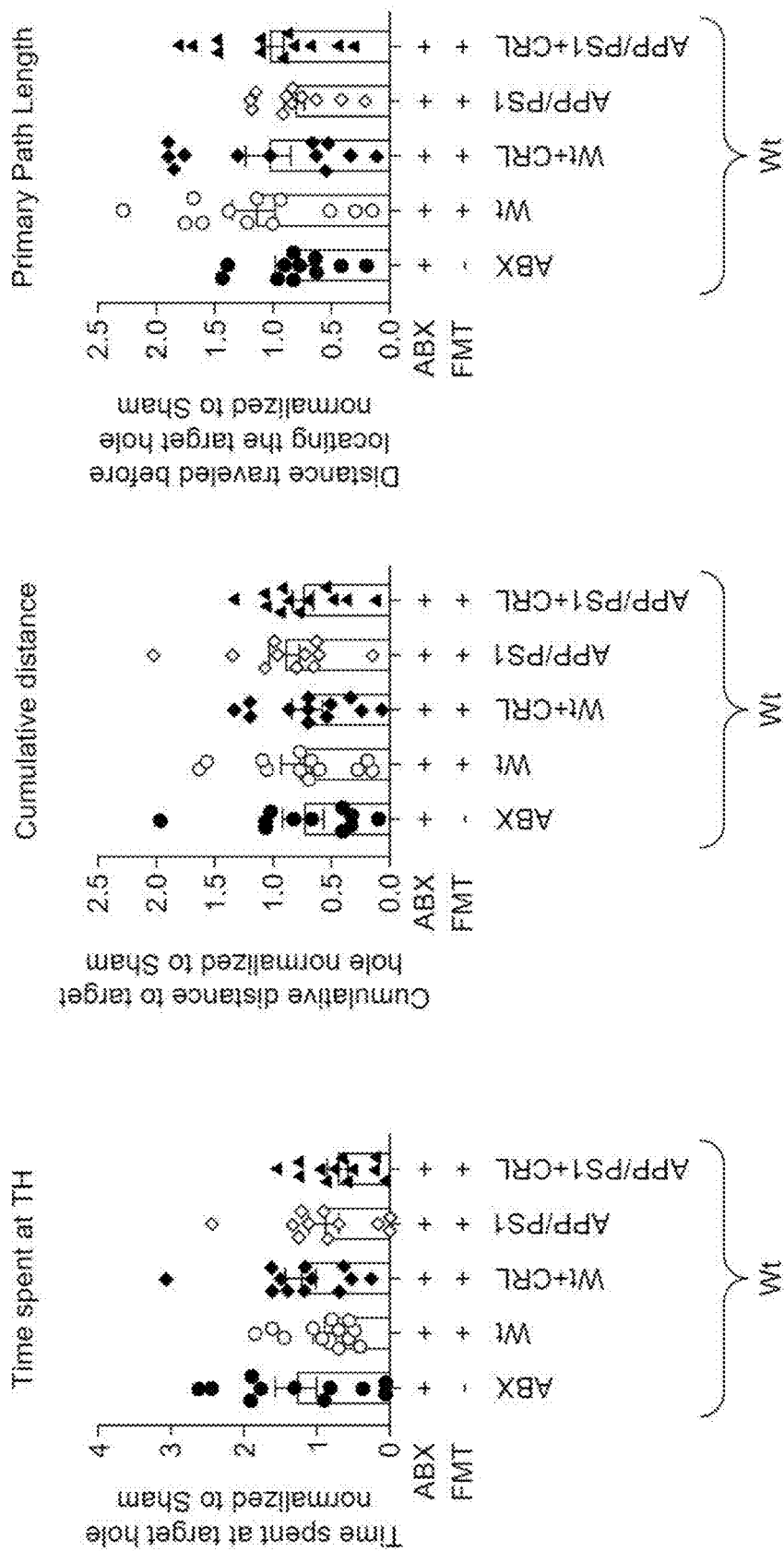
Figure 5K:
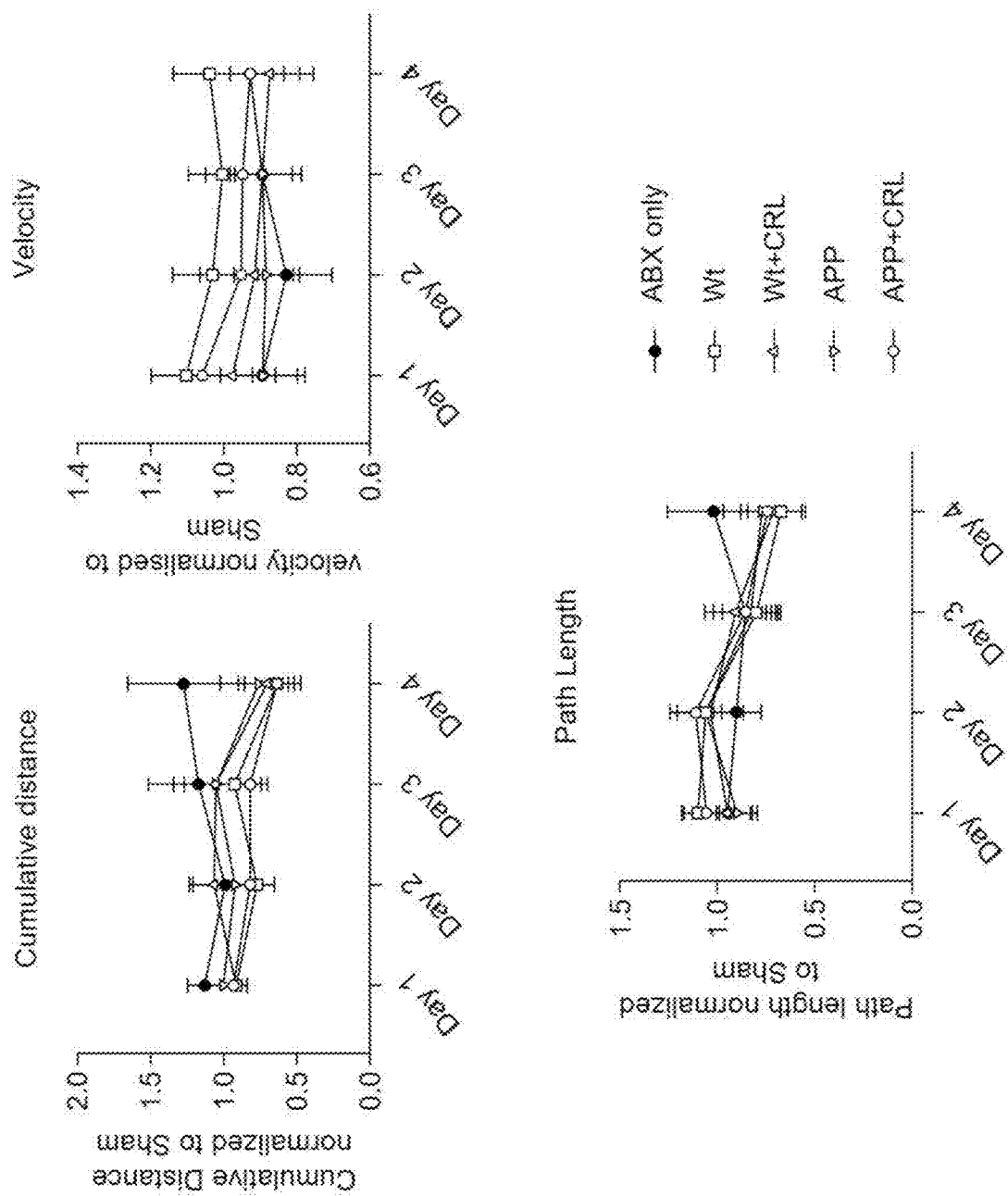

After microbial depletion and recolonization, the mice are analyzed in relation to cognitive performance by the Barnes maze experiment described in Example 1, since treatment with antibiotics and the associated dysbiosis have been reported to inhibit learning and long-term memory. See Frohlich et al., "Cognitive impairment by antibiotic-induced gut dysbiosis: Analysis of gut microbiota-brain communication," *Brain Behav. Immun.* 56:140-155 (2016). All groups are normalized to Sham and compared to the ABX group that did not receive FMTs. None of the groups show overt differences during acquisition trials in the Barnes maze (FIGS. 5H-5I, and FIG. 5K). In probe trials, AIMD mice receiving FMTs from untreated APP/PS1 mice show impaired memory (APP/PS1; frequency: 68.33%, p=0.919; latency: 140.96%, p=0.661; FIGS. 5H-5J), similar to AIMD mice not receiving FMTs (ABX; frequency: 55%; latency: 136.77%; FIGS. 5H-5J). On the other hand, AIMD mice receiving FMTs from CRL treated APP/PS1 mice exhibit a trend for improvement in memory (APP/PS1+CRL; frequency: 100%, p=0.116; latency: 60.24%, p=0.257; FIGS. 5H-5J), similar to AIMD mice receiving fecal matter from untreated Wt animals (Wt; frequency: 108.47%, p=0.041; latency: 58.83%, p=0.067). Also, despite the fact that AIMD mice receiving FMTs from Wt+CRL mice likely experienced a treatment-related infection, these mice perform as well as AIMD mice receiving FMTs from untreated Wt mice in the Barnes maze (Wt+CRL; frequency: 108.47%, p=0.041; latency: 35.71%, p=0.022; FIGS. 5H-5J).

Example 10: Summary of the Effects of Transplantation of Fecal Matter from APP/PS1 and APP/PS1+CRL Mice into Antibiotic-Depleted Wildtype Mice The effects of transplantation of fecal matter from untreated and CRL-treated APP/PS1 mice from the study of FIG. 2A into antibiotic-depleted wildtype mice are shown in FIG. 6 (right panel). As indicated in the figure, transplantation of fecal matter of APP/PS1+CRL mice leads to enhanced memory function, while transplantation of fecal matter from untreated APP/PS1 mice maintain memory deficits. As provided above, increased exploratory behavior and enhanced memory function in a Barnes Maze experiment in animals correlates to increased cognition in humans, as assessed by, e.g., a MoCA, a MMSE, and/or a Mini-Cog.

In summary, it is observed that CRL treatment causes profound changes in the gut microbiome of APP/PS1 mice that can positively impact memory, as demonstrated by fecal matter transplantation into memory impaired AIMD Wt mice and subsequent behavioral studies. Hence, alteration of the microbial and metabolic composition by CRL treatment causes mitigation of AD-like pathology and normalizes aberrant behavior in APP/PS1 mice.

Example 11: Double-Blinded, Randomized, Placebo-Controlled Clinical Study to Investigate the Effect of CRL on Memory Performance Study background. Memory is a complex cognitive function that plays a vital role in our daily lives, influencing everything from learning and decision-making to our sense of identity and personal experiences. This study investigates the relationship between CRL activity and memory function. A comprehensive study on the effect of CRL on memory will enable the development of a CRL-containing dietary supplement product to enhance memory functions in subjects. In the study, the effects of CRL treatment on memory performance, cognitive function, and mental wellbeing are assessed. The study will not only provide an understanding of the effect of lipase on memory, but also the broader implications of a patient's microbiome and lipid metabolism on cognitive function.

Subject Selection Criteria.
 a. Recruitment and Informed Consent: Eligible participants are recruited based on specific inclusion and exclusion criteria. Informed consent is obtained from all participants before their participation in the trial.
 b. Randomized, Placebo-Controlled Design: Participants are randomly assigned to either the lipase treatment group or the placebo group. This double-blind design ensures that neither participants nor researchers are aware of group assignments.
 c. Participants: A total number of 50 subjects are assigned to each of the lipase treatment group or the placebo group.
 d. Baseline Assessment: All participants undergo a comprehensive baseline health assessment, including medical history, memory tests, cognitive assessments, and lipid metabolism profile evaluations. Also, dietary habits, physical activity, and psychological well-being, are chronicled to establish a baseline health profile for each subject. Blood samples will be collected from each subject at the time of enrollment. For the purposes of this study, each participant is considered to have entered into the study once a consent form has been obtained. Each subject will be encouraged to fast 8-12 hours prior to the blood draw, but non-fasting samples will be collected if subjects are unable to do so. Approximately 30 ml of blood is then collected for a Biomarker Analysis, which is an exploratory analysis that may reveal correlations between lipid metabolism profiles and memory improvement, shedding light on the underlying mechanisms. For the blood sample, plasma and buffy coat are isolated using the established standard operating procedures, and samples are aliquoted and stored at −80° C. Additionally, demographic information is obtained from each subject, including age, education, gender, ethnicity, past disease history, and types of medication previously used and/or currently being used to examine their influence on biomarker levels. Finally, stool samples are collected from subjects to analyze the composition and diversity of their gut microbiota; high-throughput DNA sequencing and metagenomic analysis is employed to characterize the microbiome.

e. Inclusion criteria: Every subject included in the study is 35 years or older. Every subject included in the study is also able to understand written and spoken English. Participants are also able to read, write and speak the language in which psychometric tests are provided with visual and auditory acuity (corrected) that are sufficient for accurate testing.

f. Exclusion criteria: A subject is excluded from the study if they are being treated by a physician for any of the following:
  i. Cancer (except for non-melanoma skin cancers);
  ii. Chronic infectious disease;
  iii. Liver disease;
  iv. Multiple sclerosis;
  v. Stroke;
  vi. Serious psychiatric condition;
  vii. Hospitalized in the last 5 years for alcohol or drug dependence, depression, or post-traumatic stress disorder (PTSD); or
  viii. Diagnosis of MCI, dementia, or any type or Parkinson's disease.

Treatment of subjects. The treatment group receives a prescribed dosage of CRL dietary supplementation, while the placebo group receives identical-looking placebo capsules. Treatment is administered for a specified duration, e.g., 24 weeks.

Data collection. Following the informed consent process, the following procedures are performed. Although this order of administration of the procedures listed below is not strictly required, adherence to this order is strongly encouraged. Clinical survey assessments are self administered on paper format, or data is entered by the subject on a standard personal computer. A study visit may take 3-4 hours to complete, and subjects may be asked to return for additional visits within weeks or months, as needed.

a. Vital signs: Height, weight, blood pressure are recorded after being seated for 5 minutes. Pulse rate and time of this assessment are also recorded.

b. Blood sample collection: Time of collection, and last mealtime (or food consumed) with details of contents are recorded. If the subject has fasted, they consume a snack (from a variety of choices) or light meal (if they wish to bring to the clinic) prior to the blood sample collection.

c. Demographics: Subjects report information on age, education, gender, ethnicity, marital status, GW duty service (active vs. reserve/National Guard), military rank and current military status.

d. Medical Conditions: Subjects complete a checklist indicating the presence or absence of 30 medical conditions and explaining how (self/doctor) and when (year) that the condition was diagnosed, An open ended request for other medical history is also included.

e. Medication List: Subjects provide a list of all medications and over the counter dietary supplements being taken. Special attention to ensure that subjects record any Fish Oil dietary supplements being taken, as well as multi-ingredients dietary supplements that may include fish oil being taken, and the details thereof, are recorded.

f. CNS Vitals (CNS Vital Signs, LLC): CNS Vitals is a battery of neuropsychological tests that are administered on a computer or tablet. These tests are designed to be user-friendly and can be completed in a relatively short period of time, typically ranging from 30 to 45 minutes. The assessment battery includes tasks such as:
  i. Verbal Memory: Assessing the ability to remember and recall verbal information.
  ii. Visual Memory: Evaluating the capacity to remember and recall visual information.
  iii. Processing Speed: Measuring how quickly individuals can process and respond to information.
  iv. Attention: Assessing sustained and divided attention abilities.
  v. Executive Function: Evaluating skills such as planning, problem-solving, and cognitive flexibility.
  vi. Reaction Time: Measuring the speed of cognitive processing and motor response.

Additional battery tests may include determination of Neurocognition Index (NCI), and Composite Memory, Psychomotor Speed, Cognitive Flexibility, and Motor Speed tasks. CNS Vitals provides standardized scoring and generates comprehensive reports that summarize the subject's performance across different cognitive domains. These reports may assist in diagnosing cognitive impairments, tracking changes in cognitive function over time, and developing personalized treatment plans. As shown in Table 1, battery test results are expressed either as a standard score (SS), which is normalized with a mean of 100 and a standard deviation of 15, or a percentile rank (PR), which is an index on a scale of 1 to 99 of how the test subject scored compared to other subjects on of the same age.

TABLE 1

CNS Vitals Standard Scores and Percentile Ranks

| Neurocognitive Classification | Description | Standard Score (SS) Range | Percentile Rank (PR) Range |
|---|---|---|---|
| Above | High cognitive function; high cognitive capacity | >110 | >74 |
| Average | Normal cognitive function; normal cognitive capacity | 90-110 | 25-74 |
| Low Average | Slight cognitive deficit; slight cognitive impairment | 80-90 | 9-24 |
| Low | Moderate cognitive deficit; cognitive impairment possible | 70-79 | 2-8 |
| Very Low | Cognitive deficit; cognitive impairment likely | <70 | <2 |

For each battery test, if a subject's standard score (SS) is greater than 109, or within a percentile range (PR) of >74, the test subject is considered to be a high functioning test subject. A test subject with normal (average) function has a SS that is between 90 to 109, or a PR of 25 to 74. A test subject with low average function has a SS that is between 80 to 90, or a PR of 9 to 24. A test subject with low (below average) function has a SS that is between 70 to 79, or a PR of 2 to 8. Finally, a test subject with very low function has a SS that is <70, or a PR that is <2. See, e.g., Gualtieri et al., "Reliability and validity of a computerized neurocognitive test battery, CNS Vital Signs," *Arch Clin Neuropsychol* 21(7):623-643 (2006); and "CNS Vital Signs Interpretation Guide," available online at www[dot]cnsvsI[dot]com/SampleReports/CNS%20VS%20Example%20Report[dot]pdf. An increase in a subject's SS of 10 or more, or an increase in PR of at 5 or more, following CRL treatment indicates a moderate improvement in memory and cognition. Further, an increase of 20 or more in a subject's SS, or an increase of 15 or more in a subject's PR, following CRL treatment is indicative of significant memory and cognitive improvement.

g. Symbol digit modality test (SDMT): The SDMT is a neuropsychological assessment tool used to evaluate cognitive processing speed, attention, and working memory. It measures the ability to match symbols quickly and accurately to their corresponding digits according to a given key. During the test, participants are presented with a key that pairs specific symbols with corresponding digits (e.g., squares with numbers 1-9). They are then given a series of symbols and asked to orally identify and verbally express the digit associated with each symbol as quickly as possible within a specified time limit. The test typically consists of multiple trials, with varying lengths and complexity. The SDMT provides measures of both accuracy and speed in completing the task. Performance on the SDMT is assessed based on the total number of correct responses within the given time frame, as well as the time taken to complete the task. A subject's SDMT score is the summation of the number of correct substitutions within a time interval of 90 seconds, with a maximum score of 110. See, e.g., Sheridan et al., "Normative Symbol Digit Modalities Test performance in a community-based sample," *Archives of Clinical Neuropsychology* 21:23-28 (2006). An increase in a subject's SDMT score by 10 or more following CRL treatment indicates a moderate improvement in memory and cognition, while an SDMT score increase by 20 or more following CRL treatment is indicative of a significant memory and cognitive improvement.

h. Profile of mood state (POMS): The POMS is a psychological assessment tool used to measure various mood states and emotional experiences. It assesses individuals' subjective feelings across different affective domains, providing insights into their emotional well-being and psychological functioning. The POMS consists of a list of adjectives that describe different mood states, such as tension, depression, anger, vigor, fatigue, and confusion. Participants rate the extent to which they have experienced each mood state over a specific time period, typically within the past week, using a Likert scale ranging from 0 (not at all) to 4 (extremely). The POMS assesses six primary mood factors:

i. Tension-Anxiety: This factor assesses feelings of nervousness, tension, and apprehension.
ii. Depression-Dejection: This factor evaluates feelings of sadness, hopelessness, and discouragement.
iii. Anger-Hostility: This factor measures feelings of irritability, resentment, and anger.
iv. Vigor-Activity: This factor assesses feelings of energy, enthusiasm, and vigor.
v. Fatigue-Inertia: This factor evaluates feelings of tiredness, lethargy, and lack of energy.
vi. Confusion-Bewilderment: This factor measures feelings of mental cloudiness, confusion, and difficulty concentrating.

The POMS provides individual scores for each mood factor, as well as a total mood disturbance score, which reflects overall emotional distress. Higher scores on the negative mood factors (e.g., tension-anxiety, depression-dejection, anger-hostility, fatigue-inertia, confusion-bewilderment) indicate greater levels of distress, while higher scores on the positive mood factor (vigor-activity) reflect greater levels of positive mood and energy. Also, a Total Mood Disturbance (TMD) can be calculated by summation of the negative scores followed by subtraction of the positive scores, where a higher score indicates a greater degree of mood disturbance. A TMD ranges between 0 to about 200. See, e.g., McNair et al., *POMS Manual for the Profile of Mood States*, San Diego, CA: Educational and Industrial Testing Service (1971). A decrease in one or more of a test subject's negative mood scores by 1 following CRL treatment indicates a moderate improvement in the mood state of the subject. Similarly, an increase in one or more of a test subject's positive mood scores by 1 following CRL treatment also indicates a moderate improvement in mood state. Also, a decrease in one or more of a test subject's negative mood scores by 2 or 3 following CRL treatment indicates a significant improvement in the mood state of the subject. Similarly, an increase in one or more positive mood scores by 2 or 3 following CRL treatment also indicates a significant improvement in mood state. The original POMS, the short form of the POMS, or both may be administered to the subject.

i. Pittsburgh Sleep Quality Index (PSQI): PSQI is a widely used self-report questionnaire designed to assess sleep quality and disturbances over a one-month time interval. It provides a comprehensive evaluation of various aspects of sleep, including duration, latency, efficiency, disturbances, and subjective sleep quality. The PSQI consists of 19 items that assess seven components of sleep quality:

i. Subjective Sleep Quality: This component assesses overall satisfaction with sleep quality, including perceived depth and restfulness of sleep.
ii. Sleep Latency: This component measures the time taken to fall asleep after bedtime.
iii. Sleep Duration: This component evaluates the total duration of sleep obtained during the night, including both nighttime sleep and any daytime naps.
iv. Sleep Efficiency: This component calculates the percentage of time spent asleep while in bed, providing an indicator of sleep continuity and fragmentation.
v. Sleep Disturbances: This component assesses the frequency of various sleep disturbances, such as waking up during the night, nightmares, or pain interfering with sleep.
vi. Use of Sleep Medication: This component evaluates the frequency of using sleep medication to aid in sleep.

vii. Daytime Dysfunction: This component measures the perceived impact of sleep disturbances on daytime functioning, including mood, energy levels, and daytime sleepiness.

Subjects rate their experiences on each component using Likert scales, with higher scores indicating poorer sleep quality or greater sleep disturbances. The scores from the seven components are then combined to generate a global score, having a possible range of 0 to 21 points, with a higher global score indicating lower overall sleep quality. See, e.g., Buysse et al., "The Pittsburgh Sleep Quality Index: A New Instrument for Psychiatric Practice and Research," *Psychiatry Research* 28:198-213 (1989). An increase in a test subject's PSQI global score by 1 or 2 points following CRL treatment indicates a moderate improvement in sleep quality, and an increase in a test subject's PSQI global score by 3 or more points following CRL treatment indicates a significant improvement in sleep quality.

j. Multidimensional Fatigue Inventory Questionnaire (MFI-20): The MFI-20 is a self-report measure designed to assess various dimensions of fatigue experienced by individuals. It is widely used in both clinical and research settings to evaluate fatigue across multiple domains. The MFI-20 consists of 20 items that assess fatigue across five dimensions:
  i. General Fatigue: This dimension captures overall feelings of tiredness and exhaustion.
  ii. Physical Fatigue: This dimension assesses fatigue related to physical activities and exertion.
  iii. Mental Fatigue: This dimension evaluates cognitive aspects of fatigue, such as difficulty concentrating or thinking clearly.
  iv. Reduced Motivation: This dimension measures decreased motivation and energy for engaging in activities.
  v. Reduced Activity: This dimension assesses the impact of fatigue on the individual's ability to engage in daily activities and tasks.

Subjects rate the extent to which they experience each fatigue-related symptom on a Likert scale, typically ranging from 1 (not at all) to 5 (very much). Higher scores on each dimension indicate greater levels of fatigue in that particular domain. The MFI-20 questionnaire provides a comprehensive assessment of fatigue that captures its multidimensional nature. See, e.g., Smets et al., "The multidimensional Fatigue Inventory (MFI) psychometric qualities of an instrument to assess fatigue," *J. Psychosom Res.* 39(3):315-325. Increases in one or more dimensions by 1 or 2 following CRL treatment indicates a moderate decrease in the fatigue level of the subject. Further, increases in one or more dimensions by 3 or more following CRL treatment indicates a significant decrease in the fatigue level of the subject.

k. Frontal Systems Behavioral Scale (FrSBe): The FrSBe is a neuropsychological assessment tool designed to measure behavioral changes associated with dysfunction of the frontal lobes of the brain. These changes can occur due to various neurological conditions, such as traumatic brain injury, stroke, dementia, or other neurological disorders affecting the frontal regions of the brain. The FrSBe evaluates three primary domains of behavior typically associated with frontal lobe dysfunction:

i. Apathy: This domain assesses diminished motivation, lack of interest or initiative, reduced emotional responsiveness, and decreased goal-directed behavior.
  ii. Disinhibition: This domain measures impulsivity, poor judgment, socially inappropriate behavior, and lack of self-control.
  iii. Executive Dysfunction: This domain evaluates deficits in executive functions, including planning, organization, problem-solving, cognitive flexibility, and self-monitoring.

The FrSBe consists of self-report forms completed by the subject being assessed, as well as informant forms completed by a close family member, caregiver, or other person familiar with the subject's behavior. Items are rated on a 5-point scale of 1 (almost never) to 5 (almost always). The self-report and informant forms may have slightly different item sets to capture both the subject's perspective and observations from others. Scoring the FrSBe involves summing the responses to items within each domain to obtain separate scores for apathy, disinhibition, and executive dysfunction. Higher scores within each domain indicate greater impairment or dysfunction in that particular area of behavior associated with frontal lobe dysfunction. The FrSBe provides standardized scoring procedures and interpretation guidelines to assist clinicians in assessing and interpreting the results accurately. Overall, the FrSBe serves as a valuable tool in assessing and monitoring changes in behavior associated with frontal lobe dysfunction, providing valuable insights into an individual's cognitive and functional status. See, e.g., Stout et al., "Factor Analysis of the Frontal Systems Behavior Scale (FrSBe)," *Assessment* 10(1):79-85 (2003); and "Frontal Systems Behavior Scale (FrSBe)." Available online at movingahead [dot]psy [dot]unsw [dot]edu[dot]au/documents/research/outcome%20 measures/adult/Behavioural%20Function/ Website%20FrSBe[dot]pdf. Combined domain scores (FrSBe total score) of 65 points or greater are considered to indicate clinically significant frontal systems dysfunction. A reduction in the FrSBe total score of a patient by 10 points or more following CRL treatment indicates a moderate improvement in frontal systems function, and a reduction in the FrSBe total score by 20 points or more indicates significant improvement in frontal systems function resulting from CRL treatment.

l. Harvard Willett Food Frequency Questionnaire: A semi-quantitative food frequency questionnaire corpleted by the subject.

Power and statistics. A priori power estimations using G-power software for the sample size of 50 subjects includes regression for up to 5 predictors and ROC analyses and can provide an approximate power of 90% with 2-sided alpha at 0.05. These analyses are performed using SPSS 22.0 for Macintosh. The alpha level is set at 0.05 to control for type I error.

Data evaluation and assessment of CRL's effects on memory. To assess the effects of CRL on memory, a subject's scores in the CNS Vitals test, SDMT, POMS, PSQI, MFI-20, FrSBe are compared before and after CRL treatment.

Example 12: Materials and Methods for In Vitro Microbiome Studies with CRL-Containing Dietary Supplement Test Product The test product ("Product B") is a digestive enzyme dietary supplement containing three enzymes targeting lipid digestion. Each capsule contains the following: (1) 15,000 Fédération International Pharmaceutique (FIP) of CRL, (2) 20,000 Hemoglobin Unit Tyrosine (HUT) of a protease, and (3) 8,500 (alpha-amylase Dextrinizing Units) DU of an amylase. Product B is formulated to breakdown specifically lipids but also protein and carbohydrates.

Study Design

The purpose of this study is to assess the effects of exogenous enzyme activity in the Simulator of Human Intestinal Microbial Ecosystem (SHIME©) with particular focus on physical, metabolic and microbial alterations, The M-SHIME® technology, a dynamic clinical in-vitro model of the gastrointestinal tract, is used, with minor modifications. See Van den Abbeele et al., "Incorporating a mucosal environment in a dynamic gut model results in a more representative colonization by lactobacilli," *Microb Biotechnol* 5:106-115 (2012). In brief, components of the system are autoclaved for sterility and the temperature of the vessels is maintained at 37° C. throughout the entire experiment. Two conditions (Blank Control and Product B) are tested in triplicates, and one or no capsule is used per jar. Stomach and small intestine simulation are conducted in the same open vessel. The experiment starts with a two-hour gastric phase (ST), where a sigmoidal decrease of pH from 5.5 to 2.0 is performed while continuously stirring. The added SHIME® nutritional medium represents the consumption of a typical Western meal including lactose (for dairy consumption) and lipids (for fat consumption). Salt levels of the matrix are adapted from the InfoGest consensus method. See Mackie & Rigby in *The Impact of Food Bioactives on Health: in vitro and ex vivo models* (eds K. Verhoeckx et al.) 13-22 (2015). In addition, phosphatidylcholine as well as pepsin are added to the reaction. After two hours, the gastric phase is completed, and within 5 min the pH increases from 2.0 to 7.0 while continuously stirring. Once a pH of 7.0 is reached, pancreatin, trypsin and chymotrypsin are added to the media along with 10 millimoles (mM) of taurine bile acids to mimic the human digestive processes. In addition, a dialysis pouch containing a solution with pH 7.0 and a salt composition of the lumen is introduced to the vessel with a molecular weight cut-off of 3.5 kDa to mimic natural absorption processes in the SI. The dialysis pouch solution is exchanged at one and two hours. After three hours, the small intestinal phase (SI) is completed. Subsequently, the colonic phase (C) is initiated in a separate vessel. The new vessel allows anaerobic conditions throughout the entire incubation time, which is required for the anaerobic bacteria in the colon to survive. The colonic matrix in each vessel contains 10 mL of the corresponding SI suspension, 53 mL of SHIME® nutritional media representative of the human colonic conditions and 7 mL of fecal inoculum of a healthy adult human donor before the colonic incubation is started. The temperature is maintained at 37° C. while continuously shaking at 90 rpm for 48 hours.

Sample Collection

Samples are collected during the gastric (ST), small intestinal (SI) and colonic phase (C) including at: ST start, ST end, SI start, SI 1 h, SI 2 h, SI 3 h, C 0 h, C 2 h, C 24 h and C 48 h. For the SI phase, samples are collected from both the luminal content and the dialysis solution.

pH Analysis

A SenseLine F410 (ProSense) is used to analyze pH changes during the colonic phase at 0, 2, 24 and 48 h to determine the rate of fermentation through acidification of the media. Significance analysis is performed over the entire colonic incubation between 0 and 48 h using a multiple comparison 2-way ANOVA with Tukey correction. Significant differences are indicated as: *$p<0.05$ and **$p<0.01$.

Gas Pressure Analysis

A hand-held pressure indicator (WIKA, CPH6200, Lawrenceville, GA USA) with a transmitter (WIKA, CPT6200, Lawrenceville, GA USA) is used to measure gas pressure. Significance analysis is performed over the entire colonic incubation between 0 and 48 h using a multiple comparison 2-way ANOVA with Tukey correction. Significant differences are indicated as: *$p<0.05$ and **$p<0.01$.

Ammonium Analysis

Ammonium samples at 0, 24, and 48 h are analyzed colorimetric (AQ300 Discrete Analyzer) using the indophenol blue spectrophotometric method according to the manufacturer's instructions. Significance analysis is performed over the entire colonic incubation between 0 and 48 h using a multiple comparison 2-way ANOVA with Tukey correction. Significant differences are indicated as: *$p<0.05$ and **$p<0.01$.

Lactate Analysis

Lactate levels are determined using a commercially available enzymatic assay kit (R-Biopharm, Darmstadt, Germany) following the manufacturer's instructions. Results are measured on an iCubio iMagic-M9 (Shenzhen iCubio Biomedical Technology Co. Ltd., Shenzhen, China).

Short-Chain Fatty Acids Analysis

Short-chain fatty acids (SCFAs), including acetate, propionate, butyrate, and branched SCFAs (BSCFA; i.e., isobutyrate, isovalerate, and isocaproate) are analyzed according to the methods of Ghyselinck et al., "A 4-strain probiotic dietary supplement influences gut microbiota composition and gut wall function in patients with ulcerative colitis," *Int J Pharm* 587:119648 (2020). Branched SCFAs are extracted prior to analysis using liquid-liquid extraction in accordance with the methods of De Boever et al., "Fermentation by gut microbiota cultured in a simulator of the human intestinal microbial ecosystem is improved by supplementing a soygerm powder," *JNutr* 130:2599-2606 (2000). Samples are assessed at 0, 2, 24, and 48 h. At 0 h, only the blank control samples are analyzed. In brief, analysis is conducted using a Shimadzu GC2030 gas chromatograph, an autosampler, and flame-ionization detector. The injector port includes an enduro blue injector septum and a glass inlet liner with quartz wool (Shimadzu 221-75189) with a standard split. A BP21 (FFAP) GC column is used with a length of 30 m, inside diameter of 0.32 mm, and film thickness of 0.25 m. The selected carrier gas is nitrogen with a flow rate of 1.82 mL/min. Samples were split in a ratio of 10:1. Injection volume was 1 µL and the total run time set to 11.33 min. The starting oven temperature is set to 110° C., ramped to 6° C./min to 160° C. and then held for 3 min. Injector and detector temperatures are held constant at 200° C. The peak area output signal is computed via integration using Lab solutions DB software. Significance analysis is performed over the entire colonic incubation between 0 and 48 h using a multiple comparison 2-way ANOVA with Tukey correction. Significant differences are indicated as: *$p<0.05$ and **$p<0.01$.

R Packages for Shallow Shotgun Sequencing Data Analysis

Analyses are run in R 4.2.2 and data is visualized using ggplot2 (v3.4.2). The taxonomic bar- and jitterplots are assembled using phyloseq (v1.41.1). Alpha diversity metrics are calculated using phyloseq (v1.41.1) and vegan (2.6-4). The DAPC is first normalized using DESeq2 (v1.39.5) and then analyzed using adegenet (v2.1.7). LEfSe pairwise comparisons are run in base R stats4 and MASS (v7.3-54). TreeclimbR is run using TreeSummarizedExperiment (v2.6.0) and treeclimbR (v0.1.5).

Shallow Shotgun Sequencing Microbial Community Analysis

Shallow shotgun sequencing (3M reads) is conducted to analyze quantitatively (lumen) or relatively (mucus) the microbiota community. This semi-quantitative enumeration analyzes the main members of the community with at least 0.01% presence. For the quantitative luminal analysis this is combined with flow cytometry sample analysis to accurately quantify total bacterial cell counts as previously reported by Vandeputte et al., "Quantitative microbiome profiling links gut community variation to microbial load," Nature 551: 507-511 (2017). Colonic luminal samples are collected at 0 h (blank control only), 24 h, and 48 h of incubation. Mucosal environment is investigated at 48 h only. The community structure is analyzed using Discriminant Analysis of Principal Components (DAPC) where sequencing data is transformed using principal component analysis (PCA). Next, clusters are identified with discriminant analysis (DA) to maximize among-group variation and minimize within-group variation. Groups are a priori defined.

For causative analysis of taxonomic differences, after product exposure treeclimbR analysis are performed. The results are displayed in volcano plots classifying taxa into four different categories based on abundance in compared treatments: a) not significant and not biologically relevant, b) biologically relevant, but not statistically significant, c) statistically relevant, but not biologically relevant, and d) biologically and statistically significant. Statistical significance is met when p<0.05, while biological significance is based on log 2 fold changes of ≥2.0.

Shallow Shotgun Sequencing Functional Community Analysis

MetaCyc Pathways and Gene Ontology (GO) Terms databases are used to characterize the functional potential of the relative microbiota community data. Discriminant Analysis of Principal Components (DAPC) is used to assess functional beta-diversity followed by LEfSe analysis to identify the functional features. LefSe enables identification of shifts resulting from a treatment by coupling statistical significance with biological consistency and effect size estimation. Statistical significance (p<0.05) is determined using the Kruskal-Wallis and Wilcoxon tests. LDA scores of >2.0 are considered biologically relevant. LEfSe pairwise comparisons focus on the top 20 most significant features.

Figure 7A:
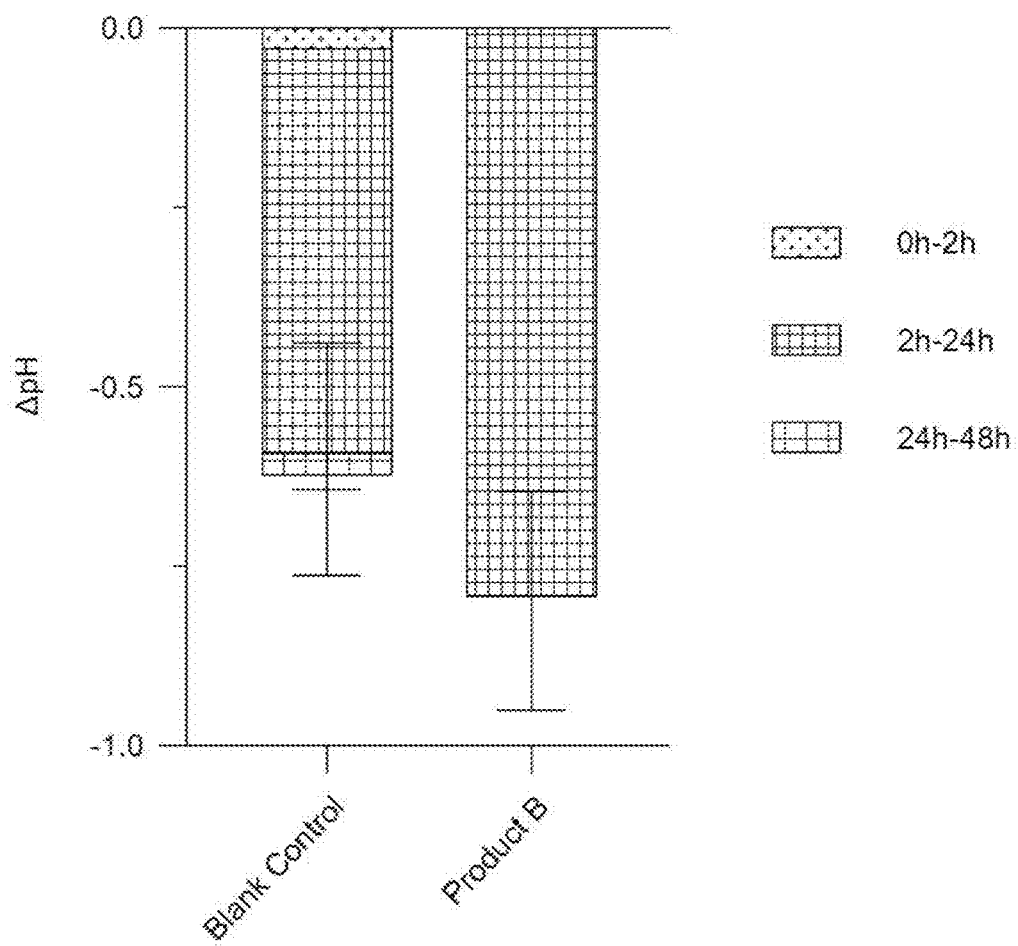
FIGS. 7A to 7I presents data showing physical and metabolic impacts of CRL activity, provided as a dietary supplement ("Product B"), on the colonic environment.
Figure 7B:
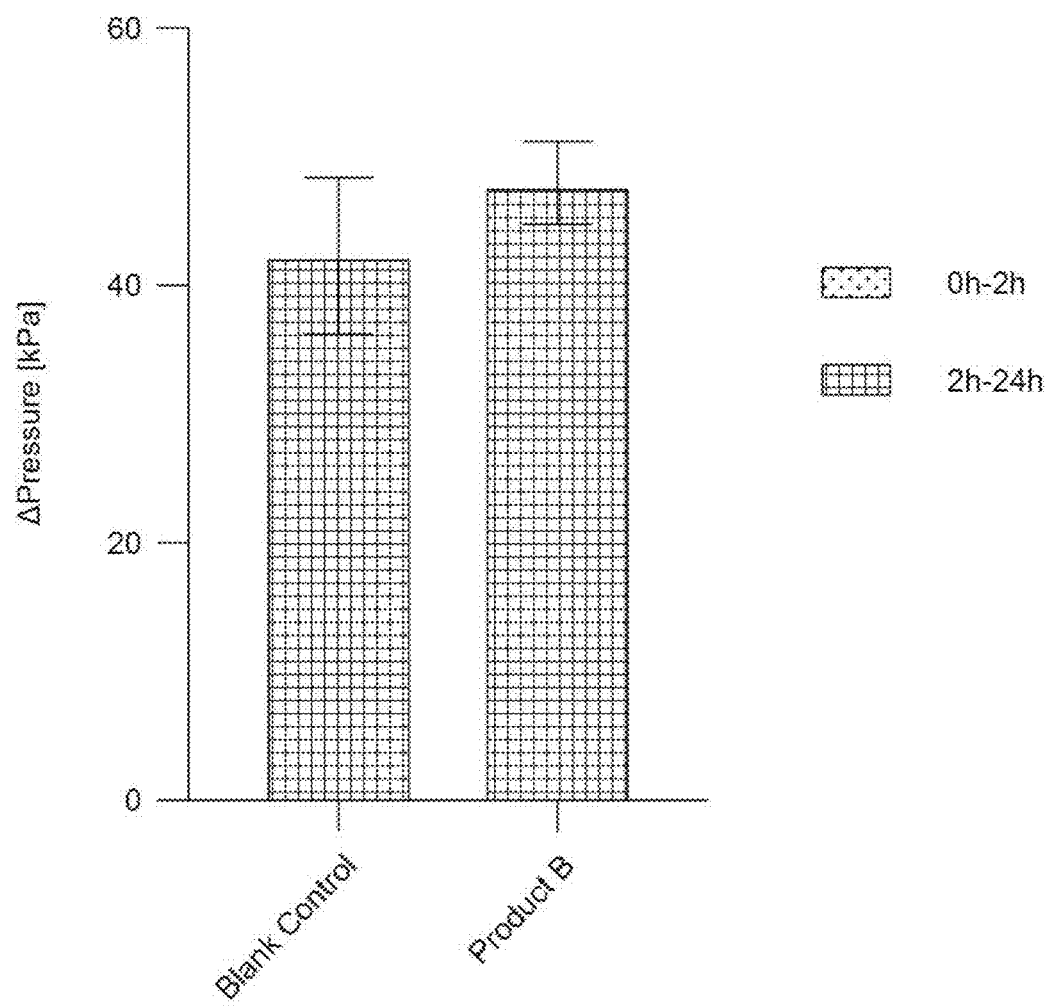

Example 13: Results of In Vitro Microbiome Studies with CRL-Containing Dietary Supplement The effects of a CRL-containing dietary supplement (Product B) in a gastro-intestinal model used to simulate the digestive processes the products would undergo before reaching the colon are investigated according to the study design of Example 12. The digested solution is then integrated into a short-term colonic stimulation model to assess Product B's effect on the physical, metabolic and microbial parameters in the colon compared to the Blank control.

pH profiles and pressure of the colonic vessel are assessed to determine the overall impact of Product B on the gut environment. The 48 h colonic phase is subdivided in three windows to determine the impact in the initial phase (0-2 h), in the saccharolytic phase (2-24 h), and finally in the proteolytic phase (24-48 h). Both conditions (Blank and Product B) show a pH reduction during 2-24 h as expected due to the saccharolytic digestion by microbiota releasing short-chain fatty acids (SCFAs) and lactate (FIG. 7A). From 24-48 h, it is expected that lactate would be metabolized into weaker acids such as propionate or butyrate. In addition, molecules such as ammonium are likely released due to the shift from saccharolytic to proteolytic digestion. Both mechanisms can halt further pH decrease, as observed in both groups between 24-48 h with no significant differences between Product B compared to Blank (FIG. 7A). Next, colonic gas release is assessed by measuring pressure differences in the vessel. While the largest change in pressure is determined during 2-24 h due to the microbial metabolic processes, no significant differences were determined between Blank and Product B (FIG. 7B). Additionally, Product B shows a trend for elevated pressure when compared to the Blank control, but no significance is reached (FIG. 7B).

Figure 7C:
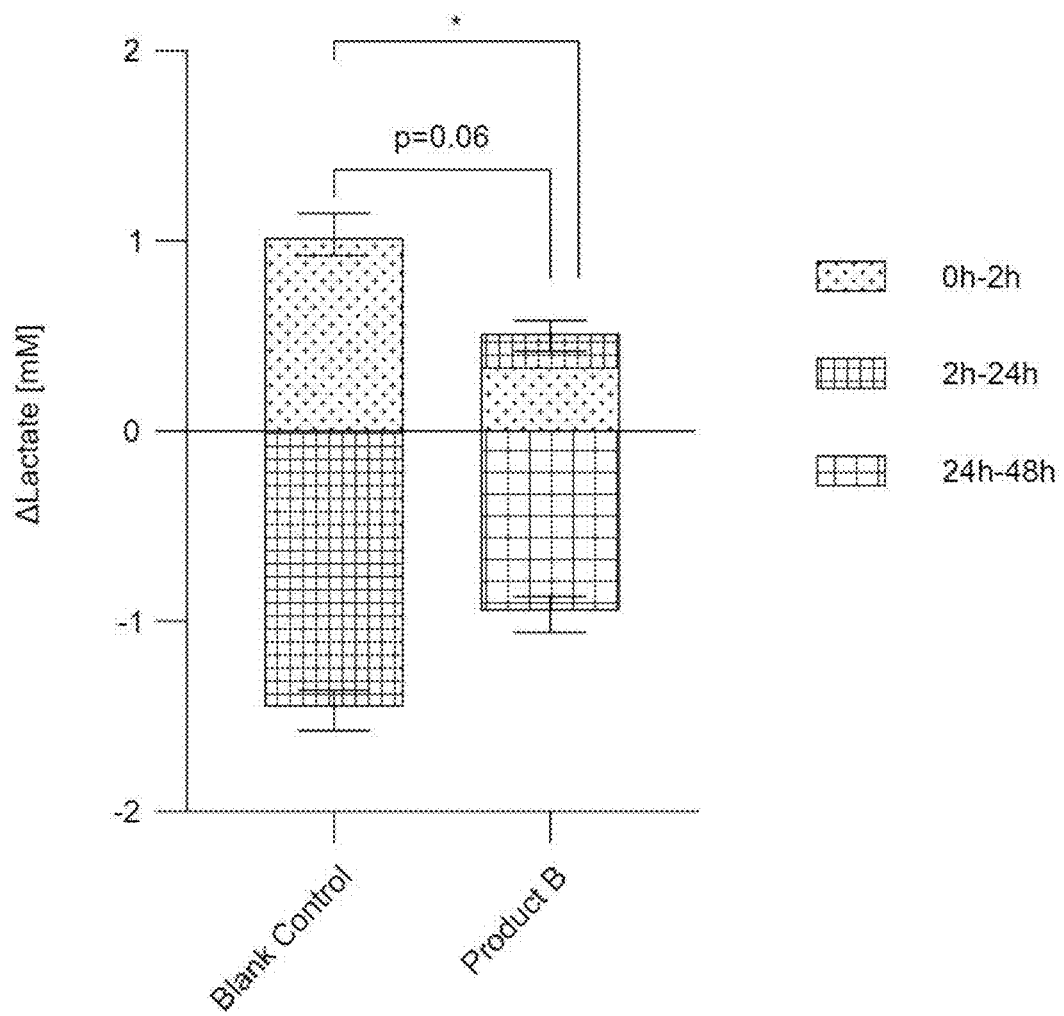
Figure 7D:
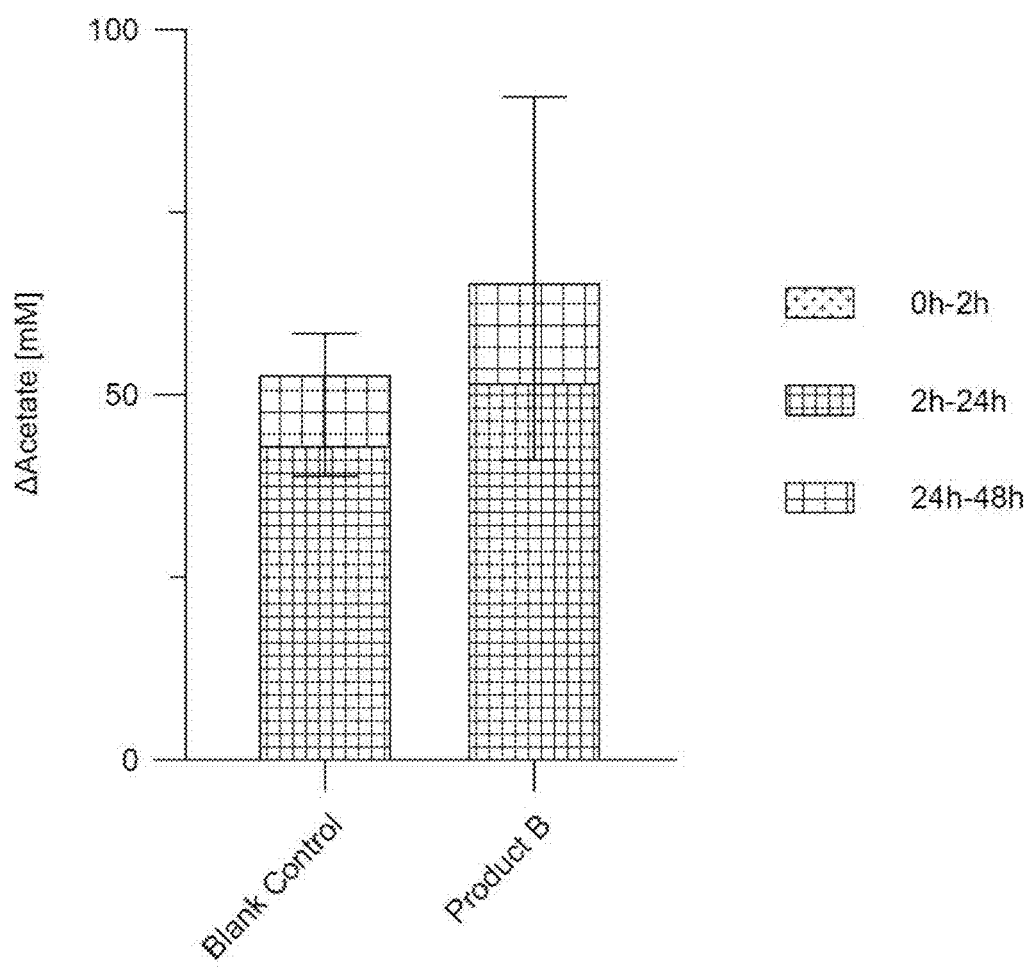
Figure 7E:
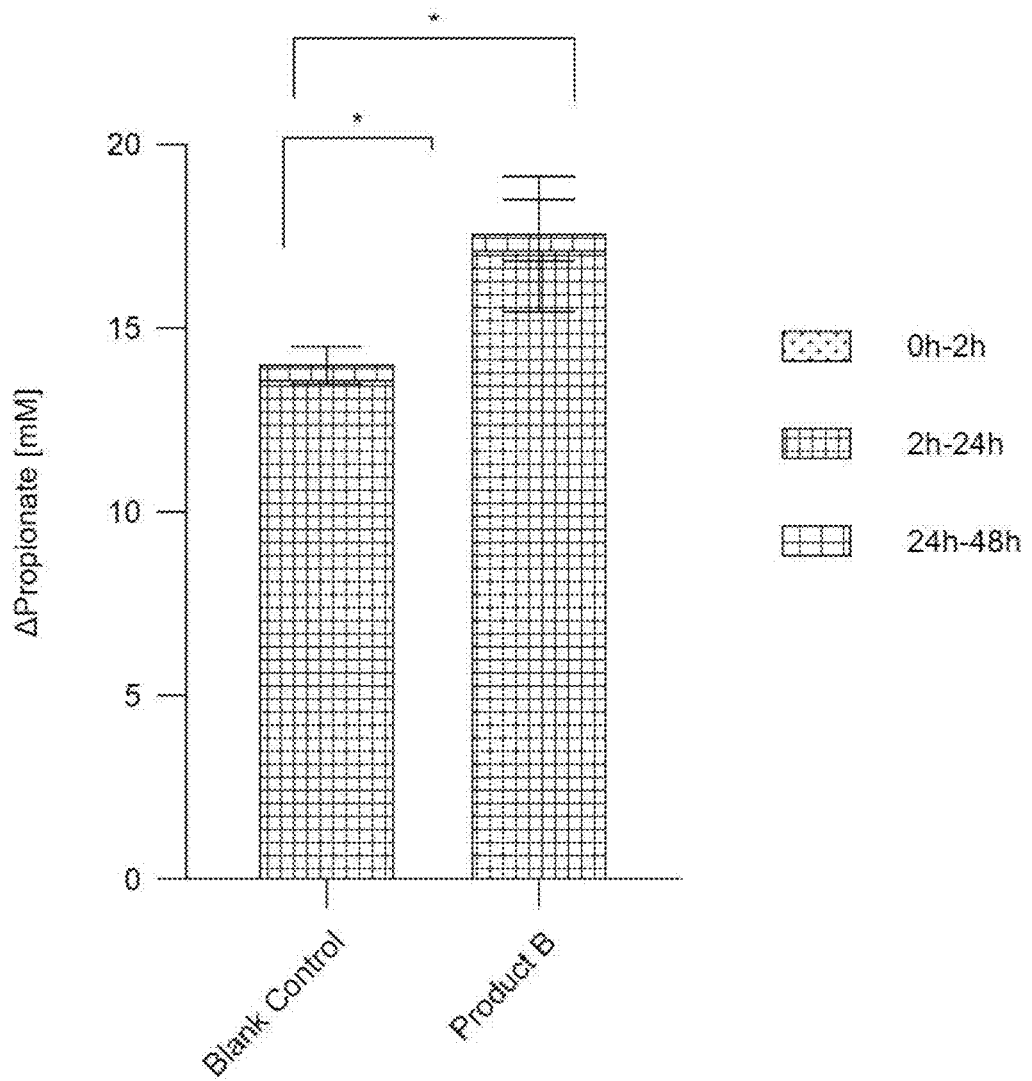
Figure 7F:
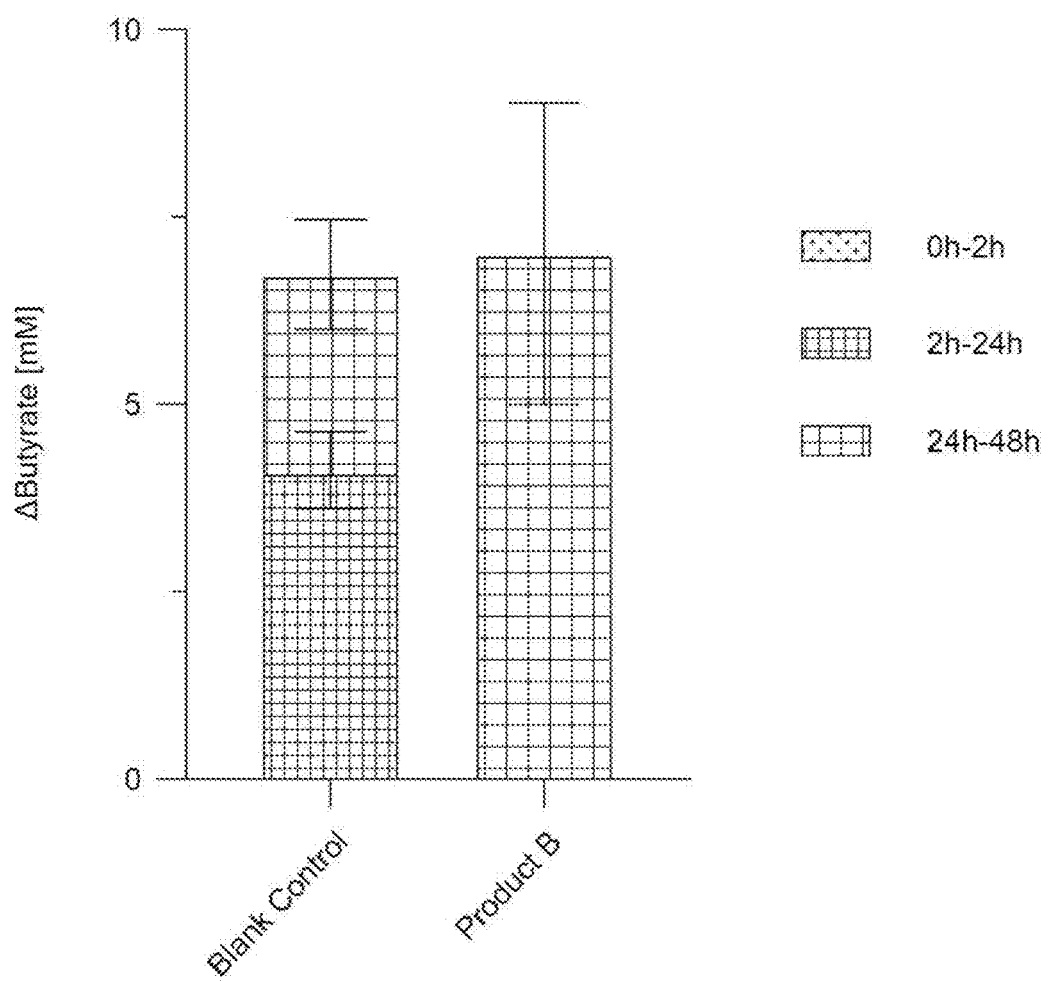
Figure 7G:
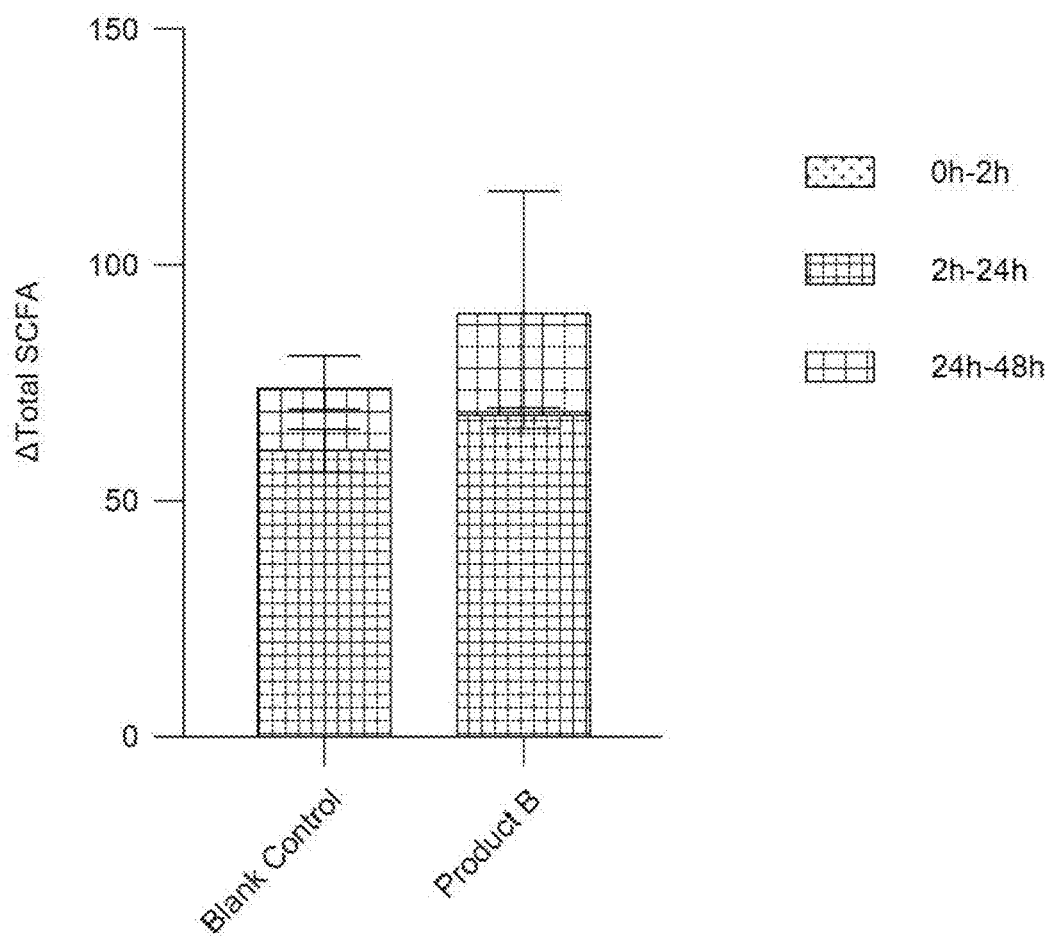
Figure 7H:
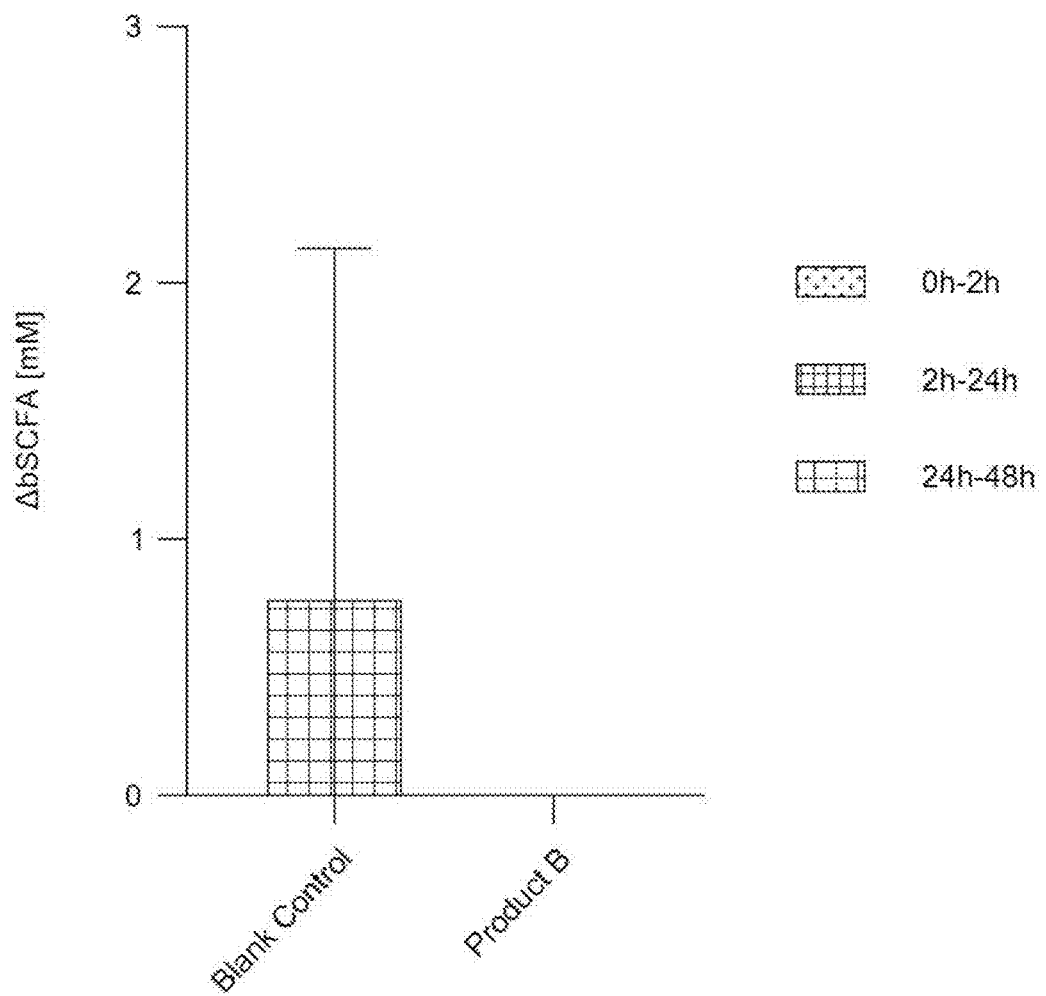
Figure 7I:
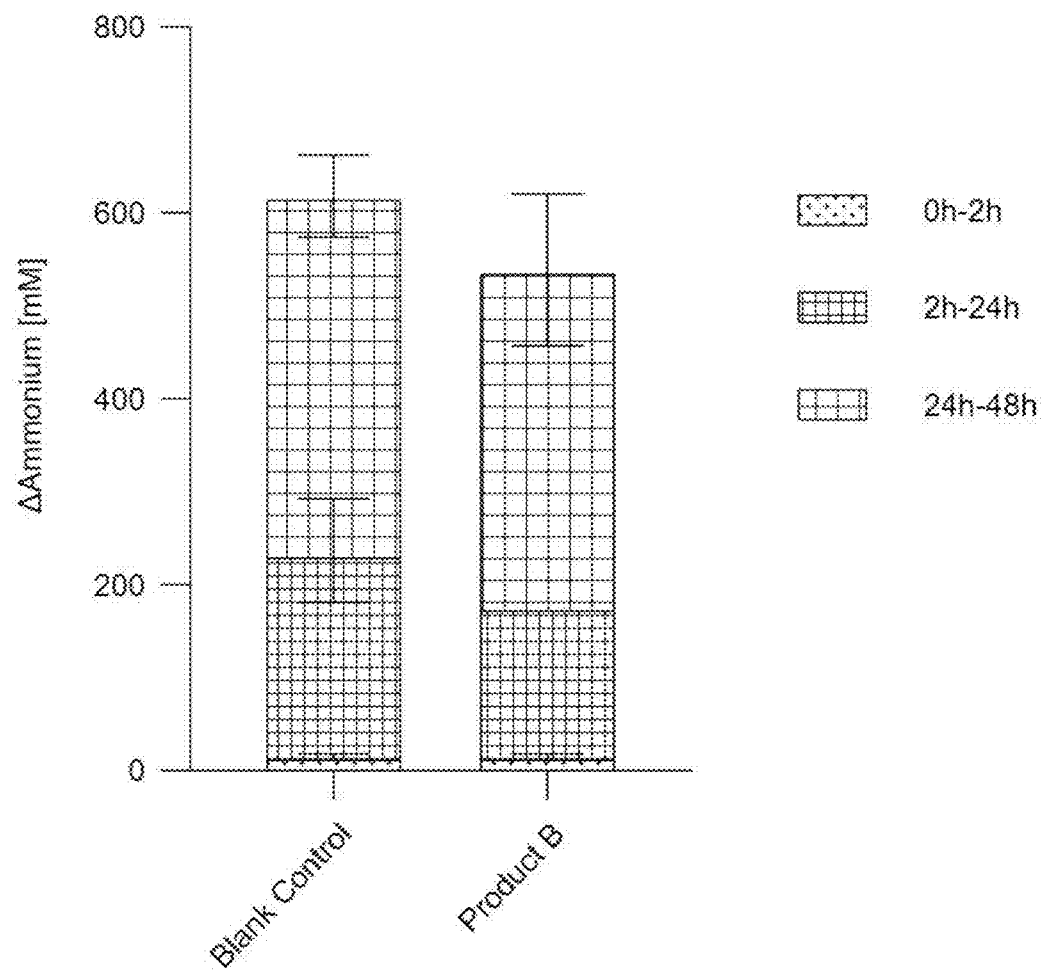

Metabolic parameters are assessed, including lactate and SCFA levels, to analyze whether the saccharolytic fermentation is impacted by the enzyme activity of Product B (FIGS. 7C to 7I). Lactate levels in the Blank Control increase between 0-2 h, confirming the microbiota's ability to metabolize nutrients (FIG. 7C). A subsequent decrease in lactate between 2-24 h in the Blank Control group demonstrates that not only has lactate been produced, but also that a cross-feeding mechanism has been established where lactate, for example, is further metabolized into butyrate or propionate. No additional changes are measured in the Blank Control group between 24-48 h. In contrast, Product B shows a lowered rate of increase of lactate during 0-2 h when compared to Blank Control, while during 24-48 h, Product B induces a decreased lactate level, during which time no changes are measured in the Blank Control group. This suggests that a cross-feeding mechanism has also established in the Product B group, but that the onset of this mechanism is delayed. Also, that Product B exhibits significantly lower overall levels of lactate suggests that the microbiota either produce less lactate than the Blank Control group's microbiota, or that lactate has already metabolized into secondary metabolites such as butyrate or propionate. Indeed, propionate levels are significantly increased in both Product B samples compared to Blank Control samples over 48 h period (FIG. 7E). While all groups showed the main increase during 2-24 h, only samples of Product A further increased during 24-48 h. As shown in FIG. 7F, butyrate levels were similar in both Blank Control and Product B samples, but timing of increases in butyrate levels varies; while Blank Control samples show increasing concentrations of butyrate during both 2-24 h and 24-48 h, Product B only exhibits increased butyrate during 24-48 h (FIG. 7F). This aligns with the delayed reduction of lactate levels in Product B, described above, since lactate is a precursor that is used by the gut microbiota to produce butyrate. Also, levels of acetate and total short chain fatty acids (SCFAs) are not significantly different between the Product B and Blank Control groups (FIGS. 7D and 7G). Finally, ammonium and branched short chain fatty acid (bSCFA) levels are investigated to assess potential adverse effects due to product exposure, and no significant differences are assessed between Blank Control and Product B for ammonium and bSCFA (FIGS. 7H and 7I).

Figure 8A:
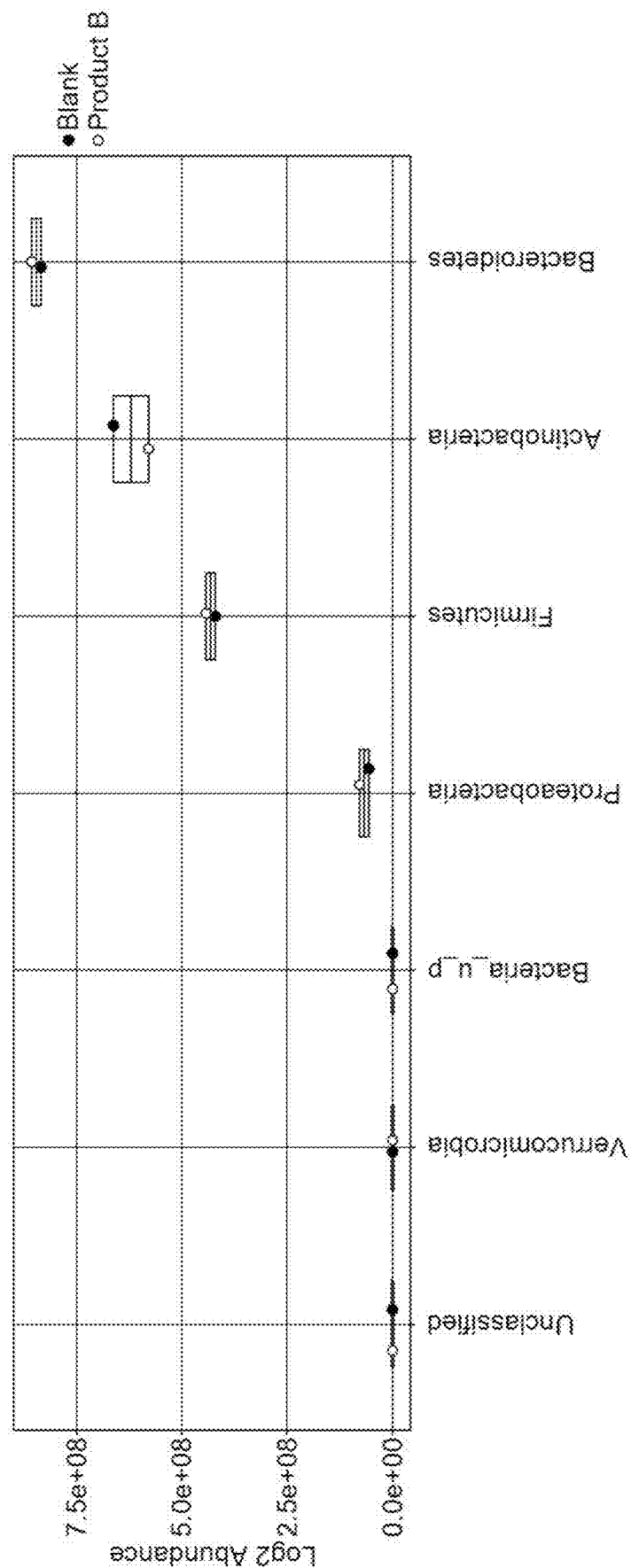
FIG. 8A presents community characterization after 48 h product exposure in the colonic phase through taxonomic analysis, showing absolute taxa abundance of luminal bacteria using flow cytometry and metagenomic data.
Figure 8B:
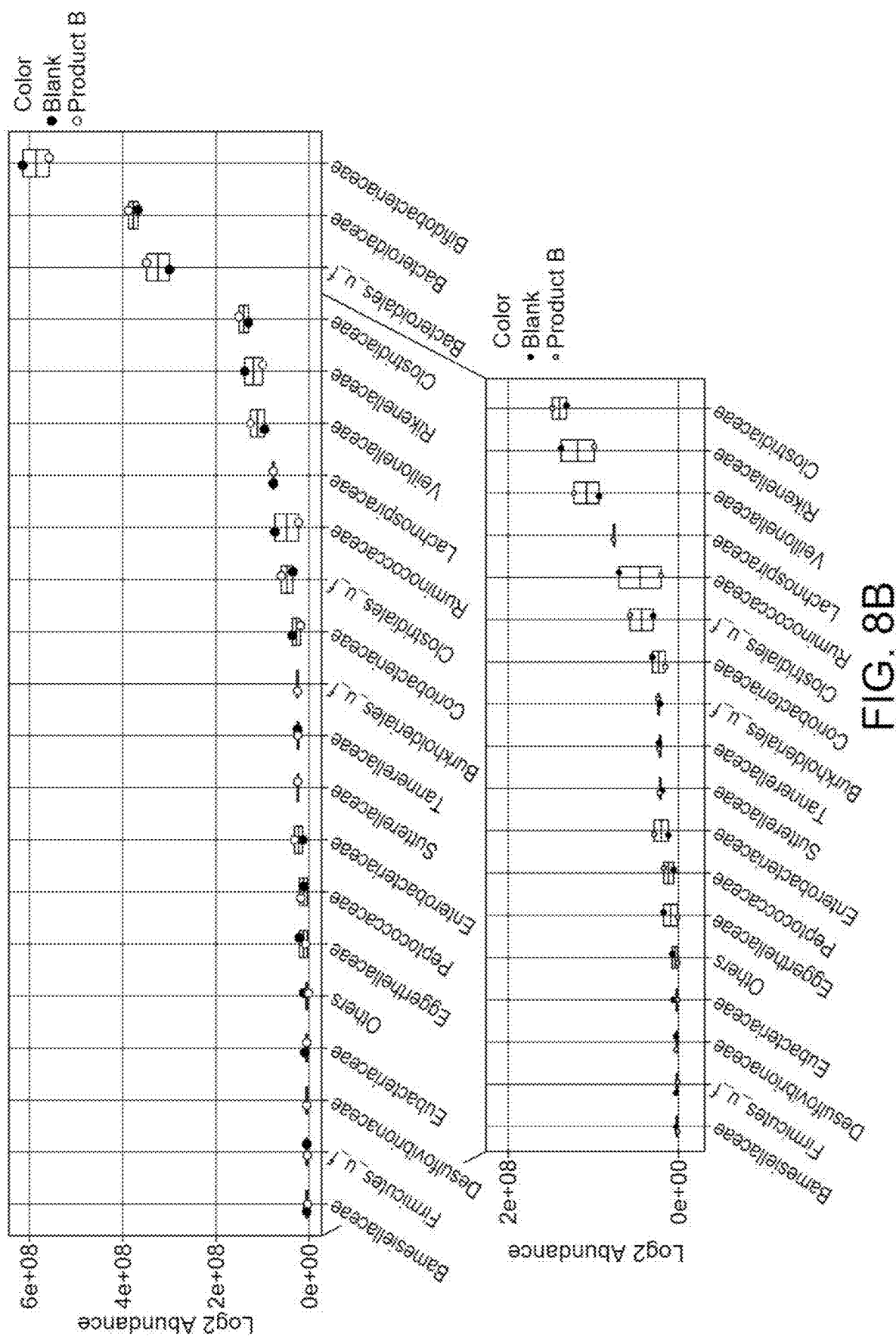
FIG. 8B presents a Jitter plot of the 20 most abundant families comparing Product B to Blank Control, showing changes in luminal environment using log 2 abundance of absolute levels at 24 h and 48 h for Product B and 0 h, 24 h and 48 h for Blank control (n=3 for each timepoint).
Figure 9A:
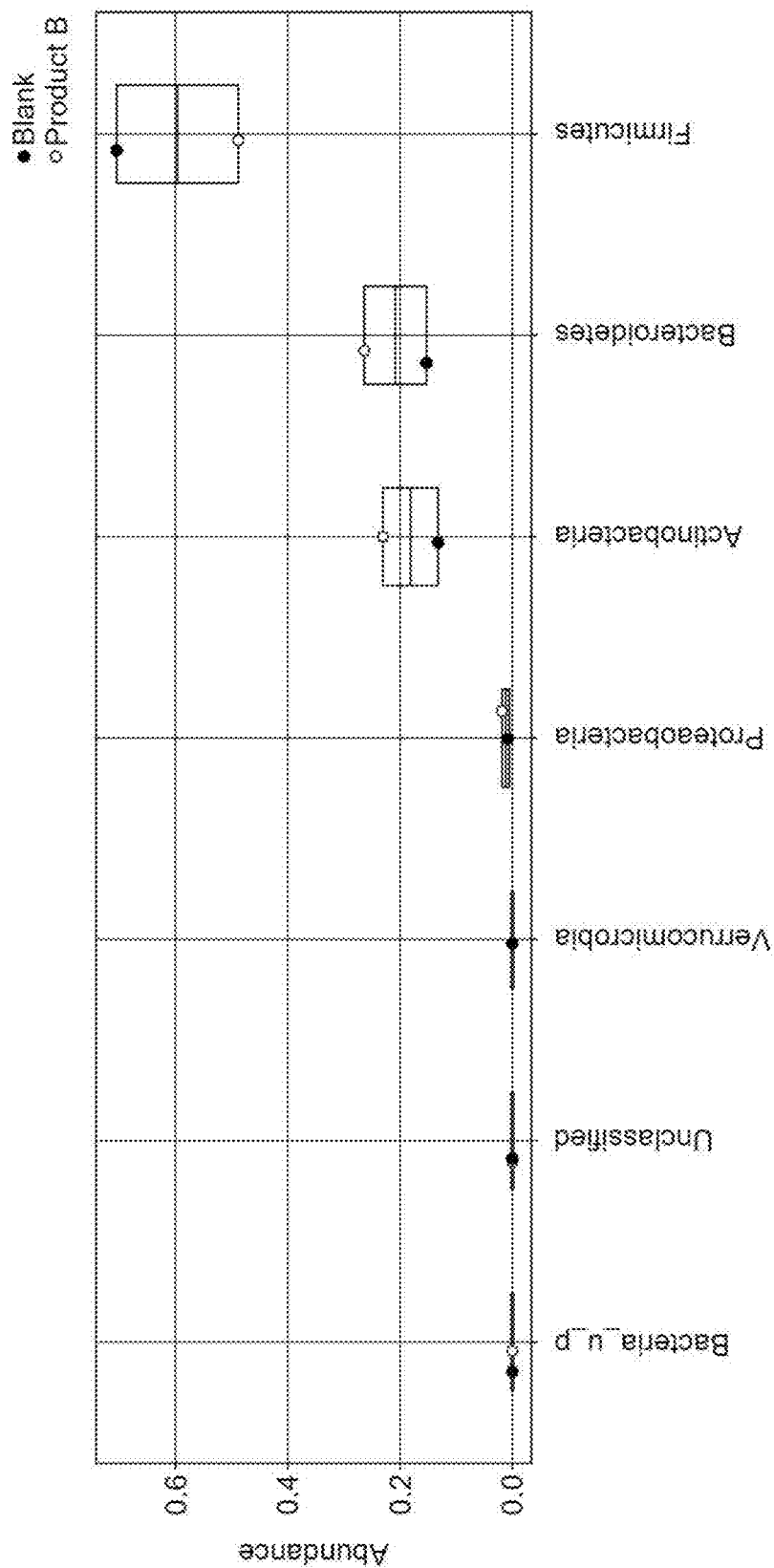
FIG. 9A presents community characterization after 48 h product exposure in the colonic phase through taxonomic analysis, showing relative Taxa analysis using metagenomic data of the mucosal layer after 48 h of product exposure.
Figure 9B:
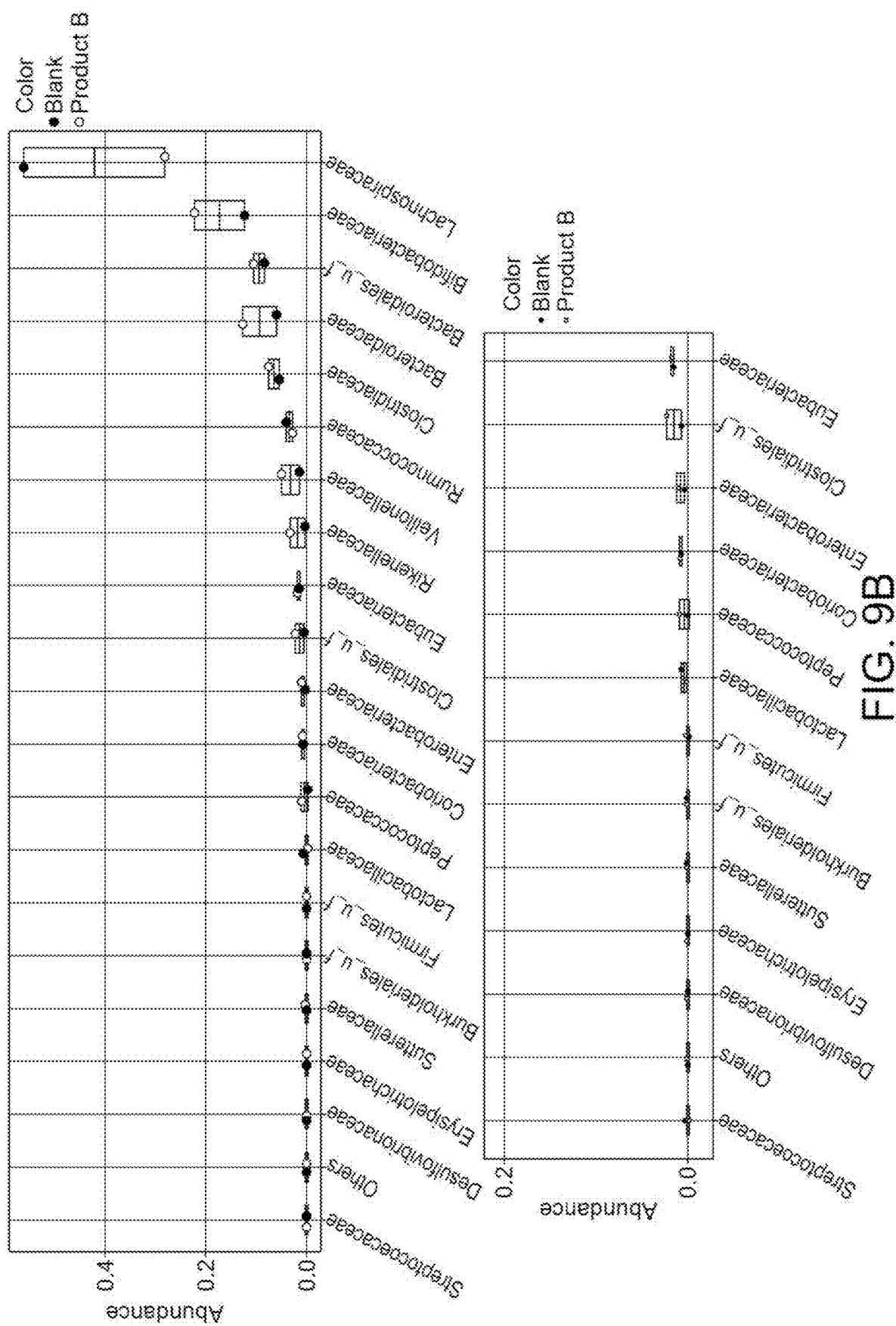
FIG. 9B presents a Jitter plot of the 20 most abundant families comparing Product B to Blank Control, showing changes in mucosal environment using log 2 abundance of relative levels at 48 h in triplicates for both Product B and Blank Control.
Figure 10:
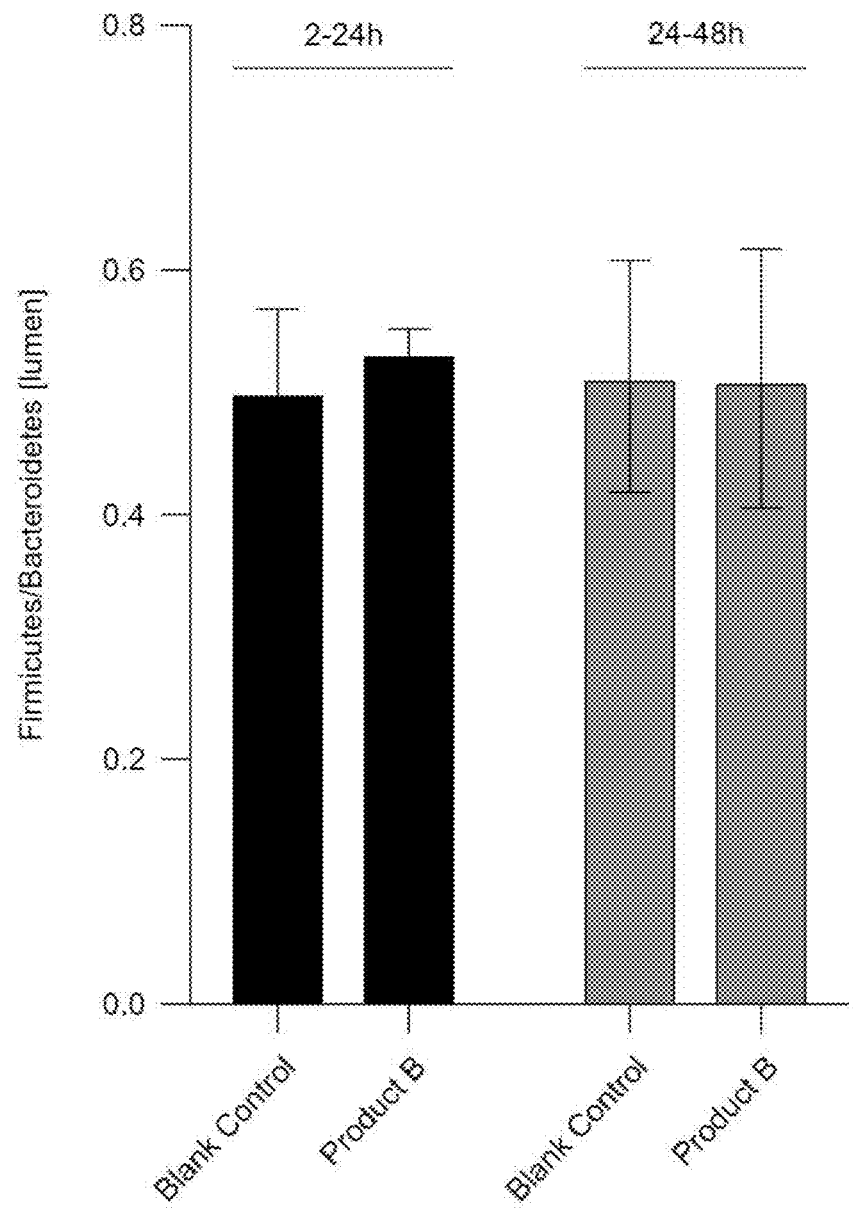
FIG. 10 presents Firmicutes-to-Bacteroidetes ratios in the lumen.
Figure 11A:
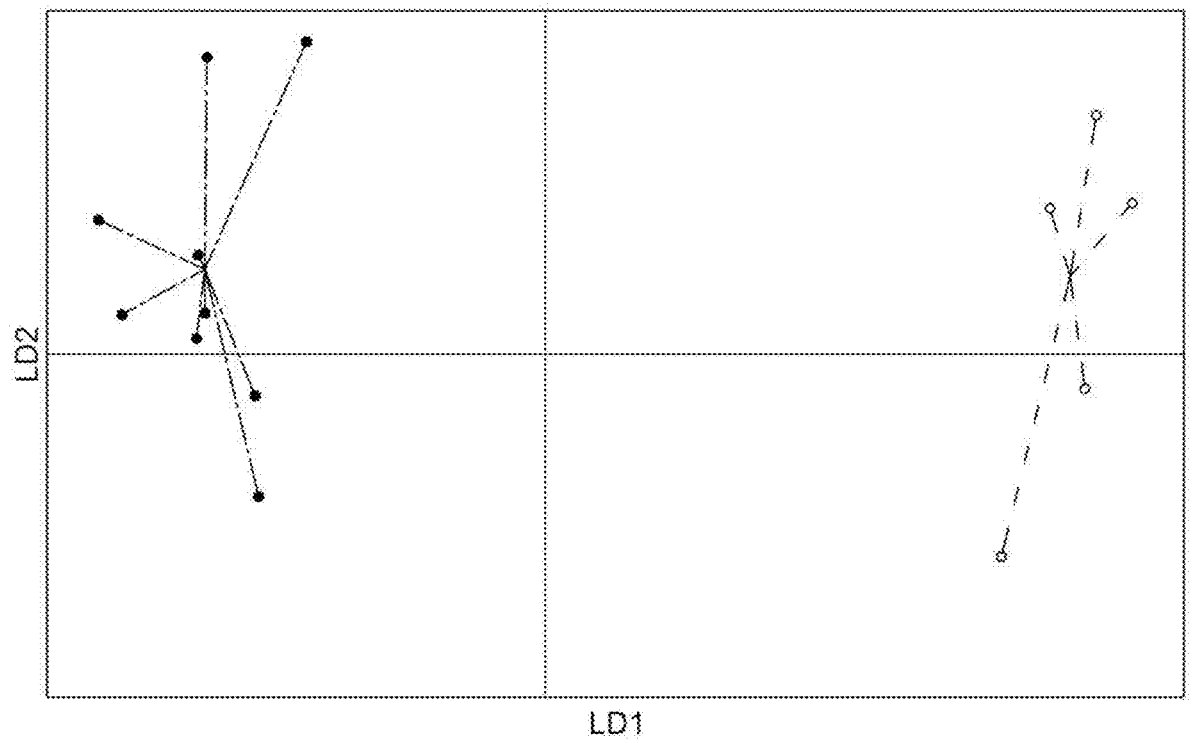
FIG. 11A presents Discriminant analysis of principal components (DAPC) of absolute abundances in lumen after 48 h, showing distinct separation between Product B and Blank Control.
Figure 11B:
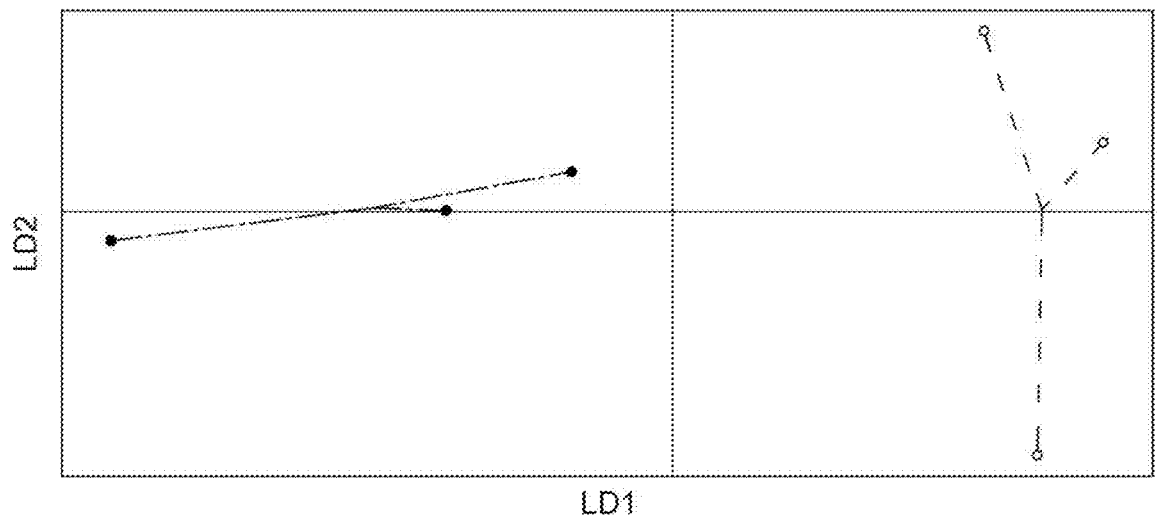
FIG. 11B presents DAPC of relative abundances in mucosal layer after 48 h, showing distinct separation between Product B and Blank Control.

A taxonomy analysis indicates that Firmicutes, Bacteroidetes and Actinobacteria are the most abundant bacterial phyla in both Product B and Blank Control samples, with Firmicutes being enriched in the mucosal layer of both groups (FIG. 8A). The elevated luminal Bacteroidetes level in the group exposed to Product B is due to increased Bacteroidaceae (FIG. 8B). In the mucosal environment, the Product B group showed similar results, with decreased Firmicutes and increased Bacteroidetes and Actinobacteria phyla (FIG. 9A). These results were driven by increases in *Bifidobacterium* and *Bacteroides* genera, and a decrease of the Lachnospiraceae (FIG. 9B) Despite these changes, there is no significant difference between the Firmicutes-to-Bacteroidetes ratio in Product B and Blank Control samples after 24 and 48 h (FIG. 10). Next, beta-diversity is assessed using discriminant analysis of principal components (DAPC) to identify overall microbial compositional shifts distinguishing the treatment and control groups after 48 h of exposure. Product B clearly separates from the Blank control in the gut lumen (FIGS. 11A and 11B). The first principal component (LD1) indicates that Product B leads to a strong shift for both mucosal and luminal environments, which suggests that Product B and its digestion products alter the gut microbiota.

Figure 12A:
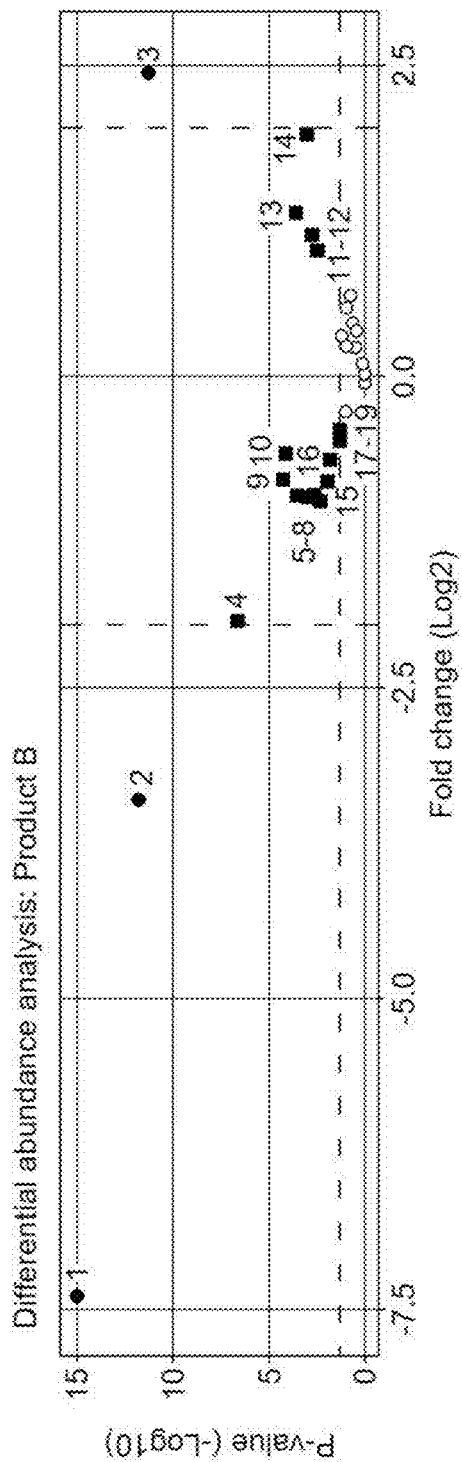
FIG. 12A presents a differential abundance analysis of Product B compared to Blank control in the luminal environment after 24 h. Negative log 10 of statistical significance is plotted against log 2 of fold change. Biological significance was reached when fold change exceeded 4, and statistical significance was reached when p-value was below 0.5 resulting in three categories: not significant and not biologically relevant; statistically significant but not biologically relevant; and biologically and statistically significant.
Figure 12B:
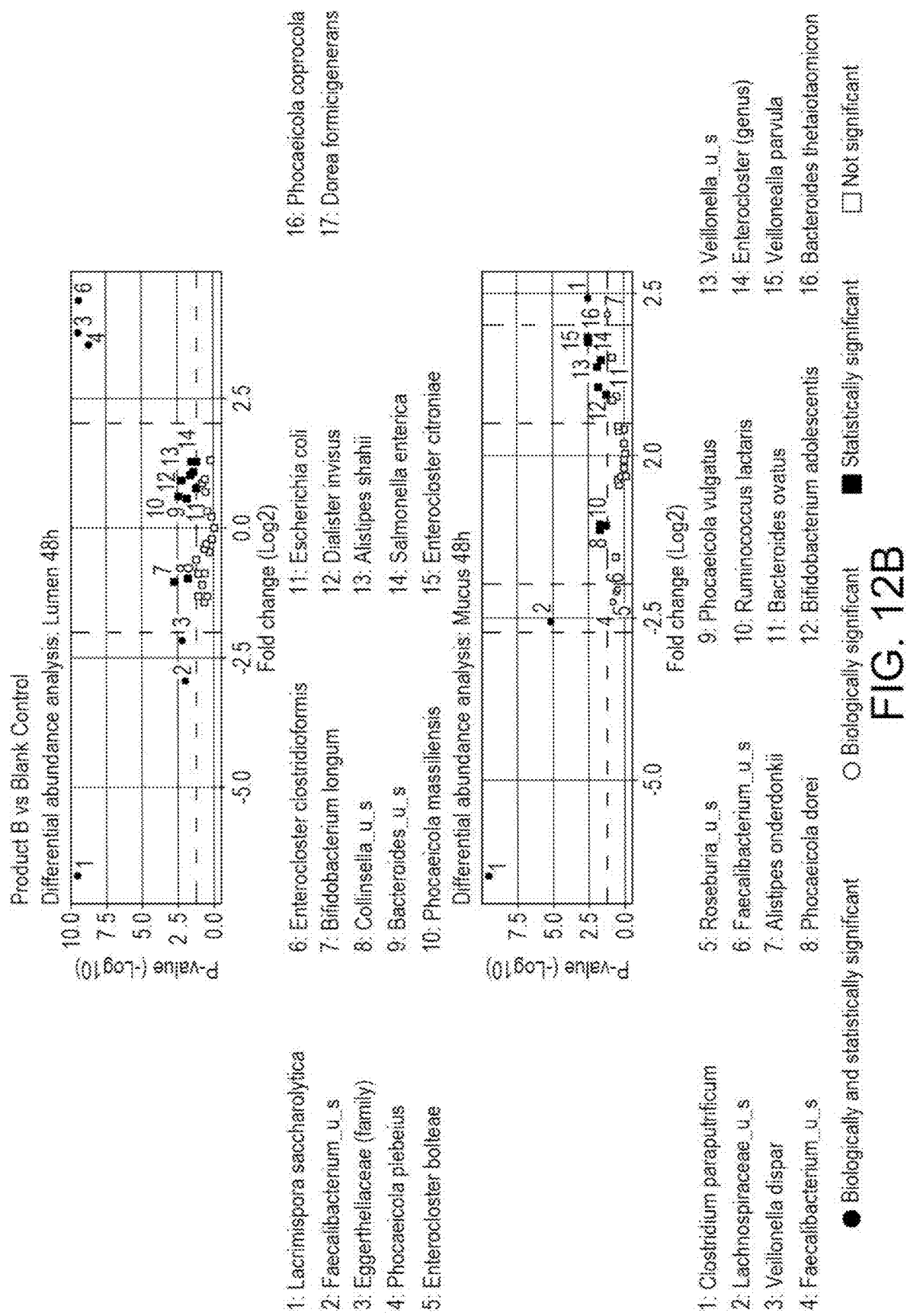
FIG. 12B presents a causative analysis of taxonomic differences after 48 h product exposure in lumen and mucosa of the colonic phase using treeclimbR analysis.
Figure 13A:
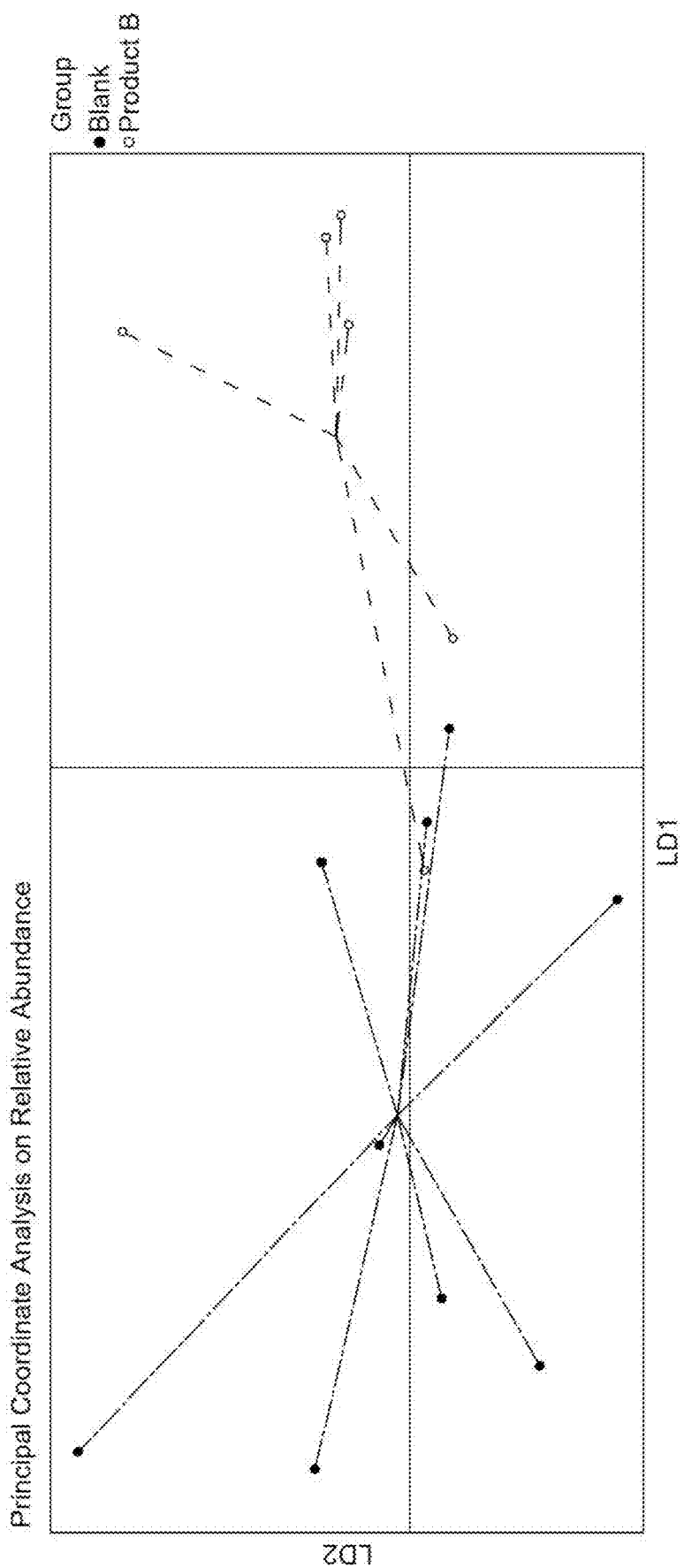
FIGS. 13A to 13D present DAPC to show differences in functionality of the microbial community (beta-diversity). Assessment of luminal environment at 24 h and 48 h for Product B and Blank Control at 0 h, 24 h and 48 h according to the Gene Ontology database is shown in FIG. 13A, and according to the MetaCyc database is shown in FIG. 13C. Analysis of mucosal environment at 48 h for Product B and Blank Control according to the Gene Ontology is shown in FIG. 13B, and according to the MetaCyc database is shown in FIG. 13D. Each dot represents one sample.
Figure 13B:
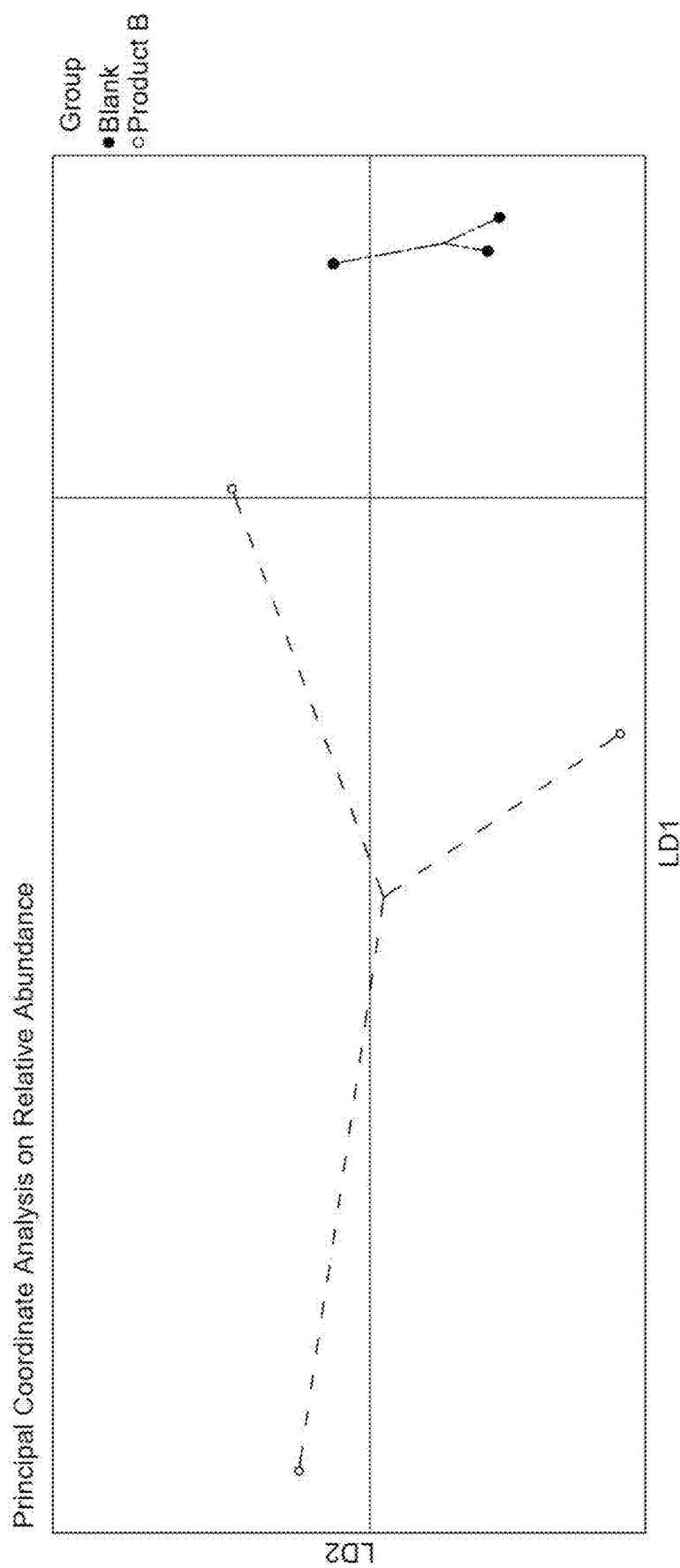
Figure 13C:
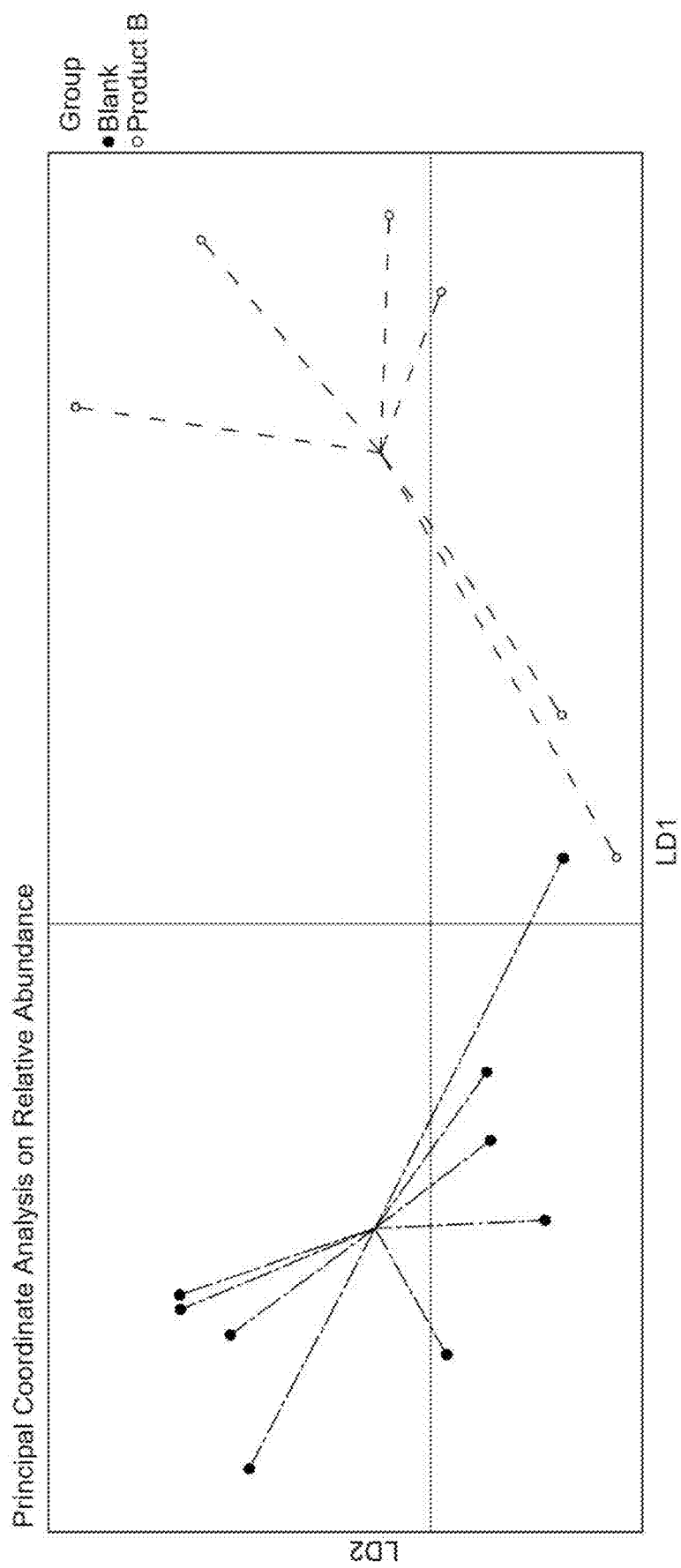
Figure 13D:
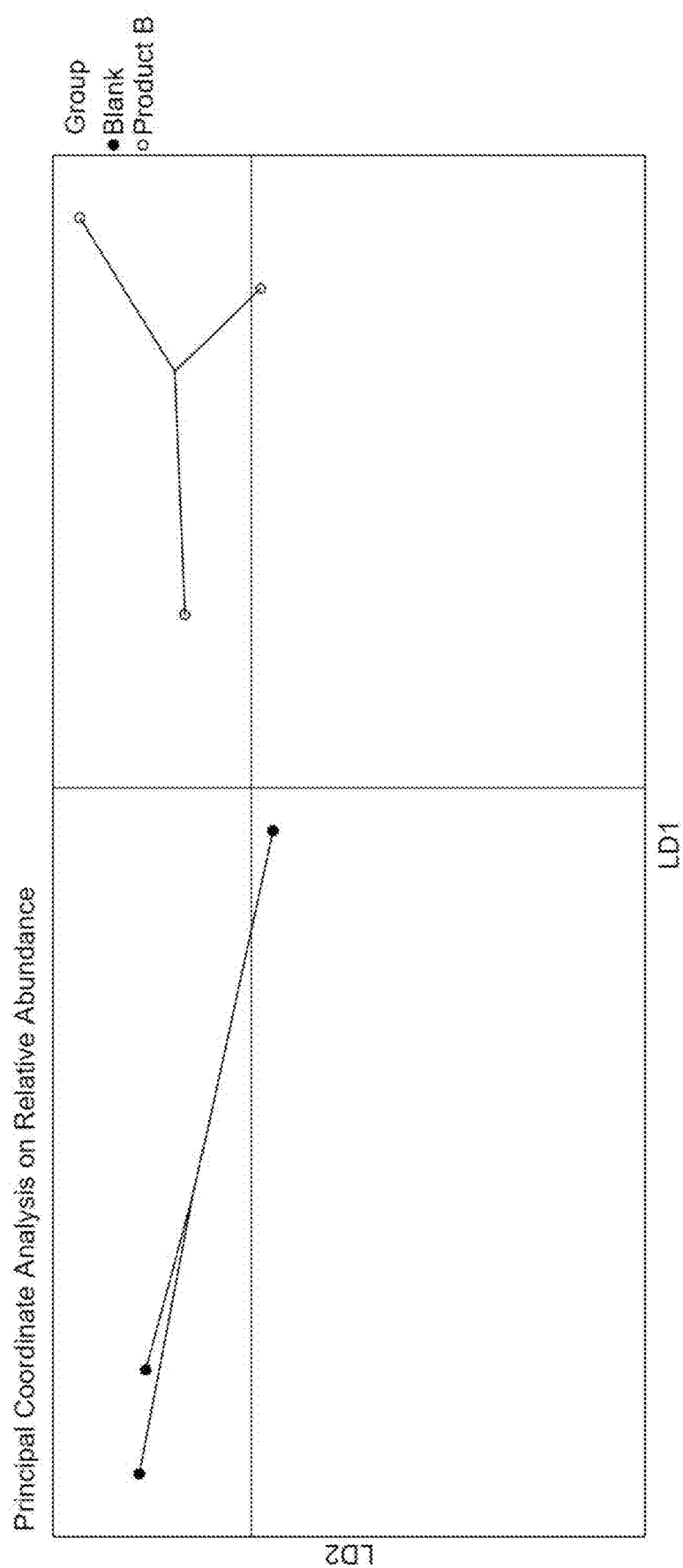

To determine which bacterial community members are driving the observed changes, TreeclimbR analysis is applied to compare the effect Product B to the Blank Control on the gut microbial community. At 24 h, the Lacrimispora genus and the Eggerthellaceae family are statistically and significantly reduced in the lumen of the Product B group, while Phocaeicola plebeius is increased (FIG. 12A). In addition, Clostridiaceae_u_g and Phocaeicola coprocola show statistically significant increases in the Product B group, while Gemmiger genus, *Bacteroides* thetaiotamicron and Phocaeicola dorei are reduced in the Product B luminal content along with three *Bifidobacterium* species (FIG. 12A). At 48 h, Lacrimispora saccharolytica, Faecalibacterium_u_s and Eggerthellaceae are significantly reduced in the Product B luminal samples (FIG. 12B), while Phocaeicola plebeius, Enterocloster boltae and clostridioformis are statistically and biologically significant. Also, Alistipes shahii, Phocaeicola *massiliensis* and Dialister invisus are significantly reduced in the gut lumen (FIG. 12B). Finally, the mucosal environment after 48 h of incubation shows a biologically and statistically significant increase of *Veillonella dispar*, while *Clostridium paraputrificum* is significantly decreased when exposed to the digested matrix of Product B (FIG. 12B).

Figure 14:
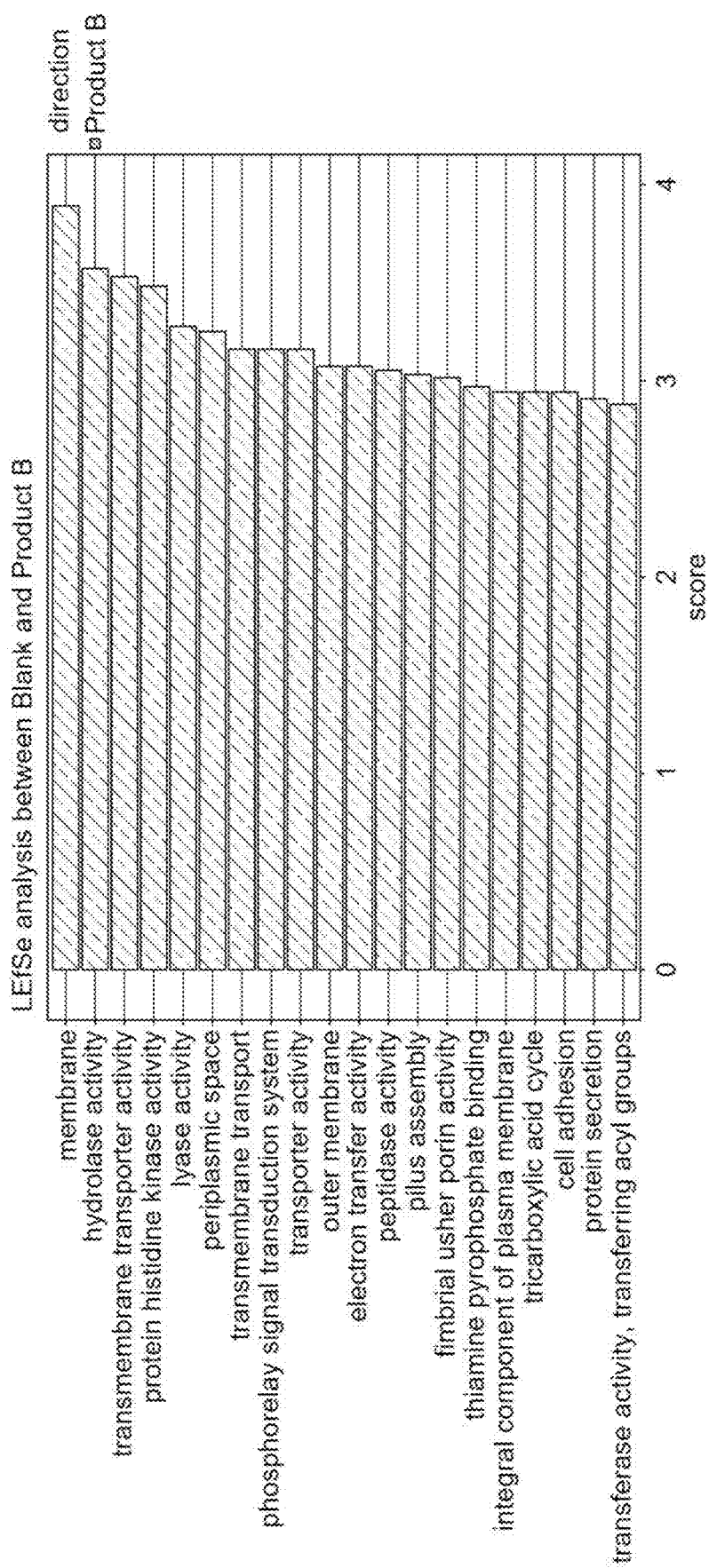
FIG. 14 presents a Linear discriminant analysis of effect size (LEfSe) in the luminal environment following 24 h of incubation. The obtained histogram plot shows differences according to the Gene Ontology (GO) database, with the x-axis in the histogram showing the LDA score.
Figure 15A:
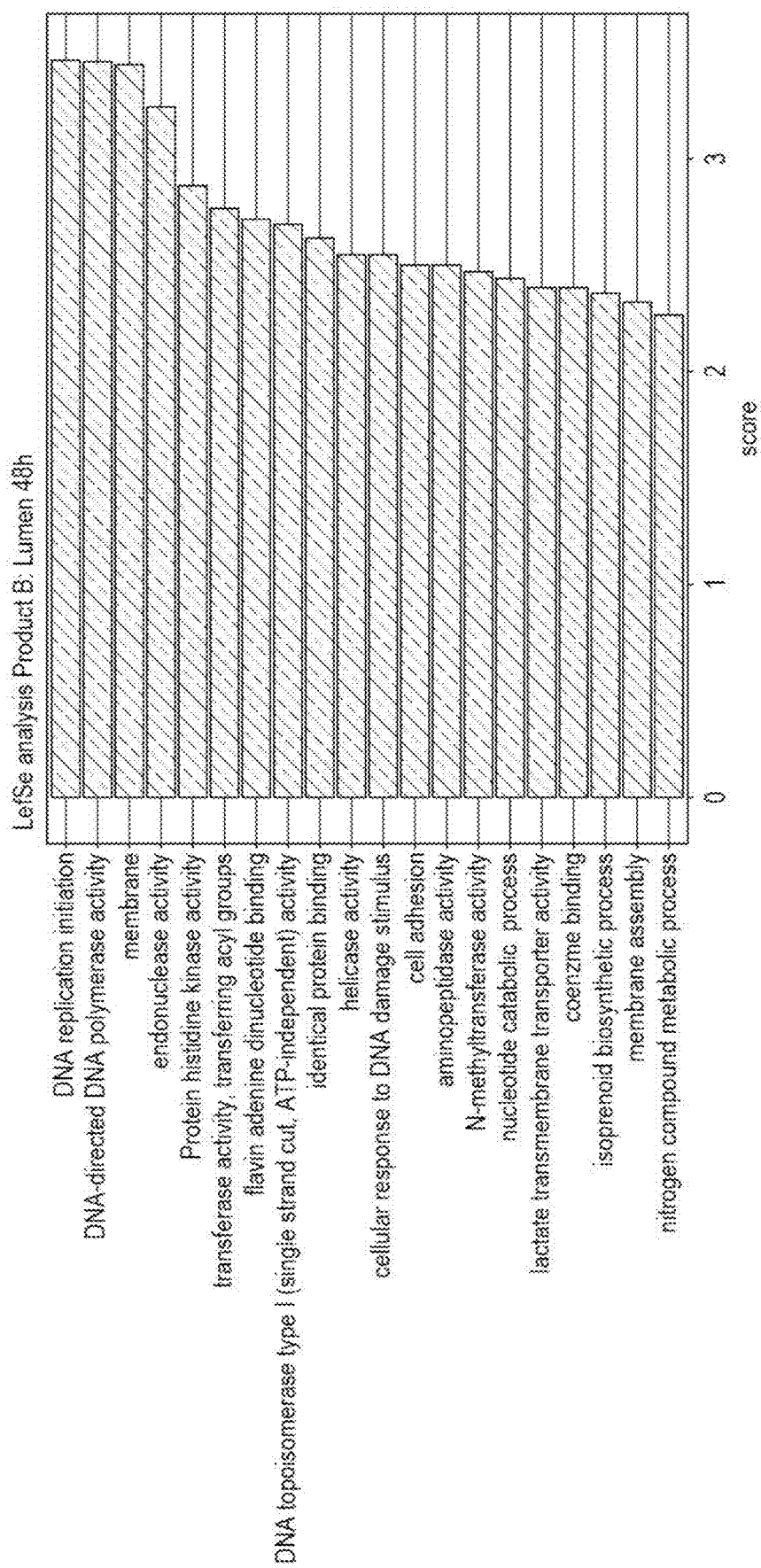
FIGS. 15A and 15B present a LEfSe in the luminal and mucosal environment, respectively, comparing Product B to Blank control after 48 h of incubation. The indicated pathways are significantly enriched features in the Product B group meeting $p<0.05$ for Kruskal-Wallis and Wilcoxon tests. LDA scores $\geq 2.0$ or $\leq -2.0$ are considered strongly enriched or depleted, respectively.
Figure 15B:
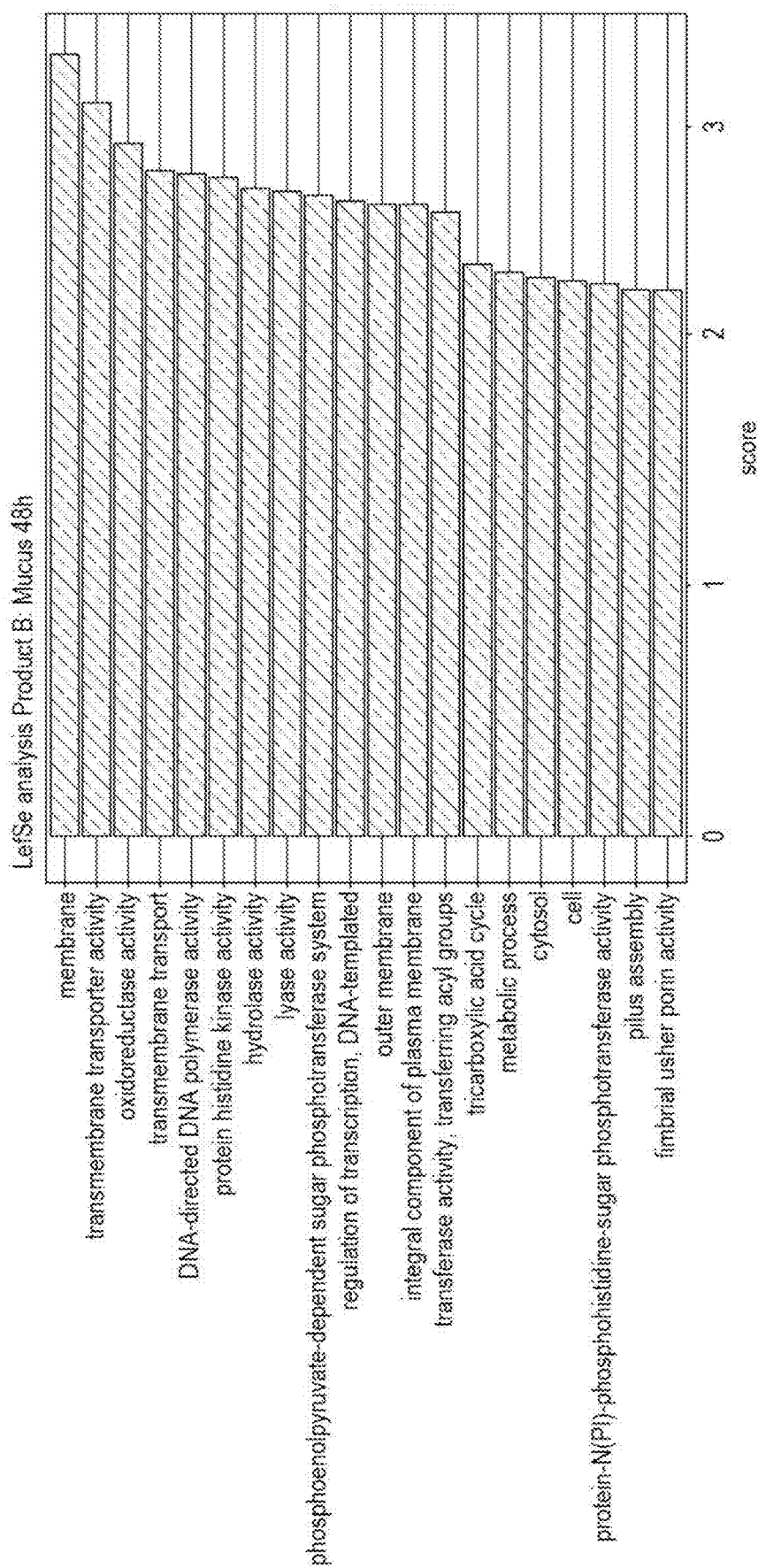

To assess how the increase and decrease of bacterial species impacts the functionality of the gut microbiome, the relative abundance of the detected functional features are analyzed by mapping the data with the Gene Ontology (GO) terms, as well as with MetaCyc pathways. Beta-diversity on a functional level is assessed using DAPC for both the luminal and mucosal environment. The Product B group shows a pronounced shift with distinct clustering from the Blank Control according to the first principal component (=LD1) in the DAPC plot (FIGS. 13A to 13D). Subsequently, pairwise linear discriminant analysis Effect Size (LEfSe) analysis is applied comparing the treatment group to the Blank Control. This analysis identifies significantly enriched functional characteristics using GO terms and the MetaCyc pathway database. After 24 h of incubation mapping against GO terms, Product B results in enhancement of membrane, outer membrane and cell components (FIG. 14). Hence, Product B promotes cell growth in the luminal environment. Metabolic activity of the bacterial community is reflected by the significant increase in transmembrane transporter genes in the Product B group (FIG. 14). Product B exposure shows an additional increase of the phospho-enolpyruvate-dependent sugar phosphotransferase system, hydrolase activity, protein histidine kinase activity, lyase activity, peptidase activity and transferase activity (FIG. 14). After 48 h, processes linked to cell growth, proliferation and mismatch repair are enhanced in Product B compared to Blank Control (FIGS. 15A and 15B). In addition, Product B shows elevated abundance of genes related to the phosphoenolpyruvate-dependent sugar phosphotransferase system (FIGS. 15A and 15B).

Figure 16:
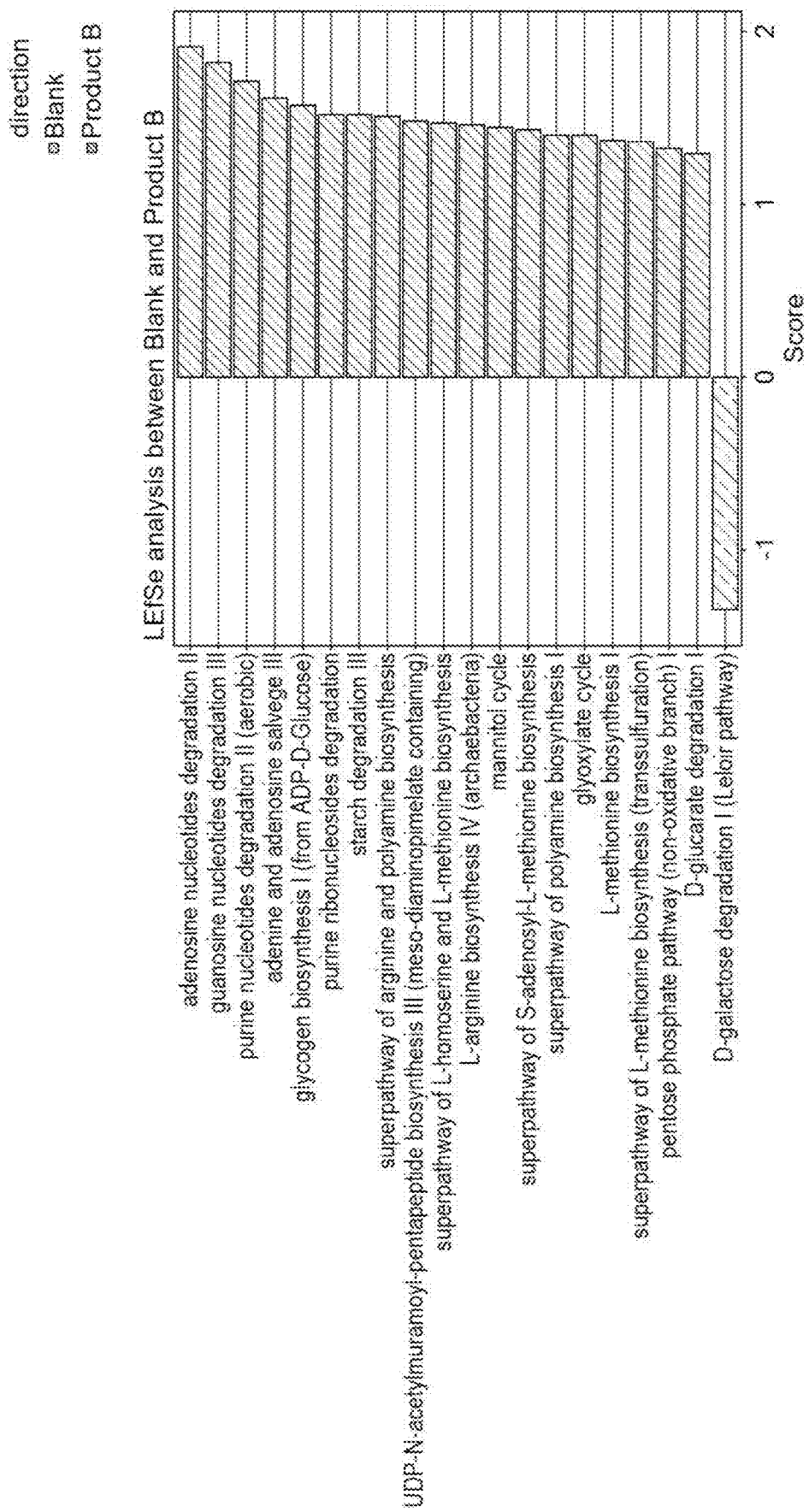
FIG. 16 presents a linear discriminant analysis of effect size (LEfSe) in the luminal environment following 24 h of incubation. The obtained histogram plot shows differences according to the MetaCyc database, with the x-axis in the histogram showing the LDA score.
Figure 17A:
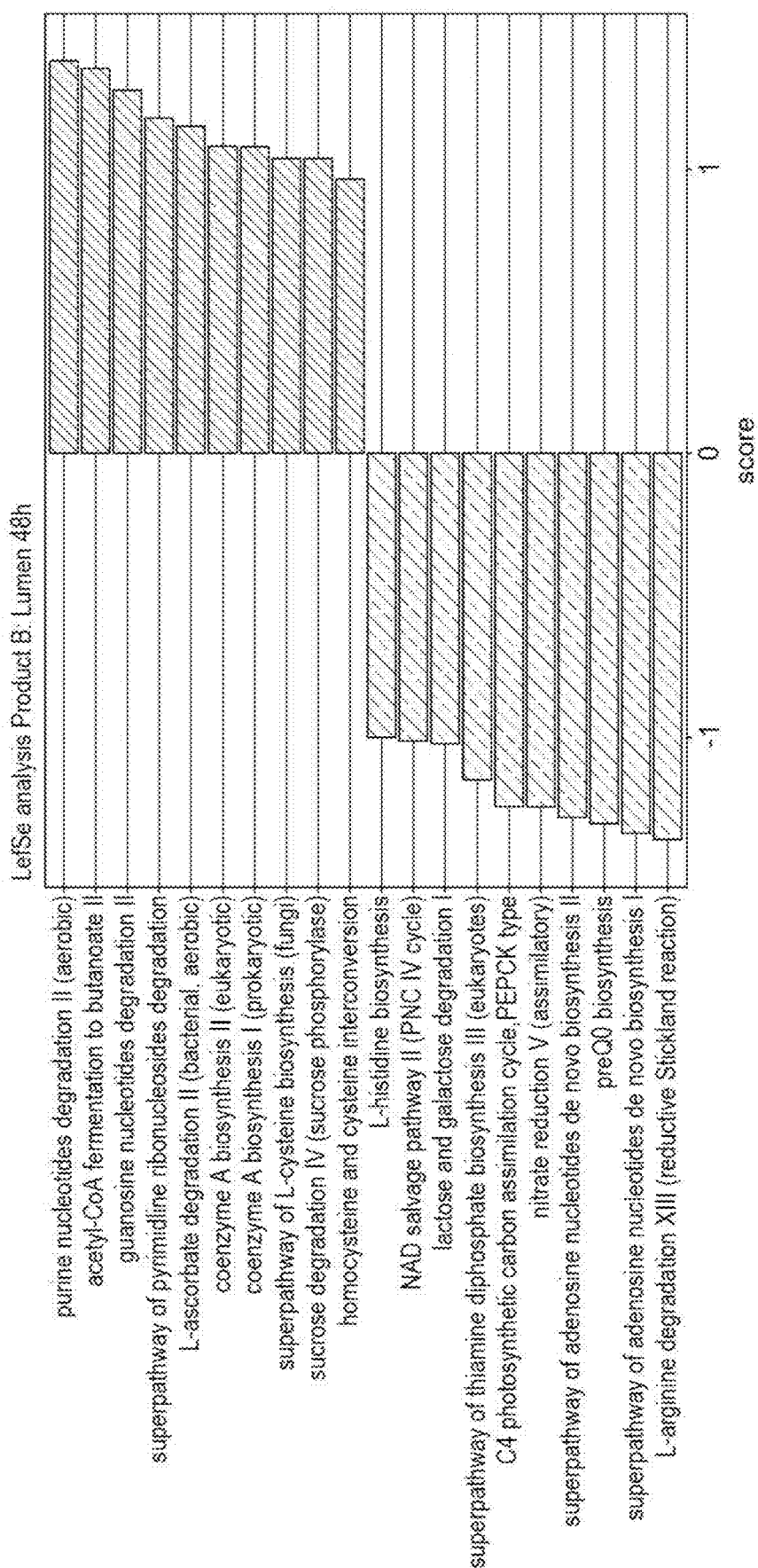
FIGS. 17A and 17B present a LEfSe in the luminal and mucosal environment, respectively, comparing Product B to Blank control after 48 h of incubation. The obtained histogram plots show the differences based on LDA scores of the functional data mapped against the MetaCyc database. The indicated pathways are significantly enriched features in the Product B group meeting $p<0.05$ for Kruskal-Wallis and Wilcoxon tests. LDA scores $\geq 2.0$ or $\leq -2.0$ are considered strongly enriched or depleted, respectively.
Figure 17B:
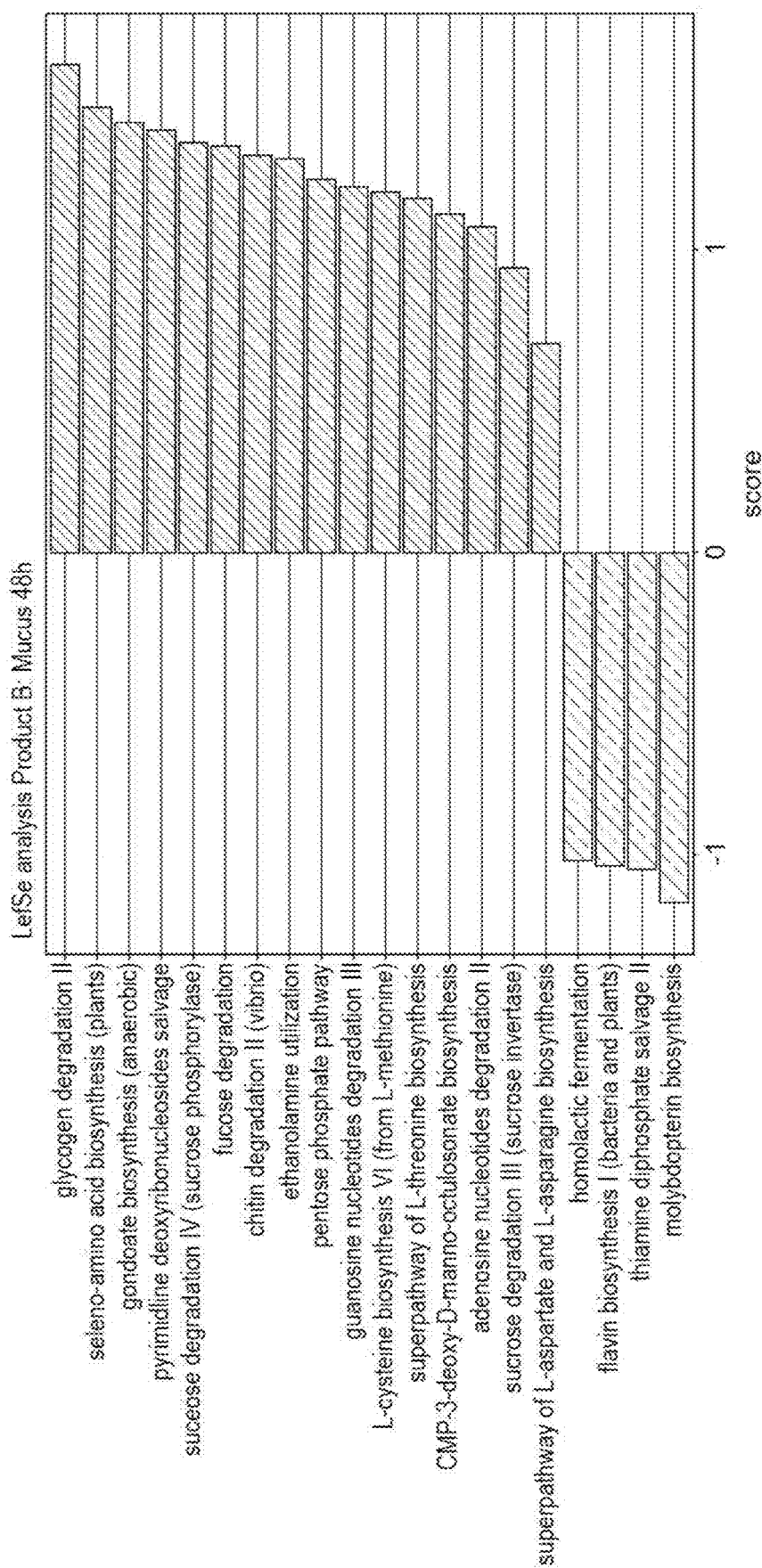

The MetaCyc analysis further reveals at 24 h that the starch degradation pathway and biosynthetic processes such as UDP-N-acetylmuramoylpentapeptide biosynthesis III are increased for Product B (FIG. 16). Also, some essential and non-essential amino acid biosynthesis for Product B are elevated, including L-methionine and L-arginine synthesis (FIG. 16). Glycogen biosynthesis I is also elevated in Product B after 24 h (FIG. 16). After 48 h, the MetaCyc analysis shows enhancement of sucrose degradation in the luminal and mucosal environment for Product B, while ethanolamine utilization, glycogen and fucose degradation are solely elevated in the mucosal environment FIGS. 17A and 17B).

Example 14: Survey Assessing the Effects of a CRL-Containing Dietary Supplement on the Enhancement of Cognitive Function Purpose of the Survey & Survey Methodology A comprehensive survey is distributed to a sample of participants who have been taking a CRL-containing dietary supplement regularly. Participants are asked to provide feedback on their experiences with the dietary supplement and indicate any observed changes in memory function. The survey includes questions pertaining to improvements in memory function, recall, focus, reductions in stress/anxiety levels, and enhancements in energy levels/fatigue management. The survey is aimed to gather insights into the perceived impact of CRL-containing dietary supplements on various aspects of cognitive performance, including memory function, alertness, focus, stress/anxiety reduction, and fatigue management as well as digestive health and overall health.

Participant Demographics

Figure 18:
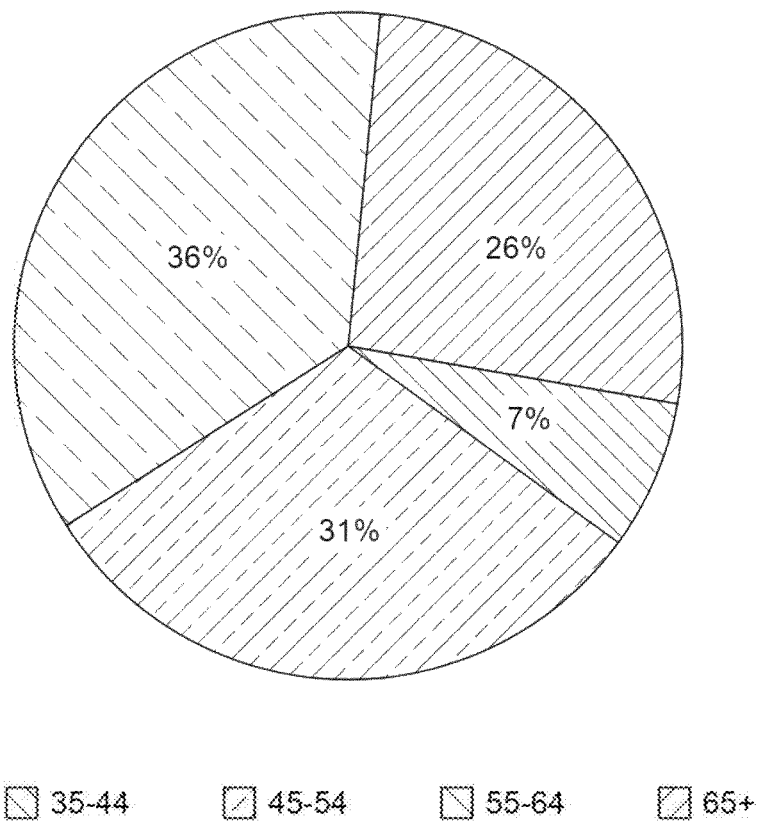
FIG. 18 presents an age distribution of participants in a survey investigating the impacts of regular use of a CRL-containing dietary supplement on cognitive function.

The participants in the survey represent a diverse demographic range, comprising individuals from various age groups ranging from 35 to 65+ years old. As shown in FIG. 18, the majority of participants fall within the adult age range, spanning from 35-45 years old (6.25%), 45-54 years (27%), 55-64 years (31.25%) and seniors 65+ (22%), reflecting a broad spectrum of life stages. This diverse demographic composition ensures that the survey findings capture a broad spectrum of experiences and perspectives regarding the effects of regular use of a CRL-containing dietary supplement on cognitive function and overall health.

The duration of use of a CRL-containing dietary supplement among participants varies, with individuals reporting different lengths of time since they began incorporating a CRL-containing dietary supplement into their daily regimen for general health reasons.

Memory Enhancement

Figure 19:
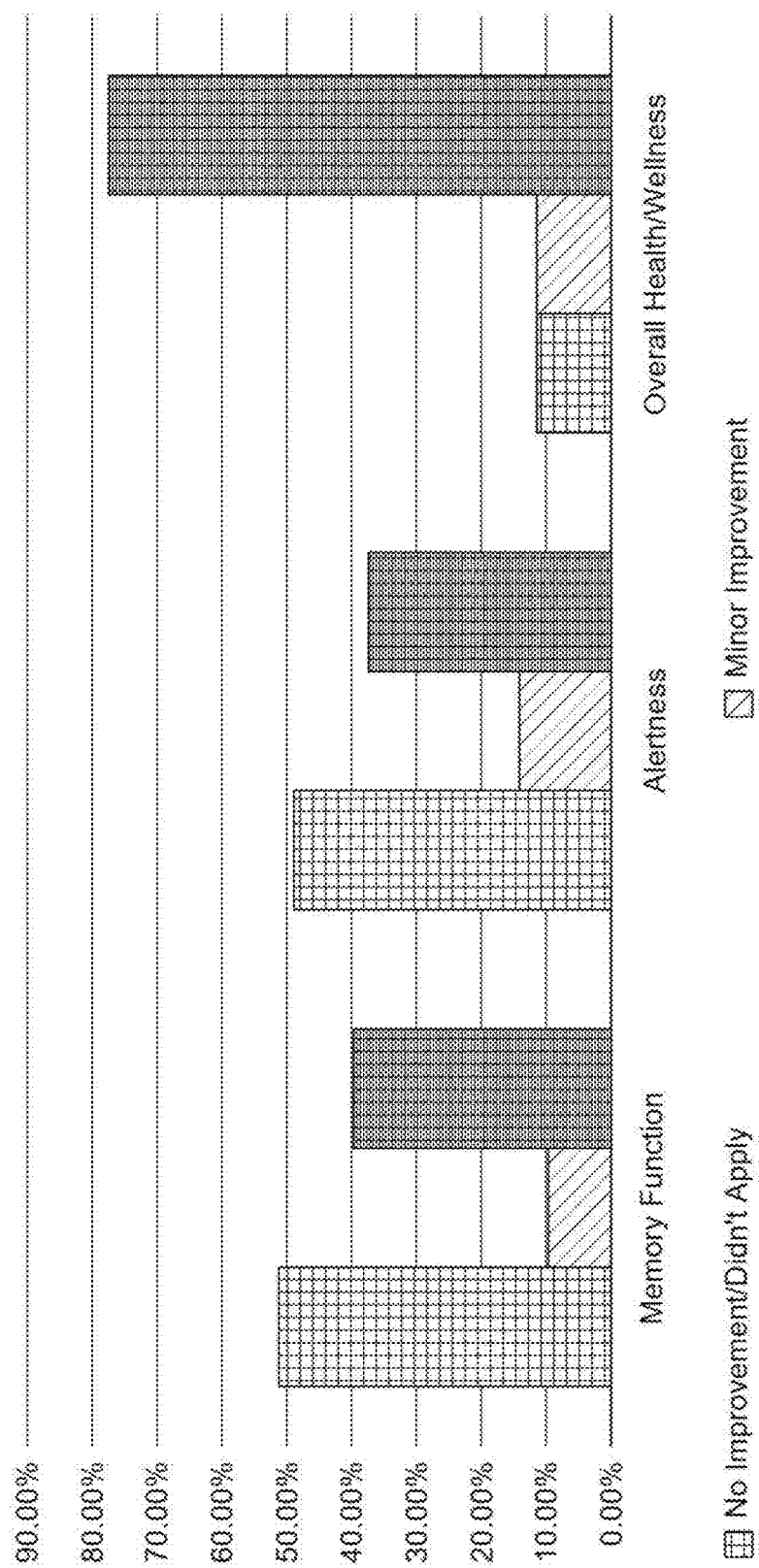
FIG. 19 presents a chart showing the percentage of participants who reported experiencing minor improvement, moderate/significant improvement, or no improvement in memory function, alertness and overall health.

The survey reveals that a significant majority of participants report perceived improvements in memory function; specifically, 39.5% of respondents indicate experiencing more than minor enhancements in their memory function after using CRL-containing dietary supplement regularly (FIG. 19).

Enhancement of Overall Alertness

A considerable proportion of participants report enhancements in overall alertness; approximately 37.22% of participants note improvements in their alertness levels following regular consumption of a CRL-containing dietary supplement (FIG. 19).

Combined Improvements

Figure 20:
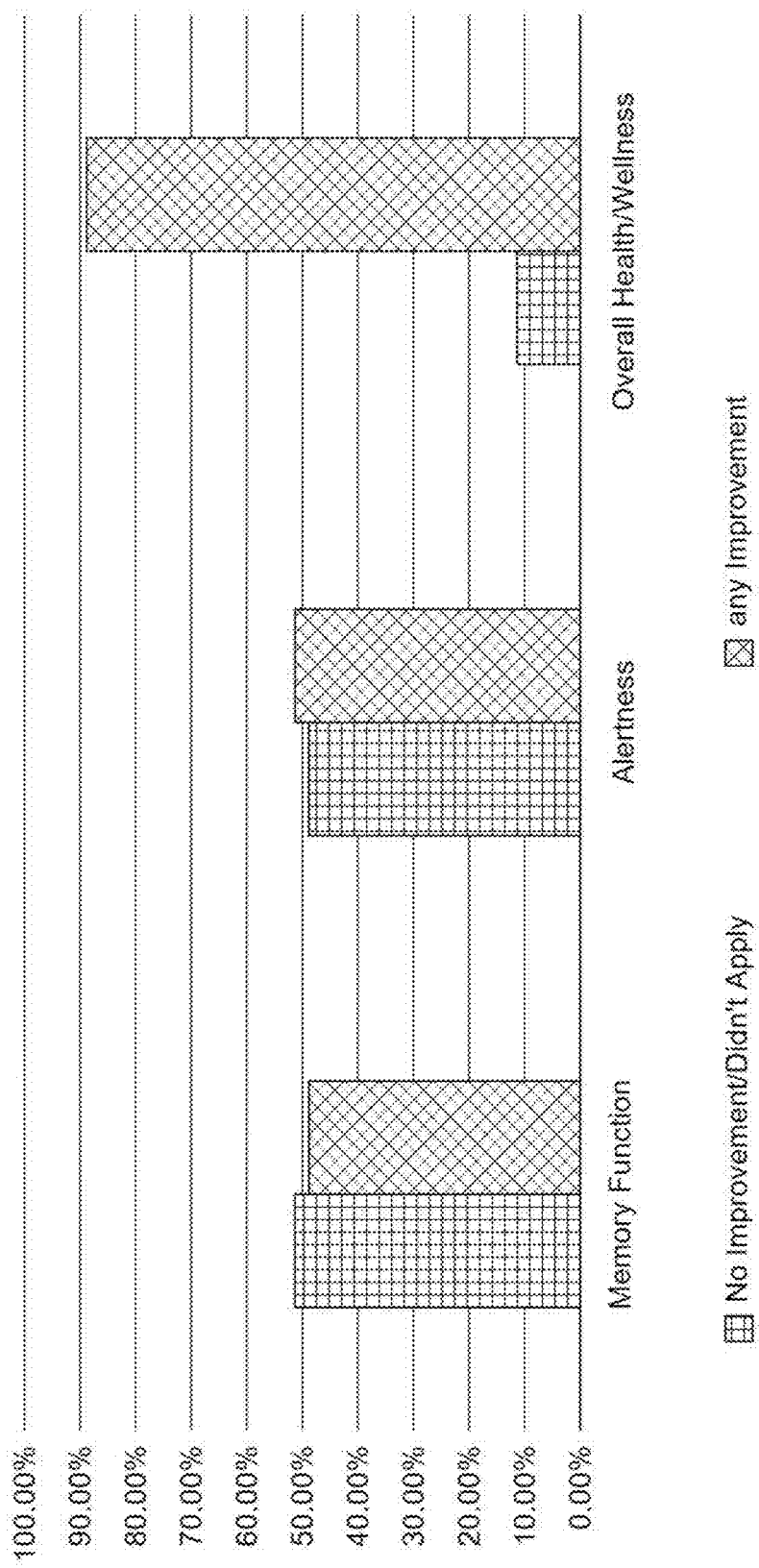
FIG. 20 presents a chart showing the combined percentage of participants who reported any improvement or no change in memory function, alertness and overall health.

As shown in FIG. 20 the combined percentage of individuals experiencing either minor or moderate to substantial improvements in memory function is 48.83%, and the combined percentage of individuals experiencing either minor or moderate to substantial improvements in overall alertness is 51.17%, underscoring a notable trend towards cognitive enhancement among regular users of a CRL-containing dietary supplement.

Recall

Figure 21:
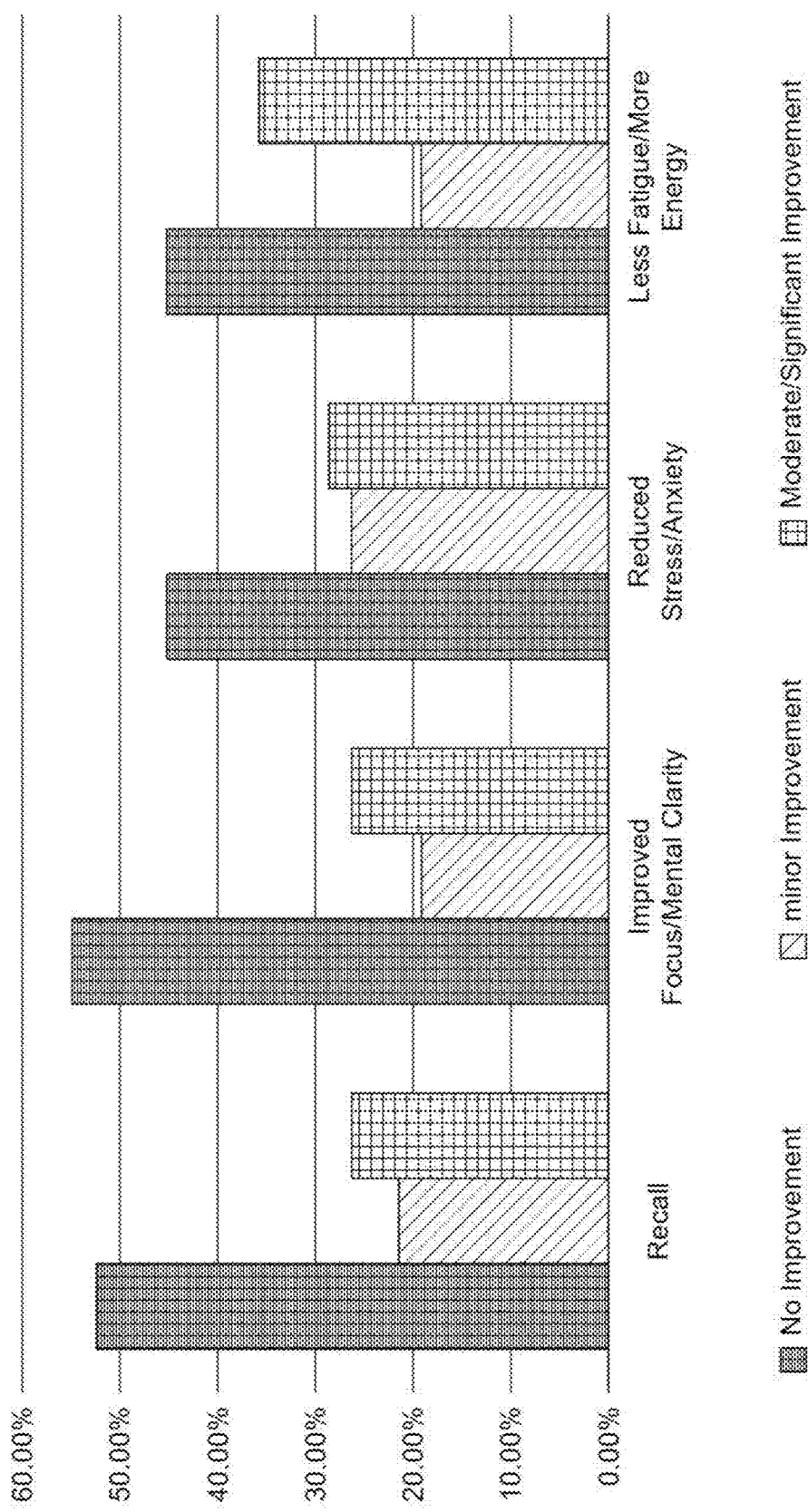
FIG. 21 presents a chart showing the percentage of participants who reported experiencing minor improvement, moderate/significant improvement, or no improvement in recall, improved focus/mental clarity, reduced stress, and reduced fatigue/increased energy.

As shown in FIG. 21, 26.2% of respondents in the survey report experiencing a significant enhancement in recall with a CRL-containing dietary supplement. Participants report an improved ability to retrieve and remember information.

Focus and Mental Clarity

As shown in FIG. 21, 26.2% of respondents in the survey report experiencing a significant improvement in focus and mental clarity. Participants report that the ability to concentrate and maintain mental acuity after regular consumption of the dietary supplement. This improvement suggests that regular use of a CRL-containing dietary supplement may effectively enhance cognitive function, particularly in tasks requiring sustained attention and concentration.

Stress and Anxiety Reduction

As shown in FIG. 21, 28.57% of respondents report feeling a reduction in stress and anxiety symptoms following regular consumption of a CRL-containing dietary supplement. This reduction in perceived stress and anxiety indicates that a CRL-containing dietary supplement may have a calming effect on the mind, potentially helping users of the dietary supplement to better manage stressors in their daily lives. Such findings are particularly relevant in today's fast-paced and demanding society, where stress and anxiety are prevalent concerns.

Reduced Fatigue and Increased Energy Level

Fatigue is a common issue that can significantly impair cognitive performance and overall well-being. As shown in FIG. 21, 35.7% of participants report feeling more energized and experiencing a reduction in fatigue. This improvement suggests that a CRL-containing dietary supplement may help individuals to overcome feelings of lethargy and exhaustion, thereby promoting greater productivity and vitality throughout the day. Thus, a CRL-containing dietary supplement may find general use in managing fatigue and increasing energy levels.

Combined Improvements

Figure 22:
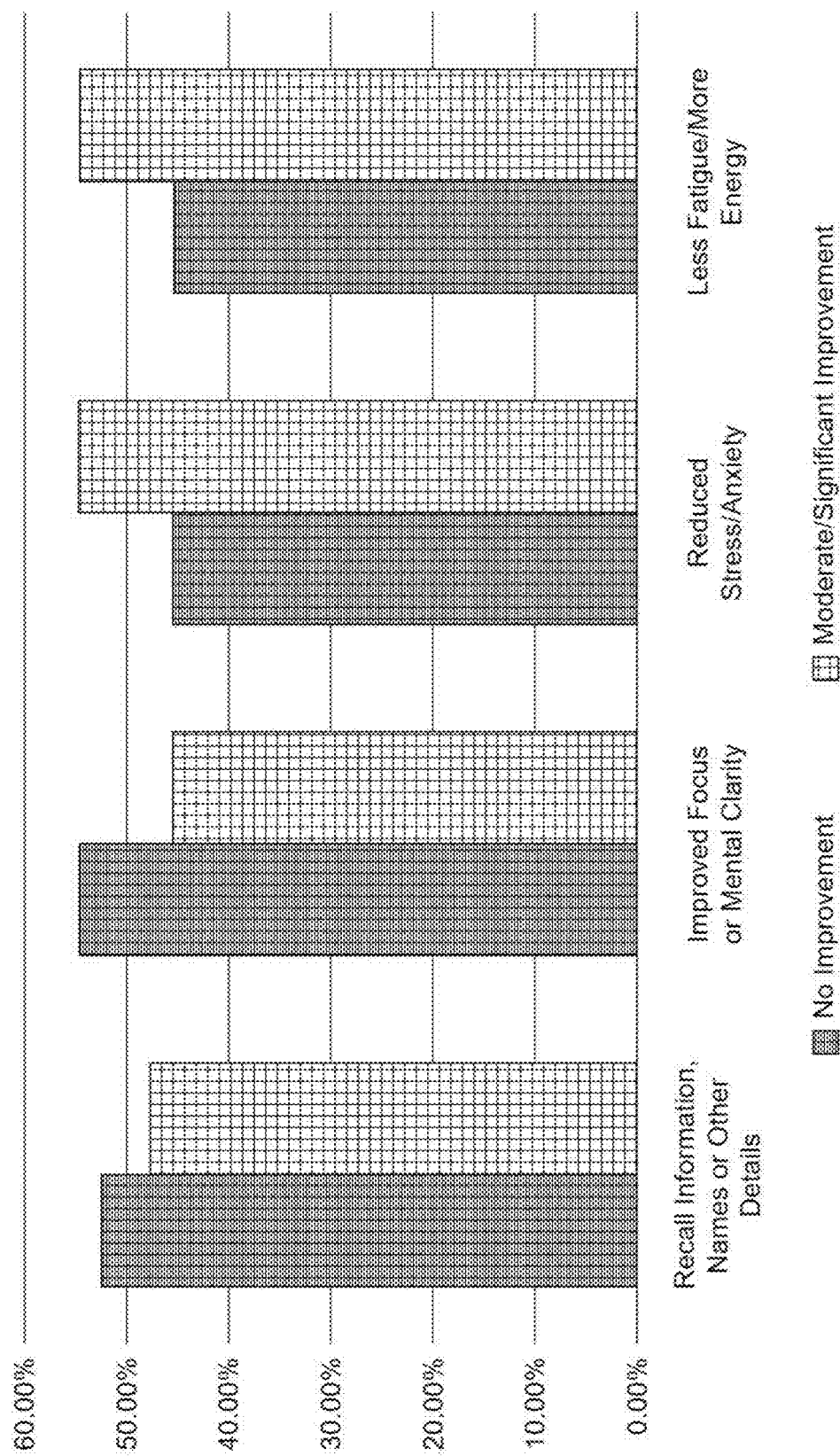
FIG. 22 presents a chart showing the percentage of participants who reported experiencing any improvement or no change in recall, improved focus/mental clarity, reduced stress and less fatigue/more energy.

The combined percentage of individuals experiencing either minor or moderate to significant improvements in recall is 47.62% (FIG. 22). The combined percentage of individuals experiencing either minor or moderate to significant improvements in focus and mental clarity is 45.24% (FIG. 22). The combined percentage of individuals experiencing either minor or moderate to significant improvements in stress and anxiety is 54.76% (FIG. 22). Finally, the combined percentage of individuals experiencing either minor or moderate to significant improvements in fatigue and energy level is 54.76% (FIG. 22). These results underscore a notable trend towards cognitive enhancement among regular users of a CRL-containing dietary supplement.

Overall Health Improvement

The survey reveals a substantial increase in perceived improvements in overall health. The combined percentage of individuals experiencing either minor or moderate to significant improvements in overall health is 88.63% (FIG. 19). It is notable that such a high percentage of participants report experiencing positive health changes beyond improved cognitive function. These changes in overall health may encompass any of increased energy levels, better mood regulation, enhanced immune function, and a general sense of well-being. Such improvements in overall health perception indicate the potential holistic benefits of regular use of a CRL-containing dietary supplement beyond cognitive enhancement alone.

CONCLUSION

The findings of this survey suggest that regular use of a CRL-containing dietary supplement may enhance cognitive function. The observed improvements in focus, memory function, recall, stress/anxiety reduction, and fatigue management among participants of the study highlight the possible benefits of regular use of a CRL-containing dietary supplement in optimizing cognitive performance and overall well-being.

While the present disclosure has been described with reference to particular embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope of the present disclosure.

Therefore, it is intended that the present disclosure not be limited to the particular embodiments disclosed as the best mode contemplated for carrying out the present disclosure, but that the present disclosure will include all embodiments falling within the scope and spirit of the appended claims.

We claim:

1. A method for improving memory function in a subject in need thereof, comprising administering a dietary supplement comprising *Candida rugosa* lipase (CRL) to the subject.

2. The method of claim 1, wherein the memory function of the subject in need thereof is assessed by a battery of neuropsychological tests.

3. The method of claim 2, wherein the neuropsychological tests measure verbal memory, visual memory, processing speed, attention, executive function, reaction time, or any combination thereof.

4. The method of claim 1, wherein the memory function of the subject in need thereof is assessed by CNS Vitals, a Symbol Digit Modalities Test (SDMT), a Profile of Mood States (POMS), a Pittsburgh Sleep Quality Index (PSQI), a Multidimensional Fatigue Inventory Questionnaire (MFI-20), a Frontal Systems Behavioral Scales (FrSBe), or any combination thereof.

5. The method of claim 4, wherein the memory function of the subject in need thereof is assessed by CNS Vitals.

6. The method of claim 5, wherein a CNS Vitals standard score (SS) of the subject in need thereof is 85 or less prior to the administering.

7. The method of claim 5, wherein a CNS Vitals standard score (SS) of the subject in need thereof is between 90 to 109 after the administering.

8. The method of claim 5, wherein a CNS Vitals standard score (SS) of the subject in need thereof is increased by 10 or more after the administering.

9. The method of claim 4, wherein the memory function of the subject in need thereof is assessed by a Symbol Digit Modalities Test (SDMT).

10. The method of claim 9, wherein a SDMT score of the subject in need thereof is 40 or less prior to the administering.

11. The method of claim 9, wherein a SDMT score of the subject in need thereof is between 45 to 50 after the administering.

12. The method of claim 9, wherein a SDMT score of the subject in need thereof is increased by 10 or more after the administering.

13. The method of claim 4, wherein the memory function of the subject in need thereof is assessed by a Profile of Mood States (POMS).

14. The method of claim 13, wherein the POMS is a POMS short form.

15. The method of claim 14, wherein the POMS short form score of the subject in need thereof is elevated prior to the administering.

16. The method of claim 14, wherein the POMS short form score of the subject in need thereof is decreased after the administering.

17. The method of claim 14, wherein the POMS short form score comprises measurements of one or more negative mood factors.

18. The method of claim 4, wherein the memory function of the subject in need thereof is assessed by a Frontal Systems Behavioral Scales (FrSBe).

19. The method of claim 18, wherein a FrSBe total score of the subject in need thereof is decreased by 10 points or more after the administering.

20. The method of claim 1, wherein the administering is for a period of 1 month to 5 years.

21. The method of claim 1, wherein the improved memory function in the subject in need thereof persists for a time period of 6 months, one year, or two years.

22. The method of claim 1, wherein the dietary supplement comprises about 30,000 Fédération International Pharmaceutique (FIP) units of CRL per tablet.

23. The method of claim 22, wherein the administering comprises administration of one or two tablets of the dietary supplement per day.

24. A method for improving cognitive function in a subject in need thereof, comprising administering a dietary supplement comprising *Candida rugosa* lipase (CRL) to the subject.

25. The method of claim 24, wherein the cognitive function of the subject in need thereof is assessed by a Montreal Cognitive Assessment (MoCA), a Mini-Mental State Exam (MMSE), a Mini-Cog, CNS Vitals, a Symbol Digit Modalities Test (SDMT), a Profile of Mood States (POMS), a Pittsburgh Sleep Quality Index (PSQI), a Multidimensional Fatigue Inventory Questionnaire (MFI-20), a Frontal Systems Behavioral Scales (FrSBe), or any combination thereof.

* * * * *